(12) United States Patent
Silverman

(10) Patent No.: US 10,796,801 B2
(45) Date of Patent: Oct. 6, 2020

(54) METHOD AND SYSTEM FOR ASSESSING, QUANTIFYING, CODING AND COMMUNIICATING PATIENT'S HEALTH AND PERIOPERATIVE RISK

(71) Applicant: David G. Silverman, West Redding, CT (US)

(72) Inventor: David G. Silverman, West Redding, CT (US)

(*) Notice: Subject to any disclaimer, the term of this patent is extended or adjusted under 35 U.S.C. 154(b) by 1316 days.

(21) Appl. No.: 14/978,276

(22) Filed: Dec. 22, 2015

(65) Prior Publication Data

US 2016/0232321 A1    Aug. 11, 2016

Related U.S. Application Data

(63) Continuation-in-part of application No. 13/459,836, filed on Apr. 30, 2012, now abandoned, which is a continuation-in-part of application No. 11/705,612, filed on Feb. 13, 2007, now Pat. No. 8,170,888.

(60) Provisional application No. 60/772,559, filed on Feb. 13, 2006, provisional application No. 60/839,112, filed on Aug. 22, 2006, provisional application No. 61/529,636, filed on Aug. 31, 2011.

(51) Int. Cl.
| | |
|---|---|
| *G16H 50/30* | (2018.01) |
| *G16H 10/60* | (2018.01) |
| *G16H 50/50* | (2018.01) |
| *A61B 5/00* | (2006.01) |

(52) U.S. Cl.
CPC .......... *G16H 50/30* (2018.01); *A61B 5/7275* (2013.01); *G16H 10/60* (2018.01); *G16H 50/50* (2018.01); *Y02A 90/26* (2018.01)

(58) Field of Classification Search
None
See application file for complete search history.

(56) References Cited

U.S. PATENT DOCUMENTS

| | | | |
|---|---|---|---|
| 6,915,265 B1* | 7/2005 | Johnson | G06F 19/328 705/2 |
| 7,195,594 B2 | 3/2007 | Eigler et al. | |
| 7,251,609 B1 | 7/2007 | McAlidon et al. | |
| 8,082,160 B2* | 12/2011 | Collins, Jr. | G06F 19/3418 705/2 |

(Continued)

FOREIGN PATENT DOCUMENTS

WO    WO91/09623    7/1991

OTHER PUBLICATIONS

O'Malley et al., "Joint-Specific Multidimensional Assessment of Pain . . . ", 2003, J Rheumatology, 30: 534-543.

*Primary Examiner* — Dennis W Ruhl
(74) *Attorney, Agent, or Firm* — Welsh Flaxman & Gitler LLC

(57) ABSTRACT

A multi-dimensional system for assessing, coding, quantifying, displaying, integrating and communicating information relating to patient health and perioperative risk includes a mechanism for inputting patient information and providing an output relating to the patient health and perioperative risk. The output includes a score for the physical condition of the patient, a score for the degree of expected surgical risk and invasiveness, a score for other vital assessments of perioperative complexity, and alphanumeric codes for other factors that may require special preoperative preparation and planning.

17 Claims, 113 Drawing Sheets

(56) References Cited

U.S. PATENT DOCUMENTS

| | | | |
|---|---|---|---|
| 8,231,541 B2* | 7/2012 | Colquitt | A61B 5/0205 60/300 |
| 2002/0103671 A1 | 8/2002 | Pederson et al. | |
| 2003/0101081 A1 | 5/2003 | Putnam et al. | |
| 2004/0224543 A1 | 2/2004 | Zhang et al. | |
| 2005/0273359 A1 | 12/2005 | Young | |
| 2014/0108042 A1* | 4/2014 | Reddy | G16H 50/30 705/3 |
| 2016/0198996 A1* | 7/2016 | Dullen | A61B 5/0024 600/301 |

* cited by examiner

FIG. 4
FIG. 4A

SAMPLE NOTE
*(based on scored positive findings as may be selected in Table 2)*
45 y/o female for radical hysterectomy with pelvic node exenteration b/o uterine cancer found during workup of slight postmenopausal bleeding.

Allergies: seasonal (2), Tegretol → rash 20 yrs ago for a single trauma-induced seizure (2), Penicillin → hives (3), Latex → short of breath (4)
Meds: (not included in this example)
Social History: >5 drinks/day x 10 yrs – prone to withdrawal (4); nonsmoking; denies drugs
Prior Surgery and Anesthesia: (surgeries not listed in this example)
    Family Hx: sister with documented episode of malignant hyperthermia (4).

CNS (1.5): negative for stroke, TIA
    + single seizure > 5 yrs ago (EtOH-related) (1.5)
PSYCH (1.5):
    + controlled anxiety (1.5)
ENDO (3): negative for thyroid, pituitary, adrenal gland
    + Diabetes mellitus: Type 2 stable on oral meds for < 5yrs (2).
    + Parathyroid: clinically signif calcium abnormality w/ confusion, somnolence, hypovolemia and polyuria (3).
CARD (3): negative for murmur, dysrhythmia
    + stable exertional angina (last episode 2 wks ago) (3); occasional use of nitroglycerin (3); old MI (3); ICD in place for h/o ventricular fibrillation (3). Cardiac-related dyspnea upon moderate exertion (<1 flight) (3); clinically insignificant MVP murmur (2); well-controlled hypertension w/o end organ damage (2). No cardiac evaluation in at least 5 years.
VASC (3):
    +s/p left transmetatarsal amputation for vascular insufficiency (3)
RESP (3): negative for COPD
    + asthma w/ rare symptoms (2); obstructive sleep apnea – AHI = 30, mild hypercarbia (3)
LIVER (3): negative for hepatitis
    + cirrhosis (Childs-Pugh A) w/ current ascites attributed to h/o alcoholism (3); PT 1.6x normal (3).
GI (1.5):
    + occasional GERD, well-controlled on meds (1.5).
KUBU (1.5): negative for renal insufficiency
    + h/o asympt stones (1.5)
GYN (3):
    + locally invasive uterine cancer w/ potential node involvement (3); chemotherapy (one dose 5-FU) two wks ago w/o sequelae (3)

Physical Exam: BP 120/80, Heart Rate 80, Oxygen sat. 98%, Temp 98.6°F; height 62 inches, wt 120 lbs.
Airway: Mouth opening > 4cm (0). Thyromental Distance 2-3 cm (3), Overbite, poor extension (2), Neck extension >60 degrees (0). Heart: regular, without murmur; Lungs: clear.

SAMPLE NOTE (cont'd)

Sample Summary at end of Note (details of categories provided in text). User can select what information should be printed in note, exported to other sites including ASPIRIN™ display and wallet card):
A3 = ASA 3/SISS™3: ENDOparathyroid, CARDihd, VASC, RESPosa, LIVER, GYNtumor
S3 = SOCU™3/SICU™3: CARD, RESP, HEME, F&E
P3 = Physical Factors Affecting Mask Ventilation (P): 3 based on: sleep apnea (3)
I5 = Intubation factors and related issues (I): 5 based on: Thyromental Distance 2-3 cm (3), Overbite, poor extension (2).
R = Risk indicators (R): Allergies [Penicillin → hives (SASRI™ = 3), Latex → short of breath (4)]; Habits [>5 drinks/day x 10 yrs – prone to withdrawal (4)]; Anesthesia-specific Risks [sister with malignant hyperthermia] (4); sleep apnea (3)]
I =Information pending and/or for review (I): cardiology consult (3) [*generated by combination of SISS™ and SICU™ in association with ACC/AHA guidelines – see text*]
N = Special Needs (N): 2 units of blood; malignant hyperthermia precautions (special anesthesia machine); latex-free setup.
Exports:
--ACC/AHA Criteria for Cardiology Evaluation: hypertension w/o end organ damage (2); prior MI (3), stable angina (3); cardiac-related dyspnea on exertion (→no reduction of score for good exercise tolerance); intermediate risk/invasiveness of surgery (3) – total points = 11 [*as per Table __-]*
--Indications of Beta-Blocker therapy: hypertension w/o end organ damage (2); prior MI (3), stable angina (3); cardiac-related dyspnea (→no reduction of score for good exercise tolerance); intermediate risk/invasiveness surgery (3) – total points = 11 [*per Tables 11a and 11b*]. (*If patient had an allergy to beta-blockers, it would co-populate this area*)
--NSQIP factors: chemotherapy two wks ago w/o sequelae (3), current ascites (3), ETOH >2 drinks/day in the 2 wks prior to admission; dyspnea (unable to climb one flight of steps without shortness of breath); angina within 30 days (3); s/p amputation for PVD (3) [*per text and Table 117a*]
--Wallet Card: 3- ENDOparathyroid, CARDihd, VASCpvd, RESPosa, LIVER, GYNtumor; 2; EKG: probable old anterior-septal myocardial infarction (3) (*score prompts option for inventive reduction of EKG to be incorporated – described later in text and in Figure 15*)

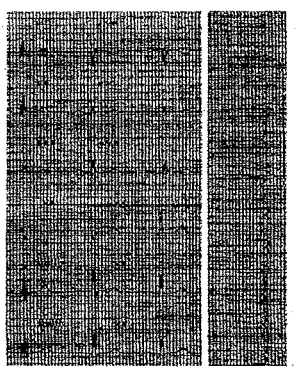

POTENTIAL ASPIRIN™ CONFIGURATIONS AND LINKS
(based on information provided in sample note of Figure 4)

a) Simple Display with Scores for modified ASA score, Surgical risk/invasiveness, Physical factors affecting mask ventilation, and Intubation predictors:
   3,3,3,5 b) ASPIRIN™ display with scores annotated with SISS™ and SICU™ delineations to provide increased information:
   $3^{ENDO,CARD,VASC,RESP,LIVER,GYN}$   $3^{CARD,RESP,HEME,F\&E}$ 3,5 c) + notification that there are items of interest in R (Risk indicators), Interim info & issues (I) and special Needs (N):
   $3^{ENDO,CARD,VASC,RESP,LIVER,GYN}$   $3^{CARD,RESP,HEME,F\&E}$ 3,5,R,I,N d) + links to aspects of systems with SISS™ ≥ 3:
   ENDO (3): Parathyroid: clinically signif calcium abnormality w/ confusion, somnolence, hypovolemia and polyuria (3).
   CARD (3): stable exertional angina (last episode 2 wks ago) (3); occasional use of nitroglycerin (3); old MI (3); ICD in place for h/o ventricular fibrillation (3). Cardiac-related dyspnea upon moderate exertion (<1 flight) (3).
   VASC (3): s/p left transmetatarsal amputation for vascular insufficiency (3)
   RESP (3): obstructive sleep apnea – AHI = 30, mild hypercarbia (3)
   LIVER (3): cirrhosis (Childs-Pugh A) w/ current ascites attributed to h/o alcoholism (3); PT 1.6x normal (3).

e) + links to airway scores
   <u>Physical Factors Affecting Mask Ventilation (P):</u> 3 based on: sleep apnea (3)
   <u>Predictors of Intubation Difficulty (I): 5 based on:</u> Thyromental Distance 2-3 cm (3), Overbite, with poor extension (2).

f) + links to Risk Indicators w/ scores ≥ 3*:
   Risk indicators (R): Allergies [Penicillin → hives (3), Latex → short of breath (4)]; Habits [>5 drinks/day x 10 yrs – prone to withdrawal (4)]; Anesthesia-specific Risks [sister with malignant hyperthermia (4); obstructive sleep apnea (3)]

g) + links to Interim Information & Issues*:
   <u>Interim Information & Issues (I):</u> cardiology consult (3); access EKG (because of score ≥ 2)

h) + links to special Needs*:
   <u>Special Needs (N):</u> 2 units of blood; malignant hyperthermia precautions (special anesthesia machine); latex-free setup.

* = an institution can establish procedures wherein terms or abbreviations (e.g., "Latex" for latex allergy precautions, "MH" for malignant hyperthermia precautions) are deemed important enough to appear in the R, I or N sections of the ASPIRIN™ display without the need to first activate the listing.

FIG. 6 (CON.)

FIG. 6B i)

|  | Patient 1 | Patient 2 | Patient #n |
|---|---|---|---|
| A | 5:<br>4:<br>3: | | |
| S | 5:<br>4:<br>3: | | |
| P (likely not needed) | | | |
| I (likely not needed) | | | |
| R | 5:<br>4:<br>3: | | |
| I | 5:<br>4:<br>3: | | |
| N | 5:<br>4:<br>3: | | |
|  | | | |
|  | | | |

FIG. 7A

| Time | Surgeon | Patient | Age | Procedure |
|---|---|---|---|---|
| 0730 | Smith, John | Doe, Jane | 84 | Cervical spine fusion, C4-C6 |

FIG. 7B

| Time | Surgeon | Patient | | Age | Procedure |
|---|---|---|---|---|---|
| 0730 | Smith, John | Doe, Jane | 3; CARD,RESP,NMS;3; 1,5 Latex;5 | 84 | Cervical spine fusion, C4-C6 |

FIG. 7C

| Time | Surgeon | Patient | | Age | Procedure |
|---|---|---|---|---|---|
| 0730 | Smith, John | Doe, Jane | 3; CARD,RESP,NMS;3; 1,5 Latex;5 | 84 | Cervical spine fusion, C4-C6 |

FIG. 8A

| | System or Dual Systems or Multisystems | Subsystem | Feature Category | System/ Subsys/ Feat Categ Code | Co-populating Code for Feat Categ, Feature and Possibly Subfeature and Descriptor(s) |
|---|---|---|---|---|---|
| | CNS | Seizures | Generalized Tonic-Clonic Seizures | 1A.01a | 01a.###$.####$.#####$ |
| | | | | 1A.01a | 01a.###$.####$.#####$ |
| | | | | 1A.01a | 01a.###$.####$.#####$ |
| | | | Generalized Absence Seizures | 1A.02a | 02a.###$.####$.#####$ |
| | | | | 1A.02a | 02a.###$.####$.#####$ |
| | | | | 1A.02a | 02a.###$.####$.#####$ |
| | | | Complex Partial Seizures | 1A.03a | 03a.###$.####$.#####$ |
| | | | | | 03a.###$.####$.#####$ |
| | | | | | 03a.###$.####$.#####$ |
| | | | Simple Partial Seizures | 1A.04a | 04a.###$.####$.#####$ |
| | | | | | 04a.###$.####$.#####$ |
| | | | | | 04a.###$.####$.#####$ |
| | | | Other Seizures | 1A.05a | 05a.###$.####$.#####$ |
| | | | | | 05a.###$.####$.#####$ |
| | | | | | 05a.###$.####$.#####$ |
| | | | Unspecified Seizures | 1A.06a | 06a.###$.####$.#####$ |
| | | | | | 06a.###$.####$.#####$ |
| | | | | | 06a.###$.####$.#####$ |
| | | Cerebral Ischemia | Asymptomatic Carotid Disease | 1B.07a | 07a.###$.####$.#####$ |
| | | | /80% narrowing bilaterally/found during preop workup | | 07a.###$.####$.#####$ |
| | | | | | 07a.###$.####$.#####$ |
| | | | TIA | 1B.08a | 08a.###$.####$.#####$ |
| | | | /crescendo pattern/transient loss of vision | | 08a.###$.####$.#####$ |
| | | | | | 08a.###$.####$.#####$ |
| | | | | | |
| | | | | | |

FIG. 8B
Alternative Coding System with augmentation of information in decimal code by letters

| | System or Dual Systems or Multisystems | Subsystem | Feature Category | System/ Subsys/ Feat Categ Code | Co-populating Code for Feat Categ, Feature and Possibly Subfeature and Descriptor(s) |
|---|---|---|---|---|---|
| | CNS | Seizures | Generalized Tonic-Clonic Seizures | 1A.01a | 01a.###$.####$ |
| | | | | 1A.01a | 01a.###A$.#### |
| | | | | 1A.01a | 01a.###B$.#### |
| | | | | 1A.01a | 01a.###AB$.#### |
| | | | | 1A.01a | 01a.###A$B$C$.#### |
| | | | | | |
| | | | Asymptomatic Carotid Disease | | |
| | | | /80% narrowing bilaterally/found during preop workup | | |
| | | | | | |
| | | | TIA | | |
| | | | /crescendo pattern/transient loss of vision | | |

FIG. 8C
Alternative Coding System Relying on Letters to Delineate Branches.

| System or Dual Systems or Multisystems | Subsystem | Feature Category/Feature/Descriptor | System/ Subsystem(A)/ Feature Category Code (B) | Co-populating Code for Feat Categ (B), Feature (C) and Possibly Subfeature D) and Descriptor(s) (Z) |
|---|---|---|---|---|
| CNS | Seizures | Generalized Tonic-Clonic Seizures | 1A1B1.0001 | B1.0001 |
| | | /Weekly seizures/often loss of bladder control | 1A1B1.0001 | B1.0001C1$3.Z304 |
| | | /poorly controlled by meds/last 1-2 minutes | 1A1B1.0001 | B1.0001C2$3.Z116a |
| | | //for 10-20 yrs | 1A1B1.0001 | B1.0001C3$D#$Z109 |
| | | | 1A1B1.0001 | B1.0001C4$#Z# |
| | Cerebral Ischemia | Asymptomatic Carotid Disease | 1A102B1.0007 | |
| | | /80% narrowing bilaterally/found during preop workup | 1A102B1.0007 | B1.0007$3C1Z111 |
| | | TIA | 1A102B1.0008 | |
| | | /crescendo pattern/transient loss of vision in left eye | 1A102B1.0008 | B1.0008$4C4$4/Z404c |
| | | //<1 hour | | Z116 |
| | | //Aspirin ineffective in past | | Z501 |

FIG. 11

FIG.11A
Risk Indicators:
Adverse Reactions to Medications

| | SASRI™=0: No problem | SASRI™=1: Not likely&minor | SASRI™=2: Mild | SASRI™=3: Moderate | SASRI™=4: Severe | SASRI™=5: Life-threatening |
|---|---|---|---|---|---|---|
| Drug Allergies (see text for more specific SASRI™ scores) | None | Minor anaphylactoid (e.g., slight itch with opioids) | Mild-Moderate anaphylactoid. Allergy to med not likely periop (e.g., a steroid cream, birth control pill) | Severe anaphylactoid. Allergy to med possible periop w/ major potential effects (e.g., penicillin) | Likely periop w/ major potential effects | Likely life-threatening exposure |
| Nonallergic Drug-Induced (DI) s/s | None known | DI drowsiness, mild NorV | DI somnolence, mod NorV | DI ↓ mental status, confusion, severe NorV | DI delirium. | DI coma |
| Adverse Material & Environmental reactions | | | Tape-induced redness. Prep solution-induced redness. Rhinitis. | Tape- or prep- induced peeling. Environmentally induced wheezing. Contrast agent-induced rash. Possible latex. | Tape- or prep-induced excoriation. Latex allergy. Contrast dye-induced anaphylactoid/tic rxn | |

FIG.11B
Habits

| | | | | | | |
|---|---|---|---|---|---|---|
| Cigarettes: Pack-yrs, current (cur) or m/y stopped | None, <1,>1m | 1-5, >1m | 1-5, cur 5-20, >1m 20+, >5y | 5-20, cur or 1m-5y 20+, cur or 1m-5y | | |
| Cigarettes s/s | n/a | None or Mild | Moderate | Severe | | |
| Alcohol:Drinks/day, cur or m/y stopped | None, Occasional | 1-2, cur 3-4, >2 w | Alcoholism (none for >6m); 3-4, *cur* | Alcoholism (none for 1w-6m); >4,*cur*(but not prone to withdrawal) | Cur Alcoholism; prone to withdrawal | Cur withdrawal; Intoxicated DOS |
| Drugs (Recreational) | None | Occasional | Addiction, none >6m w/ no sequelae. Marijuana approx 1/w; Cocaine, Heroine approx 1/m | Frequent. h/o Addiction, none 1w-6m. On methadone. | Current Addiction | Current withdrawal. Cocaine use on DOS |

FIG. 11C
Susceptibility to Problems with Anesthetic Medications

| Neuromuscular Conditions | | Inc risk of malignant hyperthermia (e.g., pediatric eye muscle surgery). Minor contraindications to succinylcholine | h/o neuroleptic-malignant syndrome. Uncertain risk of malignant hyperthermia. Intermed contraindications to succinylcholine. Pseudocholinesterase deficiency. Myasthenia gravis-responsive to Rx. | High risk of malignant hyperthermia or sux-induced hyperkalemia. Severe myasthenia gravis. |
|---|---|---|---|---|
| Postoperative Nausea and Vomiting | No known problems | Mild-mod postop N&V | Moderate postop N&V. | |
| Anesthetic-induced hepatic dysfunction | | | h/o possible halothane hepatitis. h/o porphyria | h/o halothane Hepatitis. Active porphyria. |
| | | | Severe postop N&V. | |
| | | Moderate postop N&V. | | |
| | | | h/o halothane Hepatitis. Active porphyria. | |

FIG. 11D
Conditions

| Pregnancy | Not applicable. Test negative | Undergoing termination of pregnancy | Patient Denies | Uncomplicated pregnancy. Pregnancy test indicated. | SevereN&V. High risk of Premature labor. Pre-ecclampsia | Ecclampsia; Life-threatening complications |
|---|---|---|---|---|---|---|
| Breast Feeding | | Easily stopped >24 hrs | Can be stopped 6-24 hrs | Difficult to stop > 6 hrs | | |
| Abnormal Lab Results | | | Moderate lab abnormalities. | Significant lab abnormalities | Severe lab abnormalities | Life-threatening lab abnormalities |

FIG. 11E
Susceptibility to Ventilatory Complications

| Anesthetic-specific issues: Prior Intubation | Documented easy; no report of problems. No interval changes. | No documentation; patient says no problems. No interval changes | Prior easy; significant interval changes | Prior difficulty | Prior impossible (required fiberoptic) | Required previous trach. |
|---|---|---|---|---|---|---|
| Aspiration risks | None or rare | Occasional GERD, preop therapy ordered | GERD, hiatal hernia or ↑ risk (advanced diabetes, obesity, pregnancy) readily responsive to therapy (ordered) | GERD, hiatal hernia, or ↑risk which should be responsive to preop therapy but not ordered. | GERD or hiatal hernia not reliably responsive to therapy (i.e., rapid sequence intubation likely required) | Term pregnancy, Zencker's diverticulum, Severe esophageal narrowing/obstruction, upper GI bleed |
| Obstructive Sleep-Apnea (OSA): (see legend) | | 1 catgegory | 2 categories. | 3 categories; Apnea Hypopnea Index (AHI) 21-40. | AHI > 40. | Severe hypoxia, hypercarbia |

*Categories Suggestive of Sleep-Apnea*
o  *Predisposing physical characteristics: BMI >35 kg/m², neck >17 in, craniofacial abnormalities affecting airway, anatomic nasal obstruction, tonsils touching or nearly touching.*
o  *Apparent airway obstruction during sleep: loud or freq snoring, pauses during sleep, awakens with choking sensation.*
o  *Somnolence: frequent and/or falls asleep in nonstimulating environment despite adequate "sleep*

FIG. 11F
Miscellaneous

| | | | | | |
|---|---|---|---|---|---|
| Other Anesthesia-related Physical Issues | | Potentially difficult IV Uses interpreter | Likely Difficult IV Likely Difficult positioning | | |
| Interactive Issues | | Dec mental status. | Uses interpreter. Uncooperative | Combative. Unresponsive | |
| Special Concerns | | Requests minimal resident participation. Reports awareness during previous general anesthetic | | | |
| Other Personal Issues | | Moderately anxious. Very anxious – therapy ordered | Very anxious – no therapy or despite therapy | | |
| Anticipated Analgesic Requirements | Normal for planned minor surgery | Normal for planned intermediate surgery | Normal for planned major surgery | > normal | >> normal | >>>normal |
| Other Special Issues | | | | Refuses blood products (minor surgery). | Refuses blood products (major surgery) |

| Sites of Co-Population | Surgery | HPI | Age | Allergies | Meds | Prior Anesthesia | Prior Surgery | CNS | Endocrine | Cardiac | Respiratory | Other Systems | Airway Score | Categ 3 surg | CategCard 3 Surg |
|---|---|---|---|---|---|---|---|---|---|---|---|---|---|---|---|
| Medications |   |   |   |   |   |   |   |   |   | B | B | B |   |   |   |
| CNS | A | A |   |   |   |   |   | X |   |   |   | A |   | A |   |
| Endo | A | A |   |   |   |   |   | A | X |   |   | A |   | A |   |
| Cardiac | A | A |   |   |   |   |   |   |   | X | A | A |   | A | A |
| Resp | A | A |   |   |   |   |   |   |   | A | X | A |   | A |   |
| Other system(s) | A | A |   |   |   |   |   | A | A | A | A | A |   | A |   |
| SISS™ of ASPIRIN™ |   |   |   |   |   |   |   |   |   |   |   |   |   |   |   |
| SOCU or SICU of ASPIRIN™ |   |   |   |   |   |   | B |   |   |   | A | A |   |   |   |
| Airway score (P and I of ASPIRIN™) | A | A |   |   |   |   |   |   |   |   |   |   |   |   |   |
| CBC | B | B | B |   | B |   |   |   | B | B | B |   |   | B |   |
| LYTES | B | B | B |   | B |   |   |   | B | B | B |   |   | B | B |
| BUN/creatinine | B | B | B |   | B |   |   |   | B | B | B |   |   | B | B |
| Glucose | B | B | B |   | B |   |   |   | B | B |   |   |   | B | B |
| HbA1c | B | B |   |   | B |   |   |   | B |   |   |   |   | B |   |
| LFTS | B | B |   |   | B |   |   |   |   |   |   |   |   | B |   |
| PT/PTT | B | B |   |   | B |   |   |   |   |   |   |   |   | B |   |
| Type&screen | B | B |   |   |   |   |   |   |   |   |   |   |   |   |   |
| Type&cross | B | B |   |   |   |   |   |   |   |   |   |   |   |   |   |
| EKG | B | B | B |   |   |   |   |   | B | B | B |   |   | B | B |
| Cardiac risk indices | B | B |   |   |   |   |   |   | C | C |   |   |   | B | C |
| ACC/AHA | B | B |   |   |   |   |   |   | C | C |   |   |   | B | C |
| Beta Blockers | B | B |   |   |   |   |   |   | B | B |   |   |   | B | C |
| ECHO | B | B |   |   |   |   |   |   |   | B |   |   |   | B | B |
| Stress test | B |   |   |   |   |   |   |   |   | B |   |   |   | B | B |
| Cardiac cath |   |   |   |   |   |   |   |   |   | B |   |   |   | B | B |
| Cardiac consult | B | B |   |   |   |   |   |   |   | B |   |   |   |   | B |

| | | | | | | | | | | | | | | | | | |
|---|---|---|---|---|---|---|---|---|---|---|---|---|---|---|---|---|---|
| Pulmonary Consult | C | | | | | | | | | | | | | | | | |
| PCP evaluation | B | B | | | | | | | | | | | | | | | |
| Risk indices (R of ASPIRIN™): | C | | C | C | | | | | C | | A | | | C | C | C | |
| --MH precautions | | | | | | C | | | | | | | | | | | |
| --Airway concerns | | B | | | | C | | | | | | | B | | | | |
| --? ICP concerns | | B | | | | | | A | | | | | | | | | |
| --Aspiration risk | | B | | | | C | | | A | A | | | B | | | | |
| NSQIP | B | B | | | | | | | | | | | | | | | |
| Interim Information & Issues (I of APSIRIN™) | B | B | B | B | | | | C | C | C | C | | C | C | C | C | |
| Needs (N of ASPIRIN™) | B | B | | B | B | B | B | B | B | B | B | | B | B | B | | |
| Score-Driven Provider-to-Provider "Sign-out" Report | A | A | A | A | A | A | A | A | A | A | A | | A | A | A | | |
| Score-Driven Patient "Wallet" Card | A | A | A | A | A | A | A | A | A | A | A | | A | A | A | | |
| Billing | C | C | C | C | C | C | C | C | C | C | C | | C | C | C | | |
| Quality Assurance | C | C | C | C | C | C | C | C | C | C | C | | C | C | C | | |
| Research | C | C | C | C | C | C | C | C | C | C | C | | C | C | C | | |

| | | Patient 1 | Patient 2 | Patient 3 |
|---|---|---|---|---|
| Portion of Existing Hospital Data Base | ICD-9 Codes | | | |
| | CPT Codes | | | |
| | Complications | | | |
| | Length of Surg | | | |
| | O.R. Costs | | | |
| | Length of Stay | | | |
| | Hosp Costs | | | |
| SHAPE™ 1-5 (or 0-5...) SICU™ and SICU™ Scores | Surg Invasiveness | | | |
| | F&E | | | |
| | HEME | | | |
| | EENT | | | |
| | SKIN | | | |
| | NMS | | | |
| | GENITAL | | | |
| | KUBU | | | |
| | GI | | | |
| | HEPATIC | | | |
| | RESP | | | |
| | VASC | | | |
| | CARD | | | |
| | ENDO | | | |
| | PSYCH | | | |
| | CNS | | | |

FIG. 14. Integration of ICD-9 code ("ICD") with the inventive coding and scoring FIG. 14A
Using coding shown in FIGS. 8A and 9A:
-without inventive scoring

| System | Subsystem | Feature Category | Feature Level | Subfeature Level | Descriptor Level |
|---|---|---|---|---|---|
| # | Letter | .0# | .00# | .000# | .0000# |
| # | Letter | .0# | .00# | .000# | .0000#(ICD) |
| # | Letter | .0# | .00# | .000# | .0000#(ICD) |
| # | Letter | .0# | .00# | .000#(ICD) | .0000# |
| # | Letter | .0# | .00# | .000(ICD) | .0000# |

FIG. 14B
-with inventive scoring

| System | Subsystem | Feature Category | Feature Level | Subfeature Level | Descriptor Level |
|---|---|---|---|---|---|
| #$# | Letter$# | .0#$# | .00#$# | .000$# | .0000$# |
| #$# | Letter$# | .0#$# | .00#$# | .000#$# | .0000# (ICD) |
| #$# | Letter$# | .0#$# | .00#$# | .000#$# | .0000(ICD)# |
| #$# | Letter$# | .0#$# | .00#$# | .000#(ICD)$# | .0000# |
| #$# | Letter$# | .0#$# | .00#$# | .000(ICD)$# | .0000# |

FIG. 14C
Using coding shown in FIGS. 8C and 9C:
-without inventive scoring

| System | Subsystem | Feature Category | Feature | Subfeature | Descriptor |
|---|---|---|---|---|---|
| #$# | A### | B### | C# | D# | Z(ICD) |
| #$# | A### | B### | C# | D1 | Z1001 which represents the ICD code |
| #$# | A### | B### | C# | D# | Z10#(ICD) |
| #$# | A### | B### | C# | D(ICD) | Z10# |
| #$# | A### | B### | C# | D#(ICD) | Z10# |

FIG. 14D
with inventive scoring

| System | Subsystem | Feature Category | Feature | Subfeature | Descriptor |
|---|---|---|---|---|---|
| #$# | A###$# | B###$# | C#$# | D#$# | Z(ICD) |
| #$# | A###$# | B###$# | C#$# | D#$# | Z1001 which represents the ICD code |
| #$# | A###$# | B###$# | C#$# | D#$# | Z###(ICD) |
| #$# | A###$# | B###$# | C#$# | D(ICD)$# | Z### |
| #$# | A###$# | B###$# | C#$# | D#(ICD)$# | Z# |

FIG. 16

FIG. 16A) numeric codes

| CODE | TEXT | $0 | $1 | $2 | $3 | $4 | $5 | Source | Co-population |
|------|------|----|----|----|----|----|----|--------|---------------|
| 01 | CNS | | | | 1$3 | | | | |
| A | Seizures | | | | A$3 | | | | |
| .01a | Generalized Tonic-Clonic | | | | .01a$3 | | | | |
| .001 | Poorly Controlled | | | | .01a$3.001$3 | | | P | L, C<sub>CNS4</sub>S |

FIG. 16B) predominantly letter codes for serial branching, numeric codes for details

| CODE | TEXT | $0 | $1 | $2 | $3 | $4 | $5 | Source | Co-population |
|------|------|----|----|----|----|----|----|--------|---------------|
| 1 | CNS | | | | 1$3 | | | | |
| sS1 | Seizures | | | | sS1$3 | | | | |
| FC1.001 | Generalized Tonic-Clonic | | | | FC1.001$3 | | | | |
| F1.0001 | Poorly Controlled | | | | FC1.001$3F1.0001$3 | | | P | L, C<sub>CNS4</sub>S |

FIG. 17

Score-driven Data Base with Potential Scores for Ordering and Reviewing Common Lab Tests

| | EKG | CHEST XRAY | BLOOD COUNT (CBC) | PT/PTT | ELECTROLYTES | BUN/CREATININE | GLUCOSE | LIVER FUNCTION TESTS | TUMOR MARKERS |
|---|---|---|---|---|---|---|---|---|---|
| Scored Indications — relevant cells to be identified with code for healthcare provider ordering the test or for an alternative information source (e.g., questionnaire) that generated a score-driven indication: | | | | | | | | | |
| 0=none needed | | | | | | | | | |
| 1= obtained periodically (based on age, stable conditions) | | | | | | | | | |
| 2=may be indicated preop based on age, risk/invasiveness of surgery (SOCU™) or nonspecific factors | | | | | | | | | |
| 3=advisable b/o SISS™ (eg, 3) or SISS™+SICU™ (eg, 5 or 6) | | | | | | | | | |
| 4=strongly indicated b/o SISS™ (eg, 4) or SISS™+SICU™ (eg, 7 or 8) | | | | | | | | | |
| 5=urgently needed b/o SISS™ (eg 5) or SISS™+SICU™ (eg, 9 or 10) | | | | | | | | | |
| Scored Results — relevant cells [e.g., those selected as per above] may be shaded or comparably highlighted until identified with code(s) for healthcare provider(s) reviewing result(s): | | | | | | | | | |
| 0=normal | | | | | | | | | |
| 1=borderline | | | | | | | | | |
| 2-Mildly abnormal, likely insignificant | | | | | | | | | |
| +2=value 1-10% beyond upper normal | | | | | | | | | |
| -2=value 1-10% beyond lower normal | | | | | | | | | |
| 3=Moderate abnormality, may require Rx | | | | | | | | | |
| +3=value >10% beyond upper normal but not severe | | | | | | | | | |
| -3=value >10% beyond lower normal but not severe | | | | | | | | | |
| 4 = Potentially severe abnormality, likely requires Rx | | | | | | | | | |
| +4=high value that may need to be addressed prior to surgery | | | | | | | | | |
| -4=low value that may need to be addressed prior to surgery | | | | | | | | | |
| 5=Potentially Life-Threatening abnormality, requires urgent Rx | | | | | | | | | |
| +5= critically high value | | | | | | | | | |
| -5=critically low value | | | | | | | | | |

FIG. 18
Score-driven Requesting and Reviewing of Consultations and Specialty Testing

| Consultation/Test | 0 = not indicated | 1 = assessment already performed | 2 = intermediate indication | 3 = strong indication | 4 = essential prior to procedure | 5 = essential as soon as possible |
|---|---|---|---|---|---|---|
| OTHER CONSULTS | | | | | | |
| PULMONARY FUNCTION TESTS | | | ✓ | ✓ | ✓ | ✓ |
| PULMONARY CONSULT | | | ✓ | ✓ | ✓ | ✓ |
| CARDIAC CATH | | | ✓ | ✓ | ✓ | ✓ |
| ECHOCARDIOGRAM | | | ✓ | ✓ | ✓ | ✓ |
| STRESS TEST | | | ✓ | ✓ | ✓ | ✓ |
| CARDIOLOGY CONSULT | | | ✓ | ✓ | ✓ | ✓ |
| PCP PREOP CONSULTATION | | ✓ | ✓ | ✓ | ✓ | |
| PCP HISTORY & PHYSICAL | | ✓ | ✓ | ✓ | ✓ | ✓ |
| ANESTHESIA CONSULT | | ✓ | ✓ | ✓ | ✓ | ✓ |
| ANESTHESIOLOGIST PRIOR TO DOS | | ✓ | ✓ | ✓ | ✓ | ✓ |

Scored Indication:

FIG. 19

Interim information & Issues Checklist – Paper work

| | | | | | |
|---|---|---|---|---|---|
| PCP NOTE | | | | | |
| SURGICAL CONSENT | | | | | |
| SURGEON'S FOCUSED H&P | | | | | |
| SURGEON'S COMPOSITE H&P | | | | | |
| | 0=present, in chart | 1= confirmation that item will be sent (faxed) to Chart Room | 2= confirmation that surgeon will bring on day of surgery | 3=surgeon typically brings on day of surgery | 4=message left with surgeon/surgeon's office |

5=status unknown

FIG. 20

Inventive Automated Score-driven Indications for Obtaining Liver Function Tests Based upon Integration of SISS™ and SICU™ and SASRI™ for Relevant Risk Indicator

| | SICU 0 | SICU 1 | SICU 2 | SICU 3 | SICU 4 Hepatic or SOCU 5 | SICU5 Hepatic |
|---|---|---|---|---|---|---|
| SISS™ = 0 | 0 | | | | | 2 |
| SISS™ = 1 | 1 | 0 | 1 | | 1 | 2 |
| SISS™ = 2 | 3 | 3 | 1 | 1 | 1 | 2 |
| SISS ™ = 3 | | 4 | 4 | 3 | 4 | 4 |
| SISS™ = 4 | | | 5 | 4 | 5 | 5 |
| SISS™ = 5 | | | | 5 | 5 | 5 |
| Anesth-related Issues: porphyria 3 or 4 | 4 | | | | | |
| Anesth-related Issues: porphyria 5 | 5 | | | | | |

FIG. 21A

Scored indications for Testing Based Primarily on Age and Surgical Risk/Invasiveness

| | ECG | CBC (+platelets) | Electrolytes | BUN/Creatinine | Glucose | PT/PTT | Albumin | Bleeding Time | Urine (incl. culture) | Chest Radiograph | PulmFunct.Tests | Pregnancy Test |
|---|---|---|---|---|---|---|---|---|---|---|---|---|
| Epidemiology (Age) | | | | | | | | | | | | |
| Healthy Adult <50 y/o | | | | | | | | | | | | |
| Healthy 50-69yrs | 2 | | | | | | | | | | | |
| Healthy Adult ≥70 yrs | 2 | 2 | 2 | 2 | | | | | | | | |
| Surgical Risk/Invasiveness (SOCU™ and/or SICU™) | | | | | | | | | | | | |
| STRAIGHT LOCAL (0) | | | | | | | | | | | | |
| MINOR w/ Anesth. (1) | | | | | | | | | | | | |
| LOW INTERMED (2) | | | | | | | | | | | | |
| MED. INTERMED (3) | | 2 | 2 | 2 | | | | | | 2 | | |
| HIGH INTERMED (4) | 3 | 3 | 3 | 3 | 2 | 2 | | | | 2 | | |
| MAJOR (5) | 3 | 3 | 3 | 3 | 3 | 2 | 2 | | | 2 | | |
| Cardio-Thoracic | | | | | | | | | | 3 | 2 | |
| Ortho. Prosthes (2 SKEL) | | | | | | | | | | 4 | | |
| TURP/Hysteroscopy (3 F&E) | | | 3 | 3 | | | | | | | | |
| Proc. w/ Contrast (2-3 REN) | | | | 2 | | | | | | | | |

FIG. 21

| | ECG | Consider Cardiol Eval | Consider Preop B-Blocker | Plan For A ICD, Pacer | Plan For Intraop[5] | CBC+platelets | Electrolytes | BUN/Creatinine | Glucose | Liver Function | Albumin | Calcium | Magnesium | PT/PTT[1] | Platelet Function | Urine Analysis | Chest Radiograph | PFTs | Tumor Markers |
|---|---|---|---|---|---|---|---|---|---|---|---|---|---|---|---|---|---|---|---|
| Addiction & Abuse (ABUSE) | | | | | | | | | | | | | | | | | | | |
| Human Immunodeficiency Virus (INFhiv) | | | | | | | | | | | | | | | | | | | |
| Obstructive sleep apnea (ENTosa) | ? | | | ? | | | | | | | | | | | | | | | |
| Ear, Nose, And Throat (ENT) | | | | | | | | | | | | | | | | | | | |
| Neuro-Musculo-Skeletal (NMS) | | | | | | | | | | | | | | | | | | | |
| Blood (MALIGblood) | | | | | | | | | | | | | | | | | | | |
| Hemoglobinopathy/Anemia (HEMEHb) | | | | | | ? | | | | | | | | | | | | | |
| Bleeding Diathesis (HEMEbleed) | | | | | | ? | | | | | | | | ? | ? | | | | |
| Gynecologic (GYN) | | | | | | | | | | | | | | | | | | | |
| Fluid & Electrolytes (F&E) | | | | | | | ? | ? | | | | | | | | | | | |
| Gastrointestinal (GI) | | | | | | | | | | | | | | | | | | | |
| Hepatic (HEP) | | | | | | | | | | ? | ? | ? | | | | | | | |
| Respiratory (RESP) | | | | | | | ? | | | | | | | | | | | ? | |
| Hypertension (CARDbp) | ? | | | | | | | | | | | | | | | | | | |
| Cardiac (CARD) | ? | ? | ? | | | | | | | | | | | | | | | | |
| Pheochromocytoma (ENDOpheo) | ? | | ? | | | ? | | | | | | | | | | | | | |
| Steroids/Adrenals (ENDOste$_r$) | | | | | | | ? | | ? | | | | | | | | | | |
| Diabetes Mellitus (ENDOdiab) | ? | | | | | | | | ? | | | | | | | | | | |
| Central Nervous System (CNS) | | | | | | | | | | | | | | | | | | | |

FIG. 21B

Scored Indications for Selected Testing Based Upon SISS™, SASRI™ and related factors.

FIG. 21 (CON.)

FIG. 22

FIG. 22A
Score-Based Decisions Concerning Preoperative Management of Medications

|  | Stop Aspirin? | Continue Aspirin? | Stop Plavix? | Cont Plavix? | Stop Coumadin? | Cont Coumadin? | Stop Nonsteroid Antiinflammatory? | Cont Nonsteroid Antiinflammatory? | Stop Herbals? | Cont Herbals? | Start Lovenox? | Start Beta Blocker? | Start Statin? | Start Aspiration Prophylaxis? | | |
|---|---|---|---|---|---|---|---|---|---|---|---|---|---|---|---|---|
| 0 = not indicated | | | | | | | | | | | | | | | | |
| 1 = already taken care of | | | | | | | | | | | | | | | | |
| 2 = minor to intermediate indication | / | / | / | / | / | / | / | / | / | / | | / | / | | | |
| 3 = strong indication | / | / | / | / | / | / | / | / | / | / | | / | / | | | |
| 4 = essential prior to procedure | / | / | / | / | / | / | / | / | / | / | | / | / | | | |
| 5 = urgent or too late (revised plan may be required) | / | / | / | / | / | / | / | / | / | / | | / | / | | | |

FIG. 22B
Score-Based Decisions Concerning Preoperative Management of Implanted Devices

|  | Stop Pacemaker? | Cont Pacemaker? | Stop AICD? | Cont AICD? |
|---|---|---|---|---|
| 0 = none |  |  |  |  |
| 1 = pacer, not pacer-dependent; cautery likely not required | / | / | / | / |
| 2 = ICD or pacer in pacer-dependent patient; cautery likely not required. | / | / | / | / |
| 3 = pacer in pacer-dependent patient; unipolar cautery likely required | / | / | / | / |
| 4 = ICD, possible cautery | / | / | / | / |
| 5 = ICD, likely cautery – arrangements needed | / | / | / | / |

FIG. 23
Sample Status of Prescriptions and Scripts (may be tailored to individual items)

|  | Item # 1 | Item # 2 | Item #n |
|---|---|---|---|
| 0 = no action or review required |  |  |  |
| 1 = done; confirmation likely not needed |  |  |  |
| 2 = arranged, likely accomplished |  |  |  |
| 3 = arranged; completion uncertain |  |  |  |
| 4 = still to be arranged |  |  |  |
| 5 = arrangements urgently needed |  |  |  |
|  |  |  |  |

Examples of Score-Driven Decisions

| Sample ASPIRIN™ Scores | EKG | CBC | Lytes | BUN/Creatinine | Liver Function Tests | PT/PTT | Consultation by PCP/tests | Specialty Eval (tests &/or consultaion) | Anesthesiologist assessment prior to DOS | Likely NSQIP Cardiac criteria | Likely NSQIP Respiratory criteria | Likely NSQIP Hepatic criteria | Disorder & Procedure Codes (e.g.,ICD,CPT),DRGs)* | Anesthesiologist required during procedure | Likely Unsuitable for Ambulatory center | Likely unsuitable for Fast-track Postop Discharge | Intensive Care Unit Needed Postop | Transfers between Ward, Intermed Unit & ICU** | Transfer betw Referring & level I Trauma Centers** | Special Communication During Transfer of Care** | Discharge Criteria** |
|---|---|---|---|---|---|---|---|---|---|---|---|---|---|---|---|---|---|---|---|---|---|
| Modified (including system-specific ASA Status w/o surgical procedure: | | | | | | | | | | | | | | | | | | | | | |
| 3000 | | | | | | | 1 | 1 | 2 | | | | | | X | X | X | X | | | |
| 3CARD000 | 3 | | | | | | 2 | 2 | 2 | Y | | | | | X | X | X | X | | | |
| 3HEPAT000 | | 2 | 2 | | 2 | 1 | 2 | | 2 | | | | | ± | X | X | X | X | | | |
| 4000 | 2 | 2 | 2 | 2 | | | 3 | 3 | 3 | Y | | | | | X | X | X | X | | | |
| 4CARD000 | 3 | 2 | 3 | 2 | 1 | | 3 | 3 | 3 | Y | | | | | X | X | X | X | | 5 | |
| 4HEPAT000 | 2 | 2 | 3 | 2 | 3 | 3 | 3 | 3 | 3 | | | Y | | | X | X | X | X | | 5 | |
| 5000 | 4 | 3 | 4 | 4 | 4 | 2 | 5 | 5 | 5 | ± | | | | | X | X | X | X | | 5 | |
| 5CARD000 | 5 | 3 | 4 | 4 | 4 | 2 | 5 | 5 | 5 | Y | | | | | X | X | X | X | | 5 | |
| 5HEPAT000 | 3 | 4 | 5 | 4 | 5 | 5 | 5 | 5 | 5 | | | Y | | | X | X | X | X | | 5 | |
| Surgical Risk/Invasiveness: | | | | | | | | | | | | | | | | | | | | | |
| 0300 | | 2 | | | | | | | | | | | | | Y | | | | | | |
| 0400 | 2 | 4 | 3 | 2 | | 2 | 1 | | 3 | | | | | | Y | Y | Y | Y | | | |
| 0500 | 5 | 4 | 3 | 3 | | 3 | 2 | | 4 | | | | | | Y | Y | Y | Y | | | |
| 3300 | 3 | 3 | 3 | 2 | | | 2 | | 3 | | | | | | Y | ± | Y | | | | |
| 3CARD300 | 3 | 3 | 3 | 2 | | | 3 | 2 | 4 | ± | | | | | Y | ± | Y | | | | |
| 4400 | 4 | 4 | 4 | 3 | 3 | 2 | 4 | 4 | 4 | | | | | | Y | Y | Y | Y | | X | |
| 4CARD400 | 4 | 4 | 4 | 3 | 3 | 2 | 4 | 4 | 4 | Y | | | | | Y | Y | Y | Y | | X | |
| 5500 | 4 | 5 | 5 | 4 | 4 | 5 | 5 | 5 | 5 | Y | Y | Y | | | Y | Y | Y | Y | | X | |
| Airway Scores: | | | | | | | | | | | | | | | | | | | | | |
| 1305 | | 3 | | | | | Y | | | | | | | | Y | | ± | | | | |
| 1345 | | 3 | | | | | Y | | | | | | | | Y | ± | Y | | | | |
| Risk Indicators: | | | | | | | | | | | | | | | | | | | | | |
| 22222 | | | | | | | | | | | | | | | | | | | | | |
| 22223 | | | | | | | 3 | | | | | | | | | | | | | | |
| 22224 | | | | | | | 4 | | | | | | | | | | | | | | |
| 22225 | | | | | | | 5 | | | | | | | | | | | | | | |

\* = Conversions need to be established.   \*\* = Clinical data to enable assignment of scores are presently not available.

FIG. 24

FIG. 25
Inventive Scoring of Monitoring Indices

|  | 0 | 1 | 2 | 3 | 4 | 5 |
|---|---|---|---|---|---|---|
| BPsys (mmHg) | 110-130 | +1=140to150 | +2=150to170 | +3=170to200 | +4=200to240 | +5=>240 |
|  |  | -1=90to100 | -2=80to90 | -3=70to80 | -4=50to70 | -5=<50 |
| % from target Bpsys | -10to+10 | +1=+10to20 | +2=+20to40 | +3=+40to70 | +4=70to100 | +5=>100% |
|  |  | -1=-10to-20 | -2=-20to-30 | -3=-30to-50 | -4=-50to-70 | -5 =>-70% |
| % from target Heart Rate | -10to+10 | +1=+10to20 | +2=+20to40 | +3=+40to70 | +4=70to100 | +5=>100% |
|  |  | -1=-10to-20 | -2=-20to-30 | -3=-30to-50 | =4=-50to-70 | -5 =>-70% |
| O2 sat (%) | 97-100 | 94to97 | 90to94 | 80to90 | 70to80 | <70 |
| Urine Output (ml/kg) | 0.9-2.0 | +1=2to3 | +2=3to4 | +3=4to6 | +4=6to10 | +5=>10 |
|  |  | -1=0.8to0.9 | -2=0.6to0.8 | -3=0.4to0.6 | -4=0.2to0.4 | -5=< 0.2 |
| % from Target Pulmonary Artery Pressure | -10to+10 | +1=+10to25 | +2=+25to50 | +3=+50to75 | +4=75to150 | +5=>150% |
|  |  | -1=-10to-20 | -2=-20to-30 | -3=-30to-50 | =4=-50to-70 | -5 =>-70% |

FIG. 26
FIG. 26.1

CNS (system): Seizures (subsystem): Feature Categories
Generalized Tonic-Clonic Seizures
Generalized Absence Seizures
Complex Partial Seizures
Simple Partial Seizures
Unspecified Seizures
Other -- *automatically jumps to:*
   *"Type-in (with scoring options)_____" screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Seizures" hard-coded option to further enable one to avoid to the jump which bypasses distal screens with potentially important coding and scoring).*

FIG. 26.2

CNS:Seizures (subsys):Generalized Tonic-Clonic Seizures (feat categ)/ Control (features)
Remote (1.5)
Controlled (2)
Poorly Controlled (3)
Status epilepticus (4)
Scored Type-in (select score and free type) ( 1  1.5  2  3  4  5)

The user is prompted to provide a score that provides for a scored type-in so as to insure that the information being recorded is scored. Note, the attempt to ensure that scoring is at the feature or subfeature level.

FIG. 26.3

CNS:Seizures:Generalized Absence Seizures/ Control (features)
Remote (1.5)
Controlled (2)
Poorly Controlled (3)
Scored Type-in (select score and free type) ( 1  1.5  2  3  4  5 )

The user is prompted to provide a score that provides for a scored type-in so as to insure that the information being recorded is scored. Note, the attempt to ensure that scoring is at the feature or subfeature level.

FIG. 26.4

Seizures:Complex Partial Seizures/Control (features)
Controlled (2)
Poorly Controlled (3)
Scored Type-in (select score and free type) ( 1  1.5  2  3  4  5 )

The user is prompted to provide a score that provides for a scored type-in so as to insure that the information being recorded is scored. Note, the attempt to ensure that scoring is at the feature or subfeature level.

FIG. 26.5

Seizures: Simple Partial Seizures/Control (features)
Controlled (2)
Poorly Controlled (3)
Scored Type-in (select score and free type) ( 1  1.5  2  3  4  5 )

The user is prompted to provide a score that provides for a scored type-in so as to insure that the information being recorded is scored. Note, the attempt to ensure that scoring is at the feature or subfeature level.

FIG. 26.6

Seizure Activity Descriptors:
n/a
tonic-clonic activity
loss of consciousness
loss of bowel control
loss of bladder control
"swallows" tongue
apnea
hypoxia
post-ictal confusion
post-ictal combativeness
speech-problems
twitching
staring
repetitive movements
awake but oblivious
Other – *when Other is selected on a Descriptor screen (which is, by definition, distal to the level for scoring), it simply enables an unscored type-in option on the given screen):*

FIG. 26.7

Etiology Descriptors for Seizures
n/a
Hyperexcitable focus in absence of mass
Febrile
Isolated during withdrawal
⇔Benign Intracranial Mass
 ⇔Primary Malignant Intracranial Tumor
⇔Metastatic Malignant Tumor
⇔Cerebral Trauma
⇔Cerebral Bleed
*Due to Primary Disorder of Another System (not listed above)
*Due to Unlisted Multisystem Condition (not listed above)
Unknown
Other — *when Other is selected on a Descriptor screen (which is, by definition, distal to the level for scoring), it simply enables an unscored type-in option on the given screen):*
_____
_____

FIG. 26.8

Frequency Descriptors for Seizures
n/a
h/o only one seizure
Continuously
Multiple times/day
Daily
Weekly
Monthly
Yearly
<once/yr
Other — *when Other is selected on a Descriptor screen (which is, by definition, distal to the level for scoring), it simply enables an unscored type-in option on the given screen):*
_____
_____

FIG. 26.9

> <sup>afg</sup>Acute vs. Chronic & Duration Descriptors for Seizures
> n/a
> Current
> Within past 24 hours
> Within past week
> Within past month
> Within past year
> Within past 1-5 yrs
> Within past 5-20 yrs
> >20 years ago
> Other -- *when Other is selected on a Descriptor screen (which is, by definition, distal to the level for scoring), it simply enables an unscored type-in option on the given screen):*
>
> _____
> _____
>
> (Note -- The headers for the afg Generic CNS Descriptor screens shown later are:
> a = Brain Region Descriptors
> f = Generic CNS Descriptor Screen for CNS Tests
> g = Generic CNS Descriptor Screen for CNS Treatments)

FIG. 26.10

> CNS (system):Cerebral Ischemia (subsystem):Feature Categories
> Asymptomatic Carotid Disease
> TIA
> Thrombotic Stroke
> Embolic Stroke
> Nonspecific Stroke
> *Attributable to Multisystem Condition
> Unspecified Cerebral Ischemia
> Other -- *automatically jumps to:*
>   "Type-in (with scoring options)_____" *screen at the end of the given system.*
> *(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Nonspecific Cerebral Ischemia" hard-coded option to further enable one to avoid the jump which bypasses distal screens with potentially important coding and scoring).*

FIG. 26.11

---
CNS:Cerebral Ischemia:Asymptomatic Carotid Disease/Features:
Known for > 6 months
Discovered 1-6 months ago
Discovered within past month
Other -- *automatically jumps to:*
  *"Type-in (with scoring options)_____" screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice).*

---
ᶠCNS:Cerebral Ischemia:Asymptomatic Carotid Disease/Known for >6 Months (feature):Subfeatures
Minimal occlusion, no therapy (1.5)
Minimal occlusion, therapy (1.5)
Moderate occlusion, no therapy (2)
Moderate occlusion, therapy (2)
Critical occlusion, no therapy (3)
Critical occlusion, therapy (3)
Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level.*

---
ᶠCNS:Cerebral Ischemia:Asymptomatic Carotid Disease/Known for 1-6 Months (feature):Subfeatures
Minimal occlusion, no therapy (1.5)
Minimal occlusion, therapy (1.5)
Moderate occlusion, no therapy (2)
Moderate occlusion, therapy (2)
Critical occlusion, no therapy (3)
Critical occlusion, therapy (3)
Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level.*

FIG. 26.14

> <sup>fg</sup>CNS:Cerebral Ischemia:Asymptomatic Carotid Disease/Discovered Within 1 Month (feature):Subfeatures
> Minimal occlusion, therapy (2)
> Minimal occlusion, no therapy (2)
> Moderate occlusion, therapy (3)
> Moderate occlusion, no therapy (3)
> Critical occlusion, therapy (4)
> Critical occlusion, no therapy (4)
> Scored Type-in (select score and free type) ( 1 1.5 2 3 4 5 )
>
> *The user is prompted to provide a score that provides for a scored type-in so as to insure that the information being recorded is scored. Note, the attempt to ensure that scoring is at the feature or subfeature level.*

FIG. 26.15

> CNS:Cerebral Ischemia:TIA/Features
> Single > 6 months ago
> Single 1- 6 months ago
> Multiple > 6 months ago
> Multiple 1-6 months ago
> Single within 1 month
> Multiple within 1 month
> Recent (within 1 month) plus remote (greater than 1 month ago)
> Other -- *automatically jumps to:*
> "*Type-in (with scoring options)_____*" *screen at the end of the given system.*
> (*This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice).*

FIG. 26.16

> <sup>abcdefg</sup> CNS:Cerebral Ischemia (subsys): TIA (feat. cat.)/> 6 months ago (feature)//Subfeatures
> Remote w/ subsequent seemingly effective preventative therapy (2)
> Remote w/o subsequent preventative therapy (3)
> Scored Type-in (select score and free type) ( 1 1.5 2 3 4 5 )
>
> *The user is prompted to provide a score that provides for a scored type-in so as to insure that the information being recorded is scored. Note, the attempt to ensure that scoring is at the feature or subfeature level.*

FIG. 26.17

---
<sup>abcdefg</sup> CNS:Cerebral Ischemia (subsys): TIA (feat. cat.)/ 1-6 months ago (feature)//Subfeatures
Remote w/ subsequent seemingly effective preventative therapy (3)
Remote w/o subsequent preventative therapy (3)
Other -- *automatically jumps to:*
  *"Type-in (with scoring options)_____" screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice).*

---
<sup>abcdefg</sup> CNS:Cerebral Ischemia:TIA/<1 month ago//Subfeatures
Recent w/ subsequent seemingly effective preventative therapy (medical or CEA) (3)
Recent w/o subsequent preventative therapy (3)
Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level.*

FIG. 26.19

CNS:Cerebral Ischemia:Stroke/Features
Single > 6 months ago
Single 1-6 months ago
Multiple > 6 months ago
Multiple 1-6 months ago
Single within 1 month
Multiple within 1 month
Recent (within 1 month) plus remote (greater than 1 month ago)
Other — *automatically jumps to:*
   *"Type-in (with scoring options)_____" screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice).*

FIG. 26.20

$^{abcdefg}$Cerebral Ischemia:Stroke/>6 months ago// Subfeatures
Resolved s/s w/ subsequent seemingly effective preventative therapy (3)
Resolved s/s w/o subsequent preventative therapy   (3)
Persistent minor deficits w/ subsequent seemingly effective preventative therapy (3)
Persistent minor deficits w/o subsequent preventative therapy  (3)
Persistent moderate deficits w/ subsequent seemingly effective preventative therapy (3)
Persistent moderate deficits w/o subsequent preventative therapy  (3)
Persistent major deficits w/ seemingly effective subsequent preventative therapy (3)
Persistent major deficits w/o seemingly effective subsequent preventative therapy ( 3)
Life-threatening s/s ( 4 5 )
Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level.*

FIG. 26.21

```
abcdefgCerebral Ischemia:Stroke/ 1-6 months ago// Subfeatures
Resolved s/s w/ subsequent seemingly effective preventative therapy ( 3 )
Resolved s/s w/o subsequent preventative therapy   (3)
Persistent minor deficits w/ subsequent seemingly effective preventative therapy   (3)
Persistent minor deficits w/o subsequent preventative therapy  (3)
Persistent moderate deficits w/ subsequent seemingly effective preventative therapy
(3)
Persistent moderate deficits w/o subsequent preventative therapy   (3)
Persistent major deficits w/ seemingly effective subsequent preventative therapy (3)
Persistent major deficits w/o seemingly effective subsequent preventative therapy (3
4)
Life-threatening s/s ( 4 5 )
Scored Type-in (select score and free type) ( 1  1.5  2  3  4  5 )
```

*The user is prompted to provide a score that provides for a scored type-in so as to insure that the information being recorded is scored. Note, the attempt to ensure that scoring is at the feature or subfeature level*

FIG. 26.22

```
abcdefgCerebral Ischemia:Stroke/< 1 month ago// Subfeatures
Resolved s/s w/ new preventative therapy  (3)
Resolved s/s w/o subsequent seemingly effective preventative therapy (3)
Persistent minor deficits w/ susbequent preventative therapy 3)
Persistent minor deficits w/o susbequent seemingly effective preventative therapy   (3)
Persistent moderate deficits.w/ subsequent preventative threrapy  (3)
Persistent moderate deficits.w/o subsequent seemingly effective preventative threrapy
(3)
Persistent major deficits w/ seemingly effective subsequent preventative therapy (3)
Persistent major deficits w/o seemingly effective subsequent preventative therapy (4)
Life-threatening s/s ( 4 5 )
Scored Type-in (select score and free type) ( 1  1.5  2  3  4  5 )
```

*The user is prompted to provide a score that provides for a scored type-in so as to insure that the information being recorded is scored. Note, the attempt to ensure that, scoring is at the feature or subfeature level.*

FIG. 26.23

CNS:Nonischemic Cerebrovascular Disorders (subsystem):Feature Categories
AVM
Aneurysm
⇔Bleeding tumor
⇔Bleed due to trauma
*Bleed due to low platelets
*Bleed due to coagulation disorder
*Bleed due to antiplatelet therapy
*Bleed due to anticoagulant therapy
* Bleed Attributable to Another System
Bleed due to unknown cause
Headaches
Unspecified Nonischemic Cerebrovascular Disorder
Other -- *automatically jumps to:*
   "Type-in (with scoring options)_____" *screen at the end of the given system*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Nonischemic Cerebrovascular Disorder" hard-coded option to further enable one to avoid the jump which bypasses distal screens with potentially important coding and scoring.)*

FIG. 26.24

CNS:Nonischemic Cerebrovascular Disorders:AVM or Aneurysm/Features:
No prior or current bleeding
Bleed > 12 months ago w/ low risk of repeat bleed
Bleed > 12 months ago w/ high risk of repeat bleed
Bleed 1-12 months ago w/ low risk of repeat bleed
Bleed 1-12 months ago w/ high risk of repeat bleed
Bleed 7-30 days ago w/ low risk of repeat bleed
Bleed 7-30 days ago w/ high risk of repeat bleed
Bleed within 7 days w/ low risk of repeat bleed
Bleed within 7 days w/ high risk of repeat bleed
Other -- *automatically jumps to:*
   "Type-in (with scoring options)_____" *screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice).*

FIG. 26.25

```
abcdefgCNS:Nonischemic Cerebrovascular Disorders: AVM or Aneurysm/No Bleeding//
Subfeatures
Without signs or symptoms, w/ low risk of bleed (2)
Without s/s, w/ high risk of bleed (3)
abcdefgMild s/s, w/ low risk of bleed (2)
abcdefgModerate s/s, w/ low risk of bleed (3)
abcdefgMajor s/s w/ low risk of bleed (4)
abcdefgMild s/s w/ high risk of bleed (3)
abcdefgModerate s/s w/ high risk of bleed (3)
abcdefgMajor s/s w/ high risk of bleed ( 4  5 )
Scored Type-in (select score and free type) ( 1  1.5  2  3  4  5 )
```

*The user is prompted to provide a score that provides for a scored type-in so as to insure that the information being recorded is scored. Note, the attempt to ensure that scoring is at the feature or subfeature level*

FIG. 26.26

```
abcdefgCNS:Nonischemic Cerebrovascular Disorders: AVM or Aneurysm/Ruptured > 30
Days Ago with Low Risk of New Rupture// Subfeatures
Resolved s/s (2)
Persistent minor s/s (2)
Persistent moderate s/s. (3)
Persistent major s/s. (3)
Life-threatening s/s from rupture ( 4  5 )
Scored Type-in (select score and free type) ( 1  1.5  2  3  4  5 )
```

*The user is prompted to provide a score that provides for a scored type-in so as to insure that the information being recorded is scored. Note, the attempt to ensure that scoring is at the feature or subfeature level*

FIG. 26.27

<sup>abcdefg</sup> CNS:Nonischemic Cerebrovascular Disorders: AVM or Aneurysm/Ruptured > 30 Days Ago with High Risk of New Rupture// Subfeatures
Resolved s/s (4)
Persistent minor s/s (4)
Persistent moderate s/s. (4)
Persistent major s/s.w/ high risk of repeat rupture (4)
Life-threatening s/s from rupture (4)
Scored Type-in (select score and free type) ( 1 1.5 2 3 4 5 )

*The user is prompted to provide a score that provides for a scored type-in so as to insure that the information being recorded is scored. Note, the attempt to ensure that scoring is at the feature or subfeature level*

FIG. 26.28

CNS:Nonischemic Cerebrovascular Disorders:Non-AVM, Non-Aneurysm Bleeding
/Features:
Bleed > 12 months ago w/ low risk of repeat bleed
Bleed > 12 months ago w/ high risk of repeat bleed
Bleed 1-12 months ago w/ low risk of repeat bleed
Bleed 1-12 months ago w/ high risk of repeat bleed
Bleed 7-30 days ago w/ low risk of repeat bleed
Bleed 7-30 days ago w/ high risk of repeat bleed
Bleed within 7 days w/ low risk of repeat bleed
Bleed within 7 days w/ high risk of repeat bleed
Other -- *automatically jumps to:*
    "*Type-in (with scoring options)*_____" *screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice).*

FIG. 26.29 abcdefgNonischemic Cerebrovascular Disorders: Bleeding/ > 30 Days Ago with Low Risk of Repeat Bleed or Spasm// Subfeatures
Resolved s/s (2)
Persistent minor s/s (2)
Persistent moderate.w/ low risk of repeat bleed (3)
Persistent major s/s. low risk of repeat bleed (3)
Life-threatening s/s from bleed ( 4  5 )
Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level*

FIG. 26.30 abcdefgNonischemic Cerebrovascular Disorders: Bleeding/ > 30 Days Ago with High Risk of Repeat Bleed or Spasm// Subfeatures
Resolved s/s (4)
Persistent minor s/s (4)
Persistent moderate (4)
Persistent major s/s (4)
Life-threatening s/s from bleed ( 4  5 )
Scored Type-in (select score and free type) ( 1  1.5  2  3  4  5 )

*The user is prompted to provide a score that provides for a scored type-in so as to insure that the information being recorded is scored. Note, the attempt to ensure that, scoring is at the feature or subfeature level*

FIG. 26.31 abcdefgNonischemic Cerebrovascular Disorders: Bleeding/ Within 30 Days with Low Risk of Repeat Bleed or Spasm// Subfeatures
Resolved s/s ( 2 )
Persistent minor s/s (3)
Persistent minor s/s (4)
Persistent moderate s/s. (3)
Persistent major s/s. (3)
Life-threatening s/s from bleed ( 4  5 )
Likely brain dead from bleed (5)
Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level*

FIG. 26.32 abcdefg Nonischemic Cerebrovascular Disorders: Bleeding/ Within 30 Days with High Risk of Repeat Bleed or Spasm// Subfeatures
Resolved s/s (4)
Persistent minor s/s (4)
Persistent moderate s/s. (4)
Persistent major s/s. w/ high risk of repeat bleed or spasm (4)
Life-threatening s/s from bleed ( 4  5 )
Likely brain dead from bleed (5)
Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level*

FIG. 26.33

CNS:Nonischemic Cerebrovascular Disorders: Headaches unrelated to mass, acute trauma or bleed (feat. categ.)/Type of Headache (features):
Tension
Migraine
*Arteritis
*Attributable to a Disorder of Another System(s)
Unspecified Headache
Other — *automatically jumps to:*
  "Type-in (with scoring options)_____" *screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice).*

FIG. 26.34

CNS: Nonischemic Cerebrovascular Disorders: Headaches unrelated to mass, acute trauma or bleed (feat categ)/Type of Headache (Feature) // Headache Severity (subfeatures):
    Mild (1.5)
    Moderate (2)
    Severe (3)
    Life-threatening ( 4  5 )
    Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level*

FIG. 26.35

Frequency Descriptors for Headaches
Continuously
Multiple times/day
Daily
Weekly
Monthly
Yearly
<once/yr
Other – *when Other is selected at the Descriptor level (which is beyond the level for scoring), it simply enables an unscored type-in option on the given screen)*
  Type-in (descriptor): _____

FIG. 26.36 s/s Descriptors for Headaches
n/a
Diplopia
Field cut
Other vision changes
Paralysis
Spasticity
Weakness
Numbness
Decreased sensation
Altered speech
Other – *when Other is selected at the Descriptor level (which is beyond the level for scoring), it simply enables an unscored type-in option on the given screen*

FIG. 26.37

CNS (sys): Nonmalignant Intracranial Mass (subsys): Types (feature categ):
Glioma
Benign Astrocytoma
Meningioma
Pituitary tumor
Acoustic neuroma
Ependymoma
Oligodendroglioma
Unspecified nonmalignant intracranial mass
Other -- *automatically jumps to:*
  *"Type-in (with scoring options)_____" screen at the end of the given system*
  *(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice) The present screen contains the "Unspecified nonmalignant intracranial mass" option to further enable one to avoid the jump which bypasses distal screens with potentially important coding and scoring.*

FIG. 26.38

CNS (sys): Nonmalignant Intracranial Mass (subsys): Specific Type (feature categ)/Location (features)
n/a
Frontal    Left    Right    Bilateral
Temporal   Left    Right    Bilateral
Parietal   Left    Right    Bilateral
Occipital  Left    Right    Bilateral
Pituitary
Foramen magnum
Epidural
Subdural
Subarachnoid
Unspecified Nonmalignant Mass Location
Other -- *when Other is selected on a Descriptor screen (which is, by definition, distal to the level for scoring), it simply enables an unscored type-in option on the given screen):*

_____

*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Nonmalignant Mass Location" hard-coded option to further enable one to avoid to the jump which bypasses distal screens with potentially important coding and scoring).*

FIG. 26.39

| CNS (sys):Nonmalignant Intracranial Mass (subsys): Specific Type (feat. categ.)/ Location (feature)// Scored Subfeatures |
|---|
| never associated with s/s (1.5) |
| s/p resection w/o deficit (1.5) |
| s/p radiation w/o deficit (2) |
| Minor local and/or regional s/s from tumor or therapy (2) |
| Moderate local and/or regional s/s from tumor or therapy (3) |
| Severe local and/or regional s/s from tumor or therapy (4) |
| Life-threatening local and/or regional s/s from tumor or therapy ( 4  5 ) |
| Scored Type-in (select score and free type) ( 1  1.5  2  3  4  5 ) |

*The user is prompted to provide a score that provides for a scored type-in so as to insure that the information being recorded is scored. Note, the attempt to ensure that scoring is at the feature or subfeature level*

FIG. 26.40

| CNS (sys):Nonmalignant Intracranial Mass (subsys): Specific Type (feat. categ.)/Severity Score (feat)- Prior or Ongoing Rx of Tumor (descriptors) |
|---|
| n/a |
| none |
| local excision |
| resection of regional spread |
| local chemotherapy |
| cryotherapy |
| radiation |
| Other -- *when Other is selected on a Descriptor screen (which is, by definition, distal to the level for scoring), it simply enables an unscored type-in option on the given screen):* |

FIG. 26.41

CNS (sys):Nonmalignant Intracranial Mass (subsys): Specific Type (feat, categ.)/Severity Score (feat)- Effects of Tumor or Therapy Within CNS (descriptors)

None
bcdefg Yes

Other - - *when Other is selected on a Descriptor screen (which is, by definition, distal to the level for scoring), it simply enables an unscored type-in option on the given screen):*

FIG. 26.42

CNS (sys): Malignant Intracranial Tumor (subsys): Types (feature categ)

Glioblastoma
Malignant Astrocytoma
Malignant Meningioma
*Metastases to Brain (include unknown)
Unspecified Malignancy
Other - Other - *automatically jumps to:*

"*Type-in (with scoring options)_____*" *screen at the end of the given system.*
*(This specific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Primary Malignancy" and Unspecified Metastatic Malignancy" hard-coded options to further enable one to avoid the jump which bypasses distal screens with potentially important coding and scoring).*

FIG. 26.43

CNS (sys): Malignant Intracranial Mass (subsys): Specific Type (feature categ)/Location (features)
n/a
Frontal      Left    Right   Bilateral
Temporal     Left    Right   Bilateral
Parietal     Left    Right   Bilateral
Occipital    Left    Right   Bilateral
Pituitary
Foramen magnum
Epidural
Subdural
Subarachnoid
Unspecified Malignant Mass Location
Other -- *when Other is selected on a Descriptor screen (which is, by definition, distal to the level for scoring), it simply enables an unscored type-in option on the given screen):*

_____

*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Malignant Mass Location" hard-coded option to further enable one to avoid to the jump which bypasses distal screens with potentially important coding and scoring).*

FIG. 26.44

CNS (sys):Malignant Intracranial Mass (subsys):Specific Type (feat. categ.)/Location (features)// Scored Subfeatures
    never associated with s/s (1.5)
    s/p resection w/o deficit (1.5)
    s/p chemotherapy w/o deficit (2)
    s/p radiation w/o deficit (2)
    Minor (local and/or systemic) s/s from tumor or therapy (2)
    Moderate (local and/or systemic) s/s from tumor or therapy (3)
    Severe (local and/or systemic) s/s from tumor or therapy (4)
    Life-threatening (local and/or systemic) s/s from tumor or therapy ( 4  5 )
    Scored Type-in (select score and free type) ( 1  1.5  2  3  4  5 )

*The user is prompted to provide a score that provides for a scored type-in so as to insure that the information being recorded is scored. Note, the attempt to ensure that scoring is at the feature or subfeature level*

FIG. 26.45

| Prior or Ongoing Rx of Malignant Tumor (descriptors) |
|---|
| n/a |
| none |
| local excision |
| excision to nodes w/ local edema |
| excision of nodes w/o local edema |
| resection of regional spread |
| resection of metastases |
| local chemotherapy |
| cryotherapy |
| radiaoactive implant |
| radiation |
| chemotherapy |

FIG. 26.46

Effects of Malignant Tumor or Therapy Within CNS (descriptors)
None
$^{bcdefg}\Downarrow$Yes Other -- *when Other is selected on a Descriptor screen (which is, by definition, distal to the level for scoring), it simply enables an unscored type-in option on the given screen):*

---

*(English letters superscripted before "Yes" indicate that, if "Yes" is selected, the computer will jump automatically to a series of generic CNS Descriptor screens that apply to more than one CNS subsystem so as to avoid unnecessary repetition of screens. Since the superscript also contains $\Downarrow$, this indicates that it will jump to the next Descriptor screen, upon completion of the letter-designated screen(s).)*

FIG. 26.47

Systemic or Remote Effects of Tumor or Therapy (descriptors)
None
$^{a}$Yes

Other -- *when Other is selected on a Descriptor screen (which is, by definition, distal to the level for scoring), it simply enables an unscored type-in option on the given screen):*

FIG. 26.48

CNS (sys): Other [Nonvascular, Non Mass-related] Intracranial Trauma & Injury (subsys): Feature Categories
    Gunshot
    Blunt trauma to brain
    Subdural Hematoma
    Epidural hematoma
    Central pontine myelinolysis
    Surgical scar
    *Attributable Primarily to Another System
    Unspecified Intracranial Trauma and Injury
    Other -- *automatically jumps to:*
        *"Type-in (with scoring options)_____" screen at the end of the given system.*
        *(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Intracranial Trauma and Injury" hard-coded option to further enable one to avoid the jump which bypasses distal screens with potentially important coding and scoring).*

FIG. 26.49

CNS (sys): Other Intracranial Trauma and Injury (=subsys): Type (feat categ) /Location (features)
    n/a
    Frontal    Left    Right    Bilateral
    Temporal    Left    Right    Bilateral
    Parietal    Left    Right    Bilateral
    Occipital    Left    Right    Bilateral
    Pituitary
    Foramen magnum
    Epidural
    Subdural
    Subarachnoid
    Unspecified Location
    Other -- *when Other is selected on a Descriptor screen (which is, by definition, distal to the level for scoring), it simply enables an unscored type-in option on the given screen):*

*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Location" hard-coded option to further enable one to avoid to the jump which bypasses distal screens with potentially important coding and scoring).*

FIG. 26.50 abcdefg CNS:Intracranial Trauma and Injury:Specific Type(Feat.
Categ)/Location(Feat)/Scored Severity(subfeatures)

| | |
|---|---|
| w/o significant s/s; negative workup | (1) |
| s/p intracranial trauma w/o sequelae | (1) |
| Mild post-traumatic brain injury | (2) |
| Moderate PTBI | (2) |
| Severe PTBI | (3) |
| Mild acute injury | (2) |
| Mild chronic injury | (2) |
| Moderate acute injury | (3) |
| Moderate chronic injury | (3) |
| Severe acute injury | (4) |
| Severe chronic injury | (4) |
| Long-standing life-threatening injury | (4) |
| Acute Life-threatening injury | (5) |
| Scored Type-in (select score and free type) | ( 1 1.5 2 3 4 5 ) |

*The user is prompted to provide a score that provides for a scored type-in so as to insure that the information being recorded is scored. Note, the attempt to ensure tha scoring is at the feature or subfeature level*

FIG. 26.51

CNS: Infection (subsystem)

CNS: Infection: Type (feat categ)
   Abscess
   Septic embolus
   s/p Injury
   Infected bone flap
   Encephalitis
   Jacob Creutzfeld
   Meningitis
   Unspecified Intracranial Infection
   *Attributable Primarily to Another System
   Other -- *automatically jumps to:*
      "Type-in (with scoring options)_____" *screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Intracranial Infection" hard-coded option to further enable one to avoid the jump which bypasses distal screens with potentially important coding and scoring).*

FIG. 26.52

| CNS (sys): Intracranial Infection (=subsys): Specific Type (feat categ) /Location (features) |
|---|
| n/a |
| Frontal    Left    Right    Bilateral |
| Temporal    Left    Right    Bilateral |
| Parietal    Left    Right    Bilateral |
| Occipital    Left    Right    Bilateral |
| Pituitary |
| Foramen magnum |
| Epidural |
| Subdural |
| Subarachnoid |
| Unspecified Location |
| Other -- *automatically jumps to:* |
|     "Type-in (with scoring options)_____" *screen at the end of the given system.* |
| *(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Location" hard-coded option to further enable one to avoid the jump which bypasses distal screen with potentially important coding and scoring).* |

FIG. 26.53

| abcdefgh CNS Infection: Specific Type (feat categ)/Location (feat)/Scored Severity (subfeatures) |
|---|
| n/a |
| none (1) |
| resolved w/o sequelae (1) |
| prior with mild persistent s/s (1.5) |
| prior with moderate persistent s/s (2) |
| prior with severe persistent s/s (3) |
| prior with life-threatening s/s ( 4   5 ) |
| prior with likely fatal s/s (5) |
| current with mild persistent s/s (1.5) |
| current with moderate persistent s/s (2) |
| current with severe persistent s/s (3) |
| current with life-threatening s/s ( 4   5 ) |
| Scored Type-in (select score and free type) ( 1   1.5   2   3   4   5 ) |
| *The user is prompted to provide a score that provides for a scored type-in so as to insure that the information being recorded is scored. Note, the attempt to ensure that scoring is at the feature or subfeature level* |

FIG. 26.54

| |
|---|
| <u>CNS (sys): Inc ICP (subsyst): Causes of Increased ICP (feat. Categ.)</u><br>    Pseudotumor Cerebri<br>    Communicating hydrocephalus<br>    Noncommunicating hydrocephalus<br>    Mass<br>    Trauma<br>    Bleed<br>    Ischemia<br>    Unspecified Cause of ICP<br>    Other -- *automatically jumps to:*<br>        "*Type-in (with scoring options)*_____" *screen at the end of the given system.*<br>    *(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Location" hard-coded option to further enable one to avoid the jump which bypasses distal screens with potentially important coding and scoring).* |

FIG. 26.55

| |
|---|
| <u>CNS:inc ICP (subsyst): Specific Cause (feature category)/Scored Severity (features)</u><br>Benign (2)<br>Mild -- during current improvement w/ Rx (2)<br>Moderate (3)<br>Moderate -- during current improvement w/ Rx (3)<br>Severe (4)<br>Severe -- during current improvement w/ Rx (4)<br>Life-threatening  (4 5)<br>Unspecified Severity of increased ICP<br>Other<br>    Other -- *automatically jumps to:*<br>        "*Type-in (with scoring options)*_____" *screen at the end of the given system.*<br>*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. On a scored feature or subfeature screen, it also permits scoring of the Unspecified item. The present screen contains the "Unspecified Severity of Increased ICP" hard-coded option to further enable one to avoid the jump which bypasses distal screen with potentially important coding and scoring).* |

FIG. 26.56

CNS:inc ICP (subsyst): Specific Cause (feature category)/Scored Severity (features) -
Descriptor Screen for Global CNS s/s Associated with Increased ICP n/a
⇔Headaches
⇔Seizures
Herniation
Coma
Stupor
Confusion
hallucinations
Short-term memory loss
Long-term memory loss
Combativeness
Dec cognitive function
Altered HR and/or BP
Respiratory (aspiration, arrest; refer to resp system)
Other -- *when Other is selected at the Descriptor level (which is beyond the level for scoring), it simply enables an unscored type-in option on the given screen*

⇔ *indicates that there is a system, subsystem or feature category devoted to the given item. The computer may jump to that area, allow entry of information into that area, and then return to the present screen.*

FIG. 26.57

CNS(sys): Cognitive Disorders (subsys)

CNS:Cognitive Disorders (subsys):Types (feat categ)
Mental retardation
Alzheimer's
Stupor
Coma
*Hepatic encephalopathy
*Wernicke-Korsakoff
*Acute drug/substance induced disorder
*Attributable to Another System not listed above
Unspecified Cognitive Disorder
Other -- *automatically jumps to:*
"Type-in (with scoring options)_____" *screen at the end of the given system.*
*(This nonspecific jump which bypasses distal screens may be averted by using the "Similar Type-in" option on a drop-down menu (or its equivalent) associated with each hard-coded choice on the present screen. The "Similar Type-in" allows free typing that is similar to the hard-coded choice in a manner that enables modified coding, storage, communication, linking and jumping in accordance with the hard-coded choice. The present screen contains the "Unspecified Cognitive Disorder" hard-coded option to further enable one to avoid the jump which bypasses distal screen with potentially important coding and scoring).*

FIG. 26.58

CNS: Cognitive Disorders (subsys): Specific Type (feat categ) /Scored Severity (features)
Mild (1.5)
Mild (during current improvement with Rx) (2)
Moderate (3)
Moderate (during current improvement with Rx) (3)
Severe (4)
Scored Type-in (select score and free type) ( 1 1.5 2 3 4 5 )

*The user is prompted to provide a score that provides for a scored type-in so as to insure that the information being recorded is scored. Note, the attempt to ensure that scoring is at the feature or subfeature level*

FIG. 26.59

CNS: Parkinsonism & Other CNS-based Movement Disorders (subsys): Types of Disorders (feat categ)
Parkinsonism
Huntington's
*Attributable to a non-CNS Disorder
Unspecified
Other -- *automatically jumps to:*
  "Type-in (with scoring options)_____" *screen at the end of the given system.*

FIG. 26.60 abcdefgh CNS: Parkinsonism & Other CNS-based Movement Disorders:Features of Specific Disorder
n/a
none
Minimal (2)
Minimal during current improvement with Rx (2)
Moderate (3)
Moderate during current improvement with Rx (3)
Severe (4)
Severe during current improvement w/ therapy (4)
Significant threat to life (5)
Scored Type-in (select score and free type) ( 1 1.5 2 3 4 5 )

*The user is prompted to provide a score that provides for a scored type-in so as to insure that the information being recorded is scored. Note, the attempt to ensure that, when possible, scoring is at the feature or subfeature level*

FIG. 26.61

> CNS: Other/Other// (*with special code such as 99*)
> Type-in (unscored) _____
>
> Type-in (1) _____
>
> Type-in (1.5) _____
>
> Type-in (2) _____
>
> Type-in (3) _____
>
> Type-in (4) _____
>
> Type-in (5) _____
>
> *This screen appears at the end of each system. Coding to designate jump from "Other" selections will be specially delineated; e.g., with a "99" code. Ideally, scoring for each important item in the given System already has been accomplished at the Feature or Subfeature level. This screen should serve as the final safety net, with the realization that entry on to this screen will provide less specific coding than entry within a specific Subsystem and Feature Category. Upon completion of the present screen, user is given options such as "return to the preceding screen" "proceed to next System", "jump to Feature Categories of given system," "jump to Features of given system," "jump to Subfeatures of given system," "jump to Descriptors of given system," or "jump to Interactive Index." Obviously, one simply may bypass the screen.*

FIG. 27
FIG. 27.1

> a = Brain Region Descriptors
> n/a
> Frontal      Left    Right   Bilateral
> Temporal     Left    Right   Bilateral
> Parietal     Left    Right   Bilateral
> Occipital    Left    Right   Bilateral
> Pituitary
> Foramen magnum
> Epidural
> Subdural
> Subarachnoid
> diffuse intracranial
> other nonspecific s/s
>
> Other — *when Other is selected at the Descriptor level (which is beyond the level for scoring), it simply enables an unscored type-in option on the given screen*

FIG. 27.2

```
b = Generic CNS Descriptor Screen for Global CNS s/s
n/a
⇔Headaches
⇔Seizures
⇔Increased ICP
Herniation
Coma
Stupor
Confusion
hallucinations
Short-term memory loss
Long-term memory loss
Combativeness
Dec cognitive function
Altered HR and/or BP
Respiratory (aspiration, arrest; refer to resp system)
Post-traumatic brain injury syndrome
Other — when Other is selected at the Descriptor level (which is beyond the level for scoring), it simply enables
an unscored type-in option on the given screen
```

FIG. 27.3

```
c = Generic CNS Descriptor Screen for Local Neural s/s
n/a
None
Decreased hearing
Pain
Diplopia
Field cut
Other vision changes
Other — when Other is selected at the Descriptor level (which is beyond the level for scoring), it simply enables an
unscored type-in option on the given screen
```

FIG. 27.4

--- d = Generic CNS Descriptor Screen for Peripheral Neural s/s
n/a
None
Paralysis
Spasticity
Weakness
Numbness
Decreased sensation
Altered speech
Compromised swallowing
Pill-rolling
Dystonic movements
Decreased gag reflex
Resting tremor
Intention tremor
Other — *when Other is selected at the Descriptor level (which is beyond the level for scoring), it simply enables an unscored type-in option on the given screen*

--- e = Generic CNS Descriptor Screen for Sites of Peripheral s/s
n/a
Widespread
Arm      Left   Right   Both
Leg      Left   Right   Both
Face     Left   Right   Both
Ear      Left   Right
Bowel
Bladder
Other — *when Other is selected at the Descriptor level (which is beyond the level for scoring), it simply enables an unscored type-in option on the given screen*

FIG. 27.6 f = Generic CNS Descriptor Screen for CNS Tests
n/a
physical exam
Brain scan
CT scan
MRI
EEG
Carotid ultrasound
MRA
Spinal tap
WADA
Grid for Seizure Mapping
Other —*when Other is selected at the Descriptor level (which is beyond the level for scoring), it simply enables an unscored type-in option on the given screen*

FIG. 27.7 g = Generic CNS Descriptor Screen for CNS Treatments
n/a
Steroids
Antiseizure meds
Antiplatelets meds
Anticoagulants
Diuretics
Analgesics
s/p surgery
Intravascular occlusion
Radiation
Chemotherapy
Other — *when Other is selected at the Descriptor level (which is beyond the level for scoring), it simply enables an unscored type-in option on the given screen*

FIG. 27.8

CNS: Other/Other// (*with special code such as 99*)
Type-in (unscored) _____

Type-in (1) _____

Type-in (1.5) _____

Type-in (2) _____

Type-in (3) _____

Type-in (4) _____

Type-in (5) _____

*This screen appears at the end of each system. Coding to designate jump from "Other" selections will be specially delineated; e.g., with a "99" code. Ideally, scoring for each important item in the given System already has been accomplished at the Feature or Subfeature level. This screen should serve as the final safety net, with the realization that entry on to this screen will provide less specific coding than entry within a specific Subsystem and Feature Category. Upon completion of the present screen, user is given options such as "return to the preceding screen" "proceed to next System", "jump to Feature Categories of given system," "jump to Features of given system," "jump to Subfeatures of given system," "jump to Descriptors of given system," or "jump to Interactive Index." Obviously, one simply may bypass the screen.*

FIG. 28
GENERIC SCREENS FOR MULTIPLE SYSTEMS & MULTISYSTEM CONDITIONS

FIG. 28.1

*List of Systems
   CNS
   PSYCH & PAIN
   ENDOCRINE
   CARDIAC
   VASCULAR
   RESPIRATORY
   LIVER, PANCREAS & SPLEEN
   GASTROINTESTINAL
   KIDNEY, URETER & BLADDER
   FEMALE & MALE
   NEURO-MUSCULO-SKEL & SKIN
   EYES, EAR, NOSE, & THROAT
   HEMATOLOGIC
   FLUID & ELECTROLYTES
   MULTI-SYSTEM: Nutrition
   Unknown

* means that if the given system is selected on this screen, then it automatically is selected by the computer for positive identification in data base(s) and note(s) and that its options for data entry have been enabled. Options for the user: proceed immediately to that system; proceed to that system upon completion of the given branch; accept as complete information that already has been entered into that system; or enter information into that system when it is reached during normal progression of the history and physical.

FIG. 28.2

*List of Multisystem Conditions

α = Systemic/Remote Effects of Malignancies and Their Therapy
-- Systemic/Remote Effects of Malignancy: paraneoplastic syndromes, metastases
-- Systemic/Remote Effects of Malignancy Rx: chemotherapy, radiation, surgery β = Systemic/Remote Effects of Immunosuppressive Meds (not for malignancy): steroids, cyclosporine χ = Proliferative Blood/Lymphoid (not leukemia): lymphoma, Hodgkin's, Waldenstrom's macroglobulinemia, cryoglobulinemia, multiple myeloma δ = Autoimmune, Inflammatory, Connective Tissue, and Vascular Disorders:
--Granulomatous/ Infiltrative: amyloid, neurofibromatosis, sarcoid, Wegener's
--Inflammatory & Autoimmune: rheumatoid arthritis, lupus, ankylosing spondylitis, polymyalgia, myositis, dermatomyositis, Goodpasture's, Reiter's
-- Vasculitides: polyarteritis, hypersensitivity vasculitis, polyarteritis nodosa, giant cell, Takayasu's arteritis
--Connective Tissue: scleroderma, Marfan's
--Other Syndromes: CREST, Henoch-Schonlein purpura, Klippel-Feil, serum sickness, congenital ε = Infectious: Lyme Disease, HIV, sepsis φ = Obesity: morbid, supermorbid γ = Nutrition: malnutrition, anorexia, bulimia η = Recreational Substances: alcohol, cocaine, heroin, marijuana, amphetamines \* means that if the given Multisystem Condition is selected on this screen, then it automatically is selected by the computer for positive identification in data base(s) and note(s) and that its options for data entry have been enabled. Options for the user: proceed immediately to that Multisystem Condition; proceed to that Multisystem Condition upon completion of the given branch; accept as complete information that already has been entered for that system; or enter information for that system when it is reached during normal progression of the history and physical.

FIG. 28.3

MULTISYSTEM CONDITIONS: Malignancies and Their Treatment (subsys): Type of Effects (feat categ)
*Site of Primary -- *jump to list of systems for simply acquiring name of system; details and scoring to be provided within that system(s)*
*Site of Metastases -- *jump to list of systems for simply acquiring name of system; details and scoring to be provided within that system(s)*
Resolved paraneoplastic syndrome
⇓⇑Current paraneoplastic Syndromes
Chemotherapy in past w/o significant systemic effects
Resolved systemic effects of chemotherapy
⇓⇑Current or residual systemic effects of chemotherapy
Radiation in past w/o significant systemic effects
Resolved systemic effects of radiation
⇓⇑Current or residual systemic effects of radiation
⇓⇑Unspecified effects
Other

FIG. 28.4

*MULTISYSTEM CONDITIONS: Malignancies and Their Treatment (subsys): Type of Effects (feat categ)/ Site of Primary
n/a
none
CNS
PSYCH & PAIN
ENDOCRINE
CARDIAC
VASCULAR
RESPIRATORY
LIVER, PANCREAS & SPLEEN
GASTROINTESTINAL
KIDNEY, URETER & BLADDER
FEMALE & MALE
NEURO-MUSCULO-SKEL & SKIN
EYES, EAR, NOSE, & THROAT
HEMATOLOGIC
FLUID & ELECTROLYTES
MULTI-SYSTEM
   Unknown

FIG. 28.5

*MULTISYSTEM CONDITIONS: Malignancies and Their Treatment (subsys): Type of Effects (feat categ)/ Site(s) of Metastases
n/a
none
CNS
PSYCH & PAIN
ENDOCRINE
CARDIAC
VASCULAR
RESPIRATORY
LIVER, PANCREAS & SPLEEN
GASTROINTESTINAL
KIDNEY, URETER & BLADDER
FEMALE & MALE
NEURO-MUSCULO-SKEL & SKIN
EYES, EAR, NOSE, & THROAT
HEMATOLOGIC
FLUID & ELECTROLYTES
MULTI-SYSTEM
Unknown

FIG. 28.6

*MULTISYSTEM CONDITIONS: Malignancies & Their Rx (subsys): Current Paraneoplastic Syndromes (feat categ) / Systemic Effects (features)

n/a
none
CNS
PSYCH & PAIN
ENDOCRINE
CARDIAC
VASCULAR
RESPIRATORY
LIVER, PANCREAS & SPLEEN
GASTROINTESTINAL
KIDNEY, URETER & BLADDER
FEMALE & MALE
NEURO-MUSCULO-SKEL & SKIN
EYES, EAR, NOSE, & THROAT
HEMATOLOGIC
FLUID & ELECTROLYTES
MULTI-SYSTEM Score and cumulative score code for paraneoplastic syndrome:
    (1  1.5  2  3  4  5)
    (=   +     +>)

FIG. 28.7

Rx of Malignancy (=Multisystem) (descriptors)
Chemotherapy; Agents and Dates; Remote and Systemic Effects
Radiation; Description and Dates; Remote and Systemic Effects
Remote/Systemic Effects of Chemotherapy
Remote/Systemic Effects of Radiation

FIG. 28.8

Chemotherapeutic Agents (descriptors)
Adriamicin
Bleomycin
Vincrinstine
Dexamethasone
Other
Type-in info (other drugs, dates, etc)

FIG. 28.9

Radiation Therapy (descriptors)
Rads: _____
Implants: _____
Site(s) _____
Dates: _____
Type-in info: _____

FIG. 28.10

MULTISYSTEM CONDITIONS: Malignancies & Their Rx (subsys): Current or Residual Effects of Chemotherapy (feat categ) / Systemic Effects (features)
    n/a
    none
    CNS
    PSYCH & PAIN
    ENDOCRINE
    CARDIAC
    VASCULAR
    RESPIRATORY
    LIVER, PANCREAS & SPLEEN
    GASTROINTESTINAL
    KIDNEY, URETER & BLADDER
    FEMALE & MALE
    NEURO-MUSCULO-SKEL & SKIN
    EYES, EAR, NOSE, & THROAT
    HEMATOLOGIC
    FLUID & ELECTROLYTES
    MULTI-SYSTEM: Nutrition Score and cumulative score code for systemic effects of chemotherapy:
       (1  1.5  2  3  4  5)
         (=    +      +>)

FIG. 28.11

*MULTISYSTEM CONDITIONS: Malignancies & Their Rx (subsys): Current or Residual Effects of Radiation (feat categ) / Systemic Effects (features)
n/a
none
CNS
PSYCH & PAIN
ENDOCRINE
CARDIAC
VASCULAR
RESPIRATORY
LIVER, PANCREAS & SPLEEN
GASTROINTESTINAL
KIDNEY, URETER & BLADDER
FEMALE & MALE
NEURO-MUSCULO-SKEL & SKIN
EYES, EAR, NOSE, & THROAT
HEMATOLOGIC
FLUID & ELECTROLYTES
MULTI-SYSTEM: Nutrition Score and cumulative score code for systemic effects of radiation:
(1 1.5 2 3 4 5)
( =   +   +>)

PSYCH & PAIN (sys): subsystems
psychiatric Disorder
Pain

FIG. 29.2

PSYCH&PAIN (sys): Psychiatric Disorder (subsys):

FIG. 29.3

PSYCH&PAIN DISORDERS (sys):Psychiatric (subsys):Types of Psych Disorders (feat categs):
Depression
Mild Anxiety
Pronounced Anxiety
Mild situational Anxiety
Pronounced situational Anxiety
Bipolar
Schizophrenia
Personality Disorder
Claustrophobia
Anorexia
Bulimia
Autism
*Attributable to Another System
Other

FIG. 29.4

PSYCH&PAIN Psych: Specified Type of Psych Disorders /Features
Mild (1.5)
Mild (2)
Mild as a result of improvement due to Rx (2)
Moderate (3)
Moderate (severe if not for Rx) (3)
Severe (4)
Other ( 1  1.5  2  3  4  5 )

PSYCH&PAIN:Psych:Specific Type/Features///Characteristics (Descriptors)
Suicidal ideations
Hallucinations
combativeness

FIG. 29.5

PSYCH&PAIN:Psych:Specific Type/Features///Treatments (Descriptors)
    Prior antidepressants
    Current antidepressnts
    Prior antipsychotics
    Currents antipyschotics
    Prior ECT
    Current ECT
    Counseling

FIG. 29.6

PSYCH&PAIN (sys): Pain (subys): Location (feature categories)
Site of planned surgery
Local lumbosacral spine
Local lumbosacral spine + radicular
Local cervical spine
Local cervical spine + radicular
Other

FIG. 29.7

PSYCH&PAIN (sys): Pain (subys): Specific Location (feat categ)/Features
n/a
None
Minor (1-2 on a 0 – 10 pain scale) w/o need for high-dose analgesics (1.5)
Minor (1-2 on a 0 – 10 pain scale) while using high-dose analgesics (1.5)
Intermediate (3-6 on a 0 – 10 pain scale) – not using high-dose analgesics (2)
Intermediate (3-6 on a 0 – 10 pain scale) while using high-dose analgesics (2)
Severe (7-9 on a 0 – 10 pain scale) – not using high-dose analgesics (3)
Severe (7-9 on a 0 – 10 pain scale) despite using high-dose analgesics (3)
Worst pain imaginable w/o current high-dose analgesics (4)
Worst pain imaginable despite high-dose analgesics (4)
Other

FIG. 30.
ENDOCRINE (sys): Diabetes Mellitus (susbsys)

FIG. 30.1

ENDOCRINE (sys): Diabetes Mellitus (susbsys): Types (feat. categ.)
Type 1 (insulin-dependent)
Type 2 on no meds
Type 2 on oral meds
Type 2 requiring insulin (and oral meds)
Noninsulin-dependent
Insulin-dependent
Steroid-induced noninsulin-dependent
Steroid-induced insulin-dependent
s/p pancreatic resection insulin-dependent
Gestational in past
Borderline
Other

FIG. 30.2

ENDOCRINE: Diabetes Mellitus: Type 1 (feat. categ)/ Effectiveness of Control (features)
well-controlled w/ current insulin regimen only ( 2  3 )
fair control w/ current insulin regimen only (3)
poorly controlled w/ current insulin regimen only ( 3  4 )
in need of Rx with insulin ( 3  4 )
current diabetic ketoacidosis ( 4  5 )
current nonketotic hyperosmolar state ( 4  5 )
diabetes-induced organ injury ( 2  3  4 ) (detailed below)

FIG. 30.3

ENDOCRINE: Diabetes Mellitus: Type 2 (feat categ)/Effectiveness of Control (features)
no meds currently required (1)
borderline, meds likely to be started (1.5)
well-controlled with current oral meds (2)
poorly controlled w/ current oral meds ( 2  3 )
well-controlled with current insulin + oral meds (2 3)
poorly controlled w/ current insulin + oral meds (3)
current diabetic ketoacidosis ( 4  5 )
current nonketotic hyperosmolar ( 4  5 )
diabetes-induced organ injury ( 2  3  4 ) (detailed below)

FIG. 30.4

Insulin Requirements & Administration (descriptors):
NPH
Lantus
Regular scheduled
Regular prn
Pump
*(this area can be co-populated with data from Medications)*

FIG. 30.5

| Glucose Management (descriptors) |
| --- |
| Checks glucose regularly |
| Checks glucose sometime |
| Rarely checks glucose |
| Other |

FIG. 30.6

Glucose Values (descriptors)
Typical glucose range upon awakening: ____ mg/dL to ____ mg dL
Typical glucose range during day: ____ mg/dL to ____ mg/dL
Lowest glucose w/ current regimen: ____ mg/dL
Highest glucose w/ current regimen: ____ mg/dL
Hypoglycemic s/s if < ____ mg/dL
h/o ketoacidosis. If so, give approx date: ____
recent insulin adjustment (to type-in screen for description)
diabetes-related ER visit (to type-in screen for description)
diabetes-related hospital visit (to type-in screen for description)
Other

FIG. 30.7

| Optional Table (descriptors) | Blood Glucose Levels (mg/dL) | | | | | | | | | | | | | | |
|---|---|---|---|---|---|---|---|---|---|---|---|---|---|---|---|
| | <50 | 70 | 90 | 110 | 130 | 150 | 175 | 200 | 250 | 300 | 350 | 400 | 500 | >600 | unkno |
| Range upon awakening (low and high) | | | | | | | | | | | | | | | |
| Range during day (low and high) | | | | | | | | | | | | | | | |
| Hypoglycemic s/s if < (single value) | | | | | | | | | | | | | | | |
| Lowest glucose in past yr normal settings | | | | | | | | | | | | | | | |
| Highest glucose in past yr in normal settings | | | | | | | | | | | | | | | |
| | | | | | | | | | | | | | | | |
| | | | | | | | | | | | | | | | |

FIG. 30.8

HbA1C (descriptors):
Not checked
Unknown
None recent
<7
7-9
9-11
>11
Other

FIG. 30.9

| s/s When Hypoglycemic (descriptors) |
| --- |
| light-headedness |
| dizziness |
| loss of consciousness |
| altered speech |
| sweating |
| Other |

FIG. 30.10

Diabetic Complications & Sequelae (Descriptors)

n/a
    None
    *CNS$_{CEREBVASC}$
    *CNS$_{nonCEREBVASC}$
    *ENDOCRINE$_{notDIAB}$
    $^{1,2,3}$*CARDIAC$_{CAD}$
    *CARDIAC$_{nonCAD}$
    *BP
    *VASCULAR
    *RESPIRATORY
    *LIVER & SPLEEN
    *PANCREAS
    *GASTROINTESTINAL
    *KIDNEY
    *URETER & BLADDER
    *FEMALE & MALE
    *NEURO-MUSCULAR
    *SKELETAL
    *SKIN
    *EYES
    *EAR, NOSE, & THROAT
    *HEMATOLOGIC
    *FLUID & ELECTROLYTES
    *ULTI-SYSTEM (from Table 2)

*For purposes of this example subscripts indicate: 1 = co-population of established Cardiac Risk Index, 2 = co-population of American College of Cardiology/American Heart Association Guidelines for preoperative cardiology consultation, and 3 = algorithm for determining need for perioperative beta-blockade to decrease risk of a heart attack.*

FIG. 30.11

| Descriptors Describing Plans for Therapy of Diabetes |
|---|
| n/a |
| Currently receiving effective therapy |
| Unsuccessful therapy in past |
| Currently receiving preventative therapy |
| Likely to receive additional therapy prior to day of surgery |
| $_4$Likely to receive additional therapy on day of surgery |
| Decision as to additional therapy prior to surgery to be made by PCP |
| Decision as to additional therapy prior to surgery to be made by surgeon |
| Decision as to additional therapy prior to surgery to be made by consultant |
| Decision as to additional therapy prior to surgery made by anesthesiologist |
| Anticipate improvement due to therapy prior to surgery |
| Plan to decrease therapy on day before surgery |
| Plan to decrease therapy several days prior to surgery |
| Other: _____ |
| |
| *Subscripted 4 indicates co-population of ASPIRIN™ display with information as to the need for therapy on the day of surgery* |

FIG. 31
LAB VALUES (system)
FIG. 31.1

<u>LAB (sys): subsystems</u>
Hematology
Blood chemistries
Liver function tests
Tumor markers
Urine
Unspecified
Other

FIG. 31.2

<u>LAB (system): Blood Chemistries (subsystem): Feature Categories</u>
Sodium
Potassium
Chloride
Bicarbonate
Calcium
Magnesium
Etc.

FIG. 31.3

<u>LAB (system): Blood Chemistries (subsystem): Potassium (Feature Category)/Features</u>
Normal or Below Normal
Above Normal

FIG. 31.4

```
LAB: Blood Chemistries: Potassium/Below Normal/Subfeatures
Normal (1)
Borderline low-normal and of no concern (1.5)
Slightly below normal and of no concern (1.5)
Borderline low, therapy considered ( 1.5 2 )
Slightly below normal, therapy considered (2)
Significantly below normal, therapy indicated ( 2 3 )
Significantly below normal, despite therapy ( 2 3 )
Significantly below normal requiring new or additional therapy preop ( 2 3 4 )
Dangerously below normal ( 3 4 )
Life-threatening below normal ( 4 5 )
```

FIG. 31.5

```
LAB: Blood Chemistries: Potassium/Above// Normal/Subfeatures
Borderline high-normal and of no concern (1.5)
Slightly above normal and of no concern (1.5)
Borderline low, therapy considered ( 1.5 2 )
Slightly above normal, therapy considered (2)
Significantly above normal, therapy indicated ( 2 3 )
Significantly above normal, despite therapy ( 2 3 )
Significantly above normal requiring new or additional therapy preop (2 3 4)
Dangerously above normal ( 3 4 )
Life-threatening above normal ( 4 5)
```

FIG. 32

FIG. 32.1. Examples of systems, subsystems and representative features of the SHAPE™ Individual Systems Status (SISS™) Score
A) CNS and Cognitive (CNS) system

| Code | System/subsystem/Feature Category | Status 2 Features & Subfeatures | Status 3 Features & Subfeatures | Status 4 Features & Subfeatures | Status 5 Features & Subfeatures |
|---|---|---|---|---|---|
| S1 | GNS & COGNITIVE (CNS) [CNS-based feature and subfeature codes range from 1000 to 1999; not shown because many of the items are composites of multiple features and/or feature(s)/subfeature(s) to simplify use by the healthcare provider – see text for details] | | | | |
| sS1 | Seizures | Controlled complex partial or generalized seizures. Simple partial sz. [1.5:Sz > 5 yrs ago] | Frequent complex partial with changed consciousness. Generalized seizure(s) w/ LOC despite medication. | Status epilepticus (despite Rx). | |
| FC1.0001 | Generalized Tonic-Clonic | | | | |
| FC1.0002 | Generalized Absence | | | | |
| FC1.0003 | Complex Partial | | | | |
| FC1.0004 | Simple Partial | | | | |
| FC1.0005 | Unspecified | | | | |
| FC1.0006 | Other | | | | |
| sS2 | Cerebral Ischemia | Asympt partial occlusion. | >70% carotid occlusion. h/o transient ischemic attacks, thrombotic or embolic stroke. Moderate s/s from prior stroke | Current TIAs, recent or acute stroke. Critical occlusion. LT stroke-induced s/s. | |
| sS3 | Nonischemic Cerebrovascular Disorders | s/p aneurysm clipping w/o sequelae. Recurrent moderate headache. [1.5: recurrent mild headache, occasional moderate headaches] | "Stable" aneurysm or AVM. Moderate s/s following bleed. Temporal arteritis requiring steroids. Severe headache. | Aneurysm or AVM – recently ruptured, pending rupture. Sever s/s following bleed. | Acutely ruptured aneurysm. |
| sS4 | Nonmalignant Mass | Acoustic neuroma, limited to hearing deficit. Asympt Glioma, benign Astrocytoma or Meningioma. Minor local and/or regional s/s from tumor or therapy. [1.5: Incidental finding. s/p success-ful resection w/o sequelae.] | Focal signs, Tumor or therapy causing moderate systemic effects: Pituitary tumor causing visual field deficit or hormonal instability. | Severe local and/or regional s/s from tumor or therapy. Poorly controlled ICP. High potential for herniation.↓ consciousness. LT systemic effects. | |
| sS5 | Malignant Mass | s/p chemotherapy w/o deficit; s/p radiation w/o deficit; Minor (local and/or systemic) s/s from tumor or therapy. [1.5: s/p resection w/o deficit.] | Moderate CNS and/or systemic s/s from tumor or therapy (3) | Severe (local and/or systemic) s/s from tumor or therapy (4) | |

| Code | System/subsystem/Feature Category | Status 2 Features & Subfeatures | Status 3 Features & Subfeatures | Status 4 Features & Subfeatures | Status 5 Features & Subfeatures |
|---|---|---|---|---|---|
| sS6 | Head Trauma and Infection | Mild injury (Glasgow Coma Score 13 to 15). Questionable loss of consciousness--cleared by H&P/imaging studies. Mod. post-traumatic brain injury. | Acute trauma, infection or comparable injury w/ s/s of mod CNS injury. Sympt cerebritis, encephalitis, meningitis. Glasgow Coma score 9-12. | Severe injury. Glasgow Coma Score of 6-8 | Glasgow Coma Score 3-5 |
| sS7 | ICP/Hydrocephalus | Mild elevation. Benign, asympt. | Controlled or sufficiently ↓ w/acute therapy (e.g., steroids). Symptomatic w/headaches. Pseudotumor cerebri w/ICP >20 mmHg or non-LT symptoms. | LT brainstem compression, impending herniation. | Acute herniation. |
| sS8 | Cognitive Disorders | Mild-to-mod dementia or mental retardation [1.5: evident but slight]. | Severe dementia* or mental retardation*. Significant residual deficits from CVA. Sympt Wernicke-Korsakoff syndrome. | ↓ level of consciousness. Near-comatose. | |
| sS9 | Parkinsonism & Related Movement Disorders | Mild tremor, minor gait disturbance. | Drooling, compromised swallowing, altered sensorium. Mod. ventilatory weakness, autonomic dysfunction. | LT symptoms. | |

| | Status 2 Features | Status 3 Features | Status 4 Features | Status 5 Features |
|---|---|---|---|---|
| PSYCHIATRIC & PAIN | | | | |
| PSYCH | Controlled anxiety or depression. Personality disorder. [1.5: pronounced preop anxiety] | Symptomatic psychosis not well-controlled on meds. Disruptive and combative.* | Uncontrolled, severe psychosis.* | |
| PAIN | Mild (1.5) disturbance; Moderate Disturbance | Severe disturbance | Life-threatening disturbance | |

FIG. 32.4

| | Status 2 Features | Status 3 Features | Status 4 Features | Status 5 Features |
|---|---|---|---|---|
| ENDOCRINE (ENDO) | | | | |
| Diabetes Mellitus | Well-controlled by diet. Type 2 stable on oral meds for <5 yrs w/o end-organ damage. HbA1c ≤ 7%. [1.5: borderline diabetes]. | Prone to sympt hypoglycemia or hyperglycemia (<60 or >200 mg/dL). Requires insulin to avoid glucose >250 mg/dL or ketosis. HbA1c>7%. Neuropathy (sensory, autonomic), gastroparesis, nephropathy, retinopathy, joint or collagen abnormalities (limited neck extension, poor wound healing). | Poorly controlled with severe hypo- or hyperglycemia. Ketoacidosis (being Rx'd). | Hyper/Hypo-glycemic coma. Untreated severe ketoacidosis. |
| Thyroid Mass or Dysfunction | Mild hypo- or hyperthyroidism well-controlled on meds. Nodule w/o obstructive symptoms. [1.5: s/p successful surgery or iodine therapy; long-standing, insignif enlargement] | Mod tracheal deviation; non-LT obstructive symptoms when supine. Current mod systemic manifestations of abnormal thyroid function being treated: dysrhythmias, mod. hypoventilation, myopathy, altered mental status. Graves (controlled, non LT). Active Hashimoto's thyroiditis. Metastatic tumor or therapy causing signif systemic effects. | LT airway compression. Poorly controlled thyroid function w/ dangerous systemic manifestations | Pulminant thyroid storm. Myxedema coma. |
| Parathyroid | Asympt ↑ or ↓ Ca²⁺ or relatively minor s/s (↓ energy, muscle aches, osteoporosis, renal stones). | Clinically signif. calcium abnormality w/ confusion, somnolence, hypovolemia, polyuria, ECG changes, hypertension, marked weakness, multiple fractures. Chvostek's and Trousseau's signs. | Severe calcium abnormality | |
| Pheochromocytoma | [1.5: s/p successful removal w/o sequelae] | Controlled BP and HR on alpha and/or beta blockers. Stable mild-mod. catechol-induced cardiomyopathy. | LT dysfunction or compromise: hypertensive emergency, acute pulmonary edema, severe dysrhythmias, acute ST-T changes. | |
| Other Endocrine/ Hormonal | Asympt pituitary mass w/o abnormal hormone levels. [1.5: potential drug-induced adrenal suppression from remote drug] | Signif s/s of altered prolactin (amenorrhea, galactorrhea, and infertility), ACTH (Cushing's syndrome or Addisonian), or growth hormone (acromegaly). Diabetes insipidus or SIADH requiring Rx. Clinically signif. hypo- or hyperadrenalism. Carcinoid w/flushing, intestinal hypermotility and wheezing requiring therapy. *Oral or parenteral steroid use for a chronic medical condition w/in 30 days.* | LT hormone-induced dysfunction; e.g., hypertensive emergency, acute pulmonary edema, angioneurotic edema, severe dysrhythmias, acute ST-T changes. | |

FIG.32.5

| | Status 2 Features | Status 3 Features | Status 4 Features | Status 5 Features |
|---|---|---|---|---|
| CARDIAC (CARD) | | | | |
| Ischemic Heart Disease | [Atypical chest pain – seemingly noncardiac] | Stable exertional angina. "Stable 'mild' angina" (ACC/AHA). Occasional use of sublingual nitroglycerin. "Angina occurs with strenuous or rapid or prolonged exertion at work or recreation" (Canadian Cardiovasc Soc. Class 1). "Slight limitation of ordinary activity - angina occurs walking or stair climbing after meals, in cold, in wind, under emotional stress" (Canad Class 2). "Marked limitation of ordinary activity -- angina occurs walking one or two blocks on the level or climbing one flight of stairs in normal conditions and at a normal pace." (Canad 3). New LBBB, >1 mm ST depression, deep T wave inversion or comparably worrisome ECG abnormality. Long-standing wall motion abnormalities. *Prior MI or angina w/in 6 months.* EF 25-50%. Old MI with adequate remaining function. Old MI w/ subsequent successful revascularization. s/p successful revascularization prior to lasting injury. *s/p percutaneous coronary intervention or major cardiac surgery.* Cardiac-related dyspnea at 2-4 METS. Stable with ICD* in place for h/o ventricular fibrillation. Prior CHF. Compensated CHF, stable on cardiac-meds. | LT LV compromise. Unstable angina. Acute infarction. Cardiac-related SOB or angina at <2 METS. "Inability to carry on any physical activity w/o discomfort–angina syndrome may be present at rest" (Canad 4). Prone to LT ventricular fibrillation. EF<25%. Extensive wall motion abnormalities and ischemia on cath. Sympt L main occlusion. Multiple vessel disease w/ ↓ EF. Unstable coronary syndromes (e.g., severe or unstable angina or possibly "stable" angina in a sedentary patient), uncontrolled CHF, dangerous ischemic injury-induced arrhythmias; critical valvular heart disease, acute MI (<7 days) and recent MI (7-30 days, unless confirmation of stable cardiac function and no further significant ischemic risk). | Acute, severe heart failure. |
| | | Type 1 Diabetes. Renal Insufficiency. | | |
| Nonspecific Risk Factors & Indicators for Ischemic Heart Disease | ACC/AHA "Minor" h/o Stroke; Peripheral Vascular Disease; Age > 70 yrs; Hypertension Sedentary life style (low functional capacity, "inability to climb flight of stairs with a bag of groceries; LVH, left BBB, ST-T abnormalities, rhythm other than sinus (e.g., controlled AF), on EKG. Type 2 Diabetes. [1.5: Smoking, ↑LDL, ↑ cholesterol, ↑ Homocysteine, ↑ C-reactive protein, h/o cocaine; deconditioned] | | | |

| | Status 2 Features | Status 3 Features | Status 4 Features | Status 5 Features |
|---|---|---|---|---|
| Nonischemic Cardiomyopathy | Mild wall motion abnormalities, EF > 50%. Peripheral edema. | Sympt w/ mod limitations. Compensated CHF, stable on cardiac meds. EF 25-50%. Hypertrophic cardiomyopathy w/LV outflow obstruction. s/p successful heart transplant. | Severe LT CHF or related symptoms. | Acute, severe heart failure |
| Congestive Heart Failure | Mild-moderate peripheral edema. CHF in past, now fully resolved | Compensated CHF, stable on current meds. h/o pulmonary edema in past – presently stable. EF 25-50%. *New onset or new s/s within 30 days, including abnormal exercise tolerance, orthopnea, paroxysmal nocturnal dyspnea, ↑ jugular venous pressure, pulmonary rales cardiomegaly, pulmonary vascular engorgement.* | *Severe CHF within 30 days.* Severe pulmonary edema. Cannot perform any physical activity; requires cardiac meds to function. Life-threatening pulmonary & hepatic congestion. EF<25%. | |
| Exercise Tolerance – Chest pain | [1.5=able to climb 3 flights and exercise (5-10 METS) w/o SOB or CP; limitations beyond this, but they are not directly attributable to cardiac (e.g., arthritis, obesity)]. 2=no chest pain w/ exercise but limiting SOB at 1-2 flights; or unable to evaluate by standard criteria but probably acceptable. | exertional CP at >2 flights (>4 METS) | CP at ≤2 flights (<4 METS) | Persistent pain at rest |
| Exercise Tolerance – Shortness Breath | | SOB at ≤1 flights (<4 METS). *Dyspnea upon moderate exertion (<1 flight). Unable to complete a sentence w/o needing to take a breath.* | Cardiac-related *SOB at rest* | Acute, LT SOB at rest |
| Valvular Heart Disease (AS,AR, MS,MR, TS,TR, PS,PR, MVP) | Clinically insignif. murmur including MVP; may nonethe-less require SBE prophylaxis. s/p repair or replacement, no residual damage or dysfunction. | Clinically signif. stenosis or regurgitation. Valve-induced ventricular hypertrophy or dysrhythmias. Compensated CHF. SOB at 2-4 METS. Occasional syncope or angina. LV hypertrophy. AV gradient 25 – 50 mmHg | Critical narrowing or insufficiency. Recurrent syncope. SOB at <2 METS. Uncompensated CHF. | |
| Septal Defects & Pulmonary Hypertension | Asympt ASD/VSD | RV hypertrophy. Mod pulmonary hypertension. Cor pulmonale. | Eisenmenger's syndrome. RV failure | |
| EKG | Long-standing NSST in absence of worrisome s/s or risk factors. | New LBBB, >1 mm ST depression, deep T wave inversion-or comparably worrisome ECG abnormality. NSST in context of worrisome s/s or risk factors (e.g., diabetes mellitus). Pronounced 1° block, Wenckebach. Brady-tachy syndrome. | Acute ischemia or rhythm disturbance. Sympt Mobitz 2 or complete heart block. Significant arrhythmias (high-grade AV block, symptomatic heart block, supraventricular arrhythmias with uncontrolled ventricular rate). | |
| Stress Test – EKG and symptoms | NSST w/o symptoms | CP at >4 METS; significant ST changes at >4 METS | CP at ≤4 METS; significant ST changes at <4 METS | |
| Stress Test- MIBI perfusion scan | | Old scar, ischemia of unknown origin | New (<1 month old) region of ischemia. Significant region of reversible ischemia | |
| ECHO cardiogram – wall ischemia, wall motion, eject fxn | | Long-standing wall motion abnormalities. Moderate wall motion abnormalities during exercise. EF 25-50%. | Extensive and/or new wall motion abnormalities at rest, Severe abnormalities with exercise or persantine, | |

FIG. 32.6

| | Status 2 Features | Status 3 Features | Status 4 Features | Status 5 Features |
|---|---|---|---|---|
| ECHO—valves and septum | Clinically insignif. valve abnormalities | Clinically signif. stenosis or regurgitation. Valve-induced ventricular hypertrophy or dysrhythmias. LV hypertrophy. AV gradient 25 – 50 mmHg. | Critical narrowing or insufficiency. MV area <1 cm² w/ diastolic gradient >25 mmHg. AV area < 0.7 cm² w/ gradient > 50 mmHg | |
| Cardiac Cath. | | Significant vessel disease, not imminently life-threatening. s/p successful revascularization. | Life-threatening narrowing or occlusion. Sympt L main occlusion. Multiple vessel disease w/ ↓ EF. | |
| Bradycardia (unless "normal" for patient) | Asympt borderline 1° block. Functioning pacemaker, non dependent. | Occasional light-headedness. Pacemaker-dependent. Sinus bradycardia post-ablation. Pronounced 1° block, Wenckebach. Brady-tachy syndrome. | Urgent need for pacemaker. Sympt Mobitz 2 or complete heart block. | |
| Trachy Atrial or Nodal Dysrhythmia | Asympt sinus tachycardia. Occasional sympt palpitations w/o SOB or angina. [1.5: asympt. APCs; occasional nondisturbing palpitations; s/p successful ablation] | Atrial fibrillation or flutter w/ controlled ventricular rate due to medical therapy or pacemaker. Tachyarrhythmias w/ SOB or CP Embolic potential, requiring antiembolic therapy. Untreated preexcitation or reentrant pathway syndrome. | Poor rate control. Hemodynamic instability. Active embolic events. LT or sympt high-grade atrio-ventricular block | |
| Ventricular Dysrhythmias (ICD) | Occasional unifocal VPCs – asympt | Multifocal VPCs. Occasional sympt runs of ventricular tachycardia. Functioning ICD* in place | Frequent ventricular tachycardia. Prone to ventricular fibrillation. Urgent need for ICD. | |
| Hypertension | Well-controlled w/o end-organ damage. [1.5: "white-coat" hypertension] | Poorly controlled.. | Poorly controlled w/ dangerous extremes (e.g., >220/120 mmHg). | LT extremes |
| Hypertensive Injury | No end-organ damage. Left ventricular hypertrophy | Renal injury. Moderate cardiomyopathy. | Severe cardiomyopathy. Acute hypertensive injury | LT cardiomyopathy. LT acute injury. |

| | Status 2 Features | Status 3 Features | Status 4 Features | Status 5 Features |
|---|---|---|---|---|
| VASCULAR (VASC) | | | | |
| Peripheral Vascular Disease | Early, minimally sympt stage. | Claudication. Slow-healing ulcer. Non-LT ischemic injury. Signif. stenosis of a critical vessel. *h/o revascularization or amputation for vasc. disease.* Sympt vasculitis. | LT ischemic injury. | |
| Venous Disease | Greenfield filter in place for recurrent DVT. [1.5: recent superficial phlebitis. h/o DVT due to immobility or injury] | Current DVT. Possible pulmonary emboli. h/o DVT due to persistent hypercoagulable state. | LT embolization or vessel rupture. | |
| Anomolous Vasculature | Benign AVMs. | Hereditary hemorrhagic telangiectasia or similar syndrome w/sympt bleeding. Thoracic outlet obstruction. | LT sequelae. | |

FIG. 32.9

| | Status 2 Features | Status 3 Features | Status 4 Features | Status 5 Features |
|---|---|---|---|---|
| RESPIRATORY (RESP) | | | | |
| Bronchospastic Disease (Pure Obstructive) | Rare symptoms. Prophylactic inhaler use. No recent ER visits or hospitalizations. | Daily wheezing, SOB or need for inhaler. Activity limited by wheezing. Recent exacerbation requiring systemic steroids or intubation. | Persistent sympt wheezing despite bronchodilators and steroids. | Status asthmaticus despite Rx |
| Restrictive Disorder | Minimal compromise. | Signif ↓ lung volumes and oxygenation. >50% ↓ in vital capacity. | LT ↓ lung volumes and oxygenation | |
| Lung or Mediastinal Tumor | Local lesion. s/p therapy with mild ↓ pulm function. [1.5: long-standing, asympt, likely benign mass, s/p successful therapy w/o sequelae] | Mod pulmonary symptoms. Injury to recurrent laryngeal nerve. Metastatic tumor or therapy causing signif. systemic effects. s/p therapy with mod ↓ pulm function | LT hypoxia, airway compression, effusion (due to tumor, metastases, chemotherapy or radiation). Signif. vascular compression/superior vena cava syndrome. | |
| COPD w/Mixed Obstructive/ Restrictive | Minimally sympt. Current tobacco use or >20 pack-year history. [1.5: prior h/o < 20 pack-yrs] | Emphysema or bronchitis causing SOB with <4 METS activity. Bronchospasm (see above), productive cough, RV strain, mild pulmonary hypertension. Recent exacerbation requiring steroids or antibiotics. PFTs 30-75% of predicted. *FEV1 < 75% predicted.* Needs intermittent home $O_2$. s/p successful lung reduction surgery or transplant. *Functional disability from COPD (inability to perform activities of daily living).* | SOB at rest. Fulminant pneumonia or hemoptysis. Requires continuous oxygen. Ventilator-dependent. Signif pulmonary hypertension, cor pulmonale. ARDS. FEV1<800 ml | |
| Obstructive Sleep Apnea (OSA) & Obesity-Hypoventilation Synd. | Suspected or mild OSA {1.5: one or more predisposing characteristics (Table 5) | Definite apneic episodes w/ signif ↓ $O_2$ sat. Apnea-hypopnea index (AHI) 20-40 on sleep study. Signif. daytime sleepiness. Mild polyeythemia, hypercarbia. Borderline Pickwickian. 2 or more predisposing characteristics (Table 5) | Profound hypoxia. AHI >40. Severe pulmonary hypertension, right-heart failure. SOB at rest. $CO_2$ retention. Severe Pickwickian. | |

FIG. 32.10

| | Status 2 Features | Status 3 Features | Status 4 Features | Status 5 Features |
|---|---|---|---|---|
| LIVER, PANCREAS & SPLEEN (LPS) | | | | |
| Liver Disorder | Minimal fibrosis. Mild ↑ LFTs w/o clinical significance. Asympt chronic persistent hepatitis. Local asympt tumor. Hepatitis C positive - asympt [1.5: h/o fully resolved halothane hepatitis,* hepatitis A or B] | Signif injury/dysfunction or cirrhosis. PT>1.5x normal, LFTs 2x normal. Jaundice, ascites, varices, splenomegaly. *Ascites w/in 30 days*. Mild encephalopathy, ↓ serum albumin. Sympt but not LT hepatitis (infections, drug-induced, alcoholic and nonalcoholic steatohepatitis). Childs-Pugh class A (5-6 points). Tumor or therapy causing signif systemic effects. s/p successful transplant. | Severe end-stage liver disease. LT portal hypertension, hepatorenal/hepatopulmonary syndrome, encephalopathy. Acute severe variceal bleed. Childs-Pugh class C (>9 points) and possibly B (7-9 points) | |
| Gall Bladder Disorder | Nonobstructive cholelithiasis. [1.5: gall stones in past] | Obstructive cholelithiasis. Acute cholecystitis. Tumor or therapy causing signif systemic effects | Fulminant sepsis and/or hepatic failure due to cholelithiasis. | |
| Pancreas Disorder | Local asympt tumor. s/p successful transplant | Obstructive tumor or inflammation. Acute pancreatitis. Hypocalcemia. Altered glucose. Tumor or therapy causing signif systemic effects. | LT consequences of dysfunction. | |
| Spleen Disorder | s/p splenectomy w/o sequelae. | Blood cell destruction. Stable Hematoma secondary to injury. | LT hemolysis, acute injury, impending rupture. | |

FIG. 32.11

| | Status 2 Features | Status 3 Features | Status 4 Features | Status 5 Features |
|---|---|---|---|---|
| GASTROINTESINAL (GI) | | | | |
| GERD (Gastro-Esophageal Reflux Dis-order), Hiatal Hernia & Gastroparesis* | Frequent regurgitation. Sympt hiatal hernia. Gastroparesis. [1.5: occasional; well-controlled with meds] | GERD-induced bronchospasm, voice change, pneumonia.* | LT respiratory complications.* | |
| GI Disorder | Mild-mod. local effects w/o systemic sequelae. Asympt confined tumor. [1.5: prone to GI irritability, PONV; asympt diverticulosis; s/p tumor resection – no sequelae] | Mod hypovolemia due to vomiting or diarrhea. Malnutrition. Diverticulitis. Active inflammatory bowel disease. Perforation (under treatment). Obstruction (under treatment)*. Metastatic tumor. Tumor or therapy causing signif systemic effects. Ischemic bowel. | LT fluid and electrolyte abnormalities, organ compromise. Sepsis or shock secondary to intestinal ischemia or perforation. | |

FIG. 32.12

| KIDNEY, URETER, BLADDER, URETHRA (KUBU) | Status 2 Features | Status 3 Features | Status 4 Features | Status 5 Features |
|---|---|---|---|---|
| Renal Insufficiency | Mild dysfunction. | GFR<50 mL/min. Serum creatinine >3.0 mg/dL. Mod. nephrotic syndrome. Stable on dialysis. s/s of secondary hyperparathyroidism, platelet dysfunction, ↑ BP, altered fluid and electrolytes, renal osteodystrophy. Steady ↑ azotemia and ↑ creatinine >3.0 mg/dL. Currently requiring dialysis. | Advanced hepatorenal syndrome. LT fluid and electrolyte disturbance, coagulopathy | |
| Stones | Stones (kidney, Ureter, bladder, urethra) leading to recurrent infections. [1.5: h/o or asympt stones] | Hydronephrosis secondary to stones. Significant pyelonephritis. Obstructive uropathy. | | |
| Other Kidney Disorder | Stable s/p transplant. Asympt confined tumor. [1.5: s/p tumor resection – no sequelae]. | s/p moderately successful transplant. Metastatic tumor. Tumor or therapy causing signif. systemic effects. | LT sepsis. | |
| Ureter, Bladder & Urethra | Asympt local tumor. [1.5: incontinence; s/p tumor resection – no sequelae.] | Metastatic tumor. Tumor or therapy causing signif. systemic effects. | LT sepsis secondary to obstructive uropathy. | |

FIG. 32.13

Examples of systems, subsystems and representative features of the SHAPE™ Individual Systems Status (SISS™) Score

| | Status 2 Features | Status 3 Features | Status 4 Features | Status 5 Features |
|---|---|---|---|---|
| FEMALE | | | | |
| Pregnancy* | Uncomplicated. [1.5: pt is fertile but denies (not tested)] | Pre-eclamptic. Ectopic. Premature contractions. Placenta previa/accreta. Trophoblastic disease. | Eclamptic. Acute HELLP syndrome. Severe abruption. | |
| Breast | Confined tumor. [1.5: currently breastfeeding*; s/p tumor therapy – no sequelae] | Metastatic. Tumor or therapy causing signif. systemic effects. | LT sequelae. | |
| Fibroids | Pain. Recurrent UTIs. Intermittent heavy bleeding, mild anemia [1.5: occasional pain, mild bleeding] | Sympt anemia requiring transfusion. Deep vein thrombosis (being treated). | Current microemboli secondary to vascular occlusion. | LT pulmonary embolus. |
| GYN tumor | Asympt or s/p successful therapy. | Metastatic/invasive tumor or therapy causing signif. systemic effects (ascites, pleural effusion) | LT consequences. | |
| Other GYN | Endometriosis; benign cyst; vaginal prolapse | Signif systemic symptoms. | | |
| MALE | | | | |
| Prostate | Asympt tumor or s/p successful therapy. [1.5: BPH; impotence. s/p tumor resection – no sequelae] | Metastatic tumor. Tumor or therapy causing signif systemic effects. | LT sequelae. | |
| Penis and Testes | Asympt tumor or s/p successful therapy. [1.5: incontinence; reported erectile dysfunction] | Metastatic tumor. Tumor or therapy causing signif systemic effects. | LT sequelae. | |

FIG. 32.14

| FLUID & LYTES (F&E) | Status 2 Features | Status 3 Features | Status 4 Features | Status 5 Features |
|---|---|---|---|---|
| Fluid (Volume) | Mild hypovolemia or fluid overload | Sympt fluid loss or overload. SIADH w/ water retention. Diabetes insipidus. | LT hypotension, hypoperfusion or hypervolemia. LT cardiac dysfunction | |
| Electrolytes:sodium, potassium, chloride, bicarbonate, calcium, magnesium, phosphate | Clinically insignif. Electrolyte abnormality. | Lytes markedly outside normal range and/or s/s: paresthesias, altered reflexes, weakness, multiple bone fractures, changes in mental status, seizure, non-LT ECG, HR or BP changes. Metabolic alkalosis. Metabolic acidosis. | Severe LT abnormality which requires initiation of acute Rx prior to surgery. Comatose.. Central pontine myelinolysis. Electrolyte-induced seizures. | |

FIG. 32.15

| | Status 2 Features | Status 3 Features | Status 4 Features | Status 5 Features |
|---|---|---|---|---|
| HEMATOLOGIC (HEME) (see "Multisystem Disorders" for proliferative and malignant disorders) | | | | |
| Hypercoagulable State | Asympt Factor V.Leiden, anti-thrombin III deficiency, procoagulant antibodies. | Recent or recurrent embolization. Sympt abnormal Factor V (Leiden), anti-thrombin III deficiency, protein C/S deficiency, procoagulant antibodies. Requires daily anticoagulation. | Acute pulmonary embolus. | |
| Bleeding Diathesis* | Well-controlled w/o recent need for blood products or other aggressive Rx. vonWillebrand (responsive to pre-Rx) [1.5: Persistent antiplatelet or anticoagulant Rx*] | Documented h/o of excess bleeding. Hemophilia A or B. ↓ platelets 50,000-75,000. TTP or ITP, anti-coag antibodies. | Uncontrollable bleeding. | |
| RBC & Hb Disorders, Blood Loss | Stable. Hb 7-10 g/dL or 16-18 g/dL. Relatively benign hemoglobinopathy: e.g., sickle cell trait, thalassemia minor. Porphyria* [1.5: Hb 11-12 g/dL; s/p transfusion for transient anemia] | Hb < 7 gm/dL or > 18 gm/dL. Sympt anemia. Requires transfusion. Signif. predisposition to hemolysis (e.g., G6PD Deficiency). Sickle cell disease w/ h/o vasoocclusive or hemolytic crisis. Transfusion of >4 units packed RBC or whole blood w/in 72 prior to surgery. | LT anemia. Current hemolytic or occlusive crisis, acute chest syndrome, stroke, renal injury or CHF. HbA<40%. | |
| WBC Disorders | Asympt chronic leukemia; s/p effective Rx of leukemia. s/p successful bone marrow transplant – no sequelae [1.5: mild ↓ WBC] | Dangerously low WBC. Acute leukemia. | LT WBC abnormality. | |

FIG. 32.16

| | Status 2 Features | Status 3 Features | Status 4 Features | Status 5 Features |
|---|---|---|---|---|
| EYES, EARS, NOSE, AND THROAT (ENT) | | | | |
| Airway Mass | Local and nonobstructing within airway or adjacent to airway. [1.5: s/p successful therapy - no sequelae] | Partially obstructing, compressing or distorting tumor, infection, or foreign body. Metastatic tumor to neck or other tissues. Tumor or therapy causing signif. airway compromise or systemic effects. | Severe obstruction/compromise due to tumor, metastases, chemotherapy, radiation, or infection. | |
| Vocal Cords & Larynx (nontumor) | Hoarseness. Benign vocal cord injury. s/p tracheostomy, no residual damage or dysfcn.* [1.5: prior temporary trach, healed, pregnancy-induced hoarseness.] | Sympt vocal cord injury or paralysis. Sympt but non-LT epiglottitis or laryngeotracheal bronchitis. | LT airway dysfunction. | |
| Oropharynx, Nose, & Sinuses (nontumor) | Chronic sinusitis, chronic tonsillitis. [1.5:Poor dentition, mild-mod congestion, pregnancy-induced congestion, occasional nose bleeds] | Severe nose bleeds; moderate oropharyngeal bleeding. Acute tonsilitis | LT oropharyngeal bleeding | |
| Eyes | Legally blind. [1.5: ↓ vision, cataracts; glaucoma] | Severe, uncontrolled or narrow-angle glaucoma. Open globe. Tumor. | Invasive tumor with severe CNS effects. | |
| Ears and Parotid | Local tumor. Meniere's disease. Recurrent infections. [1.5: ↓ hearing] | Invasive tumor. | | |

FIG. 32.17

| | Status 2 Features | Status 3 Features | Status 4 Features | Status 5 Features |
|---|---|---|---|---|
| NEURO-MUSCULO-SKELETAL & SKIN (NMS) | | | | |
| Lumbar & Thoracic Spine | Mod pain (local and/or radicular). Slight weakness. [1.5: occasional local discomfort] | Severe pain, requiring high-dose opioids. Pronounced weakness. Paraplegia. Bowel or bladder dysfunction. Autonomic hyperreflexia. Scoliosis with angle >60° (see also Restrictive Disorders under RESP). | Spinal shock. Scoliosis causing ventilatory failure (See also Restrictive Disorders under RESP). | |
| Cervical Spine | Mod local pain. Risk factors for subluxation (rheumatoid arthritis, diabetes w/ joint abnormalities, Down syndrome). Long-standing radicular s/s. [1.5: occasional local pain] | Quadraplegia. Severe local pain. Severe or position-sensitive radicular s/s. Severely restricted neck motion. Clinically signif instability, subluxation or Chiari malformation. | Acute transection or compression. | |
| Bone and Joint | Pain or dysfunction causing signif. limitation of activity. Active gout. [1.5: arthritis/DJD slightly limiting activity; h/o gout] | Incapacitating pain or restriction. | LT restrictions. | |
| Neural & Neuromuscular Disorders | Localized disorder (e.g., Charcot-Marie-Tooth). Mild-mod pain or weakness. [1.5: pregnancy, h/o polio, Guillain Barre] | Incapacitating pain. Generalized weakness. Compromised swallowing. Signif infiltrative, degenerative or denervating injury* (e.g., multiple sclerosis, ALS, Guillain Barre, Friedrich's ataxia). Sympt myelitis*. Myasthenia gravis requiring daily pyridostigmine. Eaton-Lambert syndrome. | Paralysis requiring ventilatory support. | |
| Myopathy* | Subclinical disorder. Mild regional s/s. Risk factors for, or h/o, malignant hyperthermia.* | Generalized weakness. Systemic s/s: cardiomyopathy, myocarditis, ↓ ventilation, ↓swallowing. Muscular dystrophy. Sympt myotonia, periodic paralysis, myositis | Paralysis requiring ventilatory support. Severe rhabdomyolysis. | |

FIG. 32.18

| Status 2 Features | Status 3 Features | Status 4 Features | Status 5 Features |
|---|---|---|---|
| MULTISYSTEM CONDITIONS | | | |
| α = Systemic/Remote Effects of Malignancies and Their Therapy<br>-- Systemic/Remote Effects of Malignancy: paraneoplastic syndromes, metastases; *spread to 1 or more sites in addition to primary site*<br>-- Systemic/Remote Effects of Malignancy Rx: chemotherapy, radiation, surgery. *Chemotherapy (not just hormonal) w/in 30 days.*<br>β = Systemic/Remote Effects of Immunosuppressive Meds (not for malignancy): steroids, cyclosporine<br>χ = Proliferative Blood/Lymphoid (not leukemia): lymphoma, Hodgkin's, Waldenström's macroglobulinemia, cryoglobulinemia, multiple myeloma<br>ε = Systemic Inflammatory Response (SIRS): Lyme Disease, HIV. *Widespread inflammatory response w/ ≥2 of the following: temp <36 or >38 degrees C, HR >130, RR > 20 breaths/min, or PaCO2 < 32 mmHg, WBC <4000 or >12000 cells/mm³, or >10% immature [band] forms); anion gap acidosis if [(Na + K) – (Cl + HCO3) >16 or if Na – (Cl+HCO3) >12.*<br>= Sepsis: = SIRS w/ positive blood culture or infective source.<br>δ = Autoimmune, Inflammatory, Connective Tissue, and Vascular Disorders:<br>--Granulomatous/ Infiltrative: amyloid, neurofibromatosis, sarcoid, Wegener's<br>--Inflammatory & Autoimmune: rheumatoid arthritis, lupus, ankylosing spondylitis, polymyalgia, myositis, dermatomyositis, Goodpasture's, Reiter's<br>--Vasculitides: polyarteritis, hypersensitivity vasculitis, polyarteritis nodosa, giant cell, Takayasu's arteritis<br>--Connective Tissue: scleroderma, Marfan's<br>--Other Syndromes: CREST, Henoch-Schonlein purpura, Klippel-Feil, serum sickness<br>= Congenital abnormalities<br>ε = Obesity: 31-45 kg/m², 46-60 kg/m² (morbid), >60 kg/m² (supermorbid)<br>φ = Nutrition: malnutrition, anorexia, bulimia; *>10% loss of body weight in the 6 months prior to surgery in absence of weight loss program.*<br>γ = Metabolic syndrome: diabetes or abnormal glucose tolerance, insulin resistance, abdominal obesity, BMI>40kg/m²; ↑□b□g↑LDL/HDL; hypertension<br>η = Recreational Substances: alcohol, cocaine, heroin, marijuana, amphetamines<br>ι = Extremes of age: 2 if <6 months, > 80 yrs; 3 if <40 wks post-conception<br>φ ↓ Activities Daily Living | | | Status 2: present but w/o signif end-organ dysfcn.<br>Status 3-5: signif. system involvement (score in appropriate systems above) |

Legend: ↑ = increased, ↓ = decreased, sympt = symptomatic, asympt = asymptomatic, mod = moderate; LT = life-threatening, signif = significant, s/p = status post, h/o = history of, b/o = because of, BP = blood pressure, HR = heart rate, CP = chest pain, SOB = shortness of breath, s/s = signs and/or symptoms of, fcn = function, dysfcn = dysfunction MRSA = methicillin-resistant strep aureus, VRE = vancomycin-resistant enterococcus * = generates a Risk Indicator letter code on ASPIRIN™ display. Greek letters for Multisystem Conditions serve as identifiers in most embodiments and as delineators of screen jumps in selected embodiments. Items in italics represent wording compatible with a widely used quality assurance tool – the American College of Surgeons National Surgical Quality Improvement Tool (NSQIP) – see text for details.

Notes & Comments:

1. These are representative statements which will undergo refinement before widespread implementation. Some brief statements of features may need to be lengthened so as to include vital information that is provided by other branches of branched-chain logic (e.g., feature categories) depicted in Tables 13-19).

2. Goals of this table are to provide: a) a template for information accrual and scoring; b) a template for importing other data (e.g., from compatible hard-coded information generated by other care givers, questionnaires); c) a means for generating modified ASA scores for the SHAPE™ data base and ASPIRIN™ display

| Row□# of Condition or Alternative entry & Date/Time stamp | Condition or Alternative Entry (hard-coded and/or text) | More Information Text,Consult,Labs) | Prefix— "From: ….□### " (Row #s of causes & inputs) | "Rx □0-5" Med, Dev, Surg, Proc, Other | Activity Status (0-5; P,R,C) | Chronic Signs&Sympts (0-5,↑↓±) | Chronic Composite (0-5,↑↓±) | Acute Signs&Sympts (0-5,↑↓±) | Acute Composite (0-5,↑↓±) | Physiologic Impact (0-5,↑↓±) | Suffix: (To: "…□#" (Row #s of sites receiving Outputs) | Date of Condition Onset | Worst Signs & Sympts (≤5) | Worst Signs & Sympts (date) | Worst Composite (≤5) | Worst Composite (date) | Potential Specific Risk Scores |
|---|---|---|---|---|---|---|---|---|---|---|---|---|---|---|---|---|---|
| Provider Code (scaled ranking) | | | | | | | | | | | | | | | | | |
| Automatic | Typical Entry in ROS | | Prepopulate from prior entries (user decides whether to modify) | | | | | | | | | User provides initial entry, updates automatically | | | | | |

FIG. 39

1st row: headers for columns on SHICT List. Shaded areas for Chronic and Acute scores indicate that typically only one set of scores (Chronic OR Acute) will be entered. 2nd row summarizes how data will be entered for given row, and thereby delineates the extent of autopopulation and prepopulation (which minimize the need for user input). User has the option to skip, review w/o change, edit or add information. Distinguishing between scaled values and condition codes and other alphanumerics can be facilitated by differing letters and symbols and number of digits as well as by font size, shading, etc. In a preferred embodiment, there is a progression in font size of numeric and alphanumeric entries from "Row □###, " " to "Rx □0-5," to "Activity Status #□" to Chronic and Acute Severity Scores and Physiologic Scores (0-5,↑↓±)

METHOD AND SYSTEM FOR ASSESSING, QUANTIFYING, CODING AND COMMUNIICATING PATIENT'S HEALTH AND PERIOPERATIVE RISK

CROSS REFERENCE TO RELATED APPLICATIONS

This application is a continuation-in-part of U.S. patent application Ser. No. 13/459,836, entitled "Method and System for Assessing, Quantifying, Coding & Communicating A Patient's Health and Perioperative Risk", filed Apr. 30, 2012, which is currently pending, This application is a continuation-in-part of U.S. patent application Ser. No. 11/705,612, entitled "Method and System for Assessing, Quantifying, Coding & Communicating A Patient's Health and Perioperative Risk", filed Feb. 13, 2007, which is now U.S. Pat. No. 8,170,888, which claims the benefit of U.S. Provisional Patent Application Ser. No. 60/772,559, entitled "Method and System for Assessing & Communicating Perioperative Risk", filed Feb. 13, 2006, and U.S. Provisional Patent Application Ser. No. 60/839,112 entitled "Method and System for Assessing, Quantifying & Communicating A Patient's Perioperative Health and Perioperative Risk", filed Aug. 22, 2006, and U.S. patent application Ser. No. 13/459, 836, entitled "Method and System for Assessing, Quantifying, Coding & Communicating A Patient's Health and Perioperative Risk", filed Apr. 30, 2012, which is currently pending, claims the benefit of U.S. Provisional Patent Application Ser. No. 61/529,636, entitled "ASA Scores", filed Aug. 31, 2011.

BACKGROUND OF THE INVENTION

1. Field of the Invention

The invention relates to a method and system for integrated assessment, coding and scoring of overall health and, more specifically, at times when communication and decision-making are particularly crucial such as in the assessment of perioperative risk.

2. Description of the Related Art

The complex physiological demands wrought by anesthesia and surgery may have a significant impact on a patient's pre-existing medical conditions, necessitating a vital role for anesthesiologists as perioperative, as well as intraoperative, physicians. While the medical imperative for this role is substantial, the health system framework required for its optimal execution is comparatively weak. The financially driven migration of inpatient surgeries to day-of-surgery admissions and outpatient procedures has virtually eliminated face-to-face conversations among clinicians at the patient's bedside on the evening prior to surgery. Moreover, the anesthesiologist caring for the patient no longer is assured access to the patient (or detailed information about the patient) prior to the day of surgery. In some centers, this lack of communication has led to establishment of pre-admission centers that integrate assessments by the anesthesiologist, surgeon, long-term care provider, and consultant. However, in many cases, the multifaceted process of preoperative assessment and preparation has become the primary responsibility of either a primary care physician without first-hand knowledge of the operative plan or of an anesthesiologist or surgeon with limited knowledge of the patient's long-term care.

Furthermore, for those institutions where preanesthesia evaluation clinics exist, they are frequently staffed by non-anesthesiologists or an anesthesiologist who will not be in charge of the patient's intraoperative care. In the absence of a well-developed information network, this opens the substantial risk of important clinical data being lost or misinterpreted within a series of information transfers. In addition, the presence of multiple care providers (for example, surgeon, anesthesiologist, internist, consultants) in the face of imprecise role definitions all too frequently results in errors of omission due to unreliable communication. The present invention was prompted to fill the void (that is, loss of the "bedside" encounter) imposed by day of surgery admissions with an even more effective, universally applicable mechanisms of assessment and communication.

These problems have been exacerbated by health care provider-electronic health record (HCP-EHR) incompatibilities and associated inefficiencies. These are attributable, in part, to health care provider's predilection for word strings and flexibility vs. electronic health record (and database) aversion for free text and lack of structure, compounded by vendor maintenance of proprietary software and lack of a universal language for electronic health record interoperability. Proclaimed consequences include an "electronic Tower of Babel" (Kush R D, Helton E, Rockhold F W, Hardison C D: Electronic Health Records, Medical Research, and the Tower of Babel. N Engl J Med 2008; 358(16):1738-1740 Apr. 17, 2008) and information hidden in "a vast sea of data," (Wang C J, Huang A T: Integrating Technology Into Health Care: What Will It Take? JAMA 2012; 307(6):569-570. doi:10.1001/jama.2012.102) amounting to an "EHR trap" (Mandl K D, Kohane I S: Escaping the EHR trap—the future of health IT. N Engl J Med 2012; 366(24):2240-2242 Jun. 14, 2012) and the conclusion that "health IT is on the wrong track." (Yasnoff W A, Sweeney L, Shortliffe E H. Putting health IT on the path to success. JAMA. 2013 Mar. 13; 309(10):989-90. doi: 10.1001/jama.2013.1474. PMID: 23483170) There is a plethora of manuscripts relating the limitations of electronic health records, with many encouraging change; however, there is a paucity of articles delineating interoperable health care provider-friendly and health care provider-meaningful ways to achieve said change. The vast majority of what euphemistically have been referred to as reforms have been generated by vendors converting electronic billing systems to enable clinical documentation that facilitates said billing and complies with regulatory requirements. Proclaimed needs for interoperable, simplified abstraction of a medical record with well-structured normalized data elements (Mandl K D, Mandel J C, Murphy S N, Bernstam E V, Ramnoi R L, Kreda D A, McCoy J M, Adida B, Kohane I S: The SMART Platform: early experience enabling substitutable applications for electronic health records. J Am Med Inform Assoc 2012 July-August; 19(4):597-603. doi: 10.1136/amiajnl-2011-000622) and facilitated capture and communication of medical reasoning (Cimino J J. Improving the electronic health record—are clinicians getting what they wished for? JAMA. 2013 Mar. 13; 309(10):991-2. doi: 10.1001/jama.2013.890) remain unfulfilled.

The impact encompasses the gamut from daily care to quality metrics, data registries, evidence-based medicine, and cost-effectiveness research. The encumbrances on anesthesiologists may be magnified as anesthesiologists assume increased roles as perioperative physicians, most notably as anchoring physicians in perioperative surgical homes, where anesthesiologists may need to access myriad records originating from multiple non-interoperable programs while being involved in 10 or more transfers of information and care among anesthesiology-based preadmission, intraoperative, intensive care and pain teams, as well as with surgeons, primary care providers, specialists, hospitalists, perioperative nursing, paraprofessionals and patients (and, ultimately, regulatory forms and data registries) before, during and after surgery.

One may have expected that many of the frustrations would have been obviated by the common listing of a patient's medical conditions, referred to as the problem list. However, this simply is a listing; and "the failure to effectively integrate the creation, updating, reorganization, and inactivation of items on the problem list into the clinician's workflow has been one of the great failures of clinical informatics" (Schiff G D, Bates D W: Can Electronic Clinical Documentation Help Prevent Diagnostic Errors? N Engl J Med 2010; 362(12):1066-106, Mar. 25, 2010). Despite being defined by the U.S. Center for Medicare and Medicaid Services (CMS) as "a list of current and active diagnoses as well as past diagnoses relevant to the current care of the patient" (Centers for Medicare & Medicaid Services (CMS), HHS. Medicare and Medicaid programs; electronic health record incentive program. Final rule. Fed Regist. 2010 Jul. 28; 75(144):44313-588. PMID: 20677415 Available at http://www.gpoaccess.gov/fr/, CMS.hhs.gov), the problem list falls far short of objectives such as those put forth in Table 1, succumbing to the extremes of entry irrelevance and redundancy vs. vagueness and omission, overlapping with other comparably hampered listings (e.g., review of systems, past medical history, ICD (International Statistical Classification of Diseases and Related Health Problems) coding), being static with little information as to a condition's activity status (ACT) or severity (SEV), and generally not being interoperable among computer systems. Although recommended by CMS for vitalizing the problem list, universal language (e.g., SNOMED (Systematized Nomenclature of Medicine)) and coding (e.g., ICD) do not eliminate HCP-EHR incompatibilities and inefficiencies, especially when limited to a static listing assigned by post-discharge coders.

TABLE 1

Objectives for Optimal Utilization of a Transformed Problem List (or Alternative Listing)

Static Assessment of Active and Inactive, Local and Systemic Conditions:
1. Activity status (ACT) of the given condition
2. Severity (SEV) at the local level
3. Impact of condition on encompassing bodily system or region (SorR) and on overall physiologic status
4. Presence of relevant therapy Dynamic Comparison Among Serial Assessments:
5. Change in ACT
6. Change in SEV
7. Change in impact on:
   a. Encompassing SorR
   b. Physiology and function
8. Change in relevant therapy.
9. Distinguish between new and preexisting morbidities (prior as well as current activity)

Filtering and Linking of Conditions:
10. Filtering according to ACT or SEV for display and retrieval; triaging and resource allocation
11. Linking among entries to: minimize redundancy; identify impact on, or impact by, other conditions Other Desirable Applications of Data: Clinical, Administrative, Investigative and Interactive
12. Identify adverse events and potential needs for scripts and alerts (e.g., ACT and SEV cutoffs)
13. Provide a foundation handoffs, ICD-10 coding, discharge summaries, wallet card/implantable chip
14. Provide basis for succinct, readily understandable means to facilitate patient-HCP (Health Care Provider) and patient-EHR (Electronic Health Record) interaction TABLE 1-continued Objectives for Optimal Utilization of a Transformed Problem List (or Alternative Listing)

15. Provide basis for:
    a. Cumulative morbidity assessment within patients (e.g., for risk and acuity indices)
    b. Cumulative quality metrics and acuity indexing
    c. Assessment of clinical outcomes, including beneficial and detrimental impacts of an intervention
    d. Integrated assessment of underlying morbidities and anticipated risks (e.g., of upcoming surgery)
16. Interoperability:
    a. Within a given patient's record
    b. Within institutions sharing a common EHR
    c. Among otherwise incompatible EHRs
17. Facilitate multi-institutional integrated data accrual for evidence-based research, comparative quality metrics, cost-effectiveness research, data registries and related "big data" applications:
    a. Propensity matching in multi-center studies.
    b. Capture anticipated as well as unanticipated new condition(s) or changes in existing ones in response to challenges or interventions to benefit evidence-based research

*While not achieved with the present problem list or currently available alternatives, each of these objectives is achieved to varying degrees by the basic and/or expanded template for uniform numericnotation with the universal language (ScaleMED ™) introduced herein.

Ironically, the problem list actually may add to problems. When an ambiguous listing is encountered during preoperative assessment, anesthesiologists often must hurriedly search through "series of often unrelated" (Detsky A S, Berwick D M. Teaching physicians to care amid chaos. JAMA. 2013 Mar. 13; 309(10):987-8. doi: 10.1001/jama.2013.620. PMID: 23483169), "bloated" (Hirschtick R E. A piece of my mind. Copy-and-paste. JAMA. 2006 May 24; 295(20):2335-6. PMID: 16720812) notes (commonly scanned from nonintegrated sources) for information about ACT and SEV, misled by outdated inclusions as well as vital omissions. If an item listed on a problem list is not addressed in the preoperative medical clearance or not apparent in other accessible notes, is the condition unimportant (outdated, negligible impact) or was it overlooked? Compounding anesthesiologists' concern for patient safety, anesthesiologists lament the day when a malpractice attorney, whose team can spend days scouring records, provides the answer for one of our patients. The inadequacies of current documentation were manifest in the detailed review of the electronic health records of 45 patients on the morning 'of same-day surgery; of 171 comorbidities noted, 0% had information as ACT or current SEV on the problem list. (Lubrano M C, Liang I, Silverman D G. Do Preoperative Records Enable Anesthesiologists to Triage and Plan Effectively? ASA 2013). In an unpublished assessment of 120 problem lists during electronic health record conversion at a community hospital, the inventor's team further observed that <10% of listings mentioned ACT or SEV; "asthma," for example, ranged from remote history of childhood asthma in an octogenarian to acute exacerbation requiring intubation.

Many have bemoaned the lack of interoperability among health care records (Mandl K D, Kohane I S: Escaping the EHR trap—the future of health IT. N Engl J Med 2012; 366(24):2240-2242 Jun. 14, 2012; Denham C R, Classen D C, Swenson S J, Henderson M J, Zeltner T, Bates D W. Safe Use of Electronic Health Records and Health Information Technology Systems: Trust But Verify. J Patient Saf 2013; 9:177Y189). In light of the problems imposed by the current electronic health record climate, there have been calls for clinician-engineered electronic health record reform (Schiff G D, Bates D W. Can electronic clinical documentation help prevent diagnostic errors? N Engl J Med. 2010 Mar. 25; 362(12):1066-9. doi: 10.1056/NEJMp0911734), with innovation and collaboration between (and among) vendors and caregivers (Denham C R, Classen D C, Swenson S J, Henderson M J, Zeltner T, Bates D W. Safe Use of Electronic Health Records and Health Information Technology Systems: Trust But Verify. J Patient Saf 2013; 9: 177Y189). However, in our only-the-dominant-survive health record era, it appears too daunting to introduce a new electronic health record program or even to suggest dramatically redesigning proprietary electronic health record "silos" (Mandl K D, Kohane I S: Escaping the EHR trap—the future of health IT. N Engl J Med 2012; 366(24):2240-2242 Jun. 14, 2012) by changing what we herein refer to as their vendor-enveloped, do-not-access ("DNA") core. In order to mitigate potential skirmishes not only with vendors but also administrators, payors and colleagues, clinician-engineered changes must avoid precipitating "IT paradox" (wherein implementation of a new technology often slows progress) (Jones S S, Heaton P S, Rudin R S, Schneider E C: Unraveling the IT Productivity Paradox—Lessons for Health Care. N Engl J Med 2012; 366(24):2243-2245 June 14) or raising angst among those who invested their institution's reserves on what has become its legacy system. Hence, reform must be (and must appear to be) easy to implement, easy to learn and easy to use, while being applicable to varied clinical, investigative and quality assessment scenarios.

In many ways, today's challenges are surprisingly reminiscent of 1941, when the ASA sought to address the variations in assessment and lack of agreement as to definition of terms by empowering a committee "to study, examine, experiment and devise a system for the collection and tabulation of statistical data in anesthesia . . . that would be applicable under any circumstances" (Saklad M: Grading patients for surgical procedures. Anesthesiology 1941; 2:281-4). The wisdom of the 1941 objectives and resultant ASA physical status score remain apparent today, enhanced by appreciation that electronic amassing of data prompts consideration of "standardized specialty-wide assessment tools" that ensure that "we are collecting the same data elements," (Tremper K K. Anesthesia information systems: developing the physiologic phenotype database. [Comment. Editorial] Anesth Analg 101(3):620-621, 2005 September) avoiding the impact of differences in surveillance strategy and definition of outcomes (Charlson M E. Ales K L. Simon R. MacKenzie C R. Why predictive indexes perform less well in validation studies. Is it magic or methods? Archives of Internal Medicine 147(12):2155-2161, 1987 December). The introduction of perioperative surgical homes introduces a new objective for the specialty of anesthesia—that the elements incorporate morbidities and factors beyond those primarily relevant to intraoperative management and that said elements be readily monitored repeatedly within and beyond the perioperative surgical homes.

It has been suggested that perioperative risk be interpreted as being influenced by two major components: the patient's physical status and the planned surgical invasiveness. Lema M J, *Using the ASA Physical Status classification may be a risky business, ASA Newsletter* 2002; 66(9).

As mentioned above, in the early 1940s, the American Society of Anesthesiologists (ASA) had the wisdom to design a simple 1 to 5 score that would enable anesthesiologists to communicate the severity of a patient's illness among themselves and with physicians in other specialties. This resulted in what is currently known as the ASA Physical Status (PS) Classification System. One of the stated purposes of the endeavor was to develop a means by which to develop statistical data about anesthetic outcomes by controlling for differences in a patient's underlying medical conditions (Saklad M., *Grading of patients for surgical procedures, Anesthesiology* 1941 May:281-284). Sixty years later—with only minor revisions despite major advances in anesthesia, surgical and medical care—the ASA PS system remains the most widely used patient classification scheme in anesthesiology.

While its simplicity is one of its strengths, it is also one of its limitations. The ASA PS score does not distinguish between disorders of different systems or the nature of different disorders within the same system. Rather, it provides a single number to represent the systemic severity of the patient's overall medical condition. Hence, a given score does not guide preparation for a patient with asthma vs. renal disease vs. cardiac disease vs. metastatic malignancy. Moreover, it does not delineate or cumulate risk based upon multiple disorders. This has prompted the inventor to hypothesize that, with respect to the ASA score, the whole is less than the sum of its parts. In a recent assessment of 220 patients that underwent preoperative assessment under my supervision at a tertiary care medical center and received an ASA physical status score of 3 (significant systemic condition), or 4 (life-threatening systemic condition):

the distribution among bodily systems was not uniform, with 55.7% having what the inventive system described herein would rate as a ≥3 (on a 1-5 scale) cardiac disorder;

30.4% of patients had two systems affected by significant dysfunction, 14.1% had three systems, and 2.1% had four systems.

Other methods of classifying patients with respect to physical condition have been developed, but these have tended to focus on discrete subpopulations. Several authorities have developed systems for stratifying perioperative cardiovascular morbidity and mortality. Palda V A. Detsky A S, *Perioperative assessment and management of risk from coronay artery disease*, [Review, Tutorial] Annals of Internal Medicine, 127(4):313-28, 1997 Aug. 15. Detsky A S, Abrams H B, Forbath N, Scott J G, Hilliard J R, *Cardiac assessment for patients undergoing noncardiac surgery. A multifactorial clinical risk index*, Arch Intern Med 1986; 146(11):2131-4. These systems typically emphasize cardiovascular evaluation to the exclusion of other disease processes. In the critical care literature, the development of risk stratification indices also has been popular. However, these systems, which include the Charlson Comorbidity index, Mortality Probability Model and APACHE score, focus on disorders with high morbidity and mortality that do not necessarily pose as high a risk as other conditions in the acute perioperative period. For example, the Charlson index provides scores of 1 and 6 for prior myocardial infarction (a finding that significantly increases the risk of an adverse cardiac event in the perioperative) and metastatic malignancy, respectively Scales D C, Laupacis A, Pronovost P J, *A systematic review of the Charlson comorbidity index using Canadian administrative databases: a perspective on risk adjustment in critical care research*, Journal of Critical Care 2005; 20(1):12-19. (As will be shown later, the indices have little in common with the major components of the present invention.

Scoring systems have also been described for specific disorders. For example, the Seventh Report of the Joint National Committee on Prevention, Detection, Evaluation, and Treatment of High Blood Pressure classifies three stages of hypertension: prehypertension (systolic 120-139 mmHg, diastolic 80-89 mmHg), Stage 1 (systolic 140-159 mmHg, diastolic 90-99 mmHg), and Stage 2 (systolic>160 mmHg, diastolic>100 mmHg) in light of the direct relationship between elevated blood pressure and risk of morbidity. Similarly, the New York Heart Association defines four classes of heart failure based on degree of physical limitation—from no limitation (Class I) to incapacitation (Class IV). Examples exist for noncardiac disorders as well. For example, the Child-Pugh score provides a means to grade the severity of liver disease based on clinical symptoms and laboratory data; and five stages of renal dysfunction have been delineated by the National Kidney Foundation based on glomerular filtration rate. Other rating systems integrate signs and symptoms to generate qualitative gradations by which the severity of the condition and the adequacy of therapeutic management are judged. For example, diabetes control is evaluated based on glycosylated hemoglobin, insulin requirements, blood glucose readings before and after meals, tendency for harmful extremes, and end-organ injury. Scoring of asthma severity is based on frequency and severity of symptoms and inhaler use.

Relative to these systems, the assignment of ASA PS is significantly more subjective. For this reason, it is not surprising that numerous studies have demonstrated significant inter-rater variability in scoring, leading some to doubt the ASA PS's clinical utility particularly when used as a communication tool among practitioners. Aronson W L, McAuliffe M S, Miller K, *Variability in the American Society of Anesthesiologists Physical Status Classification Scale*, AANA J 2003; 71(4):265-274; Mak P H, Campbell R C, Irwin M G, *American Society of Anesthesiologists. The ASA Physical Status Classification: inter-observer consistency*, American Society of Anesthesiologists. Anaesth Intensive Care 2002; 30(5):633-40; Owens W D, Felts J A, Spitznagel E L, Jr., *ASA physical status classifications: a study of consistency of ratings*, Anesthesiology 1978; 49(4): 239-43; Ranta S, Hynynen M, Tammisto T, *A survey of the ASA physical status classification: significant variation in allocation among Finnish anaesthesiologists*, Acta Anaesthesiol Scand 1997; 41(5):629-32. Nonetheless, there are several reasons why, despite its shortcomings, the ASA PS system has endured. First, it can be determined based on information obtained from a history and physical examination without the need for additional data. Second, its five-point scoring system is intuitive and easy to remember. In addition, unlike other illness severity scoring tools, the ASA PS was designed to be applied to patients of all ages, medical conditions, and degrees of health.

The ASA PS was intended to reflect the condition of an individual irrespective of the planned surgical procedure. However, without knowing the degree of surgical invasiveness planned, the ability to assess perioperative risk is limited. Hence, the need for a system by which to classify surgical severity was recognized; and several surgical risk scoring systems have been proposed. Brooks M J, Sutton R, Sarin S, *Comparison of Surgical Risk Score, POSSUM and p-POSSUM in higher-risk surgical patients*, Br J Surg 2005; 92(10):1288-92; Pasternak L R, *Preoperative evaluation, testing, and planning*, Anesthesiol Clin North America 2004; 22(1):xiii-xiv; Pasternak L R, *Preanesthesia evaluation of the surgical patient*, Clinical Anesthesia Updates 1995; 6(2):1-12; Eagle K A, Berger P B, Calkins H, et al, *ACC/AHA guideline update on perioperative cardiovascular evaluation for noncardiac surgey: a report of the American College of Cardiology* 1 *American Heart Association Task Force on Practice Guidelines* (Committee to Update the 1996 Guidelines on Perioperative Cardiovascular Evaluation for Noncardiac Surgery). 2002.}. The American College of Cardiology/American Heart Association (ACC/AHA) has divided surgeries into low-, intermediate- and high-risk in its guidelines for preoperative evaluation of patients with coronary artery disease. Eagle K A, Berger P B, Calkins H, et al, *ACC/AHA guideline update on perioperative cardiovascular evaluation for noncardiac surgery: a report of the American College of Cardiology/American Heart Association Task Force on Practice Guidelines* (Committee to Update the 1996 Guidelines on Perioperative Cardiovascular Evaluation for Noncardiac Surgery), 2002. Pasternak and colleagues proposed the Johns Hopkins Risk Classification System. Pasternak L R, *Preoperative evaluation, testing and planning*, Anesthesiol Clin North America 2004; 22(1):xiii-xiv; Pasternak L R, *Preanesthesia evaluation of the surgical patient*, Clinical Anesthesia Updates 1995; 6(2):1-12. The John Hopkins Risk Classification System employs a five-level classification based on location and extent of surgery, anticipated blood loss and fluid shift, postoperative anatomic and physiological alterations and the need for postoperative intensive care monitoring. Of note, the 3-tiered ACC/AHA and 5-tiered Pasternak rankings are not interchangeable.

The importance of having a means by which to assess surgical risk as well as preoperative patient evaluation is now well appreciated. In a retrospective study in Great Britain, Fowkes et al. found surgical condition to be the most often cited cause of perioperative death, followed by the severity of the patient's underlying medical condition. ("Anesthesia" was the third most common factor to be implicated). Fowkes F G, Lunn J N, Farrow S C, Robertson I B, Samuel P, *Epidemiology in anaesthesia. III: Mortality risk in patients with coexisting physical disease*, Br J Anaesth 1982; 54(8):819-825. More recently, the ASA Task Force on Preanesthesia Evaluation made this point clear when advising evaluation by an anesthesiologist prior to the day of surgery not only for ASA 3 or 4 patients but also for relatively healthier ASA 1 or 2 patients undergoing highly invasive, high-risk surgical procedures. American Society of Anesthesiologists Task Force on Preanesthesia Evaluation, *Practice advisory for preanesthesia evaluation: a report by the American Society of Anesthesiologists Task Force on Preanesthesia Evaluation*, Anesthesiology 2002; 96(2):485-96. Data obtained under my direction at a tertiary care center documented the effects of the ASA PS score and surgical risk/invasiveness on hospital length of stay (FIG. 1).

The relative weighting of variables and the specific formula to predict outcomes can be generated by multivariate logistic regression and other forms of analysis as well as empirical observation. For example, based on the derivation data set of the aforementioned study, the weighted influence of the ASA physical status score and the surgical invasiveness score is shown by the following regression equation generated from the data:

$$\text{Hospital Charges(\$)} = e^{[7.6+0.35(ASA)+0.56(SOCU)-0.55(ASA)(SOCU)]}$$

While, to a certain extent, the combination of ASA PS and degree of surgical invasiveness would suggest the degree of anesthetic risk, there are other factors that impact on anesthetic complexity and perioperative morbidity and mortality. If identified prior to the day of surgery, they likely would be amenable to risk management interventions. The literature is replete with recommendations as to how to characterize, plan for and manage what may be termed "non-ASA PS score, non-surgical invasiveness" factors that affect anesthetic complexity and potentially impact of patient morbidity. However, to the best of my knowledge, until the development of the present invention a system for incorporating these factors in a communicable score was lacking—hence, vital information may not be readily transmitted to the operating room schedulers and intraoperative caregivers and to databases for quality assurance, outcome, financial, resource allocation, and investigative analysis.

Complications of airway management are the most common cause of anesthetic-related catastrophes. Lee L A, Domino K B, *The Closed Claims Project. Has it influenced anesthetic practice and outcome*?, Anesthesiol Clin North America 2002; 20(3):485-501; Cheney F W, *The American Society of Anesthesiologists Closed Claims Project: what have we learned, how has it affected practice, and how will it affect practice in the future?*, Anesthesiology 1999; 91(2): 552-6; Caplan R A, Posner K L, Ward R J, Cheney F W, *Adverse respiratory events in anesthesia: a closed claims analysis*, Anesthesiology 1990; 72(5):828-33. For this reason, identification of the potentially difficult airway has been an ongoing clinical endeavor. The Mallampati score of oropharyngeal view has provided some uniformity to prediction of endotracheal intubation difficulty, but is woefully incomplete. Mallampati S R, *Clinical sign to predict difficult tracheal intubation (hypothesis)*, Can Anaesth Soc J. 1983; 30(3 Pt 1):316-317; Mallampati S R, Gatt S P, Gugino L D, et al, *A clinical sign to predict difficult tracheal intubation: a prospective study*, Can Anaesth Soc J. 1985; 32(4):429-434; Needham D M. Bellhouse C P, Dore C, *Predicting difficult intubation*, Br J Anaesth 1989; 62(4)469; Combes X, Le Roux B, Suen P, et al, *Unanticipated difficult airway in anesthetked patients: prospective validation of a management algorithm*, Anesthesiology 2004; 100(5):1146-50; el-Ganzouri A R, McCarthy R J, Tuman K J, Tanck E N, Ivankovich A D, *Preoperative airway assessment: predictive value of a multivariate risk index*, Anesth Analg, 1996; 82(6):1197-1204; Ovassapian A, Glassenberg R, Randel G I, Klock A, Mesnick P S, Klafta J M, *The unexpected difficult airway and lingual tonsil hyperplasia: a case series and a review of the literature*, Anesthesiology 2002; 97(1):124-32; Yamamoto K, Tsubokawa T, Shibata K, Ohmura S, Nitta S, Kobayashi T, *Predicting difficult intubation with indirect laryngoscopy*, Anesthesiology 1997; 86(2):316-321. Furthermore, it does not address other aspects of airway management, most notably potential difficulties associated with ventilation (e.g., via a face mask) and risk of aspiration or precipitous desaturation.

In addition to the airway, issues potentially critical to anesthesia management that should be communicated include conditions such as prior halothane hepatitis or porphyria (a disorder of blood cell enzymes); communication problems; emergency surgery; presence of an AICD (automatic intra-cardiac defibrillator); latex allergy; risk of malignant hyperthermia; morbid obesity; pregnancy; and potential for signs and symptoms of acute withdrawal. Of these, the only one that is communicated as part of the ASA score is emergency surgery, which is designated with an "E" after the numeric score to indicate that there may not be time to optimize the patient's condition preoperatively (a factor that results in a higher level of reimbursement).

It should be noted that, with current practices at a major medical center (without the information provided by the present invention), anesthesiologists reported that they either overestimated or underestimated subsequent case complexity based upon the information available on the operating room schedule in approximately 25% of cases (data obtained by my research team presented at the American Society of Anesthesiologists annual meeting in October 2006 after initial filing of this disclosure).

The need for the present invention and its potential in the perioperative period as well as for consistency, integration, communication, quality and efficiency of overall medical care is evident by the multiple urgings for change summarized in Table 2.

TABLE 2

Recent Statements That Suggest The Need for a Program Such As That Described Herein Bramhall J. The role of nurses in preoperative assessment. Nursing Times 98(40): 34-5, 2002 Oct. 1-8. When patients elect to have surgery, it is vital that they are assessed systematically in the preoperative period.
Maccioli G A: Of digital cameras and ATMs. ASCCA Interchange Newsletter 13(3): 2, 2001. How is it that medicine, a profession so critically dependent on information, is so utterly Balkanized when it comes to data?
Brown M G: Grant will allow doctors to share patient information. Connecticut Post Online. "Our current health care system still relies too much on pen-and-paper record-keeping prescribing. It is a system that vastly increases the risk of preventable errors that jeopardize our health, lessen the quality of the care we receive and increase cost," Gov. M. Jodi Rell said. "The burden will no longer be on the patient to communicate everything that is relevant about their medical condition.
Horwitz L I, Krumholz H M, Green M L, Huot S J. Transfers of patient care between house staff on internal medicine wards. A national survey. Arch Intern Med 2006; 166: 1173-1177. Transfers of care are events that are particularly susceptible to communication failure, as important information may be "lost in transition" between physicians. This is a critical issue for patient safety because communication failure is one of the most common root causes of medical error. The Joint Commission on Accreditation of Healthcare Organizations has made "a standardized approach to 'hand off' communications" one of its new National Patient Safety Goals for 2006.
MSNBC: Hospitals move toward 'paperless' age. More health-care providers switch to electronic ecords. http://www.msnbc.msn.com/id/5592501. According to a recent analysis by the Institute of Medicine, the routine use of electronic records could help reduce the tens of thousands of deaths and injuries caused by medical mistakes every year. "As patients begin to recognize that hospitals are largely in the dark ages, they will begin to demand that they get the best care possible, which is in part dependent on hospitals using electronic records," she said.
Tremper K K. Anesthesia information systems: developing the physiologic phenotype database. Anesth Analg 101(3): 620-621, 2005. As the vendors of anesthesia information systems accelerate their implementation in hospitals throughout the country, it begs the question: is it time for our specialty to develop a standardized preoperative assessment, TABLE 2-continued Recent Statements That Suggest The Need for a Program Such As That Described Herein intraoperative record, and postoperative visit? If we hope to pool our data on a large scale, it is important that we are collecting the same data elements.
Charlson M E. Ales K L. Simon R. MacKenzie C R. Why predictive indexes perform less well in validation studies. Is it magic or methods? Archives of Internal Medicine 147(12): 2155-61, 1987. Important discrepancies in performance of prognostic indexes may arise from differences in surveillance strategies and definitions of outcome.
Jollis J G. Ancukiewicz M. DeLong E R. Pryor D B. Muhlbaier L H. Mark D B. Discordance of databases designed for claims payment versus clinical information systems. Implications for outcomes research. Annals of Internal Medicine 119(8): 844-850, 1993. Claims data failed to identify more than one half of the patients with prognostically important conditions, including mitral insufficiency, congestive heart failure, peripheral vascular disease, old myocardial infarction, hyperlipidemia, cerebrovascular disease, tobacco use, angina, and unstable angina . . .
Chin T: Avoiding EMR meltdown: How to get your money's worth. There are no empirical data or surveys measuring how many de-installs occur annually, but people in the industry estimate that 20% to 33% of EMRs fail within a year of their implementation because physicians are unhappy with the systems.
Fink A S. Campbell D A Jr. Mentzer R M Jr. Henderson W G. Daley J. Bannister J. Hur K. Khuri S F. The National Surgical Quality Improvement Program in non-veterans administration hospitals: initial demonstration of feasibility. Annals of Surgery 236(3): 344-353; discussion 353-354, 2002. . . . one of the hurdles we faced in this effort was that even in these three different non-VA centers, we encountered very disparate IT systems. Ultimately we will need to develop some kind of mechanism to either circumvent these differences or to create some kind of common IT electronics interface that will facilitate data transmission.
Ledger M: Prescription: Better information technology for better health. Penn Medicine 2005, fall, 7-12. 22 kinds of mistakes which they divided into two groups: information errors generated by fragmentation of data and failure to integrate the hospital's several computer and information systems; and flaws in the interface between humans and machines.
Atherly A. Fink A S. Campbell D C. Mentzer R M Jr. Henderson W. Khuri S. Culler S D. Evaluating alternative risk-adjustment strategies for surgery. [evaluation studies] American Journal of Surgery 188(5): 566-570, 2004 November. "different risk-adjustment methodologies afford divergent estimates of mortality risk."

The problem (which is not limited to the perioperative period) is that the disparate nature of terminology, classification, coding and scoring has been allowed to metastasize, with disparate systems for clinical evaluation, special testing, decision making, communication, resource allocation, quality assurance and research applications. To date, problems in these areas have been addressed with band aids or by trying to adapt programs designed to solve a different problem.

This invention cures these problems treats the underlying "illness" by introducing a new mechanism for data entry, coding and scoring and a mechanism to enable universality among clinical, communicative, administrative and investigative components. The seamless integration of data is enabled with little or no added burden to the clinician in that main impact of the invention is on the information after it has been accrued by the patient's healthcare providers.

Limitations of Other Coding Systems:

The most widely used means for coding medical conditions is the 9$^{th}$ revision of the International Classification of Diseases (ICD, with latest version at time of this submission being ICD-9) system, as detailed in *ICD-9-CM for Physicians*. (Ingenix, Inc. 2006) codes valid Oct. 1, 2005 through Sep. 30, 2006). As noted in that text, "coding today is used to describe the medical necessity of a procedure which then facilitates payment of health services, to evaluate utilization patterns and to study the appropriateness of health care costs." As noted on p 1 of that text, ICD-9 coding is a complex process: "A joint effort between the healthcare provider and the coder is essential to achieve complete and accurate documentation, code assignment and reporting of diagnoses and procedures . . . . The entire record should be reviewed to determine the specific reason for the encounter and the conditions treated."

The following "10 STEPS TO CORRECT CODING" cited by Ingenix's 2006 version of *ICD-9-CM for Physicians* illustrates the complexity of the ICD system, which is far greater than that of the inventive system. That text states:

Step 1: Identify the reason for the visit (e.g., sign, symptoms, diagnosis, condition to be coded).

Step 2: Always consult the Alphabetic Index, Volume 2, before turning to the Tabular List.

The most critical rule is to begin a code search in the index. Never turn first to the Tabular List (Volume 1), as this will lead to coding errors and less specificity in code assignments. To prevent coding errors, use both the Alphabetic Index and the Tabular List when locating and assigned a score.

Step 3: Locate the main entry term.

Step 4: Read and interpret any notes listed with the main term.

Step 5: Review entries for modifiers

Step 6: Interpret abbreviations, cross-references, symbols and brackets. Cross references used are 'see,' 'see category' or 'see also.' The abbreviation NEC may follow main terms or subterms. NEC (not elsewhere classified) indicates that there is no specific code for the condition even the medical documentation may be very specific. The √ box indicates the code requires an additional digit. If the appropriate digits are not found in the index, in a box beneath the main term, you MUST refer to the Tabular list. Italic brackets [ ] are used to enclose a second code number that must be used with the code immediately preceding it and in that sequence.

Step 7: Choose a tentative code and locate it in the Tabular List. Be guided by any inclusion or exclusions terms, notes or other instructions such as 'code first' and 'use additional code,' that would direct the use of a different or additional code from that selected in the index for a particular diagnosis, condition, or disease.

Step 8: Determine whether the code is at the highest level of specificity. Assign three-digit codes (category codes) if there are no four-digit codes within the code category. Assign four-digit codes (subcategory codes) if there are no five-digit codes for that category. Assign five-digit codes (fifth-digit subclassification codes) for those categories where they are available.

Step 9: Consult the color coding and reimbursement prompts, including the age, sex and Medicare as secondary payer edits. Consult the official ICD-9-CM guidelines for coding and reporting, and refer to the AHA's (American Hospital Association) Coding Clinic for ICD-9-CM for coding guidelines governing the use of specific codes.

Step 10: Assign the code."

For many conditions, one needs to refer to a special section titled "Signs, Symptoms and Ill-defined Conditions" of the ICD-9 code to locate signs and symptoms. As stated on page 13 of the Ingenix text: 'In addition to the etiology/manifestation convention that requires two codes to fully describe a single condition that affects multiple body systems, there are other single conditions that also require more than one code."

The widely used CPT (Current Procedural Terminology) code provides a 5-digit code for procedures. These are grouped as "Evaluation and Management, Anesthesiology, Surgery, Radiology, Pathology and Laboratory, Medicine. CPT codes, an established means for designating specific procedures, also have significant shortcomings. As is the case for ICD codes, the CPT coding system lacks the score-based coding that typifies the inventive system. It focuses on procedures rather than diagnoses; and, for many of its codes, CPT coding ignores severity of the precipitating patient illness, the potential multi-system effects of surgery (which, as shown in FIG. 11, may be greater on a system other than that with the underlying surgical pathology—e.g., RESP after an large abdominal incision) and the nature and severity of comorbidities (problems not directly related to the planned procedure but which may impact significantly on the patient's ability to withstand the demands of a procedure such as invasive surgery or the need for/effectiveness of additional diagnosis and therapy.

The lack of a uniform language and code is evident at a major institution. The operating room scheduling system captures the CPT code and anesthesiologists bill according to Relative Value Units, which are based upon CPT codes; but many surgical offices use the ICD-9 disease code, the NSQIP quality assurance program uses specified text entries (or their equivalent), government-mandated Surgical Care Improvement Program (SCIP) measures rely upon ICD-9 codes, and hospital billing has relied upon ICD-9 procedure codes (and a system for crosswalk to establish compatible codes). Each coding system has its coding specialists.

With the foregoing in mind, an improved method and system for perioperative evaluation and communication is required that overcomes the limitations of the prior art, including:

lack of a coding and scoring system that provides consistent, suitably detailed, integrated and readily communicable information about multiple aspects of a patient's medical condition, upcoming challenges (e.g., surgery) and related factors; and lack of a uniform language, coding system and scoring system for data storage, multiple displays and reports, importing (from other sources), exporting (to multiple diagnostic and treatment algorithms), administrative purposes (quality assurance, resource allocation, and billing) and specific evidence-based research applications.

The present invention provides such a system and method for assessment, quantification and communication and then details a preferred embodiment and adaptations thereof. While the embodiments detailed herein focus primarily on integrated preoperative assessment, it is within the spirit and scope of this invention to focus on and adapt individual components for assessment in other contexts such as long-term care and management in other acute (e.g., emergency, battlefield, or intensive care) settings as well as for triaging and transferring care among healthcare providers in those contexts. Likewise, a patient may followed at standard intervals during long-term care, with additional assessments as deemed indicated, and with more frequent serial assessments during acute challenges or initiations of new therapies. As detailed later in this disclosure, score-driven communication not only would be of great value for perioperative healthcare providers but at virtually every exchange of information among healthcare providers and between healthcare providers and their patients. Further, the present invention aggressively addresses the electronic health record challenge, putting forth objectives (Table 1) for focused electronic health record reform and proposing components to meet these objectives.

SUMMARY OF THE INVENTION

It is, therefore, an object of the present invention to provide a multi-dimensional system for assessing, coding, quantifying, displaying, integrating and communicating information relating to patient health and perioperative risk. The system includes a mechanism for inputting patient information and providing an output relating to the patient health and perioperative risk. The output includes a score for the physical condition of the patient, a score for the degree of expected surgical risk and invasiveness, a score for other vital assessments of perioperative complexity, and alphanumeric codes for other factors that may require special preoperative preparation and planning.

It is also an object of the present invention to provide a method for providing an integrative mechanism of quantitative assessment and communication. The method includes inputting patient information, processing the patient information and providing an output relating to patient health and perioperative risk. The output includes a score for the physical condition of the patient, a score for the degree of expected surgical risk and invasiveness, a score for other vital assessments of perioperative complexity and alphanumeric codes for other factors that may require special preoperative preparation and planning.

Other objects and advantages of the present invention will become apparent from the following detailed description when viewed in conjunction with the accompanying drawings, which set forth certain embodiments of the invention.

BRIEF DESCRIPTION OF THE DRAWINGS

A list of Abbreviations, Acronyms and Terms used throughout the body of the present disclosure is found at the end of the present disclosure. The use of these is believed to assist in the presentation of the present invention through the use of various terms which are fully defined in accordance with the invention.

FIG. 3A provides an overview of inputs into the database and of inventive outputs, score-driven communications, exports, general applications and integration of coding and scoring with outside databases.

FIG. 4, which is composed of FIGS. 4A and 4B, shows portions of a representative preoperative caregiver note which illustrates one of several potential embodiments for inventive components including: inventive scores for individual body systems (SISS™); inventive overall surgical risk/invasiveness score (SOCU™); inventive system-specific surgical risk/invasiveness scores (SICU™); and inventive score-driven co-population of summaries and score-driven export for communication (ASPIRIN™ display, inventive transfer of care printout or electronic record, inventive wallet card to patient) and/or inventive diagnostic/treatment algorithms as detailed throughout this disclosure (Comments in italics would not be included in an actual note).

FIG. 6, which is composed of FIGS. 6A and 6B, shows how the items for co-population at the end of the note in FIG. 4 contribute to the information provided by and accessible from the ASPIRIN™ display wherein:

Figure 1:
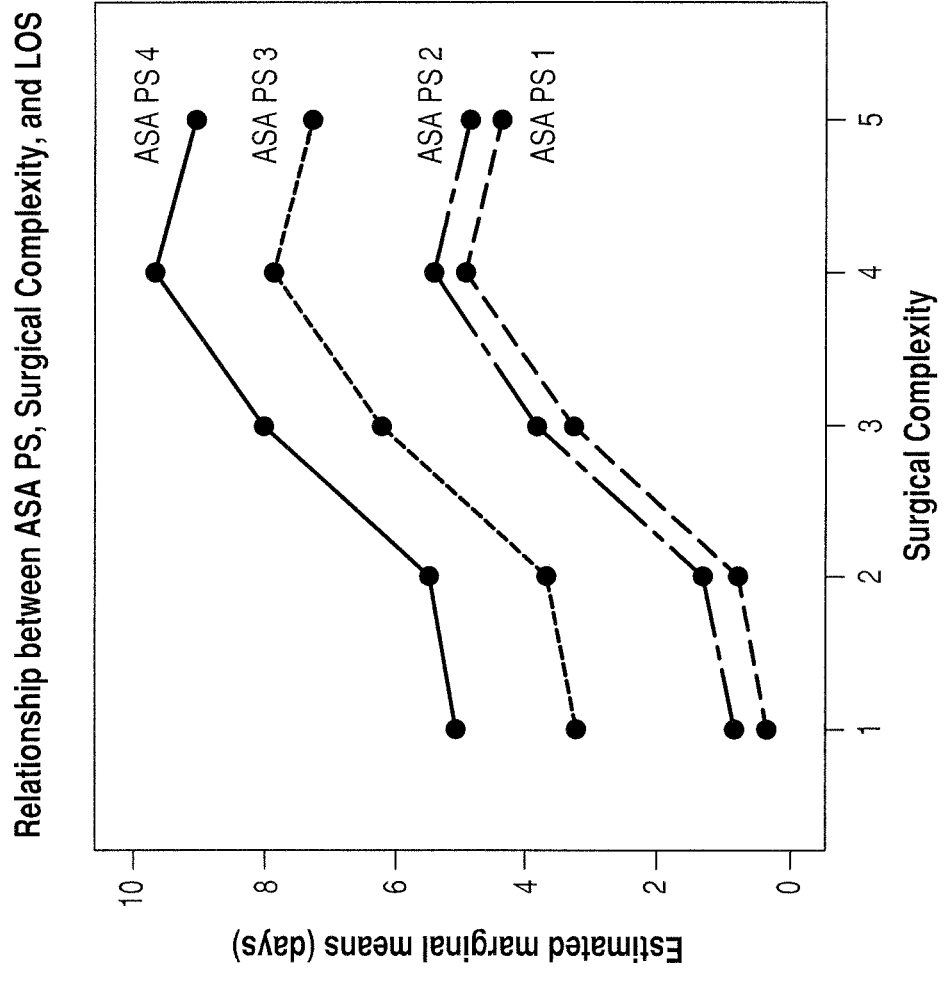
FIG. 1 is a graph showing the importance of both ASA physical status and surgical risk/invasiveness on length of hospital stay (LOS) for surgical patients.

a) example of an overall ASPIRIN™ display; and b-h) sample drop-down listings of inventive modified ASA score (SISS™), Surgical risk/invasiveness score (SOCU™ and SICU™), Physical factors affecting ventilation score, indicators of Intubation difficulty score, special Risk indicators (and scores), Interim Information & Issues (and scores), and Needs for the particular case (and the options for varied degrees of detail and linking).

i) shows a similar configuration in the form of a template that can be used for abbreviated communication in other settings; e.g., as a brief summary during physician-physician signout—printed or as the graphic user interface of a computer- or PDA-based patient log.

FIGS. 7A, 7B and 7C, collectively referred to as FIG. 7, demonstrate some of the increased information (vs. traditional listings) on an operating room schedule using the SHAPE™ score-driven system and method for the following patient: 84 y/o female with stable angina, asthma requiring daily inhalers, osteoarthritis causing limited neck range of motion (with radicular pain and numbness upon 10° extension), and a latex allergy. FIG. 7A shows a standard O.R. schedule. FIG. 7B shows an O.R. schedule with ASPIRIN™ display that relates: that the patient's condition is a modified ASA 3, with individual system (SISS™) scores of 3 for respiratory, cardiac, and neuromusculoskeletal systems; SOCU™ score of 3 indicating class 3 Surgical invasiveness; score of 1 for Physical factors primarily affecting ventilation; score of 5 for Intubation predictors (severely limited neck range of motion), and a score of 5 to indicate the highest score for a Risk indicator (latex allergy). FIG. 7C shows the O.R. schedule of FIG. 7B with addition of SICU™ score indicating that the level 3 effect of surgery is on the neuromusculoskeletal system; it also illustrative of an alternative listing for the Risk indicator (Latex$^5$)

FIGS. 8A, 8B and 8C, collectively referred to as FIG. 8, show preferred inventive mechanisms for coding (and scoring) a preferred branched-chain logic sequence of "system/subsystem/feature category/feature/subfeatures/descriptors" for the CNS system, two of its subsystems and sample FC/F/sF/D coding (represented by # or an arbitrary code) and scoring (represented by $# or $ followed by actual score). A preferred embodiment primarily uses letters for serial progression and numbers for parallel branching, as shown in FIG. 8C. The embodiments in FIGS. 8A and 8B use a number for body system, letters for that system's subsystems and a # or #+letter for the feature category (wherein the letter identifies the system with which the feature category primarily is associated (—this stays with the feature category at sites of co-population). FIG. 8A denotes F/sF/D with progressive decimals. FIG. 8B is designed to reduce the number of decimals and facilitates listing of multiple subfeatures by use of small caps after the .### feature code. The embodiment in FIG. 8C relies more heavily on letters (as opposed to progressive decimals) to delineate level of branching—each branch after Systems is designated by its abbreviation (sS, FC, F, sF, D) followed by a number (—alternatively one could use successive letters of the alphabet followed by a number). As detailed below, to facilitate co-population of different body systems and exporting to different algorithms, the code for each feature category (FC) is preceded by the code number of its predominant parent system, separated by a decimal point. Unscored descriptors (D) are coded wherein the first number groups them according to category (e.g., site, details about temporal aspects), In this figure, features (F) and subfeatures (sF) simply are numbed sequentially; special coding is also available for features and subfeatures to group them according to their primary system (not shown here, but discussed in text).

Figure 9A:
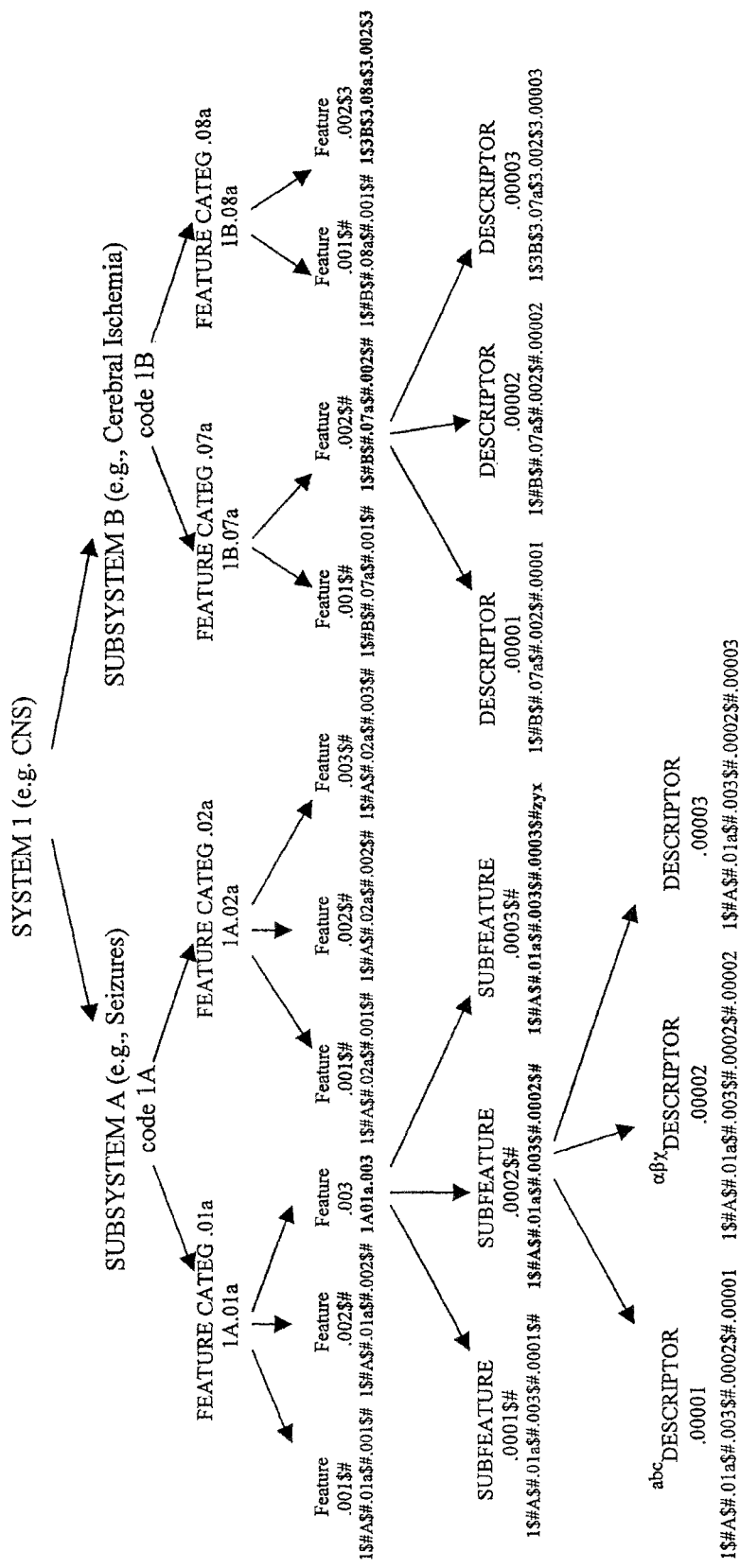
Figure 9B:
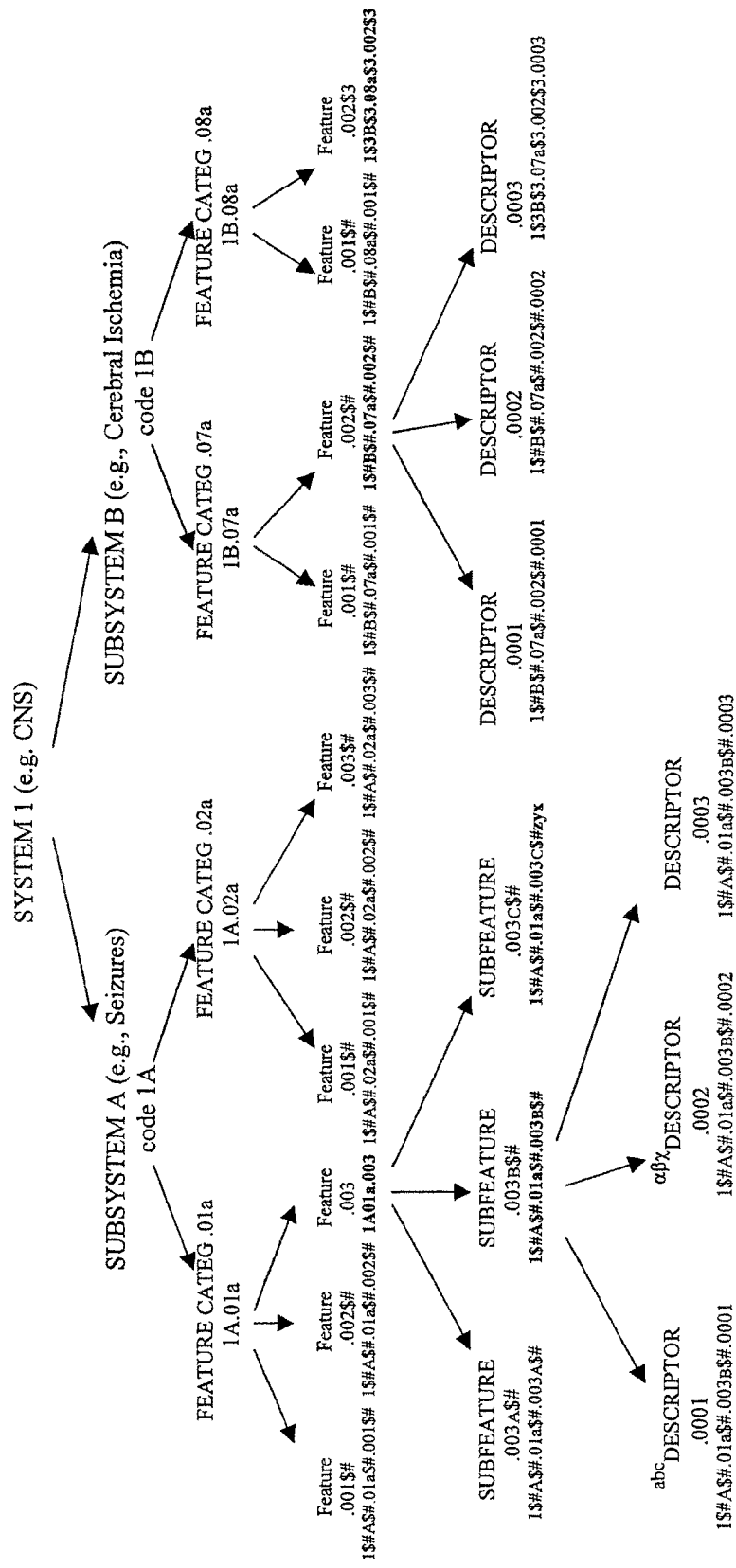
Figure 9C:
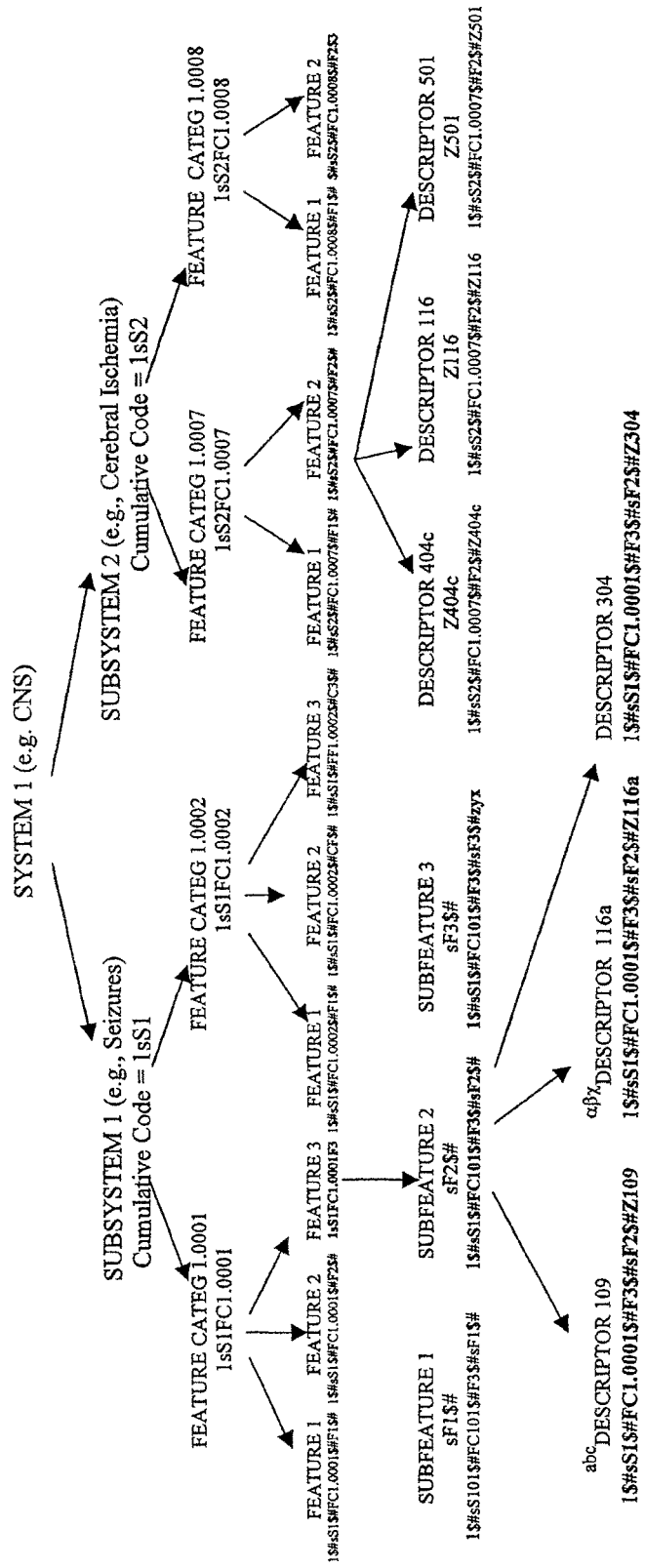

FIGS. 9A, 9B and 9C, collectively referred to as FIG. 9, show a representative section of the branched-chain logic—and related coding and scoring—in accordance with the embodiment that utilizes the coding depicted in FIGS. 8A, 8B and 8C, respectively. Codes in bold indicate a feature or subfeature code wherein a score has been included or where more distal branching is shown. The meaning of the English letters in superscripted prefix, Greek letters in superscripted letters in suffix are discussed below.

Figure 10:
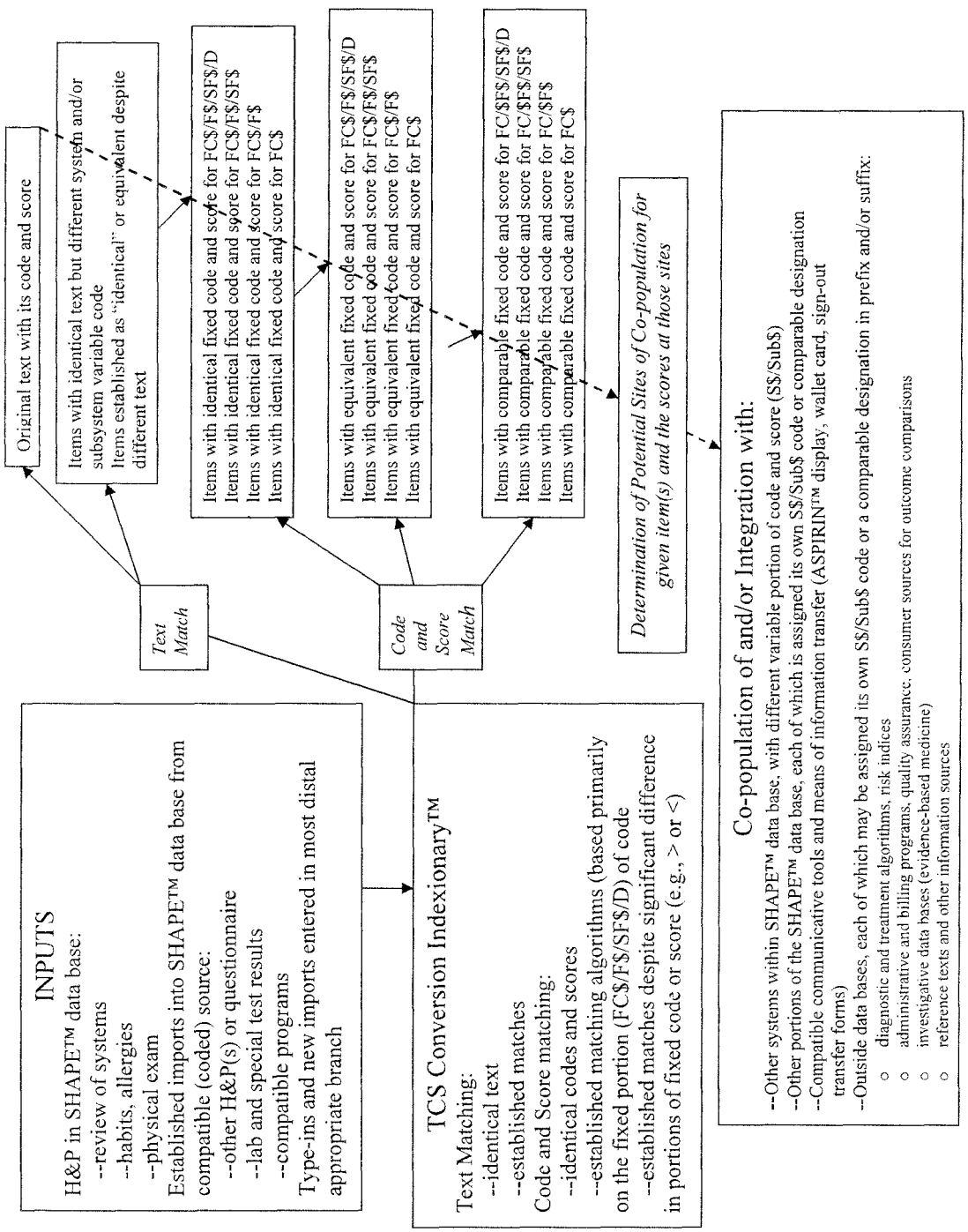

FIG. 10 illustrates the inventive text, code, and score conversion index and dictionary.

FIG. 11, which is composed of FIGS. 11A through 11F, illustrates a potential configuration for scored Risk indicators (SASRI™=SHAPE™ Alphanumeric Score for Risk Indicators) that are being introduced as a component of the invention.

FIG. 12, which is composed of FIGS. 12A and 12B, is a grid which delineates sections for common item entry (columns) and potential sites of co-population (rows) from that single entry. A=score-driven based on SISS™ and SICU™ scores, likely same score at both sites B=score-driven based on special scores assigned to variables not assigned to a body system; C=score-driven, with likely need for text, code and score conversion index and dictionary (means for universal language introduced herein to facilitate co-population and export)

FIG. 13 shows how the addition of 15-30 columns of data provided by the inventive system and method—simply as a result of its unique utilization of routine data entries—increases the robustness of the clinical information in a typical institutional database. Cells can be populated with all or part of the codes and scores described herein.

FIG. 14, which is composed of FIGS. 14A, 14B, 14C and 14D, shows the way in which the widely applied ICD-9 (ninth revision of the International Classification of Diseases) code can be incorporated (via the inventive text, code and score conversion index and dictionary) into the inventive code to generate a SHAPE™$_{ICD-9}$ code or similarly another integrated code/score such as a SHAPE™$_{CPT}$ code. The successive rows show some of the numerous potential sites of integration, including: after, or as a component of, sequential numbering at descriptor level; as a replacement for sequential numbering at the descriptor level; after, or as a component of, sequential numbering at the subfeature level; or as a replacement for sequential numbering at the subfeature level. FIG. 14A uses the sequential coding of FIGS. 8A and 8B without inventive scoring; FIG. 14B that of FIGS. 8A and 8B with inventive scoring ($#); FIG. 14C uses the sequential coding of FIG. 8C without inventive scoring; FIG. 14D that of FIG. 8C with inventive scoring. 1.### and 1.#### indicates that, in a preferred embodiment, the FC contains 3 digits after the system code and the F and sF codes contain 4 digits after the system code, consistent with preferred embodiments for coding feature categories, features and subfeatures described in text. The ICD code may be identified by a number of means, including: its unique number of digits or format; a letter code (abbreviation) or by assigning it a system number, which then would precede the actual code.

Figure 15:
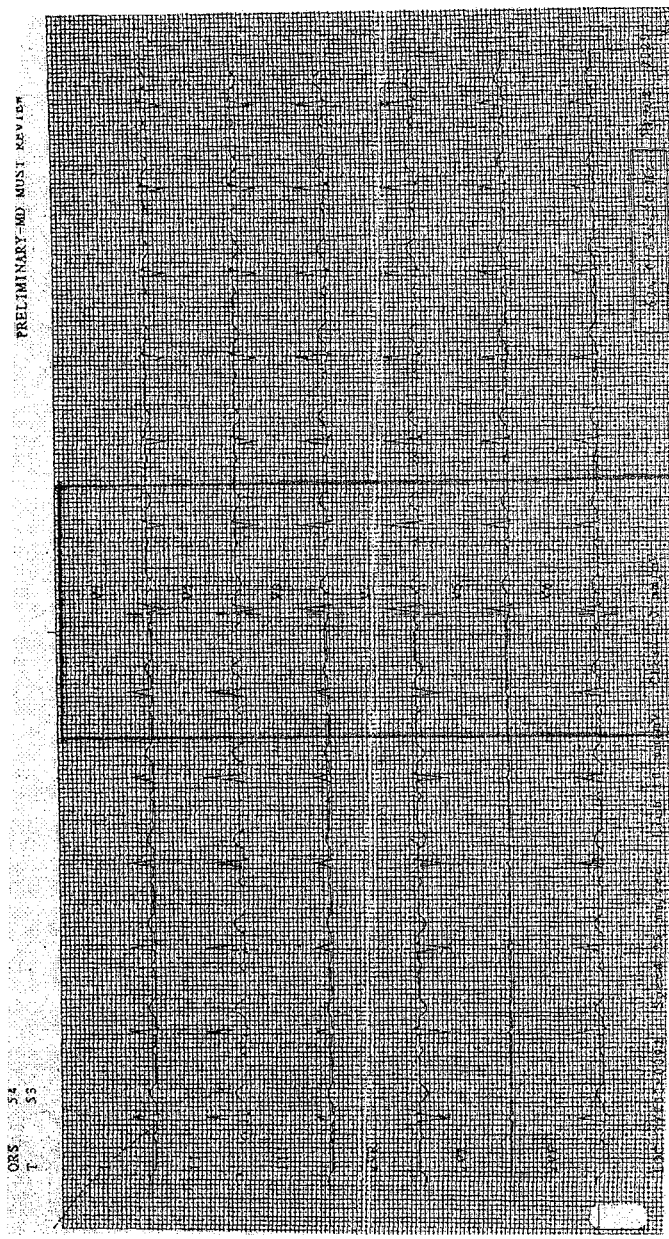

FIG. 15 shows an EKG configured for cropping for score-driven inclusion in database, relevant notes and displays and a wallet card. Its inclusion is driven by abnormalities within the EKG itself or by scores in selected systems, subsystems, feature categories, features, subfeatures or risk indicators throughout the database.

FIG. 16, which is composed of FIGS. 16A and 16B, shows details of potential embodiments of a sample section of the SHAPE™ database with text, code, and scores based on entries in FIGS. 8A, 8B, 8C, 9A, 9B and 9C. Code and score designate cells with positive responses in the given patient. Code and score in this section of the database can either be specific for given level of branching (shown) or can incorporate the codes for proximal levels of branching. A preferred embodiment includes the code beginning with that for the feature category (and, if desired, its score) for all items distal in the branched chain. FIG. 16A illustrates primarily numeric codes (with progressive numbers of decimals to designate serial branching. FIG. 16B illustrates predominantly letter codes (abbreviations) for serial branching, numeric codes for details Abbreviations in the last two columns designate source of information (e.g., P=PCP note) and sites of co-population (e.g., L=selected lab tests; $C_{CNS}4S$=drives script for consultation with a seizure specialist (neurologist); this was generated by the surgeon's entry (S) which rated the need as a grade 4 (as explained in text).

FIG. 17 is a grid that shows how the inventive score drives and chronicles ordering and reviewing common laboratory tests.

FIG. 18 is a grid that shows how the inventive score drives and chronicles requesting and reviewing of specialty consultations and specialty testing.

FIG. 19 provides the status of Interim Information and Issues (again on a graded (0-5) scale).

FIG. 20 delineates how the embodiment for driving laboratory testing delineated in FIG. 17 can be applied to liver function tests. The inventive automated score-driven indications for obtaining the tests are based upon an integration of inventive SISS™ and SICU™ scores (and, when indicated, SASRI™ for relevant Risk Indicator).

FIG. 21, which is composed of FIGS. 21A and 21B, illustrates grids that guide and chronicle ordering of laboratory tests. In its default state, grid lists the lowest likely indication score for each item based on the information that is available (in accordance with FIG. 17). As information pertaining to SISS™, SOCU™ SICU™, Medications and Risk indicators becomes available, scores for existing indications may be updated automatically and new cells may be assigned a scored indication. Score-driven decisions also may be added manually by healthcare providers. Slash in each cell enables entry of results as they are received.

FIG. 22 illustrates grids that where the inventive score drives and chronicles decisions about: discontinuing a current medication or starting a new medication (FIG. 22A); and whether to stop (inactivate) a device such as a cardiac rate management device (e.g., pacemaker or automatic intracardiac defibrillator (AICD) (FIG. 22B).

FIG. 23 shows how the current graded scoring can be adapted for other purposes such as monitoring the status of a prescription or comparable script.

FIG. 24 shows how representative ASPIRIN™ scores can uniformly drive myriad decisions with respect to basic testing, consultations, preop assessment by an anesthesiologist, suitability for fast track discharge from the post anesthesia care unit, and/or likely need for postoperative intensive care unit management. It also illustrates how the inventive system and method can be applied to nonoperative settings.

FIG. 25 shows examples of scored monitoring indices with the consistent inventive scaling—to document outcomes and drive subsequent interventions.

FIGS. 26.1-26.61 (collectively referred to as FIG. 26), FIGS. 27.1-27.8 (collectively referred to as FIG. 27 referring to generic letter coded jump screens), FIGS. 28.1-28.11 (collectively referred to as FIG. 28 referring to generic screens for multiple systems and multisystem conditions), FIGS. 29.1-29.7 (collectively referred to as FIG. 29), FIGS. 30.1-30.11 (collectively referred to as FIG. 30 referring to endocrine (system); diabetes mellitus (subsystem)), and FIGS. 31.1-31.5 (collectively referred to as FIG. 31 referring to lab values (system))

FIGS. 32.1-32.18, collectively referred to as FIG. 32, illustrates a representative listing of scores, features, and subfeatures that are separated by score for each system/subsystem. In FIGS. 32.1 and 32.2, sample coding has been included for the body system (system 1) and subsystems (sS1-9). In addition, representative feature categories had been listed for this seizure subsystem and numbered with their codes.

Figure 33:
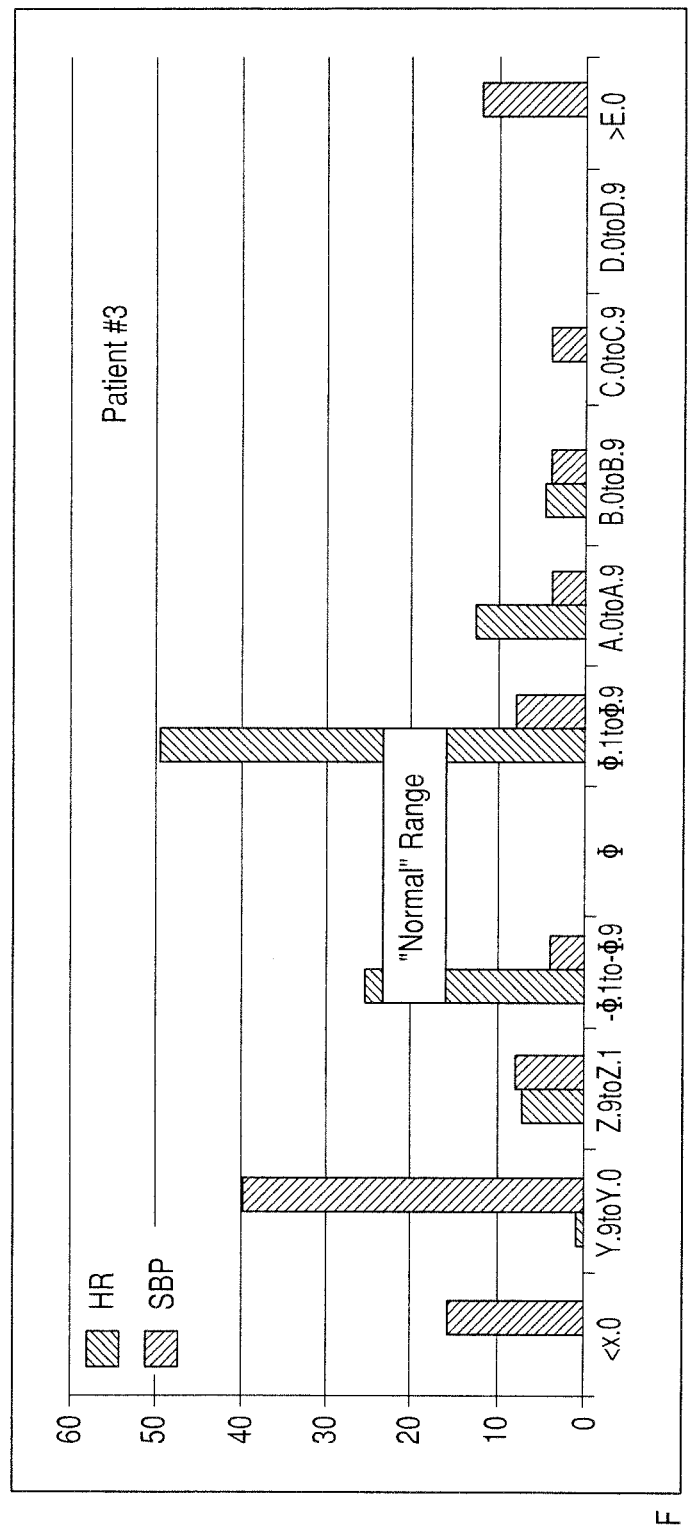

FIG. 33 is graph showing how the scaling facilitates concurrent display of the frequency distributions of heart rate and blood pressure on common axes.

Figure 34:
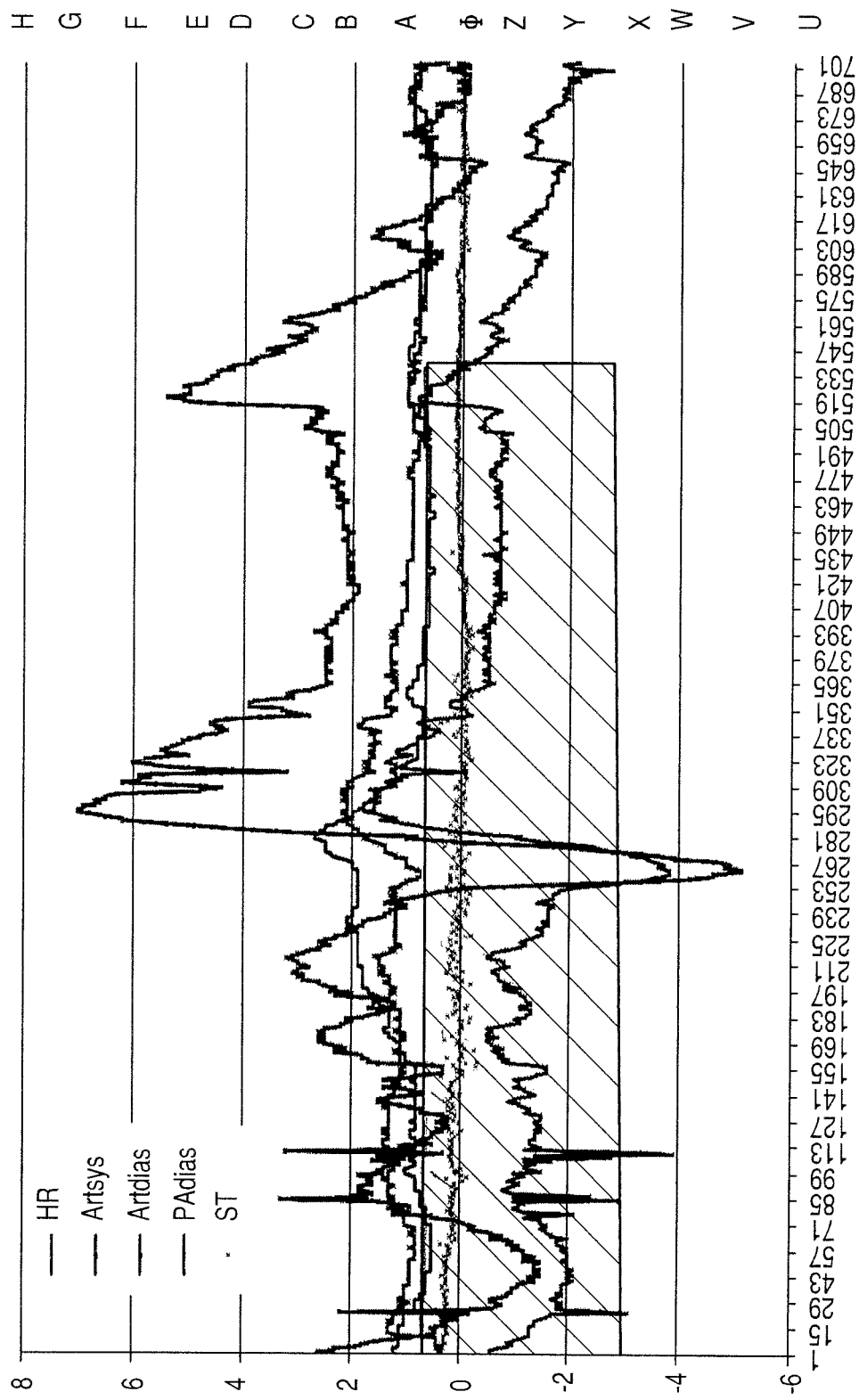

FIG. 34 illustrates continuous recording of four scaled indices during major surgery; x-axis relates successive time points; left y-axis=sequential + and − numerical categories shown for bins away from normal as shown in top row of Tables 28 and 29; right y axis=sequential + and − letter categories for bins away from normal as shown in second row of Table 21. I have introduced the lettered option for scaled values so as to eliminate any chance of confusing raw values and scaled values. While this use of dual y-axes is helpful for the present explanation, users may prefer to establish the y-axis as a logarithmic scale so as to facilitate display of the very high unscaled (original) values described with respect to Table 23.

Figure 35:
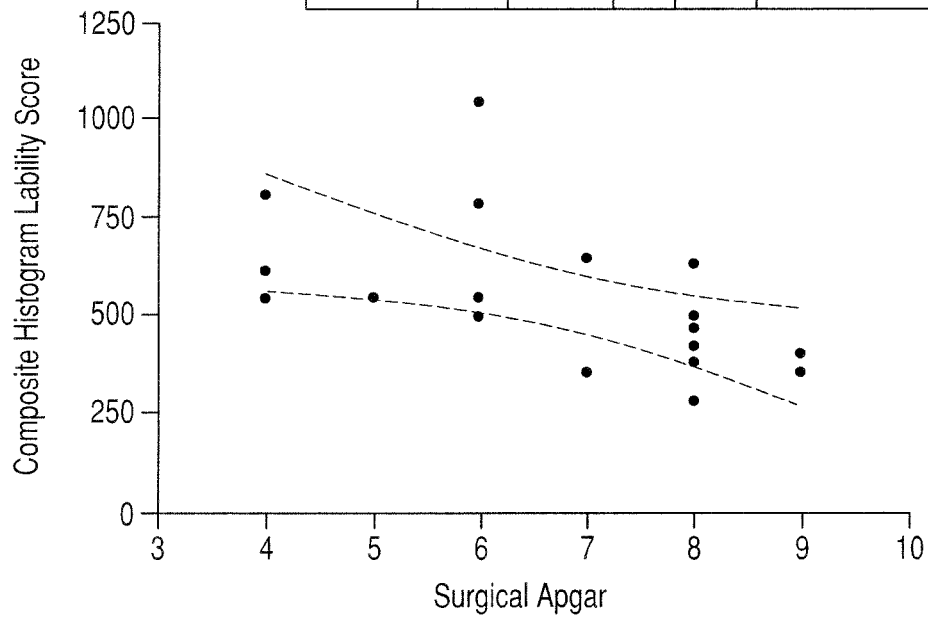

FIG. 35 shows composite scoring of heart rate, blood pressure and estimated blood loss (with the points assigned as described above) compared to a score which assigned points for highest heart rate, lowest blood pressure and blood loss. As shown by the inset, the present method offers far more detail as to the cardiovascular responses.

Figure 36:
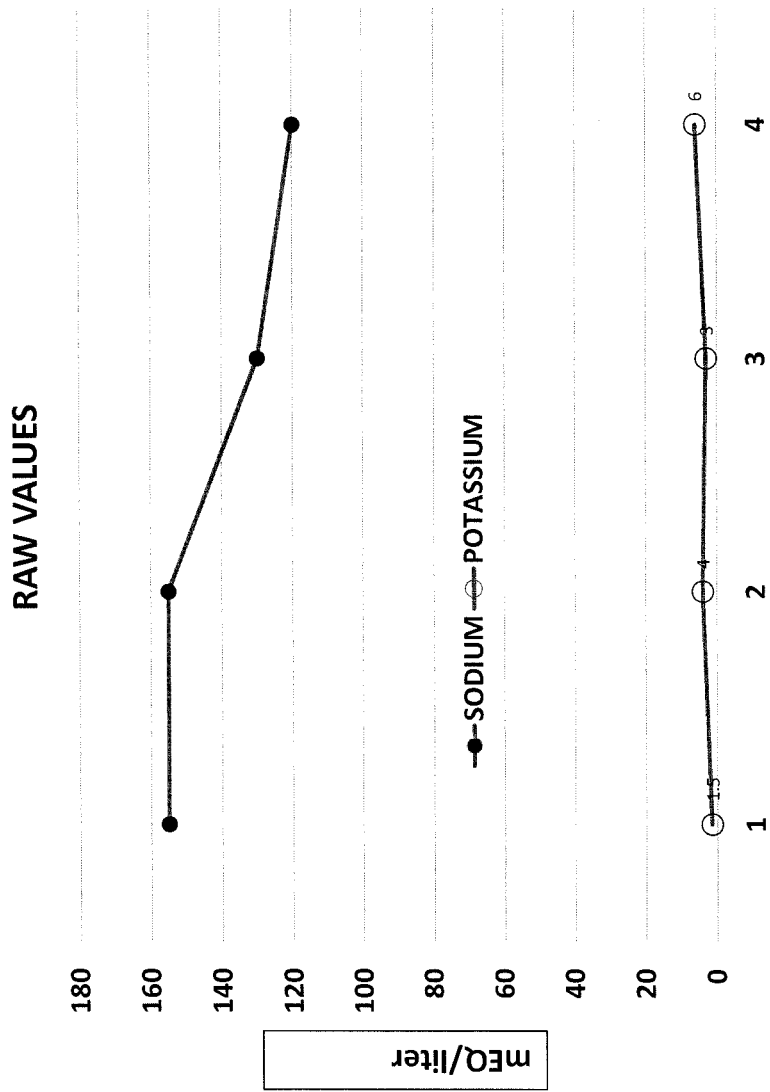

FIG. 36 illustrates the difficulty viewing laboratory tests with disparate ranges, in this case sodium (normal median=140) and potassium (normal median 4), as per prior art. Plotting raw data on traditional axes obscures vital relationships.

Figure 37:
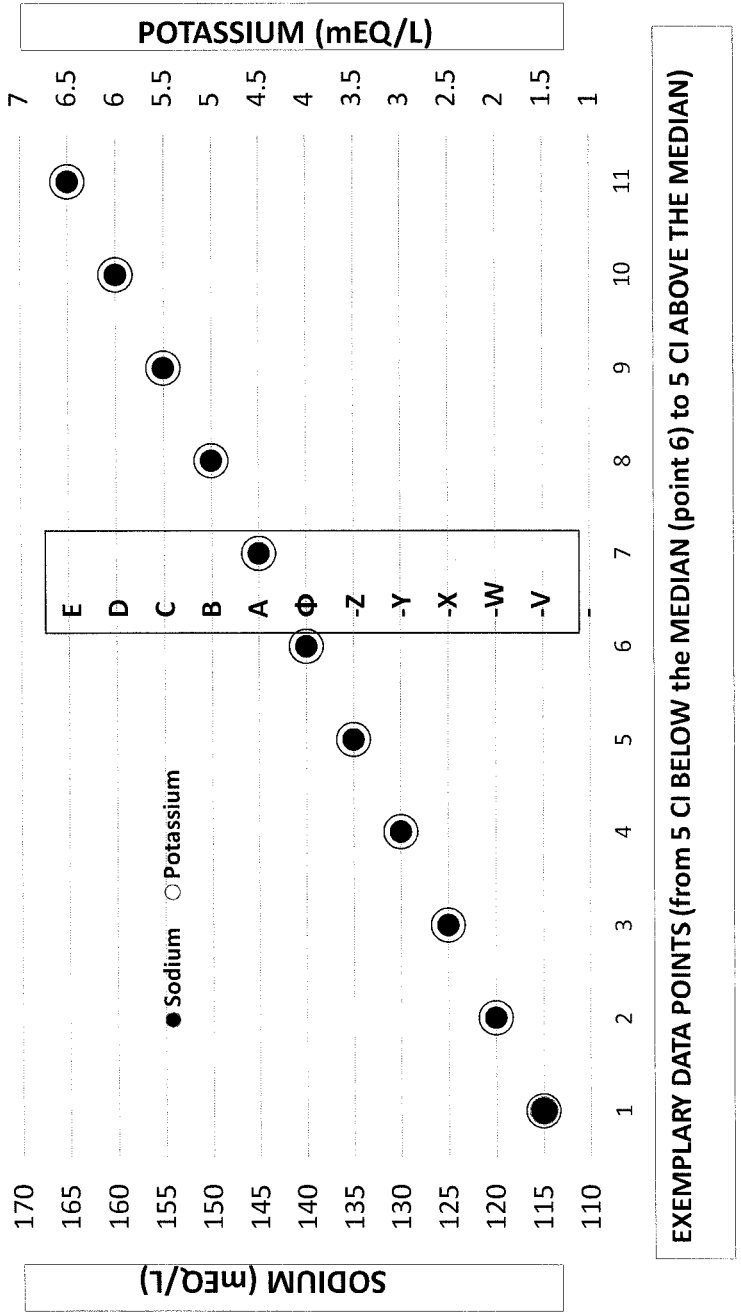

FIG. 37 illustrates how the disparate ranges of sodium and potassium can be converted k to −V to +E based upon 95% confidence interval (CI) increments for each parameter. They now can be viewed on the same scale.

Figure 38:
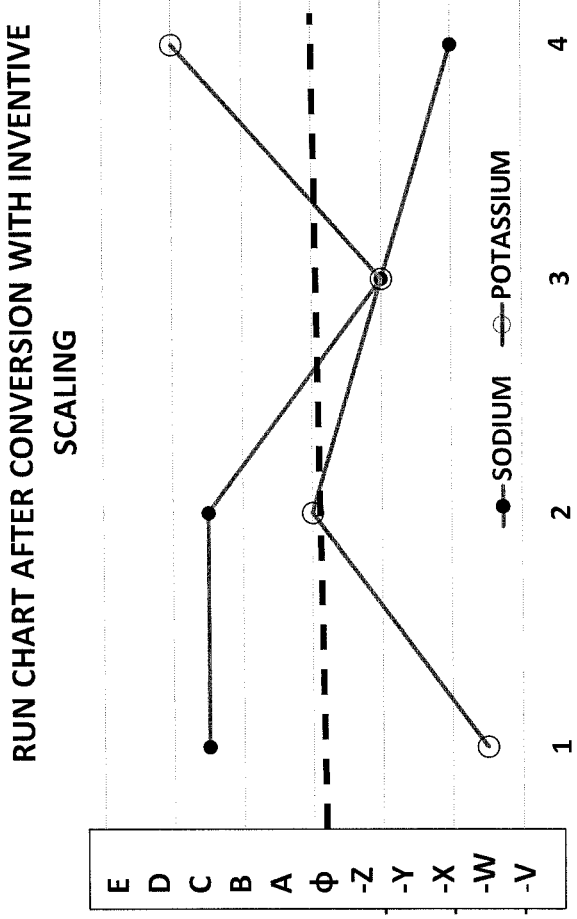

FIG. 38 shows how scaling according the increments of FIG. 37 delineates the changing relationship between sodium and potassium in the context of treatment for disturbances in these values.

FIG. 39 is designed to show how SHICCT can revolutionize record keeping, providing the "missing link" for assessment, quantification, display, and integration. A main focus of this embodiment is the mechanism of displaying the uniformly scaled data via the SHICCT (Scaled Health Information Calculating and Concatenating Tool) List (alluded to in Tables 25, 27). This replaces the classic, oft-criticized listing of the currently used Problem List; the classic Problem List is simply a listing of conditions that typically fails to include current activity status, severity (chronic vs. acute), or treatments; nor does it provide links among conditions or chart entries pertinent to these vital aspects of the condition.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

Referring to the various Tables and Figures accompanying the present disclosure, a multi-dimensional system and method for assessing, consistently coding, quantifying, displaying, integrating and communicating information relating to patient health and perioperative risk that addresses each of the factors described above is disclosed. Namely, the present system and method provides for (1) a new score for the physical condition of the patient; (2) a score for the degree of expected surgical risk and invasiveness; and other vital assessments of perioperative complexity, including scores for potential airway difficulty—(3) physical factors primarily affecting ventilation and (4) intubation-related factors —; and (5) letter codes with optional scoring for risk indicators and other factors that may require special preoperative preparation and planning (although letter codes or disclosed for (5) in accordance with a preferred embodiment, a variety of alphanumeric codes are contemplated for use in accordance with the present invention). In addition, the present invention introduces subsequently derived scores which expand upon patient condition and integrates these with other perioperative issues such as surgical risk and invasiveness. The heretofore unavailable mechanisms for assessing the multiple aspects of a patient's health described herein provides a common language, a common mechanism of coding and a common mechanism of scoring a patient's health and, in accordance with preferred embodiments detailed herein, enable calculations to assess his/her ability to withstand surgery. The branched-chain logic (shown in multiple figures and detailed below) and associated coding and scoring are consistent among bodily systems and conditions, thereby providing unique simplicity, consistency, and adaptability. The present system further provides for score-driven co-population and export, which focuses the transfer of relevant information.

Figure 2:
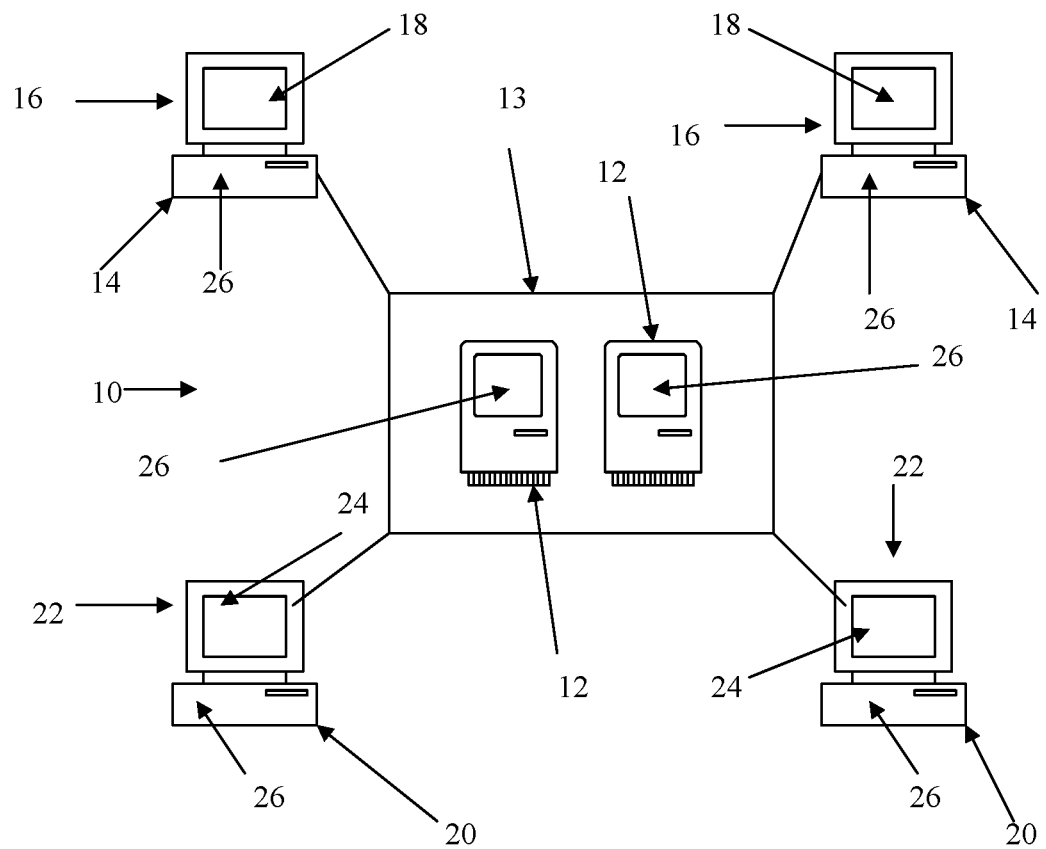
FIG. 2 is a schematic of the present system as implemented via computer-based arrangement.

As those skilled in the art will certainly appreciate, and with reference to FIG. 2, the present system 10 provides for a mechanism for inputting patient information and providing an output relating to the patient health and perioperative risk. This is implemented via a computer based system linking a variety of data source(s) 12, which cumulatively represent a database 13 of information, with data input mechanisms 14 (for example, computer stations 16 with a graphical user interface 18) for inputting relevant data to the system 10 as described below in greater detail and output displays 20 (for example, computer stations 22 with a graphical user interface 24) for retrieving desired information generated in accordance with a preferred embodiment. The present system may be limited to use at a single site or link a variety of health care facilities in a highly integrated network. The various data sources 12, input mechanisms 14 and output displays 20 are provided with well known processors 26 employed to coordinating the retrieval, processing and outputting of information in accordance with the present invention. As those skilled in the art will also certainly appreciate, the various components making up the present system may be integrated into a single station from which information is input, processed and output. Similarly, the present system may be configured in more elaborate arrangements with multiple data sources, input mechanisms and output displays, or it may be a stand alone unit.

This present system 10 is implemented by applying a method for providing an integrative mechanism of quantitative assessment and communication. The method includes inputting patient information via the data input mechanism 14, processing the patient information via the various processors 26; providing an output relating to patient health and perioperative risk via the output displays. The output includes a score for the physical condition of the patient, a score for the degree of expected surgical risk and invasiveness, a score for other vital assessments of perioperative complexity, including scores for potential airway difficulty composed of physical factors primarily affecting ventilation and intubation-related factors, and letter codes with optional scoring for risk indicators and other factors that may require special preoperative preparation and planning. The techniques employed in carrying out the present system and method are described below in greater detail. Although the present invention is described herein in a computer based system, those skilled in the art will appreciate it could be implemented in a variety of forms without departing from the spirit of the present invention.

In accordance with a preferred embodiment, the scores for the physical condition of the patient and the degree of expected surgical invasiveness are based upon ranking systems familiar to clinicians. In particular, and in accordance with a simplest embodiment, the physical condition of the patient is identified by the ASA PS of medical condition (which is modified in a unique system-specific basis in more elaborate embodiments in accordance with the spirit of the present disclosure) and the expected degree of surgical invasiveness is provided by an integration of the aforementioned ACC/AHA classification of surgical risk and the Johns Hopkins classification of surgical invasiveness (which is modified in a unique system-specific basis in more elaborate embodiments in accordance with preferred applications of the present system).

The present system offers a methodology with the simplicity of ASA PS 1-5 ranking that will serve clinical, investigative and administrative functions—useful to the clinician developing a plan for perioperative care, to the investigator seeking data for outcomes research and evidence-based guidelines, and to the administrator developing operating room case schedules as well quality assurance, productivity assessments and billing policies. This has led to the present integrative mechanism of quantitative assessment and communication which is disclosed and referenced herein under the acronym "SHAPE™" (Silverman-Holt Aggregate Preoperative Evaluation and, for more general applications, Silverman-Holt Aggregate Patient Evaluation). Among its components, SHAPE™ provides a mechanism for communicating and displaying vital information (see FIGS. 3-6).

The acronym ASPIRIN™ (ASA physical status, Surgical risk/invasiveness, Physical factors primarily affecting ventilation, Intubation predictors, Risk Indicators that identify items of potential anesthesia-related concern) is used in conveying the various components making up a SHAPE™ score. When employed within computer-based systems, the acronym ASPIRIN™ can be easily expanded so that the last two letters relate Interim Information & Issues, (Information and issues pending, as well as information which may have arrived since the original note was completed or last updated) and Needs that should be addressed (e.g., equipment, missing information, need for special medications such as preoperative antibiotics) (see FIGS. 3-7). The sequential scores are consistent with other alphanumerics in clinical medicine, including, but not limited to, "T # N # M #" to represent tumor size, nodes and metastases, and "G # P #" to represent the number of times a woman has been gravid and the number of pregnancies that resulted in live birth at >20 wks. However, and in contrast to prior clinical medicine scoring systems, ASPIRIN™ integrates varied characteristics that may otherwise be unrelated to one another (as opposed to aspects of a given condition) and that themselves may be integrative assessments as opposed to an objective measurement. In accordance with an alternate embodiment, ASPIRIN™ also may be changed to ASPIRING™, wherein the "G" stands for gas and thereby relates the anesthesia plan.

Figure 3:
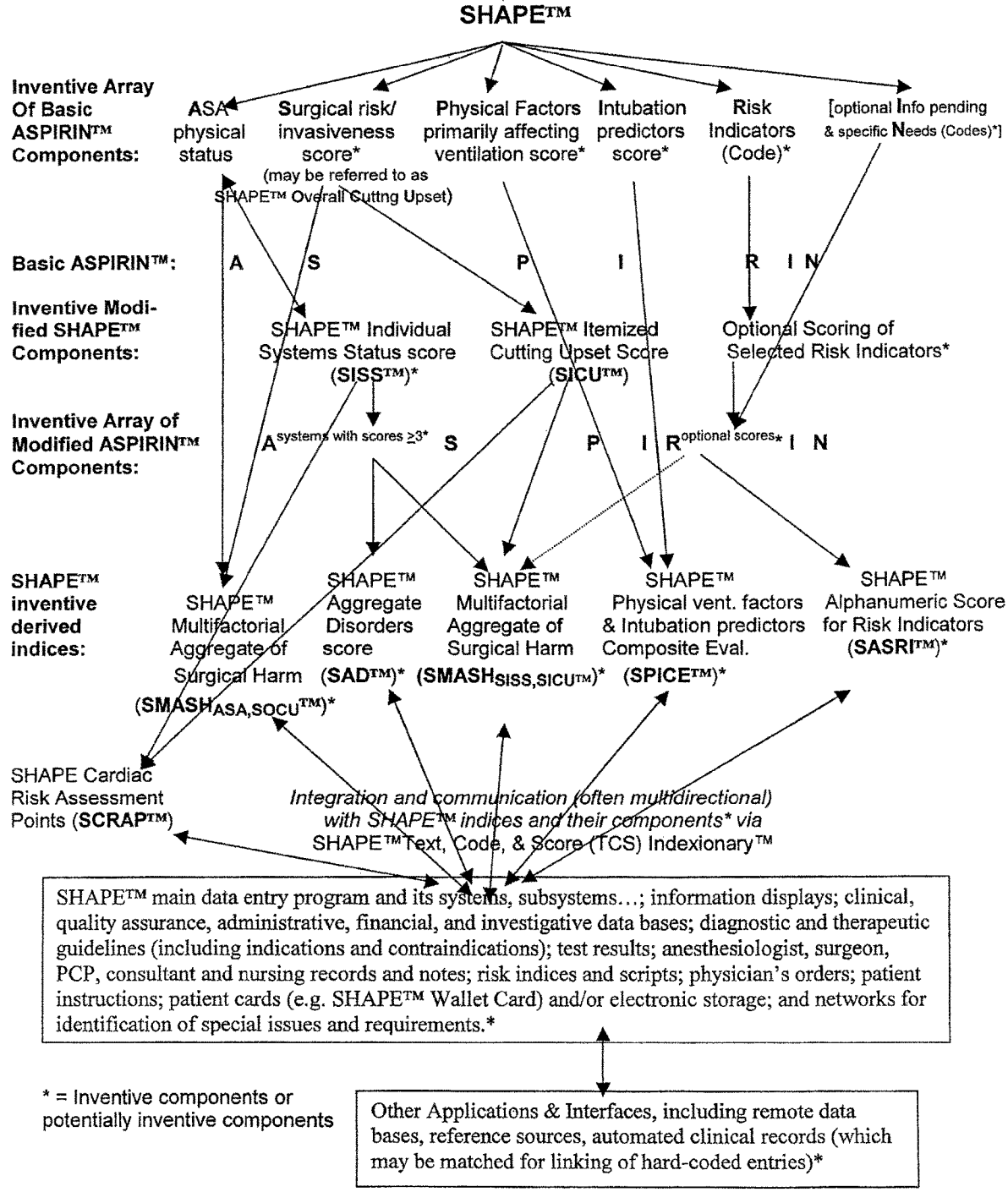
FIG. 3, which is composed of FIGS. 3A and 3B, illustrates the interactions of the inventive system.
Figure 3B:
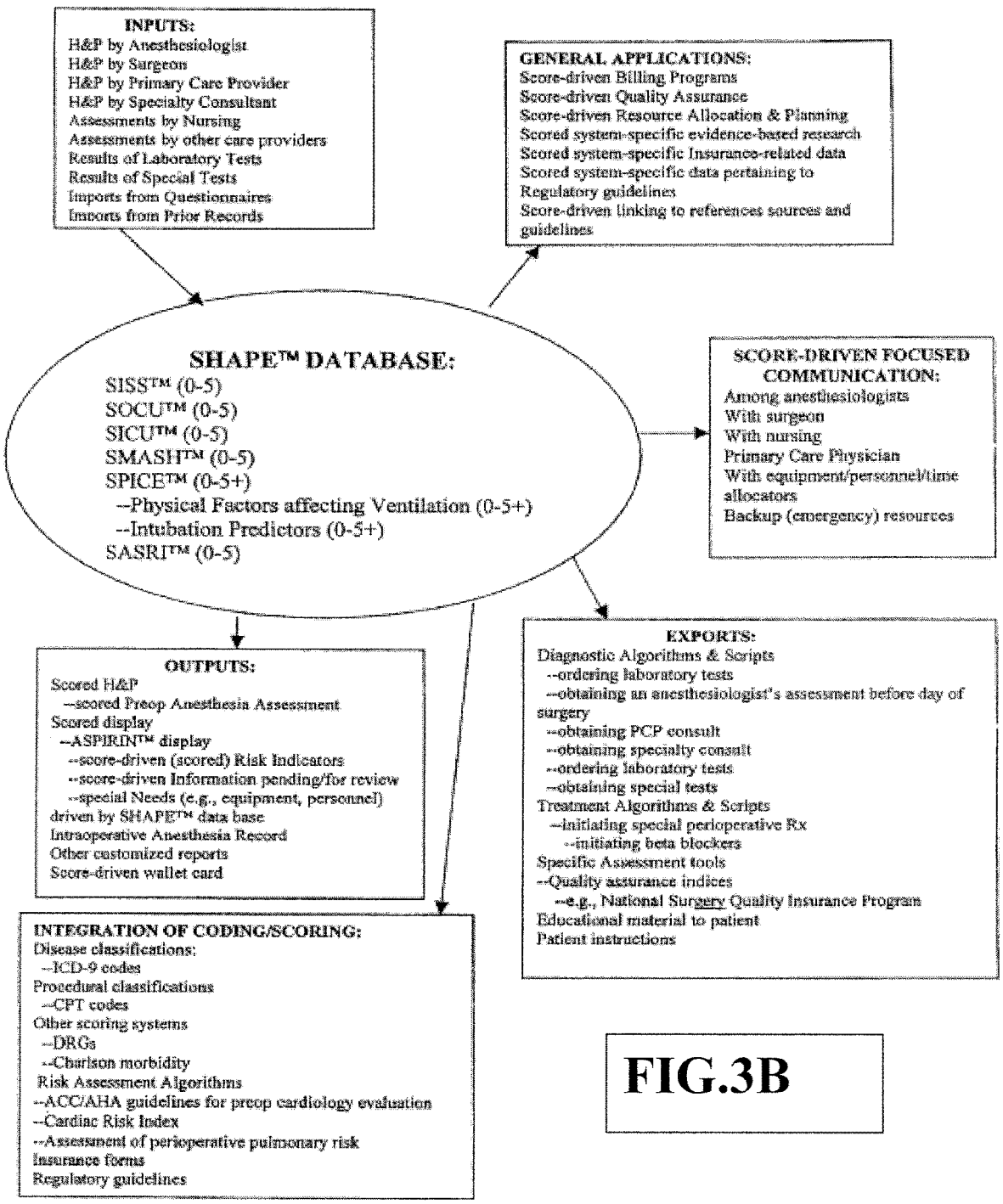
FIG. 3B is a flow chart delineating many of the inventive components of the present system and their interactions, including ASPIRIN™, SISS™, SOCU™, SICU™, SASRI™, derived indices and the SHAPE™ text, code, and score conversion index and dictionary (SHAPE™ "Text, code and score conversion index and dictionary" shown in FIG. 10).

The SHAPE™ scores simply can be displayed (FIGS. 3-7) and/or integrated to generate patient condition and surgical invasiveness sums, products or other arithmetic functions, with derived indices, including, for example, those detailed herein (lower portion of FIG. 3). The details and applications of the present system and method are presented below. Its advantages have been summarized in Table 3 and are detailed throughout the present disclosure.

TABLE 3

(Differences and) Advantages of the Inventive System of Score-Driven Consistent Coding for Assessments, Co-population and Integrated Functions:

Simple mechanisms for integrating clinical, investigative, quality improvement, research and administrative functions with heretofore unavailable common data entry, coding and scoring.
    Comparable body system-specific, as well as overall, scoring of medical conditions and surgical risk/invasiveness (with SISS ™, SOCU ™, and SICU ™)-- enabling integrated body system-specific and integrated risk assessment as well as diagnostic and treatment algorithms
    Improved discrimination among risk factors which normally constitute relatively minor disorders, with identification and optional scoring of Risk indicators (with SASRI ™), Interim Information Information and special Needs that might not otherwise be so apparent. Increased impact of an item on an upcoming anesthetic can thus be communicated without distorting its otherwise minor impact on long-term health.
    Storing and communicating multiple scored components as reflected by the ASPIRIN ™ display.
    System-specific scoring and simple communication of systems with significant disorders or other reasons for concern
    Body Interfacing with questionnaires (with comparable scores or which enable such scoring)
    Common means for documenting initial condition(s), final condition(s) and interim condition(s) based simply on scored chart entries.
    Integrative assessments of different comparably coded and scored components of the SHAPE ™ database
    Generation of score-driven summary and communication tools such as the ASPIRIN ™ display, wallet card, healthcare provider-to-healthcare provider sign-out summary
    Options for cumulative and integrative scoring of comparably scored multiple features, multiple body systems, multiple components of the SHAPE ™ database,

TABLE 3-continued

Score-driven processes based upon single, multiple, cumulative and integrated
components of the inventive database:
    Grouping items by score and, when indicated, scoring cutoffs
    Displaying items by score and, when indicated, scoring cutoffs
    Exporting items by score and, when indicated, scoring cutoffs
    Text- and score-driven/cutoff-driven co-population for other
    applications.
    Generation of integrated score-driven scripts.
    Score-driven patient transitions/disposition:
        Home without special care
        Home with special at-home care
        Extended care facility
        Level 1 trauma center
        Intensive care unit
        Step-down unit
    Score-driven triaging:
        to see anesthesiologist prior to day of surgery
        preop evaluation by PCP
        specialty consultation and/or special testing by a PCP
    Score-driven scripts for diagnostic testing:
        General laboratory testing
        Specific testing
    Specific score-driven treatment and management algorithms
        Score-driven scripts for level of patient management:
        Management of patients with overall morbidity scores
        Managements of patients with scores for specific body systems
        (e.g., cardiac score justifying possible use of beta-blocker
        therapy)
        Surgical Care Improvement Project (SCIP) measure for
        preoperative antibiotics
        Management of patients undergoing surgery with overall
        risk/invasiveness score
        Management of patients undergoing surgery with a specific
        body system-specific risk/invasiveness score
        Management of patients based upon aforementioned integrated
        assessments
Score-driven administrative data accumulation, assessment and application
    Score-driven manpower and resource planning
    Score-driven quality assurance assessments
    Score-driven assessments of personnel
    Score-driven cost predictions (and comparisons)
Score-driven visit justification and billing (with potential integration with ICD
codes, CPT codes and anesthesia billing codes. SHAPE ™ provides the
classification, uniformity, and potential multi-purpose integration that are not
provided by other methods)
Scored assessments of interim and final outcomes
    Scored assessments of test results, thereby minimizing subjectivity in
    interpretation of clinical significance (e.g. of NSST on EKG as
    described in text).
    Hemodynamic Indices
    Status at discharge
    Score-driven communication and displays
Research and the accrual of data for evidence-based guidelines:
    Classification, coding and scored stratification for outcomes research
    provide the detailed databases required for generation of meaningful
    data for documentation of perioperative morbidity, assessment of
    interventions, and generation of evidence-based recommendations.
Links to comparably coded information sources (e.g., textbooks) - based on
identical text and code as well as comparable text and code (as mediated via the
text, code and score conversion dictionary).

Where the SHAPE™ ASPIRIN™ acronym is displayed electronically (for example, on a graphical user interface of a computer system), then clicking a component (e.g., the first number or the first body system in the modified ASA score) can activate a dropdown menu. FIGS. 6 and 6-1 show some of the information that may be available and accessible. A preferred embodiment entails the provision of progressive specificity. For example, this may be achieved by a listing of positive body systems (with scores in descending order); identification of positive aspects of the body system by clicking on the given body system; or jumps to sections of the display (or other aspects of the program) co-populated with the given feature It should be noted that anesthesiologists often disagree as to whether certain relatively minor risk factors and features constitute justification for a score of "2" (as opposed to "1"). Examples are included in FIG. 32. In a preferred embodiment, SHAPE™ enables their selection and storage with a 1.5 score—without the need to complicate the SHAPE™ ASPIRIN™ display or clinical SHAPE™ indices (i.e., simply consider them a "1" for display purposes)

In this same spirit, an alternative embodiment entails modifying the 1-5 score to a 0-5 score, with 0=perfectly healthy, 1=presence of risk factors without significant signs or symptoms (2, 3, 4 and 5 would remain unchanged). It is an objective of the present invention that a uniform or consistent scoring system be introduced for each of the SHAPE™ database components and ASPIRIN™ display components. In accordance with a preferred embodiment, a 0 to 5 score is recommended for each component. However, and so as to remain consistent with anesthesiologists' logic during the initial presentation of the present invention, the 1-5 ASA score has been maintained and 1.5 has simply been inserted for most examples herein.

Additionally, other scoring systems may be employed within the scope and spirit of this invention. This may be achieved by converting other quantitative or qualitative measures to the 1-5 or 0-5 scores described above. Alternatively, a different graded range may be utilized (e.g., 0=none, 1=mild, 2=moderate, 3=severe) so long as consistency of scoring among components is maintained.

Assessment of Physical Status

As detailed later in this document, the SHAPE™ text, code and inventive score can be applied to chronic as well as acute conditions and local as well as systemic effects. The embodiments described below will focus on systemic effects in the (acute) perioperative period.

ASA Physical Status.

Because of its time-tested clinical utility, the ASA PS classification system has been chosen for use as the foundation for the present SHAPE™ representation of patient condition. However, in order to provide additional depth of information, while not forsaking its simple elegance, the present invention introduces the practice of assigning a 1 to 5 (or 0 to 5) severity score for each major organ system based on information learned from the patient history and physical examination and associated testing. The inventive system further provides the methods and algorithms to do so, thereby generating what is termed herein SHAPE™ Individual Systems Status (SISS™ or SIS™) scores (Table 4 and FIG. 32). The scoring criteria for each body system parallel the overall ASA PS classification but, by being body system-specific, are uniquely different and enable quantification of the ability of the given body system (for example, cardiac or respiratory) to withstand potential surgery-induced demands and insults—what is referred to herein as a SHAPE™ assessment of resilience.

embodiments is shown in FIGS. 8A-C and 9A-C and discussed and disclosed later in this document. Even when such detailed branched-chain logic is not evident, it is functioning and accessible in most preferred embodiments; for example, the coding of each item in FIG. 32 and delineated in FIGS. 32.1 and 32.2 is based on branched chain consisting proximally of system, subsystem and feature category codes. Except for the simplest option wherein scoring for each body system (e.g., Central Nervous System, Cardiac System) is based on the user entering a physical status score for each body system in the absence of scoring of individual features or subfeatures, the SHAPE™ methodology is implemented so that scorable choices (e.g., features and/or subfeatures) generate the proximal (e.g., system) score.

Options for arranging items are summarized as follows: 1) Grouping features within each body system or subsystem or feature category according to their default score (with an option to change that score for a given feature in a given patient) as shown in tabular form in FIG. 32 and as listed on user screens (Tables 13, 14, 15 and 17) which are described later in this document; 2) Grouping by any number of alternative means within a system, subsystem or feature category, including sequence of questioning while obtaining a history and sequential order of questions in a questionnaire. 3) Grouping of signs and symptoms based on clinical patterns. 4) Simply listing items in alphabetical order or in numerical sequence based on their respective codes. Again, scoring accompanies item selection as may be facilitated by providing a default score and the option to change a score for each individual item.

The multiple potential actions are summarized in Table 5.

TABLE 4

Comparison of traditional ASA Physical Status and proposed SHAPE ™ Individual Systems Status (SISS ™) score

| Score | Traditional ASA PS Description | Proposed Description for Individual Systems |
|---|---|---|
| 1 | Normal, healthy patient | Normal function, reserve, and resilience |
| 2 | Mild systemic disease with no functional impairment | Early stage, medically optimized disease with limited impairment of given system. Risk factors for dysfunction or compromise (of reserve and resilience) (e.g., smoking for pulmonary system). |
| 3 | Moderate systemic disease with functional limitations | Moderate disease of given system with measurable dysfunction or compromise. May benefit from optimization to minimize likelihood of perioperative morbidity. |
| 4 | Severe systemic disease that is a constant threat to life | Severe dysfunction or compromise of given system, which is a potential threat to life in the acute perioperative period. Best if condition optimized prior to surgery. |
| 5 | Moribund; not expected to survive for 24 hrs w/o surgical intervention | Acutely life-threatening dysfunction and/or compromise involving the given system (regardless of degree of upcoming surgical stress). |

In its simplest application, a user may simply score his/her entries of data for each body system—in accordance with the partial display of scored features and subfeatures that are included in FIG. 32—during the history and physical examination. As shown below, in an automated application, items such as those in FIG. 32 may be hard-coded along with their score for selection by the user—when possible without compromising simplicity, scoring is based upon entries at the feature or subfeature level. This may entail a listing of scored features and subfeatures as in FIG. 32. The details of the branched-chain logic that is employed in preferred

TABLE 5

Examples of Actions Upon Selecting a Given Feature or Sub-feature (or alternative item)

Item is recorded in H&P and database with modifiable default score
Item is recorded in H&P and database with a user-determined score
Item is recorded in H&P and database without a score (until one is subsequently assigned)
Advance distally to next scored branch (e.g., from feature to subfeature)
Jump to options to select additional unscored information (e.g., to descriptors)

TABLE 5-continued

Examples of Actions Upon Selecting a Given Feature or Sub-feature (or alternative item)

Jump to option to type-in additional information
Jump to option to modify information provided by the choice.
Item co-populates multiple portions (e.g., multiple bodily systems) of the H&P and database
Item co-populates algorithms for communication, diagnostic and treatment algorithms, quality assurance and quality improvement databases, etc. based on:
   Identical terminology
   Common terminology based on universal language (as mediated by the text, code and score conversion index and dictionary)
   Common significance based upon text and/or code + score (as mediated by the text, code and score conversion index and dictionary)

Steps in which such actions may be accomplished are summarized in Table 6.

TABLE 6

Examples of Configurative Options for Selection and Scoring

Return key (automatically selects text and default score)
Selection of score or jump option from listing (which may be abbreviated in parentheses) associated with the given item. This selection of text and desired score/option may be accomplished by:
Mouse click over desired scoring option (or, if indicated, alternative option such as "type-in")
Right-ward advance of cursor until it overlies desired score or alternative option; then pressing "return," a mouse click or comparable means of selection
Selecting options according to number, abbreviations/code, creep seek
Left mouse click over text (automatically selects text and default score).
Right mouse click over text-to access additional options (e.g. drop-down menu) which may include:
Details of more proximal branch logic
Default text that will appear in note (may be more detailed than simply what is stated for the feature or subfeature)
List potential sites of co-population within the SHAPE ™ database for the given item (i.e., other sites where the hard-coded choice appears-see text for discussion of this issue).

As detailed throughout this disclosure, major aspects of the present invention are the score-driven displays and scripts based upon SISS™ and related scores. For purposes of communication, and in accordance with a preferred embodiment of the present invention, the present invention enables that, for patients with conditions that warrant an ASA PS≥3, a code (for example, first letter or first few letters of the given system) be superscripted to the traditional ASA PS score to indicate the affected organ body system(s). For example, a patient with exertional angina, but no other major medical conditions, would be an ASA $3^{CARD}$ (for Cardiac), while a patient with long-standing insulin-dependent diabetes mellitus would receive an ASA $3^{ENDO}$ (for Endocrine). If there are abnormalities of multiple systems, these would be represented by each of the appropriate system identifications. Thus, a patient with exertional angina and insulin-dependent diabetes would be an ASA $3^{CARD,ENDO}$. In cases where multi-system ASA≥3 disease of differing clinical severity exists, the numerical score(s) that is (are) represented simply could be the system(s) with the highest score. Thus, a patient with cardiogenic pulmonary edema (worthy of an ASA 4 designation) and insulin-dependent diabetes (worthy of an ASA 3 designation) could be represented as an ASA $4^{CARD}$. Alternatively, ASA $4^{CARD>ENDO}$ or ASA $4^{CARD}3^{ENDO}$ could be used to designate both the ASA 4 and the ASA 3 disorders. Comparable annotation is shown in FIG. 4 (showing inventive components at the end of an inventive care giver note) and FIGS. 6 and 7 (showing examples of a potential ASPIRIN™ display), which demonstrate some of the increased information (vs. traditional listings on an operating room schedule) that may be generated and used for co-population of other portions of the inventive program or exported for other applications. It would be within the spirit and scope of this invention to have other mechanisms of #-systems display (e.g., systems in parentheses as opposed to as superscripts) as well as to list the systems followed by their score. For purposes of a consolidated meaningful display, it is believed that the illustrated embodiments are most effective.

The clinical importance of such system-specific data is suggested by recent data collected by my research team for presentation at the 2006 Annual Meeting of the American Society of Anesthesiologists. Of 220 patients with ASA 3 or 4 physical status, the Cardiac system was the most commonly reported system to merit such a score; this was followed by the Central Nervous System and Respiratory System. In addition, 30.4% of these patients had two systems with grade 3 or 4 level of dysfunction, 14.1% had three such systems and 2.1% had four or more such systems.

It thus should be evident that the system-specific scoring introduced herein looks at the overall ASA physical status score as being derived from the scores assigned to individual body systems (with the potential to override this score). These in turn are based upon the highest score(s) assigned to signs, symptoms and/or test results within the given body system (SISS™), typically at the feature or subfeature level. This constitutes a preferred embodiment; however, other means of consistent assignment and management of scores are within the spirit and scope of this invention.

Essentials of Coding and Scoring in Preferred Embodiments:

There are multiple options for coding and scoring database components; these will be delineated here with respect to SISS™ components. The present invention would make a significant impact simply by adding on the scoring component provided by SISS™ (and SICU™ and SASRI™) to systems and/or systems and their component features. However, the introduction of coding and scoring based upon the branched-chain logic described herein provides a unique foundation for electronic record keeping and contributes significantly to the advantages summarized in Table 3.

In most of the embodiments shown herein, there is consistent progression from system (S) to subsystem (sS) to feature category (FC) to scored features (F) and/or scored subfeatures (sF) and unscored descriptors (D). Several different means of coding and display are shown in order to illustrate the diversity of techniques that are within the spirit and scope of this invention, but also to consolidate selected displays (e.g., FIG. 9c) and to delineate means of co-population and code integration (e.g., FIG. 14). The essential aspects of a preferred embodiment are summarized in Table 7.

TABLE 7

A Preferred Means of Coding and Scoring

| | Code | Code for Hypothetical 1st | Comment | Fixed or Variable for Sites of Co-population in Given Patient | Scoring (1° = based on the item; 2° = derived from F or SF score) |
|---|---|---|---|---|---|
| System | S# or simply # | S1 or 1 | System code given to each specific system, multisystem disorder and outside database integrated with SHAPE ™ | Variable (may differ at sites of co-population) | 2°: Based on highest score for F or sF within the given S/sS/FC |
| Subsystem | sS# | sS1 | Numbered sequentially within each system | | |
| Feature Category | FC# | FC1.001 | Numbered sequentially within each system. System # (based on predominant system with given FC in given patient) is included prior to decimal. | Fixed (does not differ at sites of co-population) | |
| Feature Subfeature | F# sF# | sF1.0001 | Numbered sequentially within each system. Except for leading letters, no distinction between F and sF. # of system with which F or sF is most commonly associated is included prior to decimal. | | 1°: each F and sF has default score. If F has an sF, then score for F becomes 2° to score for sF |
| Descriptor | D# | D101 | Divided into categories, designated by first digit. | Fixed or Variable | Not scored |

The embodiment of Table 7 is shown in FIGS. 8C and 9C. Alternative embodiments, relying on equivalent S, sS, FC, F, sF, and D progression are shown in FIGS. 8A, 8B, 9A and 9B. A sample step-by-step process for data entry in accordance with this branched-logic mechanism is detailed later in this disclosure with reference to FIGS. 26-31.

Critical aspects of the preferred embodiment shown in FIGS. 8C and 9C include:

1. Primary scoring of features (F) and subfeatures (sF) where each F and sF has a score. If, however, F is followed by an sF, the score for sF predominates and default score for F becomes the score assigned to the sF. For example, a feature such as "recent myocardial infarction" may be followed by the subfeature "6 months ago, stable ($3)" or by the subfeatures "last week ($4)" and "persistent abnormal wall motion ($4)."
2. Progressive coding in association with branched-chain logic with the following unique establishment of fixed and variable code & score components:
   A fixed code for a given item's feature category/feature/subfeature(s) that, in preferred embodiments, remains with the item no matter what aspects of the database or interfaced database it co-populates (unless designated differently by the user).
   A variable proximal portion of the code which is specific for the given bodily system (e.g, Cardiac) and subsystem (e.g., Ischemic Heart Disease) or their equivalent [e.g., wherein the invention treats a grouping such as a Risk indicator as a "system" (discussed in subsequent section of this disclosure).
   An optional prefix.
   An optional suffix.

As will be shown later, the present invention also facilitates uniquely consistent and universal coding for exporting to and integration with other databases.

Options for integrating with compatible databases, with adaptable prefixes and/or suffixes and integrated scoring as above (as discussed below in greater detail).

Options for importing from programs with otherwise incompatible codes and scores or exporting to them (as discussed below in greater detail).

A key advantage of the present invention is that it accomplishes the coding and scoring without "getting in the way." The carefully configured branched logic further allows such processes to be relatively seamless and transparent. The text, code and score conversion index and dictionary allows for automated translation and universality. Instead of requiring repetitive progression down each branch, the present invention provides for default jumps (if a body system is negative) and provides options that obviate the need for user delineation of S/sS/FC/F/sF . . . . For example, a consolidated display of what some might consider all systems and sub-systems—configured to enable options for each subsystem to be viewed on a single screen—is shown in FIG. 32. FIGS. 32.1 and 32.2 indicate that, although not visible during data entry, each of the scored items is associated with a body system, subsystem and feature category coding Additionally, FIG. 32 does not distinguish between F and sF (since they are coded and scored comparably). Items are worded to be user friendly and may actually represent more than one F or F+sF; this would be evident in storage within the database and thereby enable searches based on individual as well as combined features and subfeatures.

Whereas preferred embodiments of the present invention distinguish between scored features and subfeatures vs. unscored descriptors, the user may also elect to select the information provided by a feature but to bypass the prompt to assign the default score or to select a score. That is, the user may select the item without its score. This may offer the advantage of allowing for a more speedy entry of data, in that once the feature with the highest score is selected for a given body system or subsystem, other choices could be selected without concern about scoring. However, the detailed scoring capabilities of the present invention provide for greater detail, greater consistency, and more robust population of the SHAPE™ database and co-population of other sites (e.g., when data are exported to diagnostic and treatment algorithms and related scripts). Furthermore, unless one changes the default scoring (because of his/her clinical findings), the process of scoring is transparent.

The system-based scoring for each of the body's main systems (as may be listed and modified in FIG. 32 and subsequent tables and figures) is done in large part not only to ensure communication consistent with (and superior to) the basic ASA physical status score described above, but also to take into account that without consolidation into a body system or subsystem score, the range of individually scored features and subfeatures would be unmanageable (perhaps accounting for why, to the best of my knowledge, heretofore no one has been able to effectively design a highly detailed, integrative system such as that described herein). Borrowing from an old beer commercial, one might say above SISS™—"better accuracy" and "less filling."

Scores for S, sS, FC, F and sF are represented by $# (as shown in FIGS. 8 and 9 and throughout this disclosure. Descriptors are unique—they provide valuable information but do not significantly affect the severity of the disorder; hence they are not scored. To facilitate their inclusion in the database and accommodate preferences for description terms and expressions, Descriptor codes may be grouped as shown in Table 8.

TABLE 8

A Preferred Embodiment for Coding Unscored Descriptors

| Range of Codes | Nature of Descriptors | Subdivisions | Examples | Sample Codes |
|---|---|---|---|---|
| 101-200 | Time | Time Since Onset | <1 hour | D101 |
| | | | more details | D101a |
| | | | more details | D101b |
| | | | 1-24 hours | D102 |
| | | | more details | D102a |
| | | | more details | D102b |
| | | | 1-7 days | D103 |
| | | | 1-4 weeks | D104 |
| | | | 1-6 months | D105 |
| | | | 6-12 months | D106 |
| | | | 1-5 yrs | D107 |
| | | | 5-10 yrs | D108 |
| | | | 10-20 yrs | D109 |
| | | | >20 yrs | D110 |
| | | | 1$^{st}$ NonspecificType-in | D199 |
| | | | 2$^{nd}$ Nonspecific Type-in | D198 |
| | | Frequency | Hourly | D112 |
| | | | Daily | D113 |
| | | | Weekly | D114 |
| | | | Monthly | D115 |
| | | | . . . | |
| 201-300 | Site | Region of body | Arm | D201 |
| | | Side | Left | D202 |
| 301-400 | Symptoms | Pain | Dull | D301 |
| | | | Sharp | D302 |
| | | Itching | | |
| 401-500 | Signs | Color | Erythematous | D401 |
| | | Texture | | |
| | | Temperature | | |
| 501-600 | Medications | Ineffective in past | Atenolol | D501 |
| 601-700 | Other Therapeutic Interventions | Acupuncture | Without benefit | D601 |

TABLE 8-continued

A Preferred Embodiment for Coding Unscored Descriptors

| Range of Codes | Nature of Descriptors | Subdivisions | Examples | Sample Codes |
|---|---|---|---|---|
| 701-800 | Miscellaneous Hard-coded comments | Source of information | Spouse | D701 |
| 801-900 | Miscellaneous Type-ins or Imports | | | |

Note,
if within a given feature category, the information that would be considered a descriptor in another category, provides scorable information in this new feature category, then it would listed, coded and scored as a feature or subfeature at this site.

The clinical importance of such body system-specific data is suggested by recent data collected by my research team for presentation at the 2006 Annual Meeting of the American Society of Anesthesiologists. Of 220 patients with ASA 3 or 4 physical status, the Cardiac system was the most commonly reported body system to merit such a score; this was followed by the Central Nervous System and Respiratory System. In addition, 30.4% of these patients had two body systems with grade 3 or 4 level of dysfunction, 14.1% had three such body systems and 2.1% had four or more such body systems.

It thus should be evident that the body system-specific scoring introduced herein looks at the overall ASA physical status score as being derived from the scores assigned to individual body systems (with the potential to override this score). These in turn are based upon the highest score(s) assigned to signs, symptoms and/or test results within the given body system (SISS™), typically at the feature or subfeature level. This constitutes a preferred embodiment; however, other mechanisms of consistent assignment and management of scores are within the spirit and scope of this invention. As noted above, scored features or subfeatures are within a feature category of a given subsystem, which is, in turn, a part of a body system (such as CARDIAC).

Co-population and exporting may be at any of the aforementioned levels of branching. When a given item co-populates more than one system, its FC/F/sF (and possibly D) code remains fixed while the S/sS portion of the code changes (as shown in Table 7). The distinction between body systems and subsystems should not be considered absolute or restrictive when applied to the present invention; but once a decision is made it should be maintained so as to ensure consistent coding. Thus, even though it is a specific condition, diabetes is coded as subsystem and treated as such in applications of the program (e.g., co-population and exporting).

Cumulative Scores

The ensuing sections will expand upon the present invention by describing:
1. Other aspects of SISS™ as they relate to scoring and coding
2. Describing the unique far-reaching, multifactorial yet uniform nature of the inventive program.

The SISS™ scoring permits cumulative scoring based upon the number of disorders (as may be ascertained from the number of positive feature categories) or diseased body systems and their degree of dysfunction in what is called herein the SHAPE™ Aggregate Disorders (SAD™) score (FIG. 3).

Among its many applications is the integration of clinical findings and test results. For example, the provisions for integrated details afforded by the present invention uniquely enable one to overcome the problem of introducing excessive subjectivity and potential bias when viewing findings in the context of other conditions and risk factors. For example, nonspecific ST-T (NSST) wave changes on an EKG likely would be dismissed as not clinically significant in an otherwise healthy individual without significant risk factors for coronary artery disease. However, they might prompt a cardiology evaluation (and stress test) in the presence of clinical findings or risk factors. The present invention offers potential ways for a healthcare provider or institution to address this issue:

List scenarios that constitute class 2 and class 3 findings (as shown for $CARDIAC_{EKG}$ in FIG. 32); however, a complete list of modifiers may be exhaustive and, at times, inconclusive.

Simply score the EKG finding as class 2 but automatically convert it to class 3 (which may be annotated to indicate that it has been increased as a result of integrating factors as with the symbol "Σ3") if selective factors exceed a certain cutoff; i.e., if the nonspecific risk factors and indicators for ischemic heart disease (under CARDIAC in FIG. 32) exceed a score of 2 or summate to an established cutoff. This score-driven means of basing a decision on objective criteria minimizes the current likelihood of bias that may be introduced if one simply has to make the decision that the presumed importance of the EKG should be increased because of "likely significant clinical factors."

Don't worry about the score for EKG; simply cumulate scores from relevant systems, subsystems and/or feature categories to determine score-driven actions.

Certain issues that have been taken into account for implementing the current method(s) for scoring and cumulating multiple body systems in the present invention include:

a) ensuring identification and appropriate cumulation when more than one body system has a given score (e.g., CNS, CARD and RESP all receive a score of 3).

b) preventing indiscriminant cumulation by simply adding scores such that three body systems with a score of 2 generate a higher cumulative than a single system with a score of 4 (which virtually all would agree constitutes a degree of illness more severe than three body systems with a score of 2).

These issues may be addressed in a number of ways. Multiple body systems with the same score (for different disorders) may be identified at the end of the History and Physical (FIG. 4) or as by superscripts in the ASPIRIN™ display (FIGS. 6, 7B, and 7C). If the user wishes to determine a cumulative index such as SAD™, the present invention enables assignment of an incremental value to the "modified ASA score" when there are multiple body systems that warrant a given score. For example, if both cardiac and respiratory systems were scored 3, then one could assign a cumulative score of 3.2 or $3^2$ (in accordance with a preferred embodiment, the decimal or superscript has been elected to reflect the number of body systems). If three body systems were scored 3, this could be represented as 3.3 or $3^3$. An alternative embodiment entails adding 0.2 for each additional ASA 4 body system and 0.1 for each additional ASA 3 body system. Alternatively, if one wishes to avoid a situation where an individual with three "2's" or two "3's" is assigned a higher cumulative score than an individual with a "4" (in that almost all would agree that the individual with the "4" is far sicker), one can use a formula (i.e., a correction factor) to reduce the impact when multiple body systems are assigned the same score. As for other aspects of the invention, the abundance of potential data integration and analysis can be generated from the "routine" entry of clinical data.

An alternative embodiment for scoring (regardless of the number of body systems entails conversion of the ordinal 1-5 scores to points which are reflective of relative illness and impact. For example, based on analyses of data from the initial applications (described above), preferred embodiments will enable 1-5 scores to be converted to points that take into account the dramatic rises in morbidity, length of stays and costs at greater degrees of illness (e.g., 2→2, 3→7, and 4→25 points). Comparable points may be assigned to the 1-5 surgical scores.

Thus, for example, scores of 3 for CARD and ENDO could provide a variety of SAD™ scoring options including: 6 (simple addition), 3.2 (modified for multiple systems), 14 (addition of 7+7 points), 7.6 (points modified for multiple systems).

Managing Scores and Codes for Disorders Affecting Multiple Body Systems:

The present invention is also designed to address two related vital issues—what to when a disorder of one body system also affects another body system or when more than one system is affected by a "Multisystem" condition. Ways in which this is accomplished by the present invention include:

a) providing a mechanism for designating whether multiple body systems affected by a given multisystem disorder such as those listed at the bottom of FIG. 32 should be scored independently or dependently b) providing a mechanism for designating whether the scores for a body system that is affected by another body system should be cumulated.

Preferred embodiments of the present invention address these in the following manner. When a feature or subfeature that is found in more than one body system (i.e., it constitute a disorder of more than one body system), SHAPE™ provides the following:

Codes with identical fixed FC/F/sF . . . portions of the code populate each site, with different variable S/sS portions.

Identification of what generally is the predominant system (documented with the system # at the beginning of the "FC" code that groups and identifies all feature categories within a given system) regardless of where the item currently lies.

Easy access to the body system and body subsystem of a given F or F/sF by clicking on the feature or subfeature to display the proximal S/sS/FC pathway.

Option to include combination system codes in the variable portion of the code with the designations of relative importance and directionality shown in Table 9 (below).

The invention provides a mechanism for designating scores for each of the body systems associated with a given feature or subfeature. Where two or more specific body systems are involved, unless otherwise specified by the user (see below), overlapping information would impact on the score of each system and both would be included in an inventive cumulative score, such as, SAD™. Examples of such interactions include:

a) Endstage Renal injury as a result of Hypertension—some or all of the Renal system score would be due to hypertension-induced renal injury; some or all of the Hypertension score would be due to its systemic impact on the kidney.

b) If a patient has vomiting which leads to a fluid and electrolyte disturbance, then both the GI system and the Fluid & Lytes system would reflect the conditions. Since they otherwise are independent systems, both likely would be included in a cumulative SAD™ score. In support of this decision, correction of the Fluid & Lytes problem would not necessarily affect vomiting; likewise, if vomiting suddenly stopped, it is likely the Fluid & Lytes problem would require significantly more time to resolve and might require separate therapy. (While in preferred embodiments the systemic impact score for F and sF would be the same in both systems, the local impact score may differ and the overall system scores may differ (depending on other F and sF).

Once the healthcare provider has reached the FC level for an item affecting multiple body systems, he/she may elect to continue within the given body system or jump to the system primarily affected by the disorder since this would likely have more hard-coded F, sF and ssF. In many cases, the computer will automatically jump but will give the user the option of determining how to weight the different systems (Table 9).

TABLE 9

When A Disorder of One System Affects Another System(s)

| Name of Current system | Name of Other System | Name of Other System | Name of Other System |
|---|---|---|---|
| Appearance in Note: | | | |

Normal
[in brackets]
type-in text

TABLE 9-continued

When A Disorder of One System Affects Another System(s)

| Name of Current system | Name of Other System | Name of Other System | Name of Other System |
|---|---|---|---|
| Co-populate ASPIRIN ™ and Related Displays Export to Diagnostic and Treatment Algorithms Include in cumulative SAD ™ score | | | |

Combined Code

Multisystem disorders present particularly challenges in that they do not necessarily have their own body "system." In preferred embodiments, the Multisystem paradigms can be accessed by the following means:

Selecting "Multisystem Disorder" as if it were a specific body system. This then jumps to a screen that allows one to select from Multisystem Disorder categories such as those listed at the end of FIG. 32 (specifically, FIG. 32.18) (or to type-in). The next screen would list the Multisystem Disorders within the selected category. Then, the user is prompted to select information about the given disorder and/or select specific body systems that are affected. The computer then jumps to the selected screens which are completed in routine fashion with the addition of the checklist shown in Table 10. The code for entries into the body system is then modified to reflect that the body system is affected by a Multisystem Disorder (as may be accomplished by including the Greek letter [shown at the bottom of FIG. 32.18 [followed by a number as a prefix to the body system code).

Proceeding normally through the Review of Systems until one reaches a body system that is affected by a Multisystem Disorder. A "Multisystem Disorder" option is provided within each system; selecting it will initiate a series of steps comparable to those noted above.

TABLE 10

MULTISYSTEM TABLE (check appropriate choices)

| Name of Multi-system Disorder | Name of Affected System | Name of Affected System | Name of Affected System |
|---|---|---|---|
| Appearance in Note: | | | |

Normal
[in brackets]
type-in text
Co-populate ASPIRIN ™ and Related Displays
Export to Diagnostic and Treatment Algorithms
Include in cumulative SAD ™ score
Weighting Code (vs. Multi-system Disorder):
=
>
>+
(Multi-system Condition no longer present; only sequelae remain)

Table 10 includes a prompt to define a "Weighting Code (vs. Multisystem Disorder) for each body system affected by the Multisystem Disorder. This addresses a major issue that otherwise can plague a data entry program. When a specific body system (e.g. "Cardiac") is affected by a multisystem condition (e.g., "Amyloidosis"), the interaction is more complex than between two specific body systems because the user must determine if the multisystem condition's systemic impact is:

solely due to its effect on Cardiac (—could be designated "=" in one of the multiple potential forms of dual-system designation that are consistent with the inventive system);

due to multiple effects on specific body systems, none of which merits a greater score than its cited effects on the Cardiac system (—could be designated as "+"); or due to factors wherein the multisystem disorder may have greater overall systemic impact than the effects cited for specific body systems such as Cardiac (—could be designated as "+>"). An example might be supermorbid obesity (typically assigned a score of 3) without significant organ dysfunction; the multisystem condition in and of itself may have significant impact during and after surgery. Likewise, fulminant amyloidosis may receive a higher score than its current manifestations on specific systems.

Unless otherwise specified, the systems affected by multiple conditions annotated with a "'+" or "+>" would be included in a cumulative SAD™ score.

Events Such as Surgery

SHAPE™'s text, code and inventive score can be applied to the impact of a variety of challenges and interventions, including surgery, trauma, and therapies. Consistent with the focus on embodiments addressing perioperative concerns, the embodiments described below will focus on the impact of surgery.

Surgical Risk & Invasiveness:

To be consistent with the 5-point ASA PS system, a five tiered classification scheme is used for ranking of surgical risk and invasiveness (or SHAPE™ Overall Cutting Upset (SOCU™)) as identified in the second letter in ASPIRIN™ (S) as described above in accordance with the present invention (See Table 11a). The lowest risk score of 1 would be appropriate for superficial procedures such as a breast biopsy which may require minimal sedation (comparable to the "low-risk" classifications of the ACC/AHA Guidelines and the "minimally invasive" class of Pasternak rankings). A score of 5 is assigned to highly invasive intrathoracic and intracranial procedures, those associated with massive blood loss (>1500 mL) as well as any emergent major operation (consistent with the ACC/AHA Guidelines "high-risk" classification and Pasternak's most invasive category). Scores of 2 through 4 represent the spectrum of risk between these two extremes. Since it has been concluded that the "intermediate" ranking of the ACC/AHA was too broad, it has been subdivided, in accordance with a preferred embodiment of the present invention, in accordance with the surgical invasiveness score proposed by Pasternak as well as by taking into consideration anesthetic requirements and the potential for otherwise unsuspected pulmonary or hemodynamic changes. Conversely, the score proposed by Pasternak is not consistently translatable to the low, intermediate- and high-risk ACC/AHA classifications and thus not readily applicable to established risk assessment indices and therapeutic guidelines, which include the ACC/AHA classification as to when consultation with a cardiologist is indicated prior to surgery. The 1-5 score of overall surgical risk and invasiveness (referred to as the SHAPE™ Overall Cutting Upset or SOCU™ [pronounced "sock you"] score) introduced herein is designed to provide greater precision and greater relevance to perioperative events than the ACC/AHA classifications, while maintaining compatibility with indices and guidelines that utilize the ACC/AHA classifications. In accordance with the proposed 0-5 ASA physical status score, SOCU™ would have 0=no procedure.

The integration of the 1-5 gradations of patient condition and risk/invasiveness has been evaluated in 878 patients by the inventor and colleagues at his institution (FIG. 1) and enabled creation of models that predict a substantial portion of the variation in hospital charges, length of stay, and anesthesia billing units. Both factors were positively correlated with each of the three outcome variables. For hospital LOS (length of stay), the maximum amount of variation that could be derived from knowledge of both factors was 56.7%; this was possible by defining an index equal to 0.3(ASA PS)+0.7(SOCU™). For hospital charges, the maximum amount of variation predicted by ASA PS and SOCU™ was 45.0% when an index equal to 0.35(ASA PS)+0.56(SOCU™) was used. Although both ASA PS and SOCU™ were positively correlated with anesthesia billing units and had independent predictive value, in combination, only the impact of SOCU™ was statistically significant, predicting 68.0% of the variation. (Note, this is a derivation data set that has not yet been validated in a prospective study). Moreover, the data confirm that while helpful, simply looking at the "A" and the "S" of ASPIRIN™ is not sufficient.

Another unique inventive feature is the body system-specific coding and scoring of the surgical risk/invasiveness score in a manner comparable to that for the inventive SISS™ score of patient condition. The inventive SHAPE™ Intersystem Cutting Upset (SICU™) score is employed in accordance with the present invention to delineate the intersystem impact of the planned surgical procedure regardless of the patient's underlying condition (DIFF). As per recording, communication and display based on SISS™, the body systems which are likely to be affected by the given surgery based on SICU™ can be documented for the SHAPE™ database and those likely to be most severely affected can be annotated in the ASPIRIN™ display. That is, those scored ≥3 can be cited as superscripts after the second number (corresponding to "S" for surgical risk and invasiveness) in the display. A representative embodiment for the SICU™ scoring is provided in Table 11b and shown in FIGS. 6B and 7C. Unless noted to be otherwise, the SICU™ score is based on the potential upset of each body system's role in maintaining overall patient condition (i.e., its overall systemic effect). Hence, it is possible that a vital body system such as Respiratory may receive a higher SICU™ score than the body system actually undergoing the given surgery; e.g., if a large incision is required to removal an intraabdominal mass and there is subsequent pain and compromised breathing. Additionally, removal of a kidney from someone who already requires dialysis may receive a lower KUBU (kidney, ureter, bladder, and urethra) score than less extreme renal surgery on someone whose kidneys still are functional (since the change from normal function to decreased function in the latter is of greater systemic impact). Likewise, a patient with a sarcoma of the leg may be assigned a higher score for systemic impact than an individual who underwent amputation and has remained tumor-free. Alternatively, as will be detailed later for disorders, the inventive system can be modified to score local as well as systemic impacts of an intervention such as surgery. In which case, SICU™ score likely would be higher at the site of the surgery.

TABLE 11a

Surgical risk/invasivenesss stratification for SHAPE ™ classification-also known as the SHAPE ™ Overall Cutting Upset (SOCU ™)

| Score and Description | Examples |
|---|---|
| 1 MINOR<br>Little or no blood loss, minimally invasive | Superficial procedures: Breast/Skin biopsy$^L$. Cataract surgery$^L$. Lithotripsy$^L$. Pacemake r$^{l,s}$. Colonoscopy$^L$. Cystoscopy/Bladder biopsy. Ureteroscopy. Simple D&C. Early D&E* Simple mastectomy. Simple inguinal hernia. Arthroscopy. Foot/Ankle surgery. |
| 2 LOW INTERMEDIATE<br>Minor + ↑risk of intraop instability; or<br>Relatively noninvasive Intermediate | Complex "Minor " Limited Laparoscopy (diagnostic, cholecystectomy), Hysteroscopy. TUR P$^s$. Rhinoplasty/Uvulopalatopharyngoplasty/Sinus surgery. Laser Laryngoscopy/Bronchoscopy. Simple Oral Mass excision. Tonsillectomy. Parotidectomy. Mastoidectomy. Tympanoplasty. Mastectomy or Melanoma w/nodes. Transmetatarsal Amputation. Simple Thyroidectomy, Parathyroidectomy. Vulvectomy, Vaginal Hysterectomy. Pubovaginal sling. Mid-term D&E*. Free fla p$^s$ AV fistul a$^s$. Ventriculo-peritoneal shun t$^s$. Feeding Tube. ORIF (not femur or hip ).$^s$ IC D$^{l,s}$ |
| 3 INTERMEDIATE<br>Moderately invasive, EBL 500-1500 ml | Straightforward Head and Neck surgery (functional neck dissection, extensive thyroid). Limited Intraperitoneal (open cholecystectomy, hysterectomy, simple nephrectomy, colectomy, prostatectomy). Late D&E*. Routine Spine (laminectomy, fusion). Hip or femur fx. Major Arthroplast y$^s$ (knee/hip/shoulder). Extensive Endoscopic procedure (gastric bypass, Nissen fundoplication*). Splenectomy. Major Skin and<br>Soft Tissue surgery (radical mastectomy w/flap, extensive melanoma). Carotid endarterectomy. Mediastinoscopy. Major Amputation (BKA or AKA). Facial Fractures (stable). Cranioplasty w/brain exposure. |
| 4 HIGH INTERMEDIATE<br>Intermediate + ↑risk of intraop instability due to blood loss, hypoxia, CNS effects; or<br>Major w/less risk of cardiopulmonary or CNS compromise | Video-assisted thoracoscopy. Esophagectomy. Pulmonary lobectomy. Peripheral vascular surgery (limbs) Limited intracranial surgery (e.g., acoustic neuroma, pituitary). Complex Head and Neck surgery (e.g., radical neck), Intraperitoneal (e.g., Whipple, ischemic bowel,* radical cystectomy, renal transplant). Spinal rodding. Seizure mapping. |
| 5 MAJOR<br>Highly invasive; major fluid shifts and blood loss; likely cardiac, pulmonary and/or CNS involvement) | Emergency* "high intermediate". Extensive cardiothoracic procedures. (pneumonectomy, CABG, valve replacement). Major vascular surgery (e.g., aorta). Major Intracranial procedures. Major transplant (heart, lung, liver, pancreas) |

"*indicates ↑ aspiration risk. Procedures that consistently are amenable to local and/or conscious sedation (e.g., extracorporeal shock wave lithripsy) have been annotated with an "L," in that they likely would not be influenced by anesthesia-related factors such as a difficult airway. Although qualifying as "minor" or "low-intermediate," certain procedures are associated with features that may disproportionately influence their effects on outcome variables such as length of stay and total hospital costs independent of surgical risk/invasiveness; examples, which have been annotated with a "S," include those requiring postoperative intravenous antibiotics because of hardware insertion or prolonged observation to ensure flap viability, surgical effectiveness, or device functioning. In such cases, the effect of coexisting morbidities on length of stay and costs may need to take into account obligatory lengths of stay.

TABLE 11b

SHAPE ™ Itemized Cutting Upset (SICU ™) Score.

| Surgical Procedure (with SOCU ™ score in parentheses). Selected surgical procedures are scored w/and w/o epidural for improved postoperative analgesia. | SHAPE ™ Itemized Cutting Upset (SICU ™) Score for upset by surgery (on given system's role in maintaining overall patient condition) is ≥2* | | | | | | | | |
|---|---|---|---|---|---|---|---|---|---|
| | CNS | CNSischemia | ENDO-CRINE | ENDOdiabetes | CARDIAC & BP | CARDischemia | VASCULAR | RESPI-RATORY | HEP PANC SPLEEN |
| Cataract (1) | | | | | | | | | |
| Arthroscopy (1) | | | | | | | | | |
| Laparoscopy (2) | | | | | 2 | 2 | | 2 | |
| TURP (2) | 2 | | | | | 2 | | | |
| Vulvectomy (2) | | | | | | 2 | | | |
| Radical Hysterectomy | | | | | | 3 | | 3 | |
| Extensive Thyroid (3) | | 2 | | | | 2 | | | |
| Colectomy -- open (3) | | | | | | 3 | | 3 | |

TABLE 11b-continued

SHAPE ™ Itemized Cutting Upset (SICU ™) Score.

| Procedure | | | | | | | |
|---|---|---|---|---|---|---|---|
| Carotid Endarectomy (3) | 3 | | 3 | 3 | 3 | | |
| Video-assisted thoracoscopy (4) | | | 3 | 3 | | 4 | |
| Periph Vasc Surg (4) | | | 4 | 4 | 3 | | |
| Abdominal Aortic Surgery (5) | | | 5 | | 5 | 4 | |
| Whipple Procedure (4) | | | 3 | 3 | | 4 | |
| Whipple Proc w/epidural (4) | | | 3 | 3 | | 3 | |
| CABG open heart (5) | 4 | 4 | 5 | 5 | | 5 | |
| Pneumonectomy (5) | | | 4 | | | 5 | |
| Pneumonectomy w/epidural analgesia (4) | | | 4 | | | 4 | |

Surgical Procedure (with SOCU ™ score in parentheses). Selected surgical procedures are scored w/and w/o epidural for improved postoperative analgesia.

SHAPE ™ Itemized Cutting Upset (SICU ™) Score for upset by surgery (on given system's role in maintaining overall patient condition) is ≥2*

| postoperative analgesia. | GASTRONTEST. | KID URET BLAD | FEM & MALE | NMS & SKIN | EENT & AIRWAY | HEME/BLOOD | FLUID & ELEC | MULTISYSTEM | PAIN |
|---|---|---|---|---|---|---|---|---|---|
| Cataract (1) | | | | | | | | | |
| Arthroscopy (1) | | | | | | | | | |
| Laparoscopy (2) | | | | | | | | | |
| TURP (2) | | 2 | 2 | | | | 2 | | |
| Vulvectomy (2) | | 2 | 2 | | | | | | 2 |
| Radical Hysterectomy | | 2 | 2 | | | 3 | 3 | | 3 |
| Extensive Thyroid (3) | | | | | 3 | 2 | | | |
| Colectomy -- open (3) | 2 | | | | | 2 | 3 | | 3 |
| Carotid Endarectomy (3) | | | | | | | | | |
| Video-assisted thoracoscopy (4) | | | | 2 | 3 | | | | |
| Periph Vasc Surg (4) | | | | | | 2 | | | 3 |
| Abdominal Aortic Surgery (5) | 2 | 3 | | | | 4 | 4 | | |
| Whipple Procedure (4) | 4 | | | | | 3 | 4 | | 4 |
| Whipple Proc w/epidural (4) | 4 | | | | | | 4 | | 3 |
| CABG open heart (5) | | 4 | | | | 4 | 4 | | 4 |
| Pneumonectomy (5) | | 3 | | 3 | | 4 | 4 | | 5 |
| Pneumonectomy w/epidural analgesia (4) | | 3 | | 3 | | 4 | 4 | | 3 |

*As detailed in text, one may elect to include local as well as systemic effect (e.g., the local effect of hysterectomy is greater than its systemic effect).

Together, the itemized body system scores for patient condition (SISS™) and surgical impact (SICU™) provide a heretofore unavailable:

Mechanisms for more effective prediction and assessment of the ability of specific body systems to meet and withstand the demands of surgery (i.e., SHAPE™ numeric assessment of resilience).

Mechanisms for communication of such information

Bases for score-driven body system-specific, as well as general, diagnostic and treatment algorithms (i.e., guidelines for obtaining a cardiology consult and/or when to initiate cardioprotective beta-blocker therapy)

Figure 5:
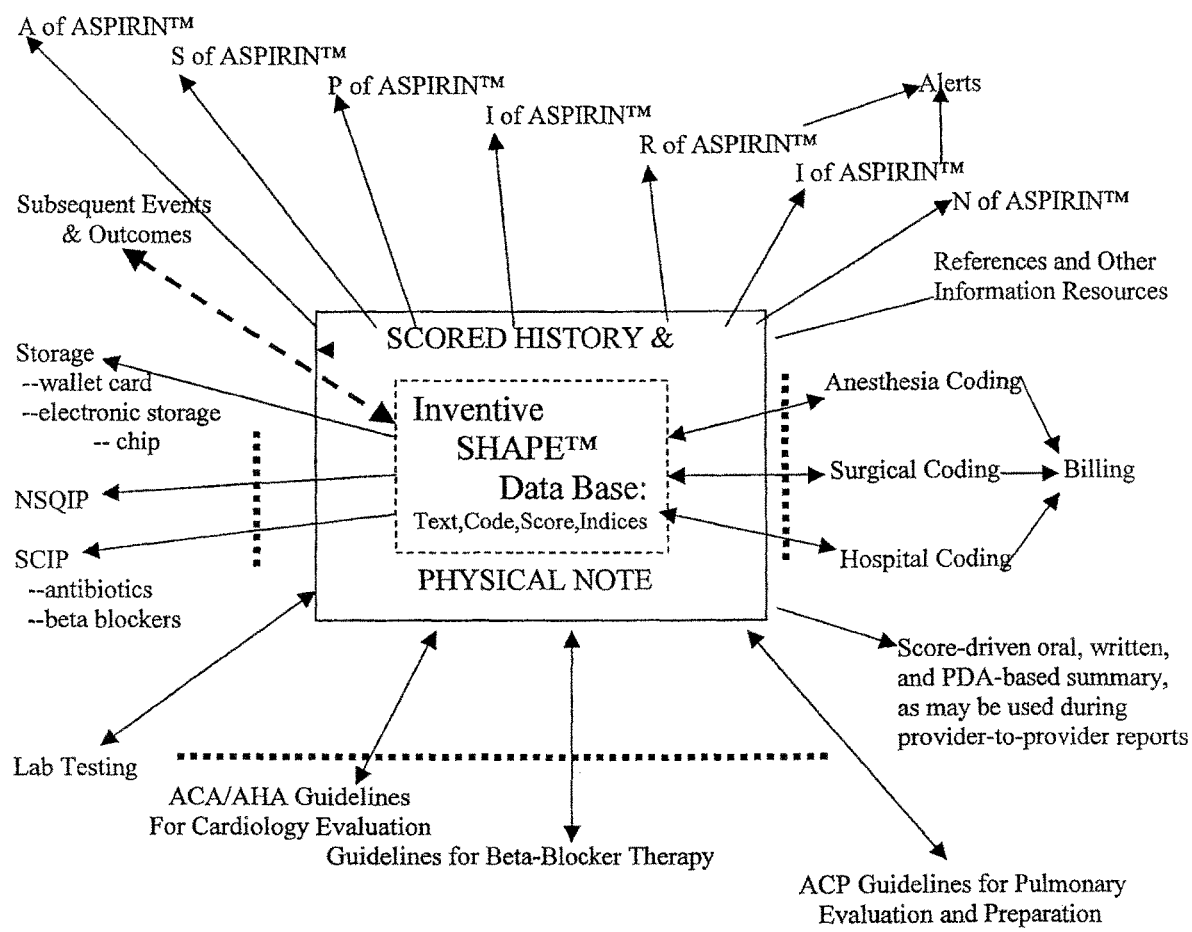
FIG. 5 shows the integrative potential of the inventive score-driven system and method just based on the information provided in a typical workup (e.g., the note displayed in FIG. 4), with a common language and scoring system that otherwise is not available. Dotted line represents the text code and score conversion index and dictionary which provide common language, coding and scoring among SHAPE™ and established databases, algorithms and scripts. Each item contains information generated based upon text, code and score (with links based on the text code and score conversion index and dictionary) entered during performance of the history and physical exam. Dashed outline shows fluidity between database and history and physical such that a one-time entry can co-populate the official note as well as the other sites of interaction. Thick dashed line represents unique bidirectional relationship between SHAPE™ and "Subsequent Events and Outcomes"—SHAPE™ not only provides data to predict outcomes but also may be updated (with associated timestamp) based on events and outcomes.

Accumulation of evidence-based guidelines for specific medical and surgical disorders as well as the myriad applications summarized in Table 3 and FIGS. 3 and 5

A key feature of the present invention is that it accomplishes this with its unique foundation of itemized scoring—a potential enormous gain for relatively little user effort that does not entail retrospective assessments of variables and assignments of scores.

Other Inventive Scored Assessments: the "PIRIN" of ASPIRIN™

SHAPE™'s text, code and inventive score also can be applied to items which, often because of the given context (e.g., perioperative), constitute a risk or management issue that is disproportionate to—or not reflected by—their "A" or "S" score. The literature is replete with recommendations, some of which are evidence-based, as to how to characterize, plan for and manage what may be termed "non-ASA score, non-surgical invasiveness factors" that affect anesthetic complexity and potentially impact of patient morbidity. However, to the best of my knowledge, a system is lacking for integrating the factors, scoring them in a consistent manner, incorporating them in a consistent communicable relative score, and applying them for score-driven decisions and actions—i.e., for using them in the manner(s) introduced herein.

The embodiments described below focus on anesthesia and overall perioperative concerns. As those skilled in the art will certainly appreciate, comparable indices could be established for other settings.

Physical Factors Primarily Affecting Ventilation & Intubation Predictors:

For anesthesiologists, airway issues are paramount—even if they have minimal impact on daily life—and hence are assigned ASPIRIN™'s "P" ("Physical factors that affect ventilation") and "I" ("Intubation factors and related issued") categories and inventive scores as summarized in Tables 12a and 12b and described below.

As discussed below, a letter/alphanumeric scored code is disclosed for other issues that have a potential impact that may be disproportionate to their "A" or "P" relative score. These "Risk indicators ("R" of ASPIRIN™) may generate score-driven communication, preparation and planning based upon an item-specific score or a generalized cutoff (e.g., ≥3).

Physical Factors Primarily Affecting Ventilation & Intubation Predictors:

Consistent with the separation of mask ventilation and intubation issues in difficult airway algorithms, the present system opts to provide groupings of "Physical factors affecting ventilation" and "Intubation factors and related issues". A list of risk factors was garnered from published studies and clinical experience, with an appreciation that, while prior investigators commonly excluded high-risk patient populations, such as obstetrical patients and those with known airway pathology, el-Ganzouri A R, McCarthy R J, Tuman K J, Tanck E N, Ivankovich A D, *Preoperative airway assessment: predictive value of a multivariate risk index*, Anesth Analg. 1996; 82(6):1197-1204; Langeron O, Masso E, Huraux C, et al, *Prediction of difficult mask ventilation*, Anesthesiology 2000; 92(5):1229-1236; Yildiz T S, Solak M, Toker K, *The incidence and risk factors of difficult mask ventilation*, J Anesth. 2005; 19(1):7-11; Bellhouse C P, Dore C, *Predicting difficult intubation*, Br J Anaesth 1989; 62(4)469; Combes X, Le Roux B, Suen P, et al, *Unanticipated difficult airway in anesthetked patients: prospective validation of a management algorithm*, Anesthesiology 2004; 100(5):1146-50; Tse J C, Rimm E B, Hussain A, *Predicting difficult endotracheal intubation in surgical patients scheduled for general anesthesia: a prospective blind study*, Anesth Analg. 1995; 81 (2):254-258; Turkan S, Ates Y, Cuhruk H, Tekdemir I, *Should we reevaluate the variables for predicting the difficult airway in anesthesiology?*, Anesth Analg. 2002; 94(5):1340-1344; Wilson M E, Spiegeihalter D, Robertson J A, Lesser P, *Predicting difficult intubation*, Br J Anaesth. 1988; 61(2):211-216; Yamamoto K, Tsubokawa T, Shibata K, Ohmura S, Nitta S, Kobayashi T, *Predicting difficult intubation with indirect laryngoscopy*, Anesthesiology 1997; 86(2):316-321. a score designed for integrative assessment and communication would have to account for these patients. Points for each item were tentatively assigned based on perceived impact. The individual factor and cumulative points for both ventilation and intubation are summarized in Tables 12a and 12b (collectively referred to as Table 5), with the realization that factors often overlap.

As noted in Tables 12a and 12b, it is possible to accumulate a score greater than 5 for the "Physical factors affecting ventilation" and "Intubation factors and related issues" groupings. The actual total, as well as the components, may prove valuable for quality assurance, outcome, and resource studies. In accordance with a preferred embodiment of the present invention, 5 has been tentatively set as a cutoff, so as to establish a level where most anesthesiologists would agree that there is sufficient concern to notify all parties as to the need for careful reassessment and planning (for example, availability of equipment for possible fiberoptic intubation, appropriate allocation of time and staffing). In addition, assigning a five-point scale maintains the consistency of the scoring system for patient condition (modified ASA class) and surgical risk (modified ACC/AHA class). The actual data are stored in the database for subsequent applications as well as to provide greater information to the patient's caregivers.

TABLE 12

Factors likely to affect airway management, divided for purposes of presentation into "Physical factors which affect mask ventilation" (4a) and "Intubation predictors" (4b). For each table, scores from each of the five categories are summated. For purposes of consistency with the ASA score and surgical risk/invasiveness score, a summated score >5 may simply be displayed as a 5. A score of this magnitude should alert the O.R. team to the potential need for special planning.

| Physical factors which affect mask ventilation | | | |
|---|---|---|---|
| Age | Score | History & Physical | Score |
| 15-55 yrs | 0 | None | 0 |
| 56-80 yrs | 0.5 | Habitual snoring | 0.5 |

TABLE 12-continued

Factors likely to affect airway management, divided for purposes of presentation into "Physical factors which affect mask ventilation" (4a) and "Intubation predictors" (4b). For each table, scores from each of the five categories are summated. For purposes of consistency with the ASA score and surgical risk/invasiveness score, a summated score >5 may simply be displayed as a 5. A score of this magnitude should alert the O.R. team to the potential need for special planning.

| | | | |
|---|---|---|---|
| >80 yrs | 1.0 | Possible sleep apnea | 2 |
| | | Probable/Definite sleep apnea | 3 |

| BMI | Score | Internal/External Airway Pathology: | Score |
|---|---|---|---|
| <30 | 0 | Present, unlikely to be significant | 0.5 |
| 31-45 | 1 | Possible moderate deformity | 2 |
| 46-60 | 2 | Obstruction/Impending Obstruction | 5 |
| >60 | 4 | | |

| Miscellaneous Factors | Score |
|---|---|
| Large Beard and/or Edentulous | 0.5 |
| Moderately distorted facial anatomy | 2 |
| Significantly distorted facial anatomy | 5 |
| Persistent Aspiration Risk (e.g., term pregnancy, Dencker's, esophageal narrowing, obstruction) | 5 |

TABLE 12(b)

Intubation Predictors and related factors[a]

| Mallampati Class | Score | Ability to Prognath | Score |
|---|---|---|---|
| I or II | 0 | No overbite, good extension | 0 |
| III | 1 | No overbite, poor extension | 1 |
| IV but improves w/vocalizing | 3 | Overbite, good extension | 0.5 |
| IV with no improvement w/vocalizing | 4 | Overbite, poor extension | 2 |
| | | Can't understand request to prognath | 0.5 |

| Mouth Opening | Score | Neck (oextension from neutral) & Sizec | Score |
|---|---|---|---|
| >4 cm* | 0 | >60, normal size | 0 |
| 34 cm* | 1 | >60, short neck | 0.5 |
| 2-3 cm | 4 | 30-60, normal neck | 0.5 |
| <2 cm | 5 | 30-60, short neck | 2 |
| | | 10-30, normal neck | 3 |
| | | 10-30, short neck | 4 |
| | | <10 or immobilized | 5 |

| Thyromental Distance | Score |
|---|---|
| >6 cm | 0 |
| 4-6 cm | 0.5 |
| 3-4 cm | 1 |
| 2-3 cm | 2 |
| <2 cm | 4 |

[a]= Score may be modified by prior intubation experiences: moderate difficulty (3), pronounced difficulty (4), impossible (5); and, if h/o easy intubation with no subsequent anatomical change, then annotate score with an "*"
TMJ = temporomandibular junction Other Risk Indicators—Anesthetic Risk—Letter Code for Risk Indicators.

Even with the inclusion of an airway risk score, the combination of modified ASA physical status and surgical risk still fails to address certain conditions that may pose additional risk or added complexity to anesthetic/perioperative management. These "Risk indicators" include anesthesia-specific, perioperative-specific, and more general conditions based upon score-driven population of entries such as Allergies, Medications, Prior Anesthetics, Social Habits, Review of System, Physical Exam and Laboratory reports. As detailed in FIG. 11 and shown in portions of FIGS. 3, 4, 6, 7C, 20 and 24, a component of the present invention is a letter/alphanumeric scored code for such issues that may have a condition that is disproportionate to their "A" or "P" or "I" relative score. The Risk indicator score that is assigned [SHAPE™ Alphanumeric Score for Risk Indicators (SASRI™)] often depends on the context (e.g., it may be higher for pre-anesthetic care than it would be for chronic medical care). Higher scores provide an indication of potential concerns for the clinicians involved with the patient's care and may be accompanied by a score-driven email notice, phone call or page as may be based upon an item-specific score or a generalized cutoff (e.g., ≥3).

SASRI™ is a major improvement over existing systems wherein the perioperative impact of a clinical condition such as malignant hyperthermia, which does not pose a physical limitation on daily life, is underestimated by the ASA physical status score. Hence, without effective communication, an anesthesiologist may not be aware of this issue until he/she reviews the chart prior to initiating the anesthetic. Even when a disorder would otherwise be evident, the score-driven categorization of specific features by SASRI™ also is central to the value of the inventive Risk indicators. For example, although the risk associated with the underlying medical condition that prompted insertion of a device such as an automatic implantable cardiac defibrillator (AICD) would have been addressed in the assignment of ASA physical status and, more specifically the system-specific ASA status (via SISS™ introduced herein), the presence of an AICD itself (and hence an alert about the need to prepare and plan for it) might not be communicated as effectively in the absence of the Risk indicator.

Examples of scoring Risk indicators are shown in FIG. 11. The generic SASRI™ scores in FIG. 11 facilitate tabular display but may be supplemented with graded scores that are more specific for a given condition. For example, adverse/allergic reactions to medications may be categorized as:

1=probably not significant risk factor; 2=potentially significant; if applicable, exposure to trigger should be minimized or avoided (common cutoff for co-population of Interim Information and Issues); 3=potentially significant; may require pretreatment; if applicable, avoid exposure (common cutoff for display); 4=likely significant; may require pretreatment; if applicable, avoid exposure; 5=critical or likely critical risk factor that may not be totally avoided The precise mechanism varies for different sources of input. For Allergies, when a drug and the accompanying reaction are selected, a default score is provided, with an option (e.g., dropdown menu) to alter that score, consistent with other areas of the inventive program. For issues such as smoking and alcohol, user options include:

selecting the hard-coded options that correspond to the different breakdowns (e.g., 3-4 drinks/day, current).

entering more specific information (e.g. 3.5 py), which the computer will store to preserve detail but also categorize under "1-5 py" for scoring, reporting, and analyses.

The healthcare provider is also prompted to rate the severity of the signs and symptoms attributable to smoking (which may be equivalent to (and co-populate) that for the features and subfeatures selected under the "RESPIRATORY" system).

The Risk indicator score that is assigned [SHAPE™ Alphanumeric Score for Risk Indicators (SASRI™)] often depends on the context (e.g., it may be higher for pre-anesthetic care than it would be for chronic medical care).

Because the score assigned to Risk indicators takes into account the subclinical impact of risk factors and the impending impact of surgery, a given feature may have a higher SASRI™ than SISS™ score—e.g, cigarette smoking (which has the potential to have serious insidious impact before causing comparable signs and symptoms).

The risk of aspiration pulmonary aspiration of gastric contents is of a magnitude in the perioperative period that it is worth documenting with a SASRI™ score, even though it already is partly addressed in the Physical factors affecting mask ventilation score.

Potentially dangerous abnormal laboratory test results (which are graded on a test-by-test basis as shown in FIG. 17 can be grouped under this heading to facilitate a last-minute review of critical data (as opposed to simply being listed under "Laboratory Tests").

Medications that need to be changed in the context of an upcoming challenge such as surgery. When medications are entered during the basic history and physical or via an alternative form of data entry (e.g., patient questionnaire), predetermined medications would co-populate one of the series of "potentially worrisome meds" screens. The assigned default score relates information as to the likely nature and severity of the issues associated with the given drug (which can be modified) . Aspects include:

Whereas someone could be maintained chronically on aspirin and Plavix, continuation of these drugs has the potential to lead to excessive bleeding during major surgery. Alternatively, discontinuing them prior to surgery likewise may pose risks. These factors, alone or in combination, can generate a risk indicator score that is relatively higher than that in the review of systems. The inclusion of this issue in Risk Indicators alerts care givers to current status and potential concerns. Additionally, based on its score (FIG. 22), it can prompt inclusion of an alert in the "*Interim Information & Issues*" section of ASPIRIN™ (see below)

The score may integrate entries from more than one aspect of the database (e.g., as for the assessment of the impact of a low potassium level in a patient on digoxin SASRI™ can generate score-driven checks and alerts by integrating scores for one or more Risk indicators or combinations of Risk indicators and SISS™ scores.

Communication and display of Risk indicators can be consistent with the # system or $\#^{system}$ display used for SISS™ of FIGS. 4, 6 and 7, wherein the highest score is listed and the items with scores above a certain cutoff would be listed after the score (with ">" separating the successive scoring tiers). Alternatively, one could simply list all items above a preset cutoff with the option to include the score after the item (e.g., Latex$^5$ or AICD$^\#$). These two alternatives are shown in FIGS. 7B and 7C, respectively. In electronic versions, clicking on the # generates a listing of scored Risk indicators In addition to co-population of Risk indicators at the time of data entry during attainment of the history and physical, there are settings where entries co-populate algorithms for cumulative diagnostic, predictive and treatment algorithms before being converted to a scored Risk Indicator. Potential results of such unique bidirectional exchange are illustrated in FIG. 11. As is evident for multiple applications of the inventive program, co-population is facilitated by the text, code and score conversion index and dictionary (FIG. 10).

In accordance with system/subsystem/feature category/ feature . . . coding, in a preferred embodiment, the data shown in FIG. 11 would be stored as Risk indicator/specific grouping/feature category (e.g., alcohol)/scored feature or subfeature. Again consistent with coding for review of body systems described above, the feature category/feature/sub feature . . . components of the code remain intact throughout the database. As noted above, it's possible that the body "system" score assigned for a given item may be different (e.g., higher) for the Risk indicator body "system" than for the body system associated with the original site of data entry; however, in preferred embodiments, the FC/F . . .

score remains unchanged. This likewise is maintained for "Interim Information and Issues" as discussed below in greater detail.

Interim Information & Issues (I):

This next component of ASPIRIN™ identifies information and issues that likely will be supplemented after completion of the given entry into the database (e.g., after the given history and physical examination). This may be referred to as "I I I™, an adaptation of the common ethnic expression when one realizes something important may be missing ("aye, aye, aye").

While certain entries are obligatory regardless of their score (e.g., a surgically focused history and physical must be in the chart), population of "I" primarily is score-driven, being based upon SISS™, SASRI™ and SICU™ scores (and related indices and score-driven diagnostic and treatment algorithms such as those described herein). Lab tests, for example, would be generated in accordance with guidelines such as those shown in FIGS. 16, 19 and 20 and listed under "I" accordingly.

The items that populate Interim Information & Issues simply can be identified by name or code. However, in preferred embodiments, the inventive system assigns "I" scores to the entries—on a scale comparable to that for A, S, P, I, and R (e.g., the uniform 0-5 code of FIGS. 17, 18, 20, and 21 or specific codes tailored to specific entries). A cutoff (e.g., ≥2) may be established to determine which items are displayed. The scores may be modified as results are received and actions are taken. The advantage of this application of the inventive scoring system is that it enables efficient access to a universal means of identifying what needs to transpire or has transpired since the last updating and review of the primary note.

A preferred mechanism for display under "I" is to group according to score. Scores at or above a certain cutoff may generate an "alert" which could be in the form of an email, page, phone call, or special notation of an available display. This may be time-dependent, e.g., an alert would be generated 24 hours before the scheduled surgery. Depending on the score, it may provide options or mandates.

It is within the scope and spirit of this invention that an aspect of embodiments of present invention addresses the different requirements for acquiring information and addressing issues among healthcare providers. For example, the anesthesiologist would be more interested in obtaining and reviewing a previous anesthetic record; a surgeon might be more interested in tests to assess the spread of a malignancy. Hence, embodiments may contain subcategories with respect to Interim Information and Issues. A preferred way to populate these subcategories is via the user's code that is entered into a given cell (FIG. 17). Each healthcare provider could initially address his/her specific concerns, while still having the opportunity to review the summated issues. The following is one such listing; this can be adapted to the specific institution: A=anesthesiologist(s); S=surgeon(s); N=nurse(s); P=primary care provider; C=cardiologist' O=other specialist/consultant; Σ=sum of all categories.

Within the electronic note, the "I" section gets repeatedly updated. The arrival of new information or the recording of new decisions may populate and co-populate the database in several ways:

Update the item's "I" score

Type-in or import the information as text in the "I" section. This enables healthcare providers to rapidly access "new" information obtained in the interim between original data entry and the present review. In the embodiments which have the aforementioned specialty designations within "I," this information could co-populate the "I" section of the relevant notes.

Co-populate and thereby update the "ASPIR" sections of database impacted by new information:

Co-populate and thereby update features of the history and physical exam and resultant note. For example, if information from a cardiac stress test becomes available, then the "Ischemic Heart Disease" and/or "Stress Test" subsystems of the "CARDIAC" system would be updated with text, code and score (and a time stamp). Consistent with the inherent bidirectional nature of score-driven links, the updated text, code and score may then co-populate "I." In order to facilitate review of the new information, the information remains under "I" until an authorized healthcare provider confirms its presence and accessibility in another portion of the database.

Co-populate and thereby update other components of ASPIRIN™; e.g., Risk indicators Co-populate and thereby update integrated assessment scores and diagnostic and treatment algorithms.

Generate new "alerts" or cancel existing one based on the newly received (and scored) information or the need for additional information.

The aforementioned is designed for interaction by healthcare providers.

While much of the co-population by new information is based on established pathways (and the text, code and score conversion index and dictionary to establish equivalency of terms), the subsequent review and integration of new information and confirmation of its scoring will be under the purview of the healthcare provider(s).

When a healthcare provider reviews new information, makes a need decision, or carries out a needed action, this leads to changes in the "I" score and its implications on other aspects of the database. For example, Risk indicators (or less commonly review of systems) will be altered if an item in that section requires an action (e.g., altering a certain medication based on its score or its combined score in concert with another factor).

A preferred embodiment includes such a provision for information under "I," with options to access details (FIG. 6)—e.g., via a drop-down menu. As an added safeguard, if critical information is pending from a given body system or Risk indicator and/or should be reviewed prior to surgery, then the SISS™ or SASRI™ can be annotated (as with asterisks or with the "I" score). These would automatically be modified in accordance with changes under "I."

Special Needs (N)

Similarly, needed equipment, supplies and actions can be addressed under "N" eeds of the ASPIRIN™ display. Needs primarily will be generated by:

selection of specific item from A of the ASPIRIN™ score (e.g., super-morbid obesity may require a large table)

S of the ASPIRIN™ score (depending on the specific needs for the specific surgery [e.g., special table, need for equipment to rapidly transfuse blood])

P and I of the ASPIRIN™ score (which may relate to the need for special airway equipment)

Score driven features of the Risk indicators

Score-driven items in Interim Information and Issues.

Listings under N can be score-driven in accordance with the options for displaying R and I. N may play a vital role in the mandated "time-out" prior to the onset of surgery. In addition to listing standard components, N could identify critical needs (display of which is score-driven) that should be included a final check (time-out) for the given patient. These could be based on components such as an "antibiotic score," a score-driven determination of which patients require antibiotics on the morning of surgery Non-Perioperative Application of ASPIRIN™ or its Equivalent ASPIRIN™ thus provides a unique array for consolidating critical information, not only in the perioperative period but in many other contexts, especially those that involve transfer of information about multiple patients. FIG. 6B (which includes section (i) of FIG. 6) shows a sample array of an electronic data sheet and display that can be utilized on institutional computers, a hand-held PDA or for generation of printouts. Obviously, the full capacity of the system for provision of additional information and links as shown for the ASPIRIN™ display above is best achieved with electronic media. Nonetheless, even the printout would be a major advance for patient safety. The indications for this are summarized by some of the quotations in Table 2.

As for multiple components of the inventive system, most or all of the information to be included in this tool simply are generated seamlessly from clinical entries into the database In each of its settings, the ASPIRIN™ display can be configured so as to readily distinguish the different lettered categories. This automatically is done by the sequence in which they are placed (e.g., A, then S, then P . . . ). However, this may be supplemented with separators such as commas, differences in font, differences in color, or including the specific letter (e.g., A, S, . . . ).

Integration of ASPIRIN™ Components:

The goals of the present invention from a patient-care standpoint include facilitating the categorization, scoring and communication of large amounts of information, highlighting potentially high-risk situations, guiding perioperative planning, and providing a mechanism by which to analyze outcomes—with a mechanism that uses analogous coding and scoring for the spectrum of conditions and the gamut of sites for potential co-population. FIGS. 7A-C illustrate how the present body system may be applied to provide additional information on an operating room schedule. A given case could result in a ASPIRIN™ score ranging from "1, 1, 0, 0" to "$5^{systems}$, $5^{systems}$, 5, 5, $5^{items}5^{item}5^{item}$," wherein score-driven superscripted body systems (body system-specific modified ASA and Surgical scores) and items (Risk indications, Interim Information and Issues, and Needs) are determined in relation to established cutoffs; i.e., communication and display of the alphanumeric presentation may be limited to scores of 3 or 4 so as to avoid listing relatively unimportant issues.

In addition to what in FIG. 3 are described as the "Inventive Array of Basic SHAPE™ Components" and the "Inventive Array of Modified ASPIRIN™ Components", the present invention also introduces "SHAPE™ Inventive Derived Indices." Many of these would not have been obtainable prior to the present disclosure of one or more inventive SHAPE™ components. Easy calculation, as well as further delineation, may be achieved through the application of a computer-based program for electronic and hard-coded data entry, automated scoring, storage, analysis, and export. This may include any component of SHAPE™ as well as imports from other compatible sources.

The data may be arrayed in columns for integrated assessment, e.g., the SMASH™ (SHAPE™ Multifaceted Assessment of Surgical Harm) indices described below.

Such integration of components enables one to more effectively delineate preoperative conditions, assess perioperative risk, and drive indications for the myriad potential applications (Table 3, FIGS. 3, 5 and 24). The drive indications include: triaging for preoperative assessments by an anesthesiologist, primary care physician or consultant (and providing code-compatible justification for such); driving recommendations for laboratory tests; planning intraoperative personnel and resource allocation; implementation of special protocols (for example, for administration of beta-blockers); planning for postoperative intensive care; quality assurance; performance assessments; and investigations. (DIFF)

Managing Scores—Inventive Indices for Assessment of Resilience and Likelihood of Morbidity:

The aforementioned factors contribute to the unique and robust quality of the SHAPE™ database and its inventive components for determination of inventive indices. As illustrated in FIG. 3, the inventive integration and indices include:

1) an aggregate score of the patient's disorders that is based upon the body system-specific 1-5 SISS™ scores (SAD™). described above. 2) What are referred to herein as SMASH™ (SHAPE™ Multifaceted Assessment of Surgical Harm) indices. The components are delineated by subscripts. Examples include:

integration of physical status (ASA score) and Surgical risk and invasiveness (SOCU™ score)—this may be expressed as $SMASH_{ASA,SOCU}$. The comma indicates that the components simply are being listed. A specific mathematical function that is used may be delineated (i.e., replace comma with + to indicated summation). Alternatively, the function may be for multiplying or weighting as discussed above. As noted above, preliminary findings from my ongoing research indicate that the combined use of ASA PS and Surgical risk/invasiveness is a more accurate predictor of length of hospital stay (LOS) and hospital charges than either one alone. SMASH™ also may be modified or supplemented to identify and take into account special issues such as Risk Indicators by providing the letter code of the given issue, including the alphanumeric score, incorporating the alphanumeric score in the SMASH™ formula, or by adding, for example, 1 point to the score (for one or more risk indicators with a score above a predetermined cutoff).

a SMASH™ index based on body system-specific scores which integrates the modified ASA physical status scores for body systems with disorders (e.g., scores ≥2) with the rating of surgical risk & invasiveness—this may be expressed as $SMASH_{SAD \times SOCU}$™. This may be accomplished by first adding the SISS™ scores for the different positive systems (to generate the SAD™ score) and then multiplying this by the SOCU™ score.

a body system-specific SMASH™ index based on a body system-specific score of physical status and a body system-specific score (same body system) as to the effect of surgery—e.g., $SMASH_{SISS \times SICU}$™.

In the forms described above, the index is constructed so that a higher score indicates a greater degree of overall risk and/or perioperative complexity. Alternatively, an inverse function (or a low number on the described index) would indicate a lesser risk—what may be referred to a greater patient resilience in the context of the anticipated demands of the planned surgery.

As those skilled in the art will certainly appreciate, an alternative mathematical function may be selected. Potential variations also include converting patient status and surgical risk/invasiveness scores to points (as discussed above) and performing manipulations other than simple multiplication. Ultimately, the optimum score will be determined with outcome studies and aforementioned analysis.

3) Comparable indices of disorders for nonoperative settings. For example, SAD™ may be used as a mechanism to document illness in a manner comparable to that proposed for the perioperative settings. Likewise, assessments of resilience can be assessed and scored in the context of nonoperative challenges. As noted elsewhere, these may be based on the scores used in the perioperative setting or for "chronic" scores as well as for scores which evaluate local as opposed to systemic impact.

4) Airway Index that integrates scores assigned in Tables 12a and 12b. For the typical embodiments which score "Physical factors primarily affecting ventilation" and "Intubation predictors", the index is termed the SHAPE™ Physical factor and Intubation Composite Evaluation (SPICE™). If the embodiment also includes a score based on reports of prior intubations, it may be termed the SHAPE™ Mask score, Intubation score, and Report score Composite (SMIRC™). These scores may be combined with the other SHAPE™ scores and indices described above (e.g., as a component of SMASH™) to generate new composite indices. Alternatively, scored information from a prior intubation may co-populate other portions of the database such as Risk Indicators and may prompt "Need" for special airway equipment.

5) Preliminary data suggest that a simple cutoff based on the SHAPE™ scores in the ASPIRIN™ display may be indicative of the need for increased concern, triaging, planning, testing and/or therapy (and to justify billing for such). As shown in FIG. 24, SHAPE™ provides the inventive tools for an institution to establish cutoffs such as:

the need to see an anesthesiologist prior to the day of surgery if the patient has:
a score≥4 in one or more categories (e.g., modified ASA, SOCU™, Intubation predictors, alphanumerics of Risk Indicators); or
≥3 in two or more categories.

the need to see a cardiologist if the patient has:
a sufficient cardiac-specific physical status score (e.g., ≥4 in the $CARD_{ischemia}$ subsystem according to SISS™),
a score≥3 in multiple systems known to predispose to cardiovascular morbidity (e.g. $CARD_{ischemia}$, $CARD_{chf}$, $CARD_{ekg}$, $CARD_{exercise}$, $CNS_{ischemia}$, $ENDO_{diabetes}$, $RENAL_{insufficiency}$),
or a score≥3 in a single system (according to SISS™) prior to a surgical with a CARD system impact score≥3 (according to SICU™).

the need to take special pulmonary precautions if a patient has:
a sufficiently pulmonary-specific physical status score (e.g., ≥4 in the $CARD_{ischemia}$ subsystem according to SISS™),
a score≥3 in multiple systems known to predispose to pulmonary morbidity
or a score≥3 in a single system (according to SISS™) prior to a surgical with a RESP system impact score≥3 (according to SICU™).

The determination of the specific cutoffs is addressed in more detail later in this disclosure and will be adjustable in accordance with future research findings.

Potential Arrays and Screens

Embodiments such as that shown in FIG. 32 direct the user to features and subfeatures. Alternatively, one could start more proximally in a branch. Table 13 illustrates a section of one of several potential arrays for collection, storage and analysis of data in accordance with the spirit of the present invention; a methodology that demonstrates more advanced inventive features in the context of more elaborate branch-chain logic is described later (with reference to FIGS. 26-31). In this example and many others, S/sS/FC/F/sF pathways and codes and scores are not shown (since they likewise would be transparent to the user. As discussed below, Table 13 and other tables presented herein may be employed as screens of a graphical user interface when the present invention is employed in a computer based system. In accordance with the embodiment displayed in Table 13, negative (column 1) indicates that the given body system and its subsystem(s) essentially are within normal limits (no ASA scores of 2, 3, 4 or 5 in traditional 1-5 range). Positive (column 2) means that significant information has been entered into the given body system or subsystem(s). "Positive" may entail a wide range of responses, including any or all of the following effects or meanings:

a) If positive is selected for a body system during real-time data entry (that is, by person performing the history and physical exam)—or if the body system is clicked on or otherwise identified in an alternative embodiment—then the body system has positive features and the program may highlight the subsystems, and their most distal branches (e.g. features) (e.g., the subsystems and features of the CARD system).

b) If positive is selected for a subsystem during real-time data entry, then the program may jump to a screen with potential scored features of that subsystem (as illustrated in Table 14 where both a sample screen for (a) features of ENDO-subsystems Thyroid and (b) a sample screen for a drop down menu for features of Hyperthyroidism are shown) or enable access to a menu (for example, drop-down). In most embodiments, choices are associated with a default score (as seen in Table 14) as well as visible alternative choices and/or a menu to access alternative items and actions (Tables 5 and 6). The individual entering the data may then select hard-coded options, click negative or positive for hard-coded options, type in the available type-in fields, or update information that already has been entered or imported. As detailed below, one may expand upon one of the selected items by clicking on that item or selecting an option such as "type-in details"; or one can enter additional information (additional items, pertinent negatives) by first selecting the "type-in more features" option (or an equivalent).

To ensure that the most critical features have been addressed, the program can mandate neg/pos selection for these features or it can specially designate them on the screen (for example, by placing them first, displaying them in larger font or identifying them with an asterisk), with agreement that those items within a subsystem or those subsystems of a system were addressed before a subsystem or system can be scored as negative. Hence, a subsequent caregiver can be assured as to what has been addressed.

The display may be a list such as Table 15 or can be a modification of the display for the given body system as shown in FIG. 32. With varying column width to accommodate the length of given entries, the FIG. 32 display could serve as the basis for the actual report as one of several alternatives to a more traditional report.

c) If implementation of the present invention provides for a data source that is populated with positive information from another electronic source (for example, data that had been entered into another computer that has been copied or emailed to the given database, data that were scanned into the current computer), it may be identified in a variety of ways including as "positive" in column 2 or by highlighting the given feature, subsystem or body system. One could view/edit data as deemed indicated. The data may have been generated by a variety of ways, including prior entry by another caregiver, the same caregiver, a patient (e.g., a questionnaire), or import from a testing facility. The source of the information can be recorded electronically, while tracking and display can be customized to user(s) preference. Depending on the degree of compatibility between the exporting and importing programs, the data may be imported as predetermined hard-coded features, as information that simply populates the appropriate system, or as information that more simply just appears in an open area of the database where it can be handled by the user. These aspects are detailed for a preferred embodiment described later (with reference to FIGS. 26-31) and may be facilitated by the text, code and score conversion dictionary (FIG. 10).

TABLE 13

| Neg | Pos | SYSTEM/Subsystem | Default Score (1-5) | Modified Score (1-5) | Cumulative Score for Given System | Maximum Score for Given System |
|---|---|---|---|---|---|---|
| | | CENTRAL NERVOUS SYSTEM (CNS) | | | X | X |
| | | Seizure disorder ($CNS_{seiz}$) | | | X | X |
| | | Cerebral Ischemia ($CNS_{ischemia}$) | | | X | X |
| | | Nonischemic Cerebrovascular ($CNS_{nonishcerebvasc}$) | | | X | X |
| | | Nonmalignant Intracranial Mass ($CNS_{nonmalig}$) | | | X | X |
| | | Malignant Intracranial Mass (Un-$S_{miling}$) | | | X | X |
| | | Head Trauma ($CNS_{trauma}$) | | | X | X |
| | | Infection ($CNS_{infect}$) | | | X | X |
| | | Parkinsonism ($CNS_{park}$) | | | X | X |
| | | Other ($CNS_{other}$) | | | X | X |
| | | Cognitive Disorder ($CNS_{cognit}$) | | | X | X |
| | | PYSCH AND PAIN* | | | | |

*Remainder of table to list all body systems and subsystems. Bottom of table then records Highest Individual System Score (most akin to traditional ASA physical status score) and the cumulative score for all positive systems (the inventive SAD ™ score).

TABLE 14 a) Sample Screen: Features of system ENDO/subsystem Thyroid
Mild hypothyroidism well-controlled on medications (2).
Mild hyperthyroidism well-controlled on medications (2).
Benign nodule w/o obstructive symptoms (2).
Significant hypothyroidism in need of new or augmented therapy (3)
Moderate tracheal deviation (3)
Non-life threatening obstructive symptoms when supine (3)
Symptomatic (nonlife-threatening) hyperthyroidism (nonlife-threatening) despite current suppression (3)
Stable on current Rx but otherwise would be prone to thyroid storm (3)
Current atrial fibrillation (3)
Current thyroid-related tachycardia (3)
Current thyroid-related hypertension (3)
Current thyroid-related bradycardia (3)
Compromised breathing due to severe narrowing or deviation (4).
Poorly controlled hyperthyroidism w/life-threateningsignificant systemic manifestations (4)
Severe hypothyroidism w/significant systemic manifestation (4)
Fulminant thyroid storm (5)
Myxedema coma (5)
Type-in details:_____
Type-in more features:_____
b) Sample Screen: Dropdown Menu for Features of Hyperthyroidism
Fulminant thyroid storm (5)
Poorly controlled hyperthyroidism w/life-threatening systemic manifestations (4)
Symptomatic (nonlife-threatening) hyperthyroidism despite current suppression (3)
Stable on current Rx but otherwise would be prone to thyroid storm (3)
Current atrial fibrillation (3)
Current thyroid-related tachycardia (3)
Current thyroid-related hypertension (3)
Mild hyperthyroidism well-controlled on medications (2).
Type-in details:_____
Type-in more features:_____

TABLE 14-continued

Depending on features selected for given program at given institution, SHAPE ™ will prevent cummulation of overlapping signs and symptoms as described in text.

TABLE 15

|  | Patient 1 | Patient 2 | Patient 3 |
|---|---|---|---|
| Mild hypothyroidism well-controlled on medications (2). |  | 2 |  |
| Mild hyperthyroidism well-controlled on medications (2). |  |  |  |
| Benign nodule w/o obstructive symptoms (2). |  |  |  |
| h/o thyroid-related atrial fibrillation |  | 2 |  |
| Significant hypothyroidism in need of new or augmented therapy (3) |  |  |  |
| Moderate tracheal deviation (3) |  |  |  |
| Non-life threatening obstructive symptoms when supine (3) |  |  |  |
| Symptomatic hyperthyroidism (nonlife-threatening) despite current suppression (3) |  |  |  |
| Stable on current Rx but otherwise would be prone to thyroid storm (3) | 3 |  |  |
| Current atrial fibrillation (3) |  |  |  |
| Current thyroid-related tachycardia (3) |  |  |  |
| Current thyroid-related hypertension (3) |  |  |  |
| Current thyroid-related bradycardia (3) |  |  |  |
| Compromised breathing due to severe narrowing or deviation (4). |  |  | 4 |
| Poorly controlled hyperthyroidism w/significant systemic manifestations (4) |  |  |  |
| Severe hypothyroidism w/significant systemic manifestations (4) |  |  | 4 |
| Fulminant thyroid storm (5) |  |  |  |
| Myxedema coma (5) |  |  |  |
| Type-in details |  |  | Trach narrowed to 3 mm |

Type-in more features:
OTHER SYSTEMS WOULD BE TABULATED SIMILARLY

Highest Individual System Score
Cumulative Score for All Positive Systems

If these were the only positive findings in these three patients, the patients' modified ASA scores would be:
Patient 1: $3^{ENDOthyr}$-to reflect the thyroid disorder.
Patient 2: 2-to reflect that patient does not have any disorders ≥3.
Patient 3: $4^{ENDOthyr,ENTnarr}$-to reflect that patient has severe thyroid disorder as well as associated severe airway compromise. Clearly this is providing much more information than a simple score of ASA 4.
$4^{ENDOthyr,ENTmass}$ to reflect that the patient has a severe thyroid disorder as well as current severe airway compromise.
More specifically, in a preferred embodiment, for an otherwise healthy patient undergoing emergency thyroidectomy (a class 3 surgery), with only these two findings, the SHAPE ™ ASPIRIN ™ display would be $4^{ENDOThyr,ENTmas}{}_{S}\ 3^{ENDOThyr}$ #, 55, 5, 0, wherein the 4 indicates the ASA status, the 3# indicates the 1-5 score that would be assigned for surgical risk/invasiveness (the superscript adds that the effect of surgery is primarily on the thyroid gland), the "5's" indicate the impact factors impacting on mask ventilation and intubation. and the "0" for the 5th digit indicates that there were no airway problems with prior anesthetics Clearly this is providing much more information than a simple score of ASA 4."

In accordance with a preferred embodiment detailed later in this disclosure, scoring can be generated at the feature and subfeature levels (as opposed to the subsystem, feature category, or descriptor level). Selection of (and/or electronic transfer of) hard-coded features and subfeatures generates a default score (in accordance with the SISS™ score introduced herein). For a hard-coded feature or subfeature, this is the score assigned to the given feature (based on user, institutional, societal, regulatory body and/or national guidelines). For a subsystem, it typically is the highest score assigned to any of the selected hard-coded features of the subsystem or entered by the user by accessing type-in more features and assigning a score to that entry. For a body system, it is the highest score assigned to a subsystem within that body system. As within subsystems, there is the option to type-in additional data within a body system—by selecting "other" for that body system, one can type in a new subsystem and features. Note, that although the single highest score likely will be selected for communication with subsequent caregivers, the component scores and cumulative feature score and subsystem scores also will be maintained in the database.

As noted above, the caregiver performing data entry can enter a modified score by assigning a higher or lower value for a feature, body subsystem or system in the given patient. This enables a caregiver to make the determination in a given patient that, for example, five class 2 $CARD_{ischemia}$ factors (for example, smoking, hypertension, long-standing NSST changes on EKG, noninsulin-dependent diabetes mellitus, high LDL lipids) may qualify for the CARD system to be rated as a 3. This option also may prove helpful if one wishes to record that a patient has improved as a result of therapy (for example, asthmatic improved after being placed on steroids). In such a case, one could adjust the score for the original hard-coded option (and use "type-in additional information"), select an updated hard-coded option, or use the option to type-in more features. Changes in scores can be tracked electronically and displayed if deemed advisable. A major advantage of the present invention is that SHAPE™ allows for clinical judgment while maintaining a database that retains a feature's base code (regardless of score) and tracks changes in scoring.

It will be understood by those skilled in the art that negative and positive are included in Table 13 for purposes of clarity Simply clicking on the noted body system could be sufficient to highlight subsystems; the presence of a default (or modified) score would signify that the body system is positive.

As noted above, for most preferred embodiments scoring occurs at the feature and subfeature levels. By way of example, Table 14 shows how features such as those listed in FIG. 32 may relate to the selectable features for the ENDOCRINE system. Table 14a illustrates organization of features in terms of similarity of score; other means, such as similarity of features, are also achievable. Instead of checking neg or pos, in the illustrated embodiment, one would simply click on the positive feature. The default score is shown in parentheses; a change in score could be accomplished by a variety of potential mechanisms including changing the actual value or entering the score in a "Modified Score" column (or viewing a dropdown menu which lists the default score first) (Table 6). If one wishes to type-in additional information about a hard-coded feature, this may be accomplished with the "type-in add'l info" option (which may not be scored (descriptor), assigned a score by the user or assigned a default score based the scored item with which it is associated). Where there is a significant likelihood of the need for multiple details about a given feature or subfeature, hard-coded descriptors may be attainable by a variety of mechanism, including drop-down menus (Table 14b). The program can keep track of these typed-in entries so that they may eventually be incorporated into future versions of the program as hard-coded options. The coded and scored entry of type-ins is detailed with preferred embodiments described later (with reference to FIGS. 26-31).

An important aspect of the inventive system is the ability to record information that is deemed important in a preoperative note without concern as to whether listing all aspects of a problem will artificially increase its score. This is most effectively addressed in a preferred embodiment with unscored descriptors described later (with reference to FIGS. 26-31). The program can automatically prevent the cumulative scoring of overlapping features with item-specific override exclusions algorithm such that, for example, "current atrial fibrillation" and "current thyroid-related tachycardia" can both be listed but would not be additive. Duplicates are handled by the text, code and score conversion dictionary discussed above and illustrated in FIG. 10. Options for managing multisystem disorders likewise was addressed above and is shown in Table 10. The embodiment illustrated in Table 14 is an example of how to establish a balance between desired detail and unwanted complexity.

The cumulative score for a body system is the total of all the scores for the subsystems within that body system. However, because of the likelihood for overlap among subsystems, unless indicated otherwise, the score for a body system is based on the highest score assigned to one or more of its subsystems. When the ability to cumulate scores is deemed preferable, the program may be modified to treat specific subsystems as separate body systems. For example, diabetes may be treated as being independent from the rest of the ENDOCRINE system.

The overall cumulative score for a patient is the total of the scores assigned to the individual body systems; i.e., the SAD™ score (bottom of Tables 13 and 15). However, in most embodiments, to maintain consistency with the standard ASA score for communicative purposes, only the highest scores would be used; e.g., the overall ASA score would be based on the highest system score (e.g., on the 1-5 or newly proposed 0-5 scale). The cumulative scores typically would not be displayed. Either way, they could be stored in a database for quality assurance, billing, and outcome studies and could contribute to the SAD™ score.

Table 15 illustrates storage of the information and scores in a database for three representative patients. For purposes of this presentation, all entries in this example are limited to system Endocrine—subsystem thyroid. However, the total database would include all body systems and other information deemed appropriate in accordance with the present invention. A more detailed database with coding is described later in this disclosure in reference to a preferred embodiment (with its accompanying FIG. 13).

Table 16 shows the logic used for a typical questionnaire, with the provision that the text (and codes and scores) be consistent with SHAPE™ if such matching is possible. Issues with respect to interfacing with questionnaires will be discussed with "Imports" later in this disclosure.

TABLE 16

Sample Portion of Questionnaire to Correspond to SHAPE ™-Thyroid:

"Any problems with your thyroid?"
"If yes, is your thyroid high or low?"
If high, subject to respond to queries relevant to hyperthyroidism and its treatment
that match
the hard-coded SHAPE ™ options.
e.g., "Is your overactive thyroid (hyperthyroidism) well-controlled on medications?"
If low, patient to respond to queries relevant to hypothyroidism and its treatment that match hard-coded SHAPE ™ shape options.

It should be understood the preoperative version of the present invention described above is one of several potential embodiments, and could be modified with additional hard-codes and expanded type-in options for assessing, recording, communicating and investigating in other settings—including nonoperative procedures, intensive care and emergency settings and long-term care—without departing from the spirit of the present invention.

For longterm management, one may wish to record more detail about the history of a patient's disease and how it is impacting on daily living. An embodiment where such modifications for chronic (longterm) conditions related to thyroid disease are preceded by a superscripted "LT" sign is shown in Table 17.

TABLE 17

Long-term and Acute Features of system ENDO/subsystem Thyroid:

Mild hypothyroidism well-controlled on medications (2).
Mild hyperthyroidism well-controlled on medications (2).
Benign nodule w/o obstructive symptoms (2).
$^{LT}$Family history of thyroid disease (2)
$^{LT}$> 10 lb weight loss prior to onset of therapy (2)
$^{LT}$somnolence prior to onset of thyroid supplementation
Significant hypothyroidism in need of new or augmented therapy (3)
Moderate tracheal deviation (3)
Non-life threatening obstructive symptoms when supine (3)
Symptomatic hyperthyroidism (nonlife-threatening) despite current suppression (3)
Stable on current Rx but otherwise would be prone to thyroid storm (3)
Current atrial fibrillation (3)
Current thyroid-related tachycardia (3)
Current thyroid-related hypertension (3)
Current thyroid-related bradycardia (3)
Compromised breathing due to severe narrowing or deviation (4).
Poorly controlled hyperthyroidism w/significant systemic manifestations (4)

TABLE 17-continued

Long-term and Acute Features of system ENDO/subsystem Thyroid:

Untreated hypothyroidism w/significant systemic manifestation (4)
Fulminant thyroid storm (5)
Myxedema coma (5)
Type-in
details:_____
Type-in more
features:_____

Such programs could also provide alternative default scores when longterm as well as acute impact of a disorder is taken into account (described later in this document). Conversely, scores can remain consistent among longterm and acute-perioperative versions if one relies on other aspects of the SHAPE™ database (e.g., history of anesthesia-specific halothane hepatitis in Risk Indicators of the ASPIRIN™ display) to identify issues that have added impact in the perioperative setting. Either way, the actual challenges could be rated with the SICU™ score or an obvious modification thereof, wherein the lowest score (e.g., 0) would be commensurate with rest. The renaming for such purposes is simple: as described, SHAPE™ can be translated as Silverman-Holt Aggregate Patient Evaluation (as opposed to Preoperative).

Potential Applications and Advantages of the Inventive System

It is contemplated the present invention may be implemented in a variety of manners dictated by the technology available to the healthcare facility. Examples of the inventive features enabled by the inventive classification and scoring system(s) introduced herein fall under the classifications of:

- previously unavailable coding and scoring of information that is free-typed (not hard-coded);
- co-population, importing and exporting among multiple information sources, fields within the given program, databases, and diagnostic and treatment algorithms;
- development of a text, code and score conversion dictionary for these integrative functions;
- development of an Integrative Index for these accessing sections of the program (which may be a component of the conversion dictionary.

Some of these aspects will be discussed immediately below; others will be included in the following description of a preferred embodiment, with the realization that they are not limited to said embodiment.

Consistent with features cited above and more detailed descriptions below, the present invention is organized to be configured to enable hard-coded choices and type-in options for cross-population (with text, code and score) of different components of the database for a variety of purposes, including: entering information into relevant body systems, arrangement of information for the given preoperative note, storage in databases, identification of special needs, communication, quality assurance, and research. (These are addressed in greater detail in the discussions of co-population and exporting—and their facilitation by a conversion dictionary and interactive index discussed below). As such, SHAPE™ includes hard-coded options for specific issues that co-populate more than one program location (Some of the multiple options for text, coding and scoring in this context have been discussed above). This unique ability to cross-populate, simultaneously edit/update, and share a common coding and scoring system among different fields within the same database (for example, cigarette smoking in Habits and potentially Respiratory) and among different databases is one of the unique benefits of the present invention. The multiple cross-system components that can be populated in the manner within the SHAPE™ database include:

a) Co-populating a body system such as Respiratory with a habit such as smoking.
b) Potential perioperative risks ("R" isk Indicators in ASPIRIN™ display) with potentially undetected or poorly communicated problems, including: latex allergy; porphyria (with resultant sensitivity to barbiturates); hallucinations in response to narcotics and sedatives (not necessarily recorded as an allergy but nonetheless important to know); contraindications to medications (e.g., succinylcholine) which may be entered and hence listed in a variety of separate systems such as Renal, and Musculoskeletal and Central Nervous System; history of halothane hepatitis; and/or notation of medications or techniques refused by the patient. These not only will populate the relevant body systems and subsystems but also may initiate special score-driven alerts (e.g., alert care givers of important "R" isk indicators or vital "I" nformation of ASPIRIN™). Consistent with the vital role of scoring to multiple aspects of this invention, decisions to co-populate the Risk Indicator section of the ASPIRIN™ display may be driven by the alphanumeric score. This reflection of perioperative risk may be greater than the body system-specific SISS™ score, hence, as stated above, the inventive universal database of body system-specific text, codes and scoring can be tailored to the perioperative setting. For example, the potential impact of gastro-esophageal reflux may differ markedly between daily life and the day of surgery. The impact of such co-population on cumulative scores such as SAD™ is addressed with respect to annotation with "=", "+" and "+>" above and in Table 10.
c) As indicated in the preceding paragraph, important "I" nformation pending also can populate or co-populate the ASPIRIN™ display and multiple database fields. Again, the consistent means of scoring may be applied (FIGS. 17, 18, 20-22)
d) Special Needs ("N" of ASPIRIN™) such as special perioperative monitoring, special anesthetic techniques, and/or the need for intensive postoperative care. Again, such listing may be driven by the condition's 1-5 score (or 0-5 score, etc). Such listing not only applies to management of medication but also devices; for example, reprogramming an automatic intracardiac defibrillator (AICD) before and after surgery. The present invention can be adapted to integrate the given patient's indications and contraindications for a given therapy. The information can be readily accessible in the cumulative database (or portion thereof) and can be displayed on operating room schedules and electronic records (including electronic anesthesia note and under "N" of ASPIRIN™ display). It likewise may be incorporated into a memo or note or transferred to a compatible computer in another office. It could lead to a prompt, which may be in the form of a letter or alphanumeric code for the given therapy or as a component of a more generalized symbol which indicates that additional therapy may be considered. As such, it enables preemptive planning and preparation, thereby reducing day-of-surgery delays and cancellations.
e) Indications for discontinuing, withholding or initiating medications perioperatively. Using comparable mechanisms of entering, grading, integrating and exporting data, the present design may alert caregivers to the presence of medications that likely should be discontinued preoperatively (for example, clopidogrel (Plavix)) and/or indications for initiating a medication preoperatively (e.g., beta-blockers, discussed in detail below). Such an alert could be in the form of any of the following based upon user preference:

a simple Risk indicator letter code;

a graded letter code as in the aforementioned SHAPE™ Alphanumeric Score for Risk Indicators (SASRI™) (FIG. 11);

co-population of the relevant subsystems (such as Plavix in HEME);

creation of a system-equivalent labeled Periop Meds (probably not necessary);

a preferred embodiment entails providing the score shown in FIGS. 22 and 23 f) Grouping or collectively exporting particular medical conditions that have a common impact despite being from different body systems. For example, what is termed by cardiologists as "plaque risk"—a compendium of cardiovascular conditions and risk factors (some of which may be subclinical) that might not otherwise be grouped together. More, specifically, the collective exporting of such data to generate cumulative scores to guide additional workups (for example, cardiac evaluation with stress test) or initiation of beta-blockers (independently or in accordance with guidelines recommended in the literature or institutional policy). The data may be derived from CARDIAC$_{ischemia}$, CARDIAC$_{chf}$, CARDIAC$_{EKG}$ VASCULAR$_{pvd}$, or ENDOCRINE$_{diabetes}$, RENAL$_{insuff}$, CNS$_{ischemia}$ subsystems or Multisystem Conditions$_{OBESITY}$, as well as Social History (e.g., smoking) and possibly other body systems or subsystems. Similarly, one may group factors that impact on a decision to employ specific forms of invasive monitoring where risks and benefits must be weighed (e.g., a pulmonary artery catheter).

g) Grouping of data that otherwise would require chart-by-chart searching to determine the presence or absence of factors deemed essential to quality assessment and improvement programs such as the American College of Surgeons National Quality Improvement Program (ACS NSQIP). All of the data required for NSQIP can be co-populated via standard SHAPE™ data entry in the review of systems (as shown in FIG. 32) or via the Risk indicators and alerts (as shown in FIG. 11). Co-population of NSQIP or rapid chart review each is facilitated by the inventive scoring system, wherein all positive NSQIP variables may be assigned a score≥3. Such unique score-driven assignment facilitates co-population and also streamlines chart review; one only has to check for entries with a score of 3 or more. While incorporating NSQIP criteria into its scored hard-coded options, SHAPE™ maintains its ability to provide its consistent means of scoring. This also enables ready identification of the body systems with one or more positive NSQIP criteria since the given system would, by default, be assigned the score of its highest positive system. This also enables:

determination of equivalent terminology via the SHAPE™ text, code and score conversion dictionary;

determination of comparable terminology via the SHAPE™ conversion dictionary that allows storage of comparable terminology for future assessment (and possible improvement of the NSQIP criteria) based upon system (or subsystem . . . ) and score.

for NSQIP criteria and criteria complexes that do not correspond to scored features within a given bodily system, SASRI™ provides scored Risk indicators and alerts (FIG. 11). As for the inclusion of Risk Indicators in the ASPIRIN™ display, the scoring facilitates categorization and determination of what qualifies for co-population of NSQIP. In the embodiment shown, the cutoff of ≥3 prompts co-population of NSQIP as well as inclusion in the ASPIRIN™ display.

The present invention also may improve the assessment of laboratory values within NSQIP wherein the lab values are recorded for approximately 13 indices. These can be scored in accordance with a graded scale such as that in FIGS. 17, 20 and 21. Again, a score beyond a preset cutoff would determine which values correspond (via universal language and scoring) to abnormal NSQIP criteria.

It should be evident that the versatility of the present invention detailed in this disclosure is attributable, in large part, to the unique scoring and unique code/score language. This leads to score-driven co-population of notes, displays, alternative systems and databases, and algorithms. Unique options for managing codes and scores are summarized in Table 3. Aspects relevant to this portion of the disclosure include:

recording (and modifying) the information within the database and the final note;

recording the code, score and possibly text in the database directly into the ASPIRIN™ display or into a summary at the bottom of the note which can then be transferred to a display;

co-populating diagnostic and treatment algorithms, indices and electronic or paper printouts with text, code and score.

With respect to the last option, it is further contemplated data for given body systems may be integrated to provide needed entries (typically at the feature or subfeature level) to co-populate with a common language and score established indices of risk assessment (that, while highly acclaimed, are not universally applied in their current form), diagnosis (e.g., whether to obtain a cardiology evaluation) and treatment (e.g., whether to initiate perioperative cardioprotection with beta-blocking drugs) algorithms. Exported entries may be generated from:

their original field of entry (e.g., a specific feature within a given system); or a section of the SHAPE™ database that was co-populated by the original entry (e.g., co-population of the Cardiac System with the selection of Type 1 diabetes in the Endocrine system; or from Risk indicators (when appropriate); or a SHAPE™-derived index such as SMASH™.

It is described below and in Tables 18a and 18b (cumulatively referred to as Table 18) how, with relatively minor, transparent and easily understandable score translations, SHAPE™ could then convert different terminologies for different cardiac-related indices into a common language and more interchangeable scores and/or could activate the terms used in a given index with equivalent or relevant features. For example, the widely acclaimed Cardiac Risk Index of Lee et al (Circulation 1999) lists six variables which primarily impact on the rate of major perioperative cardiac complications. According to that Cardiac Risk Index, the risk of an adverse perioperative cardiac outcome is directly related to the number of risk factors in the given patient. However, it is believed the classification and scoring described in the present invention overcome many of the limitations of the Cardiac Risk Index. For example, ischemic heart disease may be scored so as to enable distinctions not available from their similar "ischemic heart disease" factor; the simple variable "congestive heart failure" can be graded according to severity as well as to whether it is currently active and the grouping of a wide variety of surgeries as "major" can be improved with the SHAPE 1-5 SOCU™ classification and, more specifically, by the system-specific SICU™ classification. Such distinction may overcome the disparity between the odds ratios generated by the derivation and validation sets of the Cardiac Risk Index (Lee T H. Marcantonio E R. Mangione C M. Thomas E J. Polanczyk C A. Cook E F. Sugarbaker D J. Donaldson M C. Poss R. Ho K K. Ludwig L E. Pedan A. Goldman L. Derivation and prospective validation of a simple index for prediction of cardiac risk of major noncardiac surgery. Circulation 100 (10):1043-9, 1999 Sep. 7.

TABLE 18

Sample Application of the Common Language and Scoring Converting Cardiac Risk Index to common language and scoring of the of SISS ™ and SICU ™ of SHAPE ™-with the Generation of SHAPE ™ Cardiac Risk Assessment Points (SCRAP ™)-to the Otherwise Disparate Cardiac Risk Index, ACC/AHA Guidelines, and Indications for Beta-Blocker Use

| Surgical Risk: | Score (SICU ™, SISS ™) | Correction For Exercise Tolerance In Given Patient* | | Patient's Corrected Score |
|---|---|---|---|---|
| | | Good (Classes 1&1.5) | Questionable (Class 2) | |
| High | 5 | n/a | n/a | |
| High Intermediate | 4 | n/a | n/a | |
| Intermediate | 3 | n/a | n/a | |
| Low Intermediate | 2 | n/a | n/a | |
| Low | 1 | n/a | n/a | |
| Major Clinical Risk Factors: | | | | |
| Severe or unstable angina | 4 | n/a | n/a | Patients with |
| Uncontrolled CHF | 4 | n/a | n/a | Major Clin |
| High-grade AV block | 4 | n/a | n/a | Risk Factors |
| Symptomatic heart block | 4 | n/a | n/a | Should be |
| Surpravent arrhythmia with uncontrolled vent rate | 4 | n/a | n/a | evaluated by a cardiologist |
| *Critical Valvular heart disease* | 4 | n/a | n/a | and/or |
| Acute MI | 4 | n/a | n/a | consi-dered |
| Recent MI (7-30 days) unless confirmation of stable cardiac function and lack of further significant ischemic risk. | 4 | n/a | | for perioperative cardiac protec-tion even in the absence of surgery not undergoing surgery. |
| | X | X | X | X |
| Intermediate Clinical Risk Factors: | X | X | X | X |
| Stable "mild" angina | 3 | −2 | −1 | |
| Prior MI | 3 | −2 | −1 | |
| Compensated or prior CHF | 3 | −2 | −1 | |
| Diabetes mellitus | 3 | −2 | −1 | |
| Renal Insufficiency | 3 | −2 | −1 | |
| | X | X | X | |
| Minor Clinical Risk Factors: | X | X | X | |
| Advanced age | 2 | −2 | −1 | |
| Prior abnormal ECG (LVH, left BBB, NSST) | 2 | −2 | −1 | |
| Rhythm other than sinus(e.g.,controlled AF) | 2 | −2 | −1 | |
| Sedentary life style (low functional capacity)) | 2 | −2 | −1 | |
| History of stroke or TIA | 2 | −2 | −1 | |
| Hypertension | 2 | −2 | −1 | |
| Total Points | X | X | X | |

Comments: For Exercise Tolerance, only classes 1, 1.5, and 2 have impact on scoring in this table. Classes 3 and 4 are associated with dysfunction that is reflected in the Cardiac Risk Factors (discussed in text).
Bold indicates the six variables of the Cardiac Risk Index (discussed in text).
Italics indicate that, although it will contribute to indications for cardiac evaluation, this feature likely would not prompt initiation of beta- blocker therapy for cardioprotection.
(Note-
indications must be weighed against contraindications-not listed).

TABLE 18b

Application of Data in Table 18a for Determination of Whether to Obtain a
Cardiology Consult and/or Initiate Beta-Blocker Therapy:

Note: A cardiology evaluation is indicated for all patients with grade 4 (or 5) clinical risk
factors even if no surgery is planned. Conversely, unless required in the absence of surgery, a
consultation is not required prior to minor surgery even if multiple low and intermediate
clinical risk factors.
According to the inventive system, consult likely indicated if 6 or more points as may be
accrued by:
Low Risk Surgery (1) point with:
Unless required in the absence of surgery, a consultation is not required prior to minor
surgery even if multiple low and intermediate clinical risk factors.
Low Intermediate Risk Surgery (2 points) with:
2, 3 or 4 Intermediate Clinical Risk Factors and Poor Exercise Tolerance (+6, 9 or 12 points)
2, 3, or 4 Intermediate Clinical Risk Factors and Questionable Exercise Tolerance (+4, 6 or 8
points)
2, 3 or 4 Low Clinical Risk Factors and Poor Exercise Tolerance (+4, 6 or 8 points)
4 Low Clinical Risk Factors and Questionable Exercise Tolerance (+4 points)
Intermediate Risk Surgery (3 points) with:
1, 2, 3 or 4 Intermediate Clinical Risk Factors and Poor Exercise Tolerance (+3, 6, 9 or 12
points)
2 Intermediate Clinical Risk Factors and Poor Exercise Tolerance (+6 points)
3 Intermediate Clinical Risk Factors and Poor Exercise Tolerance (+9 points)
4 Intermediate Clinical Risk Factors and Poor Exercise Tolerance (+12 points)
2, 3, or 4 Intermediate Clinical Risk Factors and Questionable Exercise Tolerance (+4, 6 or 8
points)
3 or 4 Intermediate Clinical Risk Factors and Good Exercise Tolerance (+3 or 4 points)
2, 3, or 4 Low Clinical Risk Factors and Poor Exercise Tolerance (+4, 6 or 8 points)
3 or 4 Low Clinical Risk Factors and Questionable Exercise Tolerance (+3 or 4 points)
Appropriate combinations of Intermediate and Low Clinical Risk Factors including:
    1 Intermediate + 1 Minor and Questionable Exercise Tolerance. (+3 points)
High Intermediate Risk Surgery (4 points) with:
1, 2, 3 or 4 Intermediate Clinical Risk Factors and Poor Exercise Tolerance (+3, 6, 9 or 12
points)
1, 2, 3, or 4 Intermediate Clinical Risk Factors and Questionable Exercise Tolerance (+2, 4,
6 or 8 pts)
2, 3 or 4 Intermediate Clinical Risk Factors and Good Exercise Tolerance (+2, 3 or 4 points)
1, 2, 3, or 4 Low Clinical Risk Factors and Poor Exercise Tolerance (+2, 4, 6 or 8 points)
2, 3 or 4 Low Clinical Risk Factors and Questionable Exercise Tolerance (+2, 3 or 4 points)
Appropriate combinations of Intermediate and Low Clinical Risk Factors including:
    1 Intermediate + 1 Minor and Questionable Exercise Tolerance(+3 pts)
High Risk Surgery (5 points) with:
1, 2, 3 or 4 Intermediate Clinical Risk Factors and Poor Exercise Tolerance (+3, 6, 9 or 12
points)
1, 2, 3, or 4 Intermediate Clinical Risk Factors and Questionable Exercise Tolerance (+2, 4,
6 or 8 pts)
1, 2, 3 or 4 Intermediate Clinical Risk Factors and Good Exercise Tolerance (+1, 2, 3 or 4
points)
1, 2, 3, or 4 Low Clinical Risk Factors and Poor Exercise Tolerance (+12, 24, 36, or 48
points)
1, 2, 3 or 4 Low Clinical Risk Factors and Questionable Exercise Tolerance (+1, 2, 3 or 4
points)
Appropriate combinations of Intermediate and Low Clinical Risk Factors including:
    1 Intermediate +and 1 Minor and Questionable Exercise Tolerance. (+3 pts)
Note - The aforementioned system is in near total agreement with the detailed guidelines
based the ACC/AHA guidelines (which lack the advantages of the inventive program as
cited in the text).

The Cardiac Risk Index excluded variables that have been considered vital to other indices for risk assessment and algorithms for diagnosis and treatment. This effect may be mitigated by a common database enabled by SHAPE™ such as the one in Table 18a which enables a common language and scoring system for the otherwise disparate indices and algorithms. No longer must health care decisions be based on an index that is isolated from other indices.

Looking at the currently available and the aforementioned SHAPE™ improvements, the six Cardiac Risk Indices variables are listed below along with quotes from relevant sections of FIG. 32 and Tables 11a and 11b that either are the given Risk Index variable or list a feature (with its score) which is suited to the given Risk Index variable. Note, the score provides additional information compared to the Cardiac Risk Index—precise features as well as score—while being programmed to maintain the simplicity of use.

high-risk surgery: co-populate with entry in accordance with overall surgical risk/invasiveness (SOCU™) score of Table 11a; or more specifically, can co-populate with the score for the effect of surgery on the Cardiac system as a component of the SICU™ score (Table 11b).

ischemic heart disease: co-populate with relevant features from "Ischemic Heart Disease" in FIG. 32 and their scores (in parentheses), including: exertional angina (3); old MI (3); stable (3); old wall motion abnormalities (3); extensive wall motion abnormalities and ischemia on scan (4); unstable angina (4); angina at ≤2 METS (4)

congestive heart failure: co-populate with relevant features from "Congestive Heart Failure" in FIG. 32 and their scores, including: compensated CHF (3), stable on current meds (3); history of pulmonary edema in past— presently stable on current Rx (3); symptomatic CHF with moderate limitations (3), EF 25-50% (3); severe CHF (4); severe pulmonary edema (4); cannot perform any physical activity (4); requires cardiac meds to function (4) life-threatening pulmonary & hepatic congestion (4) EF<25% (4).

The flexibility of the present invention is shown by the ability to co-populate different subsystems within the Cardiac System for joint exporting to the Cardiac Risk Index, while retaining the option to incorporate only one of the scored subsystems (e.g., Ischemic Heart Disease or Congestive Heart Failure) in the score for the Cardiac System for use in the SHAPE™ database and subsequent inclusion in the preanesthetic/presurgical note.

history of cerebrovascular disease: co-populate with relevant features from "Cerebral Ischemia" in FIG. 32 including: asymptomatic carotid narrowing (2), >80% carotid occlusion (3), history of transient ischemic attacks (3) or stroke (3); current TIAs (transient ischemic attack) (4), recent or acute stroke (4)

The flexibility of the present invention is further shown by the ability to co-populate different body systems (e.g., CNS and Cardiac) not only for joint exporting to the listing of six variables for the Cardiac Risk Index but also, as shown in Table 18 and discussed below, to a graded system such as the ACC/AHA Guidelines. With respect to the latter, the SHAPE™ database may export the relevant text with either: its CNS System score; with the score of its co-populated inclusion in the "Nonspecific Risk Factors & Indicators for Ischemic Heart Disease" Subsystem of the Cardiac System; or with a converted score designed for the transition from SHAPE™ to the ACC/AHA Guidelines. It should be understood that, although a history of stroke is rated as 3 for the CNS system, it is rated as 2 with respect to the Cardiac system since a review of the literature prompted the ACC/AHA Guidelines Committee to consider it to be a minor clinical risk factor for perioperative cardiac morbidity (Eagle: Circulation 2002). The SHAPE™-derived ability to use a common language with the scoring options described above enables concurrent assessment of multiple indices and algorithms. For example, the Cardiac Risk Index, the ACC/AHA guideline update on perioperative cardiovascular evaluation for noncardiac surgery, and a beta-blocker score all are available from the data tabulated in Table 18. These options for managing text and scores also apply to other items, including those with respect to Diabetes and Renal Insufficiency discussed below.

insulin therapy for diabetes: co-populate with relevant statements from "Diabetes" in FIG. 32.

renal insufficiency: co-populate with relevant sections from FIG. 32, including preoperative serum creatinine>2.0 mg/dL (3): stable on dialysis (3), GFR<50 ml/min (3), advanced hepatorenal syndrome (4)."

Even simpler, SHAPE™ enables the potential to reduce the common language to scored "cardiac risk" equivalents based on $CARD_{ischemia}$, $CNS_{Ischemia}$, $ENDO_{diabetes}$, $VASC_{pvd}$, $RENAL_{insuff}$ of SISS™ and CARD of SICU™. Examples of this include the designation of the following subsystems (as shown in FIG. 32) as independent of the parent body system for purposes of co-population of cardiac risk indices and diagnostic and treatment algorithms:

the Congestive Heart Failure (CHF) subsystem in the CARDIAC system—this is one of the six factors in the revised Cardiac Risk Index and is an intermediate clinical risk factor in the ACC/AHA Guideline Update on Preoperative Cardiovascular Evaluation for Noncardiac Surgery. The flexibility of the SHAPE™ database is shown by its ability to accommodate such categorization and thus effectively generate a preoperative note and database entries, scores and displays (e.g., ASPIRIN™) while co-populating multiple diagnostic and treatment algorithms with a single language (text and/or code and/or scoring system). This may be accomplished in a variety of ways. A preferred embodiment entails generating the data for the CHF subsystem primarily from hard-coded choices in other subsystems of the CARDIAC system. The default option can then be to include the CHF subsystem in the final database and in exports for co-population of diagnostic and treatment algorithms but to not include this subsystem in the final note unless it is positive for items not included elsewhere. If a positive score in this subsystem is due to co-population from another subsystem, then the default option would be not to include CHF in a cumulative score. (As noted above, this may be designated by a notation such as "=").

the Cerebral Ischemia subsystem of CNS and the Renal Insufficiency subsystem of RENAL. These are important in and of themselves; identifying them as scored subsystems facilitates automatic exporting of the "common language" to diagnostic and scoring algorithms and related applications. These may simply be exported as "independent" subsystems to the indices and algorithms or they may be channeled to co-populate a portion of the Cardiac System such as a Nonspecific Risk Factors & Indicators for Ischemic Heart Disease Subsystem. Here, the code will reflect the feature's origin and its score may be modified if the cardiac-related impact is deemed less than the impact in its parent system.

Exercise Tolerance. As per CHF, this typically is addressed in other subsystems of the CARDIAC system or in another body system (RESPIRATORY). The default option may be to co-populate this subsystem with entries and scores from other program sections as well as to include exercise-specific items as may be generated by treadmill testing. The default option would be not to include Exercise Tolerance in a cumulative score since this does not in and of itself constitute a disorder. Of special note—the ACC/AHA Guidelines do not treat exercise tolerance as a minor, intermediate or major clinical risk factor. Instead, they rate it as a separate "good" or "poor" category which then augments or modulates the impact of the clinical risk factors. This is reflected in the inventive algorithm for converting the score assigned to exercise tolerance as a subsystem in FIG. 32 to its role as a modifier in the ACC/AHA guidelines in Tables 18a and 18b.

The Diabetes subsystem, while appropriately included under the ENDOCRINE system for organization purposes, is programmed to co-populate the aforementioned diagnostic and treatment cardiac algorithms.

For the screens for given algorithms for consultation and/or treatment, several of the criteria for the given algorithms will be matched with identical statements in the components of the SHAPE™ score. Attempts are made to include exact wording within the review of symptoms. However, at times, more than one hard-coded choice in the review of body systems can be equivalent to or consistent with a single item in the given algorithm (or perhaps vice versa). In accordance with a preferred embodiment, they can all be included and identified with a common font, number code, or color. Additionally, they can be grouped together under a common heading via indentations or a drop-down menu. A preferred method is to assign them a subscripted code that includes the numeric subscript which identified the co-population pathway (as described later with respect to the screens for Diabetes in FIG. 30).

Also there will be situations in which a relevant item in the review of body systems does not match sufficiently with an item as stated in the given algorithm, but clearly identification of this feature is consistent with overall scoring and logic of the algorithm. In which case, they could be added during the co-population process with annotation to relate that they are distinct but similar, analogous to the annotations of "Similar Type-ins" described later in conjunction with a preferred embodiment as shown with reference to FIGS. 26-31.

The integrated common language and scoring of the present invention may be referred to as SHAPE™ Cardiac Risk Assessment Points (SCRAP™). The points could be included in Risk indicators of the ASPIRIN™ display, or as an independent inventive index, or as a component of SMASH™. Decisions may be made based on the number of factors that are present, the presence of one or more factors exceeding a given cutoff and/or cumulative score.

In addition to enabling the aforementioned forms of customization for interfacing, the incorporation the text, code and score conversion dictionary (FIG. 11) enables development of a common language with a common score and a common terminology (and a mechanism for documentation terminology equivalency or similarity) that can be modified in accordance with its score for multiple sites of co-population. The inventive dictionary converts statements to a common language for co-population while also providing important details about the nature of the disorder and its severity. The unique combination of universal terminology and coding and scoring also may be applied to SHAPE™ interactions with scoring systems such as ICD-9 codes and CPT codes as discussed below in greater detail.

Thus, Table 18 uses such a common language and SCRAP™ to collectively cite the Cardiac Risk Indices of Lee and colleagues with the ACC/AHA guidelines for cardiac evaluation, as well as to generate a score for initiating cardioprotection with beta-blockers. The scores demonstrate how the SISS™ and SICU™ scores can be included in such algorithms. The values for the clinical risk factors are identical to those of the Cardiac system in the SHAPE™ database. The scores for surgery have been modified to expand the intermediate risk surgery from a single score of 3 to options for 2, 3, or 4 (as described earlier in this document). The difficulties that have hampered the inclusion of exercise tolerance in the ACC/AHA guidelines have been addressed by assigning a 1-5 ranking to exercise in the Exercise Tolerance Subsystem of the Cardiac System and then converting scores of 1 and 1.5 to −2 and a score of 2 to −1; scores≥3 have no impact on SCRAP™ The different combinations are summarized in Table 18b.

Exercise tolerance is unique among cardiac signs and symptoms in that it is a form of a daily life test: whereas poor exercise tolerance (high score on SHAPE™ 1-5 or 0-5 scale) may confirm other signs and symptoms of cardiac disease, good exercise tolerance (low score) lessens the likelihood that the patient has significant cardiac disease. The adaptation of SHAPE™ to assign negative points to diagnostic and therapeutic guidelines not only enables more effective scoring of indications (as for determining the need for a cardiac evaluation) but also enables quantification of contraindications. Negative numbers can be assigned to specific items in specific algorithms; e.g., for a history of severe allergy to beta-blockers in the beta-blocker algorithm, for the presence of severe pulmonary hypertension in a scoring system designed to determine whether one should monitor with an invasive pulmonary artery catheter (which may cause pulmonary artery rupture in a patient with severe pulmonary hypertension). The degree of negativity can be graded, with a predetermined value indicating an absolute contraindication.

Advantages of the inventive mechanism of organizing, coding and scoring in this context include those related to the introduction of a universal language with scoring, as described above. In addition, the embodiment shown in Table 18 provides more information than the ACC/AHA Guidelines which does not account for uncertain exercise tolerance and does not take into account the number of risk factors or gradation of an individual factor's severity. Additionally, increased precision is provided by the 1-5 classification of surgery (especially with the system-specific SICU™ score). The use of a common language and standardized scoring systems enables smooth transition among applications such as the SHAPE™-modified ACC/AHA Guidelines and indications for beta-blocker therapy. One simply may select different variables for different application (e.g., one might argue that valvular heart disease should not influence the initiation of beta blockers for cardioprotection) or establish a different cutoff. Whereas a score of 6 or more in Table 18 suggests the need for cardiology evaluation, scores in the range of 5-7 actually may prompt one to forego the evaluation and simply initiate cardioprotection with a beta-blocker. Likewise, accumulation of a score of 6 or more solely as a result of minor clinical risk factors might prompt use of beta blockers as opposed to a costly evaluation. Such decisions would be prompted and facilitated by listing the factors responsible for a given score. At times, information from the cardiac evaluation may be used to determine beta-blocker use (while obviously not influencing the decision to perform an evaluation because it was generated by the evaluation). In such cases, the information (e.g., from an echocardiogram or stress test) may be entered as a new potential scored "risk factor" or as justification for modifying the score of an existing factor. Thus, clearly the inventive modifications (e.g., common language and scoring) provide greater information and flexibility than either the Cardiac Risk Index or the ACC/AHA guidelines alone (or even in concert). It is further contemplated exports from SHAPE™ may be used to co-populate other indices such as those that calculate Respiratory risk or likelihood of postoperative nausea and vomiting.

It should be evident that the unique classification with scoring introduced herein provides other opportunities for heretofore unappreciated co-population and export. This may be applied to such varied areas as ordering standard laboratory and specialty tests, triaging to anesthesiologists by nonanesthesiology caregivers, determining the need for medical or specialty consultation, transfer to a tertiary care facility, justification for increased billing (e.g., because of patient complexity), planning for required operating room time and postoperative intensive care, the performance of studies to determine benefit of certain forms of monitoring and therapy, and providing patients with coded cards or electronic storage which lists significant conditions (e.g., with scores≥2 in any of the components of the ASPIRIN™ display). The latter has not been detailed prior to this section because it is dependent not only on the history and physical but also on the accompanying laboratory testing that may be prompted by the history and physical. It is, however, a vital component of the inventive program, whose unique properties are derived from the universal language, coding and scoring provided by SHAPE™. We will return to this aspect at the end of this disclosure, after the contributing components have been described.

With respect to laboratory testing, the SISS™ and SICU™ scores, or an integrated index such as SMASH™, can initiate jumps to suggested (default) testing batteries which may be modified as deemed appropriate. These can be coded (color, size, 1-5 class) in such a way so as to designate whether the test(s) is strongly indicated or simply should be considered. For example, for patients with thyroid disease a complete set of thyroid function tests likely would be indicated for a SISS™ 4 degree of dysfunction. However, they should be considered, but not necessarily obtained, for a class 2 score.

FIGS. 21A and 21Bb illustrate how driving (generating or suggesting) of testing may be accomplished. In particular, they a) show how epidemiologic factors and the surgical invasiveness score drive test and b) show how specific medical conditions identified in the score assigned in accordance with the present invention may contribute to the tests that are ordered. The integration of laboratory results is discussed with a preferred embodiment described below.

Especially when a modified ASA score of >3 is obtained for a given body system, options for optimization may be selected. This may include new therapies or generation of a consult request (FIG. 18). This can be done with a letter code, e.g., "con", and then you could have cardiac or pulmonary. This would not only notify other healthcare providers that there is additional workup being done, but also that there is a chance for further optimization. The need for, and/or pending requests for, additional information can co-populate the "I" of ASPIRIN™.

It is further contemplated the present invention can provide medical practitioners with other important information that often is lost in the communication process; for example, that the patient refuses blood or has autodonated his/her blood for use during surgery. This option can be accessible at any time but may be prompted by the surgical score assigned to the patient (for example, if the SOCU™ score is 4 or 5 or, more specifically, if the SICU™ score for impact on the Hematologic System is 4 or 5.). Provisions for its appearance are provided by "R" and/or "N" of the ASPIRIN™ display.

With respect to the ASPIRIN™ display where a graphical user interface is displayed, if deemed preferable in a given setting (for space, HIPAA compliance, etc.), data may be available but not visible to avoid cluttering and/or to maintain confidentiality Obviously, information can be stored in a computerized database. It also can be coded. Additionally, the presence of additional information can appear as an icon which generates a drop-down menu or jump by clicking on it or with a simple mouse over.

Of note, the EKG is the one pictoral component of the patient's record for which text and/or score often is insufficient. Textual descriptors do not relate nuances of the actual tracing or enable optimal comparisons of EKGs obtained at different dates and times. If the score for the EKG is 1 in the current 1-5 (or 0 in the proposed 0-5) system, then the report of the EKG generally is sufficient. However, a score of ≥2 may trigger inclusion of an EKG, if it is available electronically, in the note (If this option is available, it may be activated automatically by selecting a relevant feature in EKG subsystem, by choosing an include EKG option in the program; or access to the EKG may be obtained in the Information section of the ASPIRIN™ display (as shown in FIGS. 5 and 15).

Working Through the Beginning Screens of a Typical Embodiment:

A typical embodiment of the program and graphical user interface screens begins with industry-standard recording or importing of basic information about the patient (e.g., name, medical record #, date of exam, date of planned surgery, name of surgeon). Typically, the name of the surgical procedure is recorded at the time of surgical scheduling Otherwise, it can be hand-entered at this time, preferably by selecting from a pick list. Ideally, the information that already is hard-coded will include not only the standard codes for the surgical procedure but also the inventive surgical risk/invasiveness score (1-5 or 0-5) and the inventive SICU™ score, wherein the anticipated impact on specific systems is delineated for scores where the impact is 2 (or another predetermined value). The healthcare provider performing the history and physical typically will include a description of the present illness at the beginning of his/her note. This can be designed to co-populate the affected body system and relevant Risk indicators. The screens will also provide the option to jump immediately to that system and work off its screens (and hard-coded choices).

The screens for Allergies, Medications, Social History/Habits, Prior Surgeries and Anesthetics will be similar to that of other body systems with the added provisions for co-population (e.g., of different sections of the SHAPE™ program and ASPIRIN™ display). Allergies ideally will be selected from a pick list. The selected allergy will be hard-coded to co-populate other screens such as the Risk indicator screen of the ASPIRIN™ display or to specific body systems in the review of body systems. For all other entries as well as type-ins, a user-generated jump will be available (e.g., right clicking, clicking a button which prompts such co-population, or selecting from a drop-down menu). Medicines will be handled similarly to allergy.

Social History/Habits (e.g., tobacco, alcohol, drugs) likewise will preferentially be selected from pick lists, with hard-coded choices for inventive co-population of relevant patient body systems (e.g., smoking may automatically be recorded as 1.5 in the RESPIRATORY system) and other aspects of the database. Prior surgeries will ideally be obtained from a pick list with options for type-in as in other parts of this program. Prior anesthetic experiences likewise will be obtainable from a pick list with options to type in as per above and options for co-population.

The review of body systems may begin with a screen which lists all possible body systems (including the aforementioned option to select a Multisystem disorder). One option is to select all the body systems that are positive so that the computer can subsequently enable all of those in sequence. However, since it is likely that the information will be recorded during the patient examination, it may be preferable to proceed through each body system sequentially as the history is being obtained. Thus, if one adhered to the sequence shown below, she/he would begin with the CENTRAL NERVOUS SYSTEM (CNS). If one clicks "negative" for CNS, then the computer will proceed to the next body system, PSYCH. If one clicks "positive" for the CNS system, then more specific choices will be enabled. Depending on the given embodiment, this may entail a variety of options for data entry, including:

the choices for CNS in FIG. 32;

CNS-specific choices on screens comparable to those shown for Endocrine in Tables 13 and 15;

screens with progressive branching in accordance with the preferred embodiment described below with reference to FIGS. 26-31.

For each body system, the final note can be configured either to simply ignore all negatives or to display the negative subsystems as a group which is designated as being negative (e.g., "Negative for . . . "). Those skilled in the art will certainly appreciate there are multiple alternative configurations that would be suitable for the aforementioned selection process; e.g., a drop-down menu with "No" as the default.

It should be noted that there are different options for graphically displaying the different body systems. For example, to consolidate, Eyes, Ears, Nose and Throat may be grouped together. However, in most embodiments each body system would have its own number. Additionally, certain subsystems may be listed separately. This is particularly valuable when one is citing factors for cardiovascular risk indices and cardiovascular diagnostic and treatment indices. In such cases, $CNS_{cerebrovsc\ ischemia}$, $ENDO_{diabetes}$, $CARD_{ischemia}$, and $VASC_{pvd}$, may selectively co-populate the CARD system.

The inventive mechanism of coding and scoring systems according to a 1-5 scale may be accomplished in a variety of ways, each of which has its advantages and disadvantages:

Simply having the user assign a score to each positive system as summarized below

---

CNS (1 1.5 2 3 4 5)
PSYCH (1 1.5 2 3 4 5)
PAIN (1 1.5 2 3 4 5)
ENDOCRINE (1 1.5 2 3 4 5)
CARDIAC (1 1.5 2 3 4 5)
VASCULAR (1 1.5 2 3 4 5)
RESPIRATORY (1 1.5 2 3 4 5)
LIVER (1 1.5 2 3 4 5)
PANCREAS (1 1.5 2 3 4 5)
SPLEEN (1 1.5 2 3 4 5)
GASTROINTESTINAL (1 1.5 2 3 4 5)
KIDNEY (1 1.5 2 3 4 5)
URETER, BLADDER & URETRHA (1 1.5 2 3 4 5)
FEMALE & MALE (1 1.5 2 3 4 5)
NEUROMUSCULAR (1 1.5 2 3 4 5)
SKELETAL (1 1.5 2 3 4 5)
SKIN (1 1.5 2 3 4 5)
EYES (1 1.5 2 3 4 5)
EARS (1 1.5 2 3 4 5)
NOSE, & THROAT (1 1.5 2 3 4 5)
HEMATOLOGIC (1 1.5 2 3 4 5)
FLUID & ELECTROLYTES (1 1.5 2 3 4 5)
MULTI-SYSTEM (1 1.5 2 3 4 5)

---

Base the system score on scored aspects of the system (automatic, electronic transfer, or type-in).

Select hard-coded items grouped according to score on the screens for a given system (as shown in FIG. 32 and Tables 13 and 15)

Select scored hard-coded items grouped according to relationship among items.

Select scored hard-coded items on feature and subfeature screens according to the branched-chain logic of a preferred embodiment (discussed below and shown FIG. 7 and FIGS. 26-31).

Embodiments with Coding and Scoring Based Upon Branched-Chain Logic:

The next section of this disclosure will focus on a preferred mechanism for arranging hard-coded choices with branched-chain logic and for adding information from free typing or importing from other data sources. The section also addresses the use of the text, code and score conversion dictionary illustrated in FIG. 10 and the associated interactive index. The last aspects of the invention to be described will be: the integration SHAPE™ with other coding systems; and the integration of the information generated by the history and physical exam, imports from other sources and laboratory testing into a score-based patient information card (or comparable electronic storage) that records positive information based on the SHAPE™ score in a universal language with an established code.

FIG. 9 shows a representative section of the branched-chain logic—and related coding and scoring—in accordance with a preferred embodiment of the present invention. The progressive SHAPE™ branched logic first entails division into body systems, consistent with a typical H&P assessment and then progressive, coded branching to more specific (distal) items: System→Subsystems→Feature Categories→Features→possible Subfeatures and optional Descriptors. Each branch is associated with a specific coding scheme (as detailed in Table 7). These are added sequentially as one proceeds to more distal branches.

This progression from body system to subsystem to subfeatures and descriptors is consistent with the general to specific questioning of patients. The unique advantages of SHAPE™ are generated largely by its mechanisms of scoring based on bidirectional branch-chain logic:

If, based on the healthcare provider's assessment, a given body system is within normal limits, then the body system is assigned a score of 1 (in 1-5 scoring range or 0 in 0-5 range) and predesignated branches corresponding to known negatives are automatically assigned the same low score. This constitutes proximal to distal scoring.

Conversely, if there are positive features or subfeatures within a body system, then it is scored "positive" and its subsystems are enabled. For each positive subsystem, the feature categories are enabled. For each positive feature category, the scored features, and possibly scored subfeatures and unscored descriptors, are enabled. With rare exceptions, scoring is at the level of relevant features and subfeatures, which then are consolidated into a single score for the parent feature category (based on highest score of a feature or subfeature), which in turn contributes to a score for the parent subsystem (default based on highest score of one of its feature categories), which in turn contributes to a score for parent system (default based on highest score of one of its subsystems), which in turn contributes to an overall ASA score for the patient (default based on highest score of one of its systems). This constitutes distal to proximal scoring. Descriptors relate information like right or left side or they enable a non-scored type-in to add information; it may help to explain a score but does not generate a score. This overall process uniquely enables optimal recording of all information for performance and recording the history and physical exam, an organized system for database maintenance, and a unique means of scoring that is compatible with the traditional use of the ASA physical status while communicating and storing a much greater degree of detail. Details of potentially overlapping features and subfeatures may be recorded, coded and scored regardless of whether they should be scored independently, since the score of the feature category is based solely on the highest score within a feature category. Likewise, for subsystems and systems. Hence, the SHAPE™ scoring algorithms can be transparent and noncumbersome to the user of such means of data acquisition. Additionally, the progressive branching of subsystems into feature categories and features is consistent with the branch logic commonly used for questionnaires and electronic records, where positive responses commonly generate more specific choices; this will be addressed in relation to importing (below).

Specifically, FIG. 9 shows:

one of the body systems (e.g., CNS), with two of its subsystems, each of which has two feature categories.

These in turn have features, one of which has subfeatures, one of which has descriptors; another feature simply has descriptors.

The score for each proximal portion will be the same as the feature score unless another limb of the branch has a positive feature with a higher score.

Text, code and score potentially can be entered collectively in a single field or in separate fields. However, although grouped or presented with the text for scored features and subfeatures in data acquisition screens, scores should be stored in independent fields for score-based assessments, analyses and integrative indices. The branching and coding may be flexible. If deemed necessary, additional levels, such as subsubfeatures may be added for a complex system such as Cardiac (although this has not found to be necessary).

A preferred obtain for coding is shown in Table 7. However, coding for features, subfeatures, and descriptors can be:

Simply based on the given system; or

Sequential within each level of branching; or

Adapted to include established codes (e.g., ICD-9 codes for specific conditions as established by governmental and nongovernmental regulatory agencies) within the desired level of branching. For example, if a given feature is equivalent to that assigned a code of 22222 in another program (e.g. ICD-9 codes), the 22222 could be included at the appropriate level of branching its inclusion at the subfeature level of branching may be further identified at 0.00022222.

Recording of the history and physical may be supplemented by: selecting a type-in option relevant to the hard-coded choice with its score (discussed later); and enabling an Import relevant to the hard-coded choice with its score (discussed later); and entering a less specific type-in or Import that is not associated with a hard-coded choice (as discussed below in greater detail)

The specific score relating to systemic significance (impact) of a given condition in a given body system typically stays with it within the given body system and, in preferred embodiments discussed previously, remains with it in a fixed FC/F/sF code. However, in other embodiments, alternative scores may be assigned for co-population of other body systems and other areas of co-population (databases, diagnostic and treatment algorithms such as that shown in Table 18a). Eventually, if deemed indicated, one could:

assign weights to components of an integrated equation (such as that shown above for the equation predicting hospital costs);

convert scores to points (as shown above); and convert scores to constants (as for Exercise Tolerance in Table 12a)

Unless modified by the user, the jump after a hard-coded choice is predetermined. This predetermined jump may take one of the following forms: remaining on the current screen so as to enable selection of another choice on the screen; jumping to the next more distal branch on the screen (e.g., from feature category to feature); and moving in parallel manner to another screen within a given branch. This would occur in the following settings: move from one descriptor screen to the next descriptor screen under the same feature or sub-feature; jump from one system to the next if one clicks negative for the system; or jump from one sub-system to the next if one clicks negative for the sub-system. These may be optional, or one may just simply skip negative systems, sub-systems, or feature categories.

Jumping to another system, subsystem, or feature category or to generic descriptors, as may be mediated by an interactive index and designated by arrows, letters and/or symbols.

Looking at the pathways for a potential embodiment in more detail:

selection of a system is followed by a jump to a screen of its subsystems;

selection of a subsystem is followed by a jump to a screen of its feature categories; and selection of a feature category is followed by jump to a screen of either its:

Scored features—choices associated with inventive SHAPE™ Individual System Status (SISS™) scores. Selection a scored feature records the item as well as its score. It may keep the user on the same screen or may cause the program to next jump to: unscored descriptors; back to a more proximal portion of the branch chain (e.g., another feature category or a list of subsystems); to another body system which either is concurrently affected by the condition being described in the present system or is next in the logical sequence of the history and physical.

Unscored features—choices that are not associated with a score (or only have a tentative score); instead, they provide information that is deemed important before the scoring screen is accessed. Selection of an unscored feature from this screen causes a jump to a list of scored subfeatures—as for scored features, each subfeature is associated with a SISS™ score. Selection of a scored subfeature records the item and its score. It then may keep the user on the same screen or may cause the program to next jump to: unscored descriptors; back to a more proximal portion of the chain (e.g., another feature, feature category or list of subsystems); another system (as per scored features above).

selection of a descriptor records the descriptor. It may keep the user on the same screen or may cause the program to next jump to:

another descriptor screen;

back to a more proximal portion of the chain (e.g., another subfeature, feature, feature category or list of subsystems);

to another system (as per scored features above)

Alternatively, the proximal to distal jumping within a given branch may be interrupted by a diversion designated by superscripted letters, symbols or arrows proximal to a screen header or one or more of its hard-coded choices. Examples of potential predetermined pathways include:

⇒ means jump to a specific screen that is not distal to the present screen or next in the typical sequence of successive feature categories, subsystems or systems.

⇐ means return to the screen that initiated a jump to a screen rather than to the next more distal screen or the screen next in the logical sequence of successive feature categories, subsystems or systems.

⇔ means that there is another portion of the same system that also pertains to the given item. User could either: jump to that section at this time and then return to the present screen; or the user may elect to first complete the present screen and access the other screen(s) at a different portion of the program.

⇊ means after jumping to next (more distal) screen in a sequence (e.g., from feature category to feature, of from scored feature to descriptor), the computer immediately returns to the original screen to enable additional choices on that screen.

⇒⇓ means after jumping to other screens (as indicated by letter codes) which are outside the proximal to distal branched logic, the computer jumps to the next distal screen in the present sequence.

* means that if another specific system or Multisystem Condition is identified by selecting the given hard-coded option on this screen, then that system automatically is selected by the computer for positive identification in database(s) and note(s) and its options for data entry are enabled. Options for the user: proceed immediately to that system; proceed to that system upon completion of the given branch; accept as complete information that already has been entered into that system; or enter information into that system when it is reached during normal progression of the history and physical. (The relationships among a multisystem disorder and the systems it affects are described earlier.)

a, b, c, d, . . . (English letters) take the user through a sequence of jumps through screens that generic for a given system; e.g., generic CNS descriptor screens as shown in association with the preferred embodiment described below.

Alpha (α), beta (β) . . . (Greek letters) indicate jumps to Generic Multisystem screens e.g., alpha (α) causes a jump to the Multisystem Condition screens devoted to Systemic/Remote Effects of Malignancies and Their Therapy.

If multiple jumping options exist after completing such a generic screen, then the user may select the next screen from the inventive Interactive Index (discussed later). In order to minimize any confusion with respect to scoring in the current preferred embodiment, no access to generic screens is programmed until after the Scored Feature or Scored Subfeature level.

Unless the letters are accompanied by ⇔ or ⇒⇓ to indicate return to the present screen or a subsequent Descriptor screen, upon completion of the letter-designated screen(s), the computer will automatically jump to the next Feature Category or Subsystem with an alternative option to access the Interactive Index. The exception—if one selects "Other" from the present screen, then the default is for the computer to bypass the letter-coded superscripts (discussed below).

A subscripted numerical prefix may be used to document co-population of diagnostic and treatment algorithms that are based on information such as that designated by the given item (e.g., diabetes is a risk factor in Cardiac Risk Indices and a potential indication for perioperative beta-blocker administration).

It should be understood that these letters and symbols would not necessarily be visible to the user. However, they could be accessed by administrative personnel to document prescribed pathways and modify them as deemed indicated.

Before delineating major components of the embodiment of the inventive program shown in FIG. 9 and detailed in FIGS. 26-31, relevant inventive components are addressed with respect to:
 entry of data—coded and scored type-ins; coded and scored imports; and
 organization and interfacing—the interactive index and the conversion dictionary.

Coded and Scored Type-Ins:

Although a mechanism for free typing is available at all times (e.g., via a pen icon), the present invention is designed so the user preferentially selects hard-coded choices. Nonetheless, at times, one may wish to enter information that is different from the hard-coded choices. Without the present invention, this typically has meant that the information is simply recorded in an unspecified portion of a database or note, while sacrificing specificity of coding and the potential for selective scoring. The latter limitation was not appreciated to be a problem prior to the introduction of the inventive scoring herein. SHAPE™ has multiple type-in options which are designed to maximize specificity of coding and scoring while minimizing complexity for the user.

If the information is closely associated with a given hard-coded choice on a given screen, then user can select what I have called the "Similar Type-in" option that is available for each hard-coded choice and enter the information as prompted (e.g., if hard-coded choice said "evidence of heart attack six months ago" and user wanted to type "chest pain with troponin leak six months ago"). The Similar Type-in option may be accessed by one of several potential options, including a drop-down menu or right-click menu associated with this hard-coded choice. The advantages of this approach are that:
 it provides for entry of the type-in information into a relevant portion of the database;
 it provides appropriate specificity of coding, storage, linking and jumping; and
 if the hard-coded option is associated with a score, then this facilitates the assigning of and recording of the score for the type-in.

A preferred option for coding is for the Similar Type-in to have the same basic code as the hard-coded choice followed by a letter suffix such as the letter "a" (i.e., the basic code before the letter suffix would document the commonality with a hard-coded choice; the letter would designate that it is a type-in). The database would include the annotated code and associated text. The closeness of the match may be delineated by a second letter chosen by the healthcare provider (e.g. a=exact, b=equivalent, c=similar). Options for storing and communicating the hard-coded choice and type-in include:
 Type-in only for database and note
 Hard-coded and type-in for database and note.
 Hard-coded and type-in for database, but only hard-coded for note
 Hard-coded and type-in for database, but only type-in for note
 Hard-coded and type-in for note, but only hard-coded for database.
 Hard-coded and type-in for database, but only type-in for note Even when there is not an associated hard-coded choice, the invention provides for specific coding and scoring:
 On screens where it is very likely that potential type-in information may not be closely associated with a hard-coded choice, selecting "Unspecified" will enable entry of the type-in on the given screen; the type-in then would be assigned codes that designate the branching proximal to and including the given screen. On feature or subfeature screens with scoring, "Unspecified" may be replaced with a "Scored Type-in" option. Here, the user is prompted to select a score for the free-type information. As for the "Unspecified" type-in option, the "Scored Type-in" option enables appropriate coding for a system, subsystem, feature category, etc. In addition, it allows scoring in the context of the scores assigned to other hard-coded choices on a given screen.

On Descriptor screens, the selection of "Other" places the cursor at the beginning of a section (on the given screen or an alternative screen) for free-typing.

A System Type-in screen at the end of each system serves as a safety net for recording, coding, and even scoring information pertaining to the given system. This screen should not be used when more specific options are available, since entry of type-in information onto this screen will provide less specific coding than entry within a specific Subsystem and Feature Category. Upon completion of the present screen, the default option is to proceed to the next system. However, the other jumping options are available. These System Type-ins may have a default code that is indicative of their nonspecific nature (e.g., 0.0000 . . . 99, 98, 97). This will facilitate storage, as well as future editing and moving.

There also are provisions for a "Miscellaneous System" to enable recording of information that subsequently can be distributed to a specific system for coding and scoring.

These inventive methods overcome the major problems with free text—as noted by Kazanjian (Kazanjian P E, Tremper K K, O'Reilly M, Kheterpal S: *The electronic pre-anesthesia form: An integral component of a new anesthesia information management system*, Seminars in Anesthesia, Perioperative Medicine And Pain 23(2):133-150, June 2004), "free text entries such as 'low platelets' could not be recognized and accounted for by the data processing engine." The present invention ensures inclusion of a coded and, if indicated, scored entry in the database which can then be treated comparably to a hard-coded entry.

Many of the options for coded type-ins shown in the aforementioned preferred embodiment are applicable to less intricate approaches such as directed selection of features in FIG. 32. Here, right clicking on a scored option can enable options for typing in free test associated with the coded item. Less specific but nonetheless scored entries can simply be entered into the appropriate scoring column of a given subsystem cited in the table (or in the overall system). Again, options may be elicited by right-clicking or its equivalent.

Imported Information:

The program is designed to facilitate entry, coding and scoring of information imported from other electronic sources such as a computer, fax, or scanner (e.g., patient questionnaire, discharge summary, physician's note, other database). The inventive keys to this are entry at the appropriate branch level and establishment of compatibility with text, code and score conversion dictionary (FIG. 10). Imported information falls into several categories which may be handled in a variety of compatible ways, including:

Information that is worded identically to hard-coded choices in SHAPE™, primarily as a result of deliberately matching the text and codes of the external source (e.g., questionnaire) with the SHAPE™ database. In such a case, the imported information may be batch transferred to the appropriate system, subsystem, feature category, feature, subfeature and/or descriptor. It is identified as an import by a means such as a letter suffix which may be specific for the given source. Ideally, the import will occur in bulk or in segments (based on word match, headings, question numbers or codes) but could be done on an item-item basis.

Information that is similar to a given hard-coded choice but not worded identically can be directed to that hard-coded choice but would be annotated specially, as with double letters so to indicate the source (first letter) and that it is similar to (but not identical with) the SHAPE™ hard-coded item. When a common import meets the criteria of having items that are similar but not equal, then the conversion can be established so that bulk transfer may occur as for identically worded and coded sources. If deemed desirable, the code from the source (e.g., of the questionnaire) could be included in the SHAPE™ branched-logic code (i.e., as described below for inclusion of ICD-9 codes). Such interfacing may be mediated by the conversion dictionary, one of whose functions is the delineation of the relationship between different text fields.

Information that is relevant to the History and Physical but not specific to a given hard-coded option may be imported at the appropriate branch level as a text field or its equivalent (i.e., like a type-in) and be coded according to that level with a special numeric code (e.g., 95, 94, 93, . . . 90) followed by a double letter suffix to designate that it is an import that is not associated with a coded hard-coded choice (or an alternative form of coding) Imported items could then be scored and/or moved to other portions of the SHAPE™ database so as to enable their use for SHAPE™'s multifaceted functions.

Matching between the import source and SHAPE™ may be based on a number of formats, including:

word match;

codes;

numbering sequence of the questions; and subheading/section.

The handling of imports in this manner provides a uniform way for entering them, coding them, and scoring them in the appropriate sections of the program. It also facilitates tracking them so the program may be updated to become more compatible with other means of data entry (e.g., electronic transfer, faxing, scanning). The number of steps required to ensure such entry will depend on the system compatibility.

Ideally, the names and coding of the information in the source of import (e.g., questionnaire) will be matched to SHAPE™. However, if this is not possible, the inventive system includes a conversion dictionary that defines the text, coding (and scoring) interface between SHAPE™ and each source of information. This enables matching to a hard-coded choice in the SHAPE™ program. As for free-typing, letters in a suffix may identify the entry as an import, identify its source, and define the degree of similarity to existing hard-coded entries. For example, if the SHAPE™ program contained a hard-coded option "recent CHF with pulmonary symptoms" that was assigned the code 0.0001$3 and the source of the imported information had a statement "recent pulmonary edema", then "recent pulmonary edema" would be entered into the program at the level of the aforementioned hard-coded option with a code akin to 0.0001A$3aa. The specific letter code suffix would be specific for the given source of input.

Organization and Interaction:

The conversion dictionary mentioned throughout is at the heart of interfaces with imports, as well for co-population with the SHAPE™ data and exports. Searching and display can be at the level of any or all of the following:

Text

Coding (with suffixes)

Coding and scoring

The conversion dictionary could be expandable; if you have a new type-in or import and click yes, then it could be included in the conversion dictionary.

To simplify aforementioned selection and scoring hard-coded items as well as related type-ins and imports, selection of a hard-coded choice could generate a drop-down menu (or equivalent). Two examples follow:

For an embodiment where selection of scored items is via drop-down menus, the menu for each hard-coded choice on a System, Subsystem, Feature Category or Unscored Feature Screen also may contain:

No (default)

Yes

Similar Type-in which allows for free typing in a manner that enables modified coding (e.g., same basic code plus a letter suffix), storage, communication, linking and jumping in accordance with the hard-coded choice.

Exact Import that is matched to an electronic input source (e.g., matched questionnaire)

Similar Import that enables importing from another portion of SHAPE™ or another electronic source with modified coding (e.g., same basic code plus a letter suffix), storage, communication, linking and jumping in accordance with the hard-coded choice.

a bidirectional jump to Conversion Dictionary to determine if there is relevant information from other sources or if there is co-population of other sections of the database with equivalent or similar entries.

For an embodiment where selection is via drop-down menus, the menu for each scored hard-coded choice on a scored Feature or scored Subfeature screen may contain:

No (default)

Yes (1)

Yes (1.5)

Yes (2)

Yes (3)

Yes (4)

Yes (5) (where sequence of numbers is arranged such that default score is listed first)

Scored Type-in which allows for free typing in a manner that enables modified coding (e.g., same basic code plus a letter suffix), storage, communication, linking and jumping in accordance with the hard-coded choice. Moreover, since the hard-coded choice is scored on this screen, the "similar" text will receive the default score assigned to the hard-coded choice. As for the hard-coded choice, the menu (or linking) allows one to select an alternative score.

Exact import (as above).

Similar import (as above).

The interaction of the different components of the SHAPE™ databases and related sites of import and export can be facilitated by an Interactive Index which may be integrated with the conversion dictionary. In its expanded state, this would include all the screens of the SHAPE™ database. Compressed states would facilitate navigation, which may be accomplished by text and/or code, with creep seek based upon successive typing of codes or text. Examples of the collective applications of importing and interfacing and utilization of the conversion dictionary and integrative index to achieve outcomes such as those cited in Table 3 include:

Improved input from Questionnaires—Although the present questioning technique is consistent with established art for comparable questionnaires, other questionnaires do not quantify information in accordance with the present invention, do not enable entry of data as described herein (for example, with matched terminology), and do not provide options for data management illustrated in FIG. 3 and/or described herein. For example, customization to achieve compatibility with the computerized acquisition, analysis, cumulation, display and communication program, most notably its characterization for a scoring system as present in accordance with the present invention.

Customized importing of EKGs and other "figures" wherein it is helpful for a care provider to be able to review a tracing, specifically when the 1-5 score indicates a predetermined level of pathology The need to include the actual tracing may be driven by score assigned to the findings in the appropriate subsystem(s) of the Cardiac System (as shown in FIG. 32). This will drive decisions as to where to display EKG (e.g., ASPIRIN™ Display; a compressed "SHAPE™ wallet" card described below).

Integrated development of diagnostic, treatment and communication scripts based upon the cumulated positive findings (e.g., above a certain score) in the varied aspects of the database, including the history and physical, SICU™ rating of surgical risk/invasiveness, scores assigned to laboratory results (discussed in subsequent description of a preferred embodiment). These may focus on specific medical conditions and/or specific surgical procedures.

Identifying items that are germane to specific risk indices such as the factors that should be considered in a patient with documented or suspected ischemic heart disease.

Interfaces concerning such issues as information, policies, guidelines and alternatives institutional material on the given computer or internet: for example, pharmacy, labs, policy manuals, other offices, educational material:

PDA's which can interface with the main program to enable partial or complete transfer of patient data or other information;

electronic texts and related materials; of note, the inventor has edited one review book in anesthesia and is editing a mini-text (with accompanying PDA version) wherein the code assigned in accordance with the present invention terminology and text terminology can coincide for rapid jumping and transfer (—vital information could be directed to desired part of database);

other resource material on Internet;

risk indices and related material (stored on computer or via web) to enable the score assigned in accordance with the present invention to be immediately compatible with the terms used in that index and thereby enable automated calculation of the given index; for example, there could be terms and fields for the established Cardiac Risk Index and for the American College of Cardiology/American Heart Association guidelines for preoperative cardiac evaluation; and likewise could jump to site that gives precise recommendations for SBE (subacute bacterial endocarditis) or DVT (deep vein thrombosis) prophylaxis that could be down-loaded to portion(s) with the relevant code assigned in accordance with the present invention with corresponding terminology.

FIGS. 26-31 include graphical user interface screens of a preferred embodiment that deals with the Central Nervous (CNS) system, the Psychiatric and Pain system, the Diabetes subsystem of the Endocrine system ($ENDO_{diabetes}$) and Laboratory Results. These were selected because they cover a wide range of configurations and demonstrate a wide range of program components that relate to branched-chain logic and coding and related scoring. As those skilled in the art will appreciate, this form of branched-chain logic is but one of many ways of coding and scoring that is within the scope and spirit of this invention. As clinical experience is gained with the program(s), screen headings, hard-coded choices, and jumping pathways may be changed while remaining consistent with the inventive coding and scoring disclosed herein.

After the list of body systems, the next screen would be a list of the different subsystems of the CNS system. The user either could highlight all positive subsystems or proceed through the positive subsystems sequentially. Either way, selection would enable (activate) screens more distal in the body system. If a subsystem is negative, it simply may be skipped.

If one selected the Seizures subsystem, then this would initiate a jump to a screen of feature categories for the Seizure subsystem (FIG. 26.1). The pathway and its standardized punctuation (System: Subsystem: Feature Category/Features//Subfeatures-Descriptors) have been included in many of the headings for purposes of clarity in this demonstration. These details could be available for training sessions but would not be needed for day-to-day use by an experienced user. The user would select the feature category that is most appropriate or otherwise type in an alternative. This would cause a jump to the feature screen for the given feature category. The first such screen is shown here as a series of scored features under the heading Control of Generalized Tonic-Clonic Seizures (FIG. 26.2). The numbers in parentheses represent the default score for the given feature. The "Scored Type-in" option is explained briefly in italics and was described in the discussion of Type-ins above. The subsequent screens illustrate what would happen if one had selected Generalized Absence Seizures (FIG. 26.3), Complex Partial Seizures (FIG. 26.4), or Simple Partial Seizures (FIG. 26.5).

After the user selects a scored feature on the "CNS: Seizures (subsys):Generalized Tonic-Clonic Seizures (feat categ)/Control (scored features)" screen, the subsequent jump is to the first of four seizure-specific Descriptor screens (FIGS. 26.6-26.9). On each screen, the user would select the relevant hard-coded unscored descriptor(s).

Some of these are preceded by a "⇔" which indicates that the item also is addressed on other screens within the same system (e.g., a subsystem or feature category that has additional information about this item). User could jump to that section at this time but probably best simply to access it when you come to it in the program.

The English letters preceding the fourth of these Descriptor screens indicate that, unless otherwise directed, the computer will jump to a series of generic screens (which are shown in FIGS. 27.1-27.7).

The first letter-coded Generic CNS screen is "a" (=Brain Region Descriptors). This allows one to select one or more of the hard-coded choices or to type in additional information about the location of the seizure focus. As stated above, these descriptors describe the nature of the seizures but are not in and of themselves associated with a specific score.

"n/a" (not applicable) or its equivalent allows one to quickly jump to the next screen. The need for this may be avoided on a given screen when a "skip" is built into selected choices on a preceding screen.

The computer next jumps to "b" (=Generic CNS Descriptor Screen for Global CNS Signs and Symptoms (s/s)).

After "b" the computer will jump to screens "e" (Sites of Peripheral s/s), "f" (CNS Tests) and then to screen "g" (CNS Treatments). Notice on the CNS Treatments screen that the hard-coded choices for Radiation and Chemotherapy are preceded by an * to enable entering information about Multisystem involvement (as per the bottom of FIG. 32).

Other items are preceded by an asterisk ("*") which indicates interaction with another system (in accordance with list shown on FIG. 28.1). If one jumps to the screens of that system at this time (via menu option or via Interactive Index), then the computer will automatically return to the screen from which the bidirectional jump originated (or the user can access the Interactive Index after entry into the new screen(s) is completed.

If one selects the Cerebral Ischemia subsystem, then the screen would jump to the feature categories that are shown. Selection of a given feature category jumps to a screen with the features for that category. As opposed to the Seizures subsystem, where scoring was at the feature level, in the present subsystem unscored features have been included for each feature category. Selection of an unscored feature enables a scored subfeature screen and causes a jump to that screen. Consistent with the aims of the present embodiment, jumps to descriptors are configured so that they occur after the scoring so as to ensure consistency and inclusion of desired details in the final note and database without concern about affecting scoring by the degree of description that is provided. (While helpful, this is not a requirement for other applications of SHAPE™). As for other screens, the jumps to generic screens (FIGS. 27.1, 27.6 and 27.7) occur after the selection of a hard-coded choice. Although not shown here, the generic screen may be customized so the most relevant choices for a given jump to that screen may be highlighted (or similarly designated).

The first feature category of "CNS: Cerebral Ischemia" (FIG. 26.10) is "Asymptomatic Carotid Disease". If this is selected, a series of unscored features is provided (FIG. 26.11). Selection of a hard-coded choice on this screen causes a jump to a subfeatures screen (FIG. 26.12, 26.13 or 26.14) which illustrates two unique aspects of the program noted above: scored subfeatures (after unscored features or features with a tentative score, as opposed to more established default score); and letters in the prefix designating the jumping pathway after choice selection on the given screen. Each scored subfeature is associated with a default score, which may be changed by the user. This screen also provides an option for Type-in with a prompt for the user to select a score. This obviates a major shortcoming of other data acquisition programs—where Type-ins typically are not coded or scored. As noted above, free-typing would be associated with a hard-coded choice and the type-in option would be accessed via that choice so as to optimize coding and scoring.

Selection of TIA (trans ischemic attack) or stroke initiates similar jumps to an unscored features screen (FIG. 26.15) which delineates timing and then to a scored subfeatures screen (TIA on FIGS. 26.16-26.18; stroke on FIGS. 26.19-26.22). Notice that the heading for each subfeature screen in this part of the program is preceded by a series of English letters which take one sequentially through the screens for generic CNS descriptors a-g (FIGS. 27.1-27.7). The sequence of Generic CNS Descriptors for TIA or Stroke bypasses the screens specific to seizures; instead, it includes screens that detail neurological signs and symptoms.

There is also an option on the "Cerebral Ischemia: Feature Categories" screen for typing information about other forms of cerebral ischemia if they should occur by selecting "Unspecified Cerebral Ischemia" or "Other" as described below.

If one selected the subsystem for Nonischemic Cerebrovascular Disorders (FIG. 26.23), then he or she would see the list of feature categories beginning with AVMs and Aneurysms. Each feature selection causes a jump to a subsequent screen of unscored features (FIGS. 26.24-26.32). Although these features may very well influence the score and thus are taken into account, the score is not officially assigned until the program jumps to one of the subfeature screens based on the hard-coded feature options. As before, most of the scored subfeatures are associated with a default score but there are other options. After the subfeature is selected, the computer jumps to the lettered generic CNS screens (a-g in FIGS. 27.1-27.7) delineated in the screen header. Exception—if "Other" is selected on the Nonischemic Cerebrovascular Disorders screen, the computer will jump to the type-in screen for typing and scoring at the end of the screens for the given system.

The last feature category for the Nonischemic Cerebrovascular Disorders subsystem is the Headaches feature category. If one selects this feature category, then one jumps to an unscored feature screen for Type of Headache. Depending on which feature is selected from this screen, one jumps to the scored subfeatures of mild, moderate, severe, or life-threatening (FIGS. 26.33-26.36).

If one selects the CNS subsystem of Nonmalignant Intracranial Mass, then s/he would jump to the feature category screen which lists different nonmalignant masses (FIG. 26.37). The subsequent unscored feature screen lists potential tumor locations (FIG. 26.38). The subfeature screen contains scored hard-coded choices (FIG. 26.39). This screen is followed by two descriptor screens (FIGS. 26.40-26.41; the "Yes" selection on the second screen is preceded by English letters delineating jumps to generic CNS screens (FIGS. 27.2-27.7).

If one selected the CNS subsystem for Malignant Intracranial Mass, then s/he too would go to a screen of different types (feature categories) (FIG. 26.42) and then to the unscored feature screen listing different potential locations (FIG. 26.43). Scoring again is at the subfeatures screen (FIG. 26.44). This is followed by several descriptor screens (FIGS. 26.45-26.47). The "Yes" option of the "Effects of Malignant Tumor or Therapy Within CNS" descriptor screen (FIG. 26.46) is preceded by letters delineating jumps through the generic CNS descriptors (FIGS. 27.2-27.7). Upon completion of the letter-coded jumps through the generic CNS descriptors, the computer will proceed to the next descriptor screen within the Malignant Intracranial Tumor subsystem.

On the next descriptor screen, with the header "Systemic or Remote Effects of Tumor or Therapy (FIG. 26.47), the "Yes" is preceded by the Greek letter "alpha" (α) which indicate a jumps to the Multisystem screens related to systemic/remote effects of malignancies and their treatment (as shown at the bottom of FIG. 32 and detailed in FIG. 28.2 in its series of multisystem conditions). The ensuing screens describe effects of the malignancy and its treatment (FIGS. 28.3-28.6). Depending on the selection, one will jump to screens with additional descriptors that include lists of chemotherapeutic agents and their remote/systemic effects (FIGS. 28.7 and 28.8). The next screen illustrates what would happen if one selected radiation, either alone or in conjunction with chemotherapy. It prompts the user to include whatever information might be relevant and available (optional) and then jumps to the relevant side effect screen where one is prompted to either say that there were no side effects or to list them and their impact.

Note the special form of scoring for this Multisystem condition in the embodiment. On these Malignancy screens, there are no specific scored features; such specified scoring is reserved for individual systems. Instead, there is a prompt for the user to supply an overall score for the features of the systemic effects of chemotherapy feature category (FIGS. 28.6, 28.10 and 28.11). As stated earlier in this document, s/he is then prompted to state whether this score should be labeled with an "=," "+," or "+>" (Table 7). Note, also that since the score that is assigned is not necessarily for a specific feature or subfeature, the descriptors are not restricted to the most distal point of branching.

The next screen dealing specifically with the Central Nervous System concerns Intracranial Trauma and Injury (FIG. 26.48). After selecting a feature category which will be listed in the note, the user jumps to a common feature screen for all of the listed feature categories (FIG. 26.49). Scoring occurs at the subfeature level (FIG. 26.50).

The next series of screens handles CNS infection in a similar manner (FIGS. 26.51-26.53). Some (a partial representation) of the potential infections that may be included on this list are included as feature categories. For each of the specific infections, the user jumps to a common feature screen that has the signs and symptoms along with their scores.

The next series of screens deals with ICP (intracranial pressure) (FIGS. 26.54-26.56). Again, the feature category screen lists potential causes (see FIG. 26.54). Then there is a common screen which lists and scores the signs and symptoms (see FIG. 26.55). Of note, provisions for an item such as ICP are unique in that it is also listed as a sign/symptom in the generic CNS screen for global CNS signs and symptoms (FIG. 27.2). Because it is listed as a separate sub-system, its inclusion in the generic CNS screen for global CNS signs and symptoms is preceded by a double-sided arrow. This arrow would prompt a jump to the ICP signs and symptoms feature screen so as to ensure that the details of increased intracranial pressure are addressed at this time or at another portion of the program (discussed above).

The next screens deal with altered cognition (FIGS. 26.57-26.58). As per increased ICP, this also is listed as a general CNS descriptor for other conditions (FIG. 27.2).

The final two screens of FIG. 26 deal with the sub-system of Parkinsonism and other CNS-based movement disorders (FIGS. 26.59-26.60). The feature category screen lists two of the many potential disorders that can be listed on this screen. The next screen shows the features of the specific disorder; their severity is rated on this screen. The letters preceding the header indicate that there are jumps to other CNS screens to enable selection of unscored descriptors.

At the end of each system, there is the option to type-in and score "Other." The score for the system (and its scored components) may be displayed. If a score has not been determined or if the user wishes to modify the assigned score, s/he is prompted to do so before moving on to the next system.

Then, on to the next system or subsystem: PSYCHIATRIC DISORDERS and PAIN (FIGS. 29.1-29.7). Of note on these screens is the design which enables documentation of the use and effect of therapy and its influence on the score. This provides two important pieces of information—current signs and symptoms and what they would be in the absence of therapy.

FIG. 30 shows typical screens for diabetes mellitus. They are included not only to show the consistency of the branch logic and scoring for another system, but also because diabetes has important implications for other systems and for co-population of risk assessment indices and diagnostic and treatment algorithms; and its features are closely tied to its use of medications. Therefore, I have selected to use it as another example of the inventive system.

The header on FIG. 30.1 indicates Endocrine System: Diabetes Mellitus subsystem/Feature Categories. The next two screens are at the scored feature level—depending on the choice that is selected, the computer will jump to either the screen with the scored features concerning control of Type 1 (FIG. 30.1) or Type 2 diabetes (FIG. 30.2). Depending on the hard-coded choices, there are then several potential jumps to descriptor screens which include: insulin requirements (FIG. 30.4); glucose management (wherein the user is prompted to type in important data that is important to the note and database) (but will not have any new impact on scoring) (FIG. 30.5); Glucose values (FIG. 30.6) with an optional table is provided to enter such data about descriptors (FIG. 30.7); HbA1C levels as an indication of diabetic complications and sequelae with options of n/a (not applicable), none, or any one of the various bodily systems (FIG. 30.8); and Interactions with other systems are designated by an *, with potential jumps to systems that may affect or be affected by diabetes (FIG. 28.1).

For purposes of simplicity, selections that may be available on a given screen may actually be an integration of 2 or more features or a feature and a subfeature. For example, it may state "severe hypertensive nephropathy". This would tell you that there is a severe nephropathy (feature) and there is a hypertensive nephropathy (also a feature). By way of another example, it may state "Pronounced hypoxia requiring continuous oxygen". This is actually a feature and a subfeature combined, wherein pronounced hypoxia could either be a 3 or 4, but the requirement for continuous nasal oxygen would be a 4. If feature category would be 4, and a given item itself together is 4 to 4. However, in the database, it would be listed as 2 separate entries: pronounced hypoxia requiring continuous $O_2$. For this particular patient, the pronounced hypoxia would be scored a 4 in the database, because it provides that number from subsequent subfeatures. Regardless of its score, its total would be that of pronounced hypoxia.

The flexibility of SHAPE™ for co-populating different body systems, displays and notes and for exporting to diagnostic and treatment algorithms as well as different databases and programs is vital with respect to a disorder such as diabetes. Applications include:

Co-population of other body systems affected by this disorder. Even if a diabetic patient does not have evidence of diabetic-induced cardiovascular disease, the presence of this risk factor could be documented with a CARDIAC score of 2 (consistent with its inclusion as a Minor Cardiovascular Risk Factor in Table 18).

Co-population of algorithms that weigh cardiovascular risk factors and treatment regimens (e.g., the perioperative administration of beta-blockers in patients at risk for a myocardial infarction as delineated by subscripts 1-3 in the Diabetes screens). Scored as well as unscored data may be transferred automatically; the prescribed paths may be designated, as by a numerical subscript before the hard-coded choice.

Co-population of the ASPIRIN™ display, such as to designate need for therapy on the day of surgery (e.g., subscript "4" on the Descriptors Describing Plans for Therapy of Diabetes screen (FIG. 30.11)

The universal application of the present invention thus has been demonstrated with respect to attaining, storing and co-populating (with exporting) the information attained during the history and physical exam. The present disclosure will next illustrate how information from two forms of testing—routine laboratory testing (with accepted ranges of normality) and EKGs (wherein clear cut criteria may not exist) may be included.

Laboratory tests could be recorded as per routine in the institution laboratory database but also co-populate sections of SHAPE™ where they can be recorded, coded and scored for storage in a Laboratory (LAB) "system" (or as a subsystem in FLUID & LYTES) as well as with specific body systems (e.g., liver function tests with liver), and/or Risk Indicators, Interim Information and Issues and where they can be used for analysis, display and distribution to interfaced notes, algorithms etc. Again, the 1-5 (or 0-5) system is used in a series of screens as illustrated for the lab values for potassium (FIGS. 31.1-31.5).

Inventive formulas convert lab values to scores. One such method is shown in FIG. 17. Alternatively, one could establish other criteria. For example, if normal range for potassium is 3.5-4.5 mEq/l, then 3.3-3.6 may be scored as "borderline low-normal" which is scored 1.5 in the current example; 2.7-3.2 as slightly below normal (score of 2); 2.0-2.6 as significantly below normal (score of 3). Abnormal values that generate the specified cutoff can trigger score-driven jumps to screens which list medications that commonly cause or are affected by the given abnormality (e.g., low potassium can lead to digitalis toxicity, diuretics can lead to low sodium). Likewise, the abnormal values can be linked to relevant medical conditions and to surgery which may exacerbate the disorder (e.g., transurethral resection of the prostate with bladder irrigation would be identified by the SICU™ score as affecting electrolytes (exacerbating hyponatremia).

Links will influence level of concern and decisions with respect to treatment of abnormal chemistries. For example, if patient is taking digitalis, this would not only be listed in medication screen but also co-populate CARDIAC system with the option for a separate screen that records Factors Affected by Electrolytes. This would be co-populated with relevant entries from Medications, Fluid and Electrolytes, Kidney, GI as well as sections from the SICU™ score for the upcoming surgery. Hence, the present invention has scoring options for a number of the hard-coded choices.

An institution would have the option of tailoring the program so that Lab Results is a subsystem of FLUID & LYTES. The problem with this is that lab results often do not become available until after the History and Physical are obtained Thus, such a wide range of "late arriving" information that can be relevant to multiple systems might best be handled separately. Conversely, system-specific tests preferably should be included in the associated body system—e.g., cardiac stress test in CARDIAC or pulmonary function tests in RESPIRATORY.

In certain situations, the textual description associated with a score may not be sufficient to effectively relate the abnormality. Although criteria for scoring an EKG have been provided in FIG. 32, in the acute perioperative setting it is difficult to include sufficient hard-coded criteria to effectively describe potential EKG abnormalities. Hence, if an EKG is sufficiently abnormal, the coding and scoring of the present invention can prompt access to the actual tracing (FIG. 10 by special notation in the ASPIRIN™ display (and relevant sites of co-population) if an electronic version is available (as shown in FIG. 3). Otherwise, it may prompt the inclusion of a printed copy with the preoperative note.

In addition, the concise database of text, code and score can be applied to provide patients and their caregivers with compact information about an individual's health status. Data can be stored in common language or code, preferably according the logical branched-chain code described below and with respect to FIGS. 26-31. Selection of information for such storage will depend on the scores of the coded features. For example, it may be limited to conditions which merit a predetermined score (e.g. ≥3) in any of the many components such as SISS™, SMASH™ or the ASPIRIN™ display. If listing is only in code, then the code will relate the system, subsystem, feature category and feature as per FIG. 7, with desired provisions for HIPAA-compliant (i.e., privacy protected) access to all components or selected components with coding. Even without an extensive dictionary, one may readily access a key which relates the codes of individual systems; identification of the systems affected may require little memorization than that required to memorize the names and sequence of the nine planets. Additionally, scores beyond an established cutoff (e.g., ≥2) may drive optional storage of additional information beyond that of coded text (typically of test results), including:

Actual laboratory results

A copy of the patient's EKG since, as noted above, the tracing often is worth a 1000 words. However, while the coding described above allows for consolidated presentation of coded conditions with a sufficient score, printout of an EKG typically is on 8×11 inch paper. Therefore, in order to meet the space confines enabled by score-driven selection of data for card storage, the EKG will be consolidated with inventive processes. In a trial among colleagues at Yale-New Haven Hospital, I confirmed that the configuration shown in FIG. 10 is the smallest that enables visual interpretation of the abnormalities typically responsible for a score≥2. It may be stored as a second wallet-sized card (fits in a holder) or on the back of main information card (described above). Such an EKG may be derived by digital reduction of a commercially available option to configure parallel columns of leads (I, II, III, V1, V2, and V3 on the left; aVR, AVL, aVF, V4, V5 and V6 on the right). The computer can then select the last beat on the left side and the first beat of the right side, with automated industry standard or manual artifact rejection. A rhythm strip may be included thereby enabling visualization of virtually all features summarized by the code and score. To improve communication, this miniaturized EKG can similarly be incorporated in notes such as the official history and physical report, again driven by a cutoff score (which could be overridden by the user).

Systemic Vs Local; Current Vs. Longterm:

For simplicity, features and subfeatures shown herein generally have been associated with a single score—that being the score that reflects systemic impact in the preoperative context. However, as noted above, other alternatives may be indicated in other settings and within a given setting so as to reflect such issues as:

Systemic and Local effects

Current and Longterm effects, with potential subdivisions of current into preoperative, acute, intensive care, and emergency Different forms of the present invention can be adapted to the four potential scoring combinations. However, one score is provided as the default score for the given version; e.g., "systemic/current" for the version displayed in FIG. 32 and FIGS. 26-31, and throughout this document for preoperative assessment. Such uniform scoring can be tailored to the given form. However, one also could retain the options to enable selection of more than one score for a given item so as enable listing of systemic vs. local and current vs. longterm characteristics. This concurrent scoring may take the form of a uniform sequence such as systemic current/local current-systemic longterm/local longterm. As noted above, the default score can be changed for each entry. A preferred option is a drop-down menu. To accommodate changes because of systemic/local or current/longterm categories, this drop-down menu similarly can enable changing options (with appropriate sequences and/or coding).

The systemic and local effects, as well as the acute and chronic effects of a given condition may be recorded with separate programs with options for automated co-population of items with equivalent scores in multiple programs. Alternatively, two or more scores can be provided in a single database. Options include:

Concurrent scoring of systemic and local effects of a disorder. A convention may be established wherein, if both are included, they are configured "systemic/local."

Concurrent scoring of current and longterm effects of a disorder. A convention may be established wherein, if both are included, they are configured "current/longterm"

Concurrent scoring of "systemic/local" and "current/longterm." This may be accomplished as "systemic current/local current-systemic long term/local longterm."

The implications of this approach are delineated in Table 19. It may be particularly helpful in delineating the systemic as well as local effects of the history of present illness, i.e., the reason for surgery. Such detailed distinctions would not be necessary for most conditions. Institutions and/or individuals may determine when multiple scoring would be indicated and which components should be included.

Table 19. Examples of Concurrent Scoring Using the Proposed 0-5 Scale.

(Systemic Current/Local Current-Systemic Longterm/Local Longterm

Macular degeneration causing progressive loss of vision in one eye (wherein effect on the given organ is greater than the systemic effect): 2/3-2/4.

Acute myocardial infarction (wherein the local and systemic effects are comparable): 4-3/4-3.

Controlled hyperthyroidism in patient scheduled for thyroidectomy and subsequent hormone replacement: 2/3-2/2.

Patient with severe as a consequence of severe colitis who is scheduled for resection of the relatively small section of severely diseased bowel: 3/4-1/2

In a preferred embodiment, the default score for each included component will be provided (e.g., current systemic for the preanesthetic assessment, with a drop-down or right-click menu for selecting additional scores.

Interfacing with Other Coding Systems—Overview:

The inventive features described earlier for interfacing with diagnostic and treatment algorithms—e.g., the use of a common language, as facilitated by a conversion dictionary, to document the equivalency (or similarity) of different terms and the use of a score to relate severity—are also relevant to interfacing with other coding systems. Here we see the flexibility of the SHAPE™ system as a means of exporting inventive codes and scores or portions thereof as well as a means for incorporating codes from other systems into the systemic coding and inventive scoring introduced herein.

Potential Applications, Integrations, and Advantages of the Inventive System with Respect to Other Coding Systems:

Many of the advantages of the present system are due to its underlying structure. Whereas a program such as ICD-9 is driven by coding (and accompanying acceptable text), the present invention is driven by systematically obtained clinically relevant text, which in turn systematically generates coding and scoring on a consistent scale.

The present invention of coding and scoring—with its accompanying scorable universal language—provides the details (nature of a patient's disorders and their scored severity), classification, uniformity, and potential multi-purpose integration that are not provided by other methods. The present invention enables scored coding of conditions, lab results, responses to challenges and therapy, and outcome according to categories such as bodily system and severity of disorder/dysfunction. Moreover, it does so at the time of information entry (into clinical note, primary database, and sites of co-populaton)—not by retrospective case-by-case chart review or reliance on recollection in association with coding texts.

The potential for bidirectional information exchange afforded by the present invention enables much-needed systematizing and universalizing of the information sent to or generated by a variety of sources (many of which have been discussed above), including other coding systems. Many are included below to show the universal nature of the inventive system in accordance with Table 3:

different types of visits and different types of encounters questionnaires lab testing (ordering tests, reviewing results)

events (e.g., intraoperative occurrences such as the direct effect of surgery as well as intraoperative and postoperative effects on blood pressure, blood volume, respiratory function, etc.). These not only are scored as outcomes (FIG. 25)—which may be predicted in accordance with the preoperative SHAPE™ database, ASPIRIN™ assessment and derived indices but also as a source of new input into the database—e.g., the RESPIRATORY system may change from a SISS™=2 to a SISS™=4 because of pain-induced ventilatory compromise.

Quality assurance and facilitated compliance with established criteria; e.g. NSQIP criteria within a given system.

Facilitated compliance with standards of care and quality improvement measures; e.g., SCIP measures for antibiotics (based on an inventive score for infection in the "S" of ASPIRIN™

Accrual of data for evidence-based research

Billing based on nature and severity of primary illness, related procedure(s) and nature and severity of comorbidities Other forms of co-population described above when deemed relevant to coding.

Advantages—Integrated Adherence to Required Assessments and Billing Regulations in Accordance with Quality Clinical Care: Current Regulatory Requirements for History and Physical and Coding:

The application of the present invention and its methods to the perioperative period should be viewed in the context of current requirements. Prior to surgery, regulatory agencies currently require:

a surgically focused history and physical exam which focuses on the nature and severity of the surgical problem—signed by the surgeon; and a general history and physical which includes allergies, current medications, social habits (smoking, alcohol, drugs), prior surgeries, review of bodily systems, physical examination (including heart, lungs and vital signs), and relevant laboratory testing (what is relevant is often a subject of debate that may be systematized by the inventive system).

These two components, which are not necessarily incorporated in the same note (e.g., the former may be completed by the surgeon, the latter by the patient's primary care physician), have different coding requirements; i.e., as noted above, the surgical procedure commonly is defined by a CPT code while the patient's morbidities are defined by ICD-9 codes.

Inventive Solutions: Overview

If and when a universal form of coding based on the inventive system is established, then it would be practical to either abolish the other coding systems or, perhaps more appropriately, incorporate the other system(s)'s code in the SHAPE™ data (as detailed below).

Inventive Solutions: Incorporating Established Codes within the Inventive Code/Score A preferred embodiment for uniform coding and scoring of different sources of information entails reliance on the inventive system of coding and scoring, with incorporation of the ICD code into items where an ICD-9 code currently is deemed indicated. An example is the general history and physical described above. Options are provided in Table 20.

In light of the inventor's goal to maintain consistency within the SHAPE™ database, the preferred embodiment retains sequential numbering for the level of branching (e.g., feature, subfeature, or descriptor) for which the code from the alternative source (e.g., the ICD-9 code) applies. There are several potential methods for including both the sequential code and the ICD-9 code, including:

Listing the sequential code and following this with the ICD-9 code which may be designated in a variety of ways including preceding it by a dash or enclosing the ICD-9 code in parentheses (as shown in Table 20).

Listing the sequential code and embedding the ICD-9 at the appropriate level of branching after the sequential code (again, set off by punctuation)

Replacing the sequential code with the ICD-9 code in the appropriate cells (FIG. 14) (preceded in a preferred embodiment by the appropriate number of decimal points to designate the branch level) so long as the program cites it in the corresponding cell assigned to the given item in the database.

Table 20. Examples of Options for Interfacing the Present Invention with Other Coding, e.g. ICD-9

1. Include terms associated with specific ICD-9 codes as hard-coded options. Selection could automatically include the ICD-9 code.

2. Include hard-coded choices or screens that are consistent with categories or subcategories of the ICD-9 system. Selection could automatically jump to a screen wherein the relevant codes and text are listed and/or interface with the appropriate section of the ICD-9 program.

3. Provide options to jump from a given item to a screen(s) with potentially applicable ICD-9 codes and associated terms.

4. Adapt Conversion Dictionary (described in text) to list text and coding synonyms for SHAPE™ vs ICD-9 and enable jumps between them.

5. Click of ICD-9 code, prompting reverse jump to SHAPE™ (Less advantageous because this eliminates many of the advantages of the inventive system, including time of entry coding and scoring, storage in accordance with inventive branched-chain logic).

FIG. 9 illustrates in tabular form how the present invention may be adapted to include the ICD-9 code (or an alternative code) within the inventive coding system. "a" shows this without an inventive score; "b" shows this with an embodiment for the inventive score ($#) at each level of branching.

The behind the scenes conversion and integration may be accomplished in a variety of ways including:
  prescribed item-by-item code incorporation
  prescribed item-by-item code conversion
  prescribed item-by-item integrative index for identical text
  based upon a conversion dictionary which establishes equivalency of different texts
  user determination of text matching
  establishing programs based upon a universal language (text, code, score) so as to minimize the need for specific conversions for different means of data entry and recording Inventive Solutions: Incorporating the Inventive Code/Score in Established Code(s)

If one is performing a surgically focused history and physical or seeing a patient for a focused examination of a specific disorder, then—until the proposed uniform means of coding and scoring described herein is universally adopted (if and when)—it may be more practical to include such information from SHAPE™ in the other (e.g., ICD-9 or CPT) code. While inclusion of the entire SHAPE™ code (as described above) would provide the most complete information and coding, a reasonable compromise would be to simply include a portion of the code and the system or feature score. Adaptation for procedures may be as simple as modifying the CPT code with the SOCU™ score of the inventive system. This enables the code to provide an indication of risk/invasiveness that otherwise might not be evident. Likewise, the codes for anesthesia relative value units can be annotated similarly.

This incorporation of information from the inventive system may be accomplished for classification systems such as the ICD-9 codes and CPT code in a number of ways, including:
  modifying the ICD-9 code so that it lists the system-specific score (e.g., SISS™, SICU™) as may be accomplished by "$#" wherein # is the 1-5 (or 0-5 or other established range) score.
  assigning all or part of the coding for branch logic to the ICD-9 code
  One may export the system code so as to help in categorizing for quality assurance and research purposes. Inclusion of more distal branches will provide greater specificity. Simply providing this level of documentation could unify coding systems with respect to a common logic for organization and a common means of assessing severity.

The system code may be generated from a common list of systems or via computer by creep seek typing which generates the code for the system in addition to its name. Subsystem code may be generated as per above, with the potential to facilitate this with a dropdown menu when a system is selected electronically. Scoring can be generated by the means described for scoring above, with the potential to generate the score electronically if the selection is generated electronically as may be enabled by arrays such as those in Tables 11 and 11b, as well as FIGS. 26-32.

The actual steps may entail a variety of potential means, including:
  simply copying the relevant information from SHAPE™ (e.g., relevant portions of code and score, by hand or electronically) to the ICD-9 code. Equivalence of different textual descriptions may be mediated via the conversion dictionary described above
  providing automated options for selecting a score when assigning the ICD-9 code.

The first of these two options is preferable because then the score is assigned at time of entry of the clinical assessment, without the need to review the record to identify the information needed for such coding and scoring. The advantages of incorporating established codes within the inventive code may be appreciated in the following example: a patient with advanced diabetes and associated atherosclerotic cardiovascular disease sees a physician because of a nonhealing foot infection with evidence of systemic infection. Since this involves multiple systems, it is cumbersome, at best, to capture the multiple presenting problems and relevant comorbidities with current coding. Incorporating the inventive codes and scores likewise could be cumbersome. However, generating the inventive codes and scores (for each system as it relates to the patient's status) as a basic component of the history and physical examination—with incorporation of the established billing codes as deemed indicated—should be far more efficient (and less prone to inadvertent, arguable, or deliberate misrepresentation). Such misrepresentation is a costly process for Medicare and private insurers and for those obligated to justify that they were in compliance.

Alternatively, one simply could add an ASA score to a code such as the ICD-9. However, we believe that is best accomplished with automated conversions described above or template-driven assignments, where there are provisions in the template for any or all of the following:
  score assigned in SHAPE™ or in a comparable program based on the information disclosed herein
  system code in SHAPE™ or in a comparable program based on the information disclosed herein
  more complete code assigned in SHAPE™ with or without the score The aforementioned inventive options for coding and scoring will enable storage in a common database, with the realization that certain cells may not include the full extent of branch-chain logic (e.g., by branching only to the subsystem level). This should provide far greater universality than simply storing according to an ICD-9 code or a CPT code.

Inventive Solutions: Application to the Anesthesia Preoperative Note:

The typical preoperative assessment by an anesthesiologist, the initial focus of many of the embodiments described herein, contains elements of both a specific surgically focused and general history and physical examination. The surgical problem, which may be described at the beginning of the note, as per common practice, in a "history of present illness" commonly referred to as "HPI," may affect multiple systems as is the case for multiple system disorder.

For example, a thyroid abnormality requiring surgery may cause: difficulty swallowing, shortness of breath when lying flat, hoarseness secondary to recurrent laryngeal nerve involvement, hypertension, an abnormal cardiac rhythm (e.g., atrial fibrillation), weight loss, and anxiety. The interaction of the inventive code/score and established codes may be depend on the configuration of the actual note—are the consequences of the abnormal thyroid listed under HPI, under Endocrine/Thyroid, or under the other affected systems. A preferred embodiment entails partial co-population of the relevant sections, with details provided upon jumps to the affected systems/subsystems/feature categories. With such an arrangement, the incorporation of other codes into the inventive system likely would be more efficient that the exportation of inventive codes and scores to means for ICD-9 and CPT coding Clearly, if the latter is employed, the surgical procedure itself (its system code and its system-specific SICU™ score or overall SOCU™ score) could be exported to the other means of coding (e.g., CPT code). However, simply doing that alone would sacrifice potential useful data in that it would not take into account the multiple-system effects of many surgeries that are delineable with the inventive SICU™ score. Again, the inventive system offers the advantage of coding at the time of information entry as opposed to having to match a code to a diagnosis by retrospective review.

This is in contrast to the information provided by the inventive text and its code: nature of the disorder, signs and symptoms, uniformly scored severity of the signs and symptoms (systemic impact and local impact if deemed indicated), and their response to therapy.

Advantages of the Present Invention

The integrative function of the inventive program and the associated inventive indices provide for integrated assessments of disorders and challenges and interventions that are not attainable with other programs (Table 3). Among the components unique to the present invention is the score-driven ability to:
  launch general laboratory testing and specialized testing and score their results;
  direct score-driven triaging to an anesthesiologist and score anesthesiologist's findings;
  generate and justify consultation by the patient's PCP or a specialist and score those findings
  allow for typing free-text which is coded and scored (as described herein)
  maintain a database well-suited for displaying, reporting, analyzing, co-populating, importing and exporting information
  grade significance from different perspectives, including systemic vs. local, acute (perioperative) vs. longterm
  generate score-driven records (e.g., wallet card)
  accelerate the identification of variables and outcomes of QA programs (e.g., NSQIP) and provide a common score-based language for identifying and coding common factors.

Many of the advantages of the present system are due to its underlying structure. Whereas a program such as ICD-9 is driven by coding (and accompanying acceptable text), the inventive system is driven by systematically obtained clinically relevant text, which in turn systematically generates coding and scoring on a consistent scale. Whereas to the inventor it appears that the inventive system should replace a complex system such as ICD-9, it is more realistic to assume that the systems could be integrated with matching of terms analogous to that for Importing and Exporting. Table 20 lists ways in which SHAPE™ could be interfaced with the coding of ICD-9.

The widely used CPT (Current Procedural Terminology) code provides a 5-digit code for procedures. These are grouped as "Evaluation and Management, Anesthesiology, Surgery, Radiology, Pathology and Laboratory, Medicine. As is the case for ICD codes, the CPT coding system lacks the score-based coding that typifies the inventive system. As noted in Table 11b, surgeries impact on multiple systems and thus may be not be amenable to the same branched-chain logic as medical conditions. Adaptation for procedures may be as simple as modifying the CPT code with the SOCU™ score of the inventive system. This enables the code to provide an indication of risk/invasiveness that otherwise might not be evident. Likewise, the codes for anesthesia relative value units can be annotated similarly.

Thus, the present invention provides the basis for detailed scored coding based on branched-chain logic with the potential for: 1) incorporation of an existing code such as ICD-9 and CPT; 2) incorporation of the inventive score in those existing codes. Likewise, there can be integration at specific levels between the inventive system and existing programs that assign codes to health care information. Such codes could be augmented with the inventive scores (e.g., SISS™, SOCU™ and/or SICU™) and other aspects of the inventive system, including: amending coding in accordance with the inventive coding and scoring for branched-chain logic; adapting inventive means for categorizing and scoring type-ins and imports; providing for score-driven displays, scripts, exports, and data transmission and storage.

Overall Database

The overall database can be constructed in a variety of ways, examples of which are shown in FIGS. 13, 14 and 16. The coding of this embodiment is in accordance with the branched-chain logic shown in FIGS. 26-31. The unpopulated database may include all potential entries (positive as well as negative, likely as well as unlikely) and allot space for imports and type-ins (as shown in this arrangement) or it may be configured so that only the selected (positive) entries are entered. The "$" columns enable each scored item to be entered into the appropriate column; the proposed 0-5 scale is shown in this figure. Although potentially requiring more storage space, it may be preferable to assign separate cells to each potential score for a given item.

Other optional aspects of the database include management of potential type-ins and imports. Established items should be hard-coded into the database. For other items, the database can be "expanded" to absorb new entries or cells, with rows and/or columns reserved for type-ins or imports related to a given hard-coded item. The "reservation" could include all or part of the code and default score (with the potential for customization according to the source of import as with a letter suffix). If the potential source is an established source of import, then the actual text may accompany the code in the reserved cell(s) comparable to the arrangement for hard-coded choices. These provisions for add-ins and type-ins can be in columns to the right of the standard hard-coded choices or can be established for entry immediately below the relevant hard-coded choice.

A separate column can designate the source of the information (e.g., current H&P, surgeon's note . . . ). Another column can designate as to sites of co-population and sites of export, in coordination with relationships defined in the conversion dictionary and/or interactive index.

Even if it co-populates multiple regions, a given feature, subfeature or descriptor maintains its level-specific code throughout the database; however, if it co-populates different feature categories, subsystems or systems, the proximal portion of its code will differ.

In embodiments where scoring is based solely on scores assigned to features and subfeatures, it is obvious that scores assigned to more proximal branch levels are based upon the scores associated with the more distal features and subfeatures. Conversely, in embodiments where the level of hard-coded scoring is not limited to features and subfeatures, then it may be important to distinguish between hard-coded and derived scores (e.g., by assigning to different columns, annotating with a letter code, etc).

Additionally, other scoring systems may be employed within the scope and spirit of this invention. This may be achieved by converting other quantitative or qualitative measures to the 1-5 or 0-5 scores described above. Alternatively, an alternative graded range may be utilized (e.g., 0=none, 1=mild, 2=moderate, 3=severe) so long as consistency of scoring among components is maintained.

Whereas the detailed clinical information within the SHAPE™ database would be accessible for integration with a hospital's data network via established links based upon criteria such as name, birthdate and medical record number, inclusion of all data on each patient in a common database likely would be cumbersome. The present invention's consolidation of patient data enables efficient integration of vital data with links to sources of greater detail. FIG. 13 shows how the addition of approximately 15-30 columns increases the robustness of the clinical information in the database from the common listing of demographic data, costs and established codes (e.g., codes for International Classification of Disease (ICD-9) and Current Procedural Terminology (CPT) classifications)—the limitations of which are discussed later in this text—to body system by body system delineation of medical conditions (nature and severity) and, if deemed indicated, comparable delineation of surgical impact, risk indicators and integrated assessments. This provides ready access to such information for functions such as billing, resource allocation, predicting personnel and time requirements, quality assurance, auditing and research. The coding and scoring described herein enable simple linking to the details within the inclusive SHAPE™ database; e.g., more specifics as to the nature of a patient's class 3 disorder(s) of the Cardiac system as summarized at the end of the sample note (FIG. 4) and enabled by the ASPIRIN™ display (FIGS. 6 and 7). The optional linking to the detailed information—as may be indicated for detailed billing, quality assurance (e.g., to confirm adherence to diagnostic and treatment algorithms), medicolegal documentation and research—is mediated by a single cell (e.g., a patient's score for the Cardiac system) in the integrated hospital database, as opposed to a complex array of codes (e.g, ICD-9) which in and of themselves do not indicate disease severity and require a dictionary to identify the nature of the given disorder. To limit the size of the integrated database long-term, a patient's surgical procedure(s) could simply be consolidated according to its overall severity with an inventive code that integrates the risk/invasiveness score and the CPT code, with a link from that single cell to the itemization provided by the SICU™ score when more details are needed about a specific procedure.

FIGS. 17 through 24 are grids, wherein the inventive score is used to consistently assess components of the SHAPE™ database and thereby populate components of the ASPIRIN™ display, co-populate other portions of the SHAPE™ database, co-populate other databases, and drive related algorithms and scripts.

FIG. 17 is a grid that shows how the inventive score drives and chronicles ordering and reviewing common laboratory tests. Code(s) for appropriate healthcare provider(s) to be entered in appropriate cells. One or more healthcare providers should be identified (as having reviewed the results) in each "Results" cell for tests cited as "Indicated" (as may be demarcated by shading).

The Sample Codes for Relevant Healthcare Providers and Information Sources are as follows:

A=Anesthesiologist
C=Consultant
P=PCP
S=Surgeon
H=Automatically generated by History and Physical
L=Automatically (electronically) entered from Laboratory (but not yet reviewed by a healthcare provider
Q=Questionnaire The codes may be generated simply by clicking in the cell or item (after electronic sign-in to the computer) which, in turn, would automatically identify and timestamp the entries of the given healthcare provider.

FIG. 18 is a grid that shows how the inventive score drives and chronicles requesting and reviewing of specialty consultations and specialty testing. The code for the source of request is entered to left of the "I" (based on coding described with respect to FIG. 17); code(s) for healthcare provider(s) reviewing the information to the right of the "/." The noted codes are those as per FIG. 17, and pre-DOS=prior to day of surgery. For many cells, the same healthcare often will designated before and after the "/."

FIG. 19 provides the status of Interim Information and Issues (again on a graded (0-5) scale). Items in this figure, as well as in related figures and tables can be coded so as to generate a "stop" or "alert" or be a component of the pre-incision "time-out" if not documented satisfactorily.

FIG. 20 delineates how the embodiment for driving laboratory testing delineated in FIG. 17 can be applied to liver function tests. The inventive automated score-driven indications for obtaining the tests are based upon an integration of inventive SISS™ and SICU™ scores (and, when indicated, SASRI™ for relevant Risk Indicator).

If the patient has active hepatic (liver) disease (e.g., SISS 4 or 5 for Hepatic system), would likely obtain liver function tests periodically and prior to virtually any challenge. If patient has history of prior liver disease, then decision to obtain liver function tests would depend on combination of the nature and severity of the condition (SISS™ score) and hepatic risk/invasiveness of the planned procedure (e.g., SISS™=3+SICU™=3 provides much greater indication than either score alone). As for other aspects of the inventive program, decisions may be overridden and institutions can establish different cutoffs (without compromising the inter-institutional recording and storage of data entry since that may be entered in accordance with established clinical guidelines and is not influenced by what one subsequently does with the entries).

FIG. 21 is a grid that guides and chronicles ordering of laboratory tests. The default "Y" (or demarcation such as shading) indicates testing may be indicated; it may be replaced a 0-5 number as per laboratory indications (FIG. 17).

FIG. 22 is a grid that shows how the inventive score drives and chronicles decisions about discontinuing a current medication or starting a new medication and/or whether to stop (inactivate) a device such as a cardiac rate management device (e.g., pacemaker or automatic intracardiac defibrillator (AICD). The appropriate cell(s) is/are shaded (by co-population) if given medication is listed in history and physical or in another source of information (e.g., questionnaire) or, in the case of possibly initiating a medication, if a designated indication (as mediated via text, code and score conversion index and dictionary) is recorded. If item is activated without a score, then cells may simply be shaded. Clearly, only one of the two columns concerning a drug typically needs to be completed (and the program readily can be adapted to reflect this).

Code(s) for source(s) of request to address the issue entered to the left of the "/" (based on coding described with respect to FIG. 17); code(s) for healthcare provider(s) generating the order to the right of the "/." As per FIG. 17, the same healthcare often would be designated before and after the "/." A "/" (or an entry to the left of the blank) may not be needed, unless the healthcare provider who identifies the need to make a decision defers the decision to a colleague (e.g., to the cardiologist).

Uniform terminology is provided in left-hand column for simplicity. However, by clicking on a cell, one can discern medication-specific or device-specific scoring graduations that—while remaining compatible with the more general terms—provide more relevant information. For example:

FIG. 24 shows how representative ASPIRIN™ scores can uniformly drive myriad decisions with respect to basic testing, consultations, preop assessment by an anesthesiologist, suitability for fast track discharge from the post anesthesia care unit, and/or likely need for postoperative intensive care unit management. It also illustrates how the inventive system can be applied to nonoperative settings. FIG. 24 illustrates how potential scores may automatically drive the testing, consults and decisions. These decisions may be adjusted in accordance with clinician input. As for the related grids shown herein, clicking on the cell can provide additional details and/or transfer to a more specific grid or to sites of co-population.

*=Columns for ICD9 and CPT codes included herein for completeness;
Y=usually yes;
±=maybe;
Y=likely indicated;
±=borderline; numbers in cells indicate strength of indication (0 to 5 scale) as per FIG. 16; and
X=not applicable because no surgical procedure cited in ASPIRIN™ score.

Looking toward the future of the present system, the following features will be primary sources for future development:
  progressive coding with a fixed variable component
  consistent coding of any or all of the following:
    system-specific ASA score, system-specific assessments of physical status, overall physical status, system-specific scoring of surgical impact, scoring of overall surgical impact
    risk indicators
    indications for testing
    factors affecting ventilation, factors likely to affect intubation
    outcome
    monitoring indices
    criteria for triaging
    quality assurance
    establishing a network of integrative indices based simply on scored assessment of data on routine history and physical and laboratory testing
    use of a conversion dictionary and integration of different features to facilitate textual descriptions, coding that enables relative searching and retrieval, and effective scoring used to interact with other databases
    means to integrate data from other databases Although specific body systems are referred throughout this disclosure in an effort to describe preferred embodiments, those skilled in the art will appreciate the present invention may be applied to a variety of body systems without departing from the spirit of the present invention.

Further to the system described above with reference to FIGS. 1-32, the following figures and tables describe various alternate embodiments for the entry, display, editing, integration, copopulation and exporting of elements calculated in accordance with system described above. The aim is to delinate applications of the invention within an electronic health record (HER). The present embodiment discloses forms of uniform scoring of multiple variables to construct what it is referred to herein as a Scaled Health Information Calculating and Concatenating Tool (SHICCT). This constitutes a preferred mechanism for the determination and integration of inventive scores into the core elements of a HERs.

In accordance with a preferred embodiment, Scaling (i.e., scoring) is on a 0-5 scale (S) of increasing severity and/or acuity and/or restrictions. The invention applies this to a spectrum of Health Information (HI). In addition to Calculating (C) scores on a per-condition or single variable (e.g., blood pressure or heart rate or surgical invasiveness or a laboratory test) basis, the present system enables Concatenation (C) of multiple scored variables on a common scale; disparate variables no longer have to be viewed separately as "apples and oranges" since the uniform scoring transforms them all into a common parameter="fruit." This was demonstrated previously with reference to the system disclosed in FIGS. 1-32, in the form of common scoring, calculations involving multiple variables and readily discernible alphanumeric displays. Having already established the uniform scoring (which, in a preferred embodiment is on a 0 to 5 scale; but clearly would be amenable to another uniform scale), the applications are illustrated within an integrated network such as the proposed Tool (T).

The essence of this continuation is summarized in the following Tables 21-27:

TABLE 21

EXEMPLARY CALCULATIONS INVOLVING TEXT

Automated or User-Activated Uniform Scaling of Text:
  Converting text describing a condition to a scaled value on the common scale
  Converting text identifying a condition to a scaled value on the common scale
  Converting text describing a risk factor to a scaled value_on the common scale
Integrative Calculations:
  integrating uniformly scaled values:
    calculating from text for multiple factors impacting a given condition or system
    calculating from multiple conditions or systems (e.g. SAD score in original disclosure)
  generating mathematically derived scores from the integrated scaled values (e.g., SMASH score in original disclosure)
  assigning points to uniformly scaled values (linear assignment, exponential assignment, etc)
  Determining whether scoring on the common scale should be applied at the level of the condition (or parameter) or at a higher level parent category or overall.

TABLE 22

THE LANGUAGE OF UNIFORM SCALING s:
    Preferred scale is 0 to 5, but an alternative uniform scale could be established within the spirit of this invention
    Conversion of text, unscaled values (e.g., test results) or unscaled scores or points (e.g., for disparate indices of risk and morbidity) to the established common scale Exemplary Alphanumerics:
    Combined letters and numbers for identification and quantification of a system, region, subsystem or condition
    Combined letters and numbers for identification and quantification of test results
    Combined letters and numbers for identification and quantification of the effect of challenges and interventions
    Combined letter and numbers to provide multiple information about uniformly scored parameters (e.g., current smoking status and uniformly scaled categorization of accumulated pack years for smoking)

Symbol-numerics:
    Transient changes in severity: ±
    Uncertainty as to severity: >, < indicates that as additional information is accrued, the condition may be worse or better than currently believed
    Changes in severity that do not warrant a change in score: ↑↓

TABLE 23

MEANS OF ACCOMPLISHING UNIFORM SCALING BY CONVERSION FROM UNSCALED VALUES (EXEMPLARY 0 to 5 SCALE)

Uniform Scale:
    Integer scaling of test value(s) or monitoring parameter(s) abnormalities from 0 (normal or baseline) to +5 (five bins above normal), with gradations, recorded as increased bin #, indicative of progressive distance above normal to a maximum distance of +5 as may be applied to test values and monitoring indices scored with the uniform scale wherein the uniform sequencing for values above normal would be akin to:
        0+1, +2, +3, +4, +5
    And uniform sequencing for values below normal would be akin to:
        −5, −4, −3, −2, −1, 0;
    Scaled score is determined by formulae such as:
        Amount above normal = actual value − normal
        % Above normal = 100 × (actual value − normal)/normal Bin Boundaries may be set by:
    Local consensus, guidelines put forth by experts, regulators or governing bodies so as to reflect gradations akin to borderline abnormal, mildly abnormal, moderately abnormal, severely abnormal, near-fatally/fatally abnormal.
    Math-based Bin Cutoffs: in accordance with predetermined arithmetic ranges wherein such ranges may be based on mathematical determinations such as:
        Median and confidence intervals (CI) for normal values and progressive CI increments from the median value
        Mean and standard deviation (SD) for normal values and progressive SD increments from the mean value
        Documented threshold that indicates a significant difference from normal values and progressive fractions and/or multiples thereof
        Established thresholds for gradations of the progressive severity of abnormal values.

Assigning Points to Compilations of Features Pertaining to a Condition
(e.g. particularly otherwise disparate scorings of indices for asthma, liver disease, . . .)
    Converting independent scores assigned to aspects of a patient's medical condition to a scaled value on the common scale
    Assigning the uniform scale score to an independent compilation of factors related to patient health status wherein the compilation's score is based on the number of factors with or without weighting for perceived importance (e.g NSQIP = National Surgical Quality Improvement Program), wherein the conversion to the uniformly scaled score is calculated with a formula such as:
        Scaled Value/5 = # points for the given patient/# of total potential points within the index
    Solving for Scaled Value on the 0 to 5 scale:
        (# points for the given patient/# of total potential points within the index) × 5

Special Considerations:
  Decimals
    Arithmetic scaling may generate scaled scores which subdivide bins into decimals wherein the precise value is expressed as #.## and additional detail is provided by:
        documenting, tabulating, or graphing the more precise value
        utilizing the more precise value in subsequent calculations

TABLE 23-continued

MEANS OF ACCOMPLISHING UNIFORM SCALING BY CONVERSION FROM UNSCALED VALUES (EXEMPLARY 0 to 5 SCALE)

Compatible Letter Code
    Comparable use of a letter and symbol code such as V, W, X Y, Z, ϕ, A, B, C, D,
    E, wherein the letter code is used so as to avoid potential confusion with unscaled
    raw values that may fall within or near the range of −5 to +5.
    Decimals can be expressed as A.1, A.2, A.3 or A.a, A.b, A.c . . .
Extension Beyond "5":
    When one is recording multiples of CI or SD, it is possible to exceed 5 bins from
    normal. The default is to list the next bins as all-inclusive >5 or <−5 (or >E, <V).
    Options include:
        maintaining all scaled values (even if >5) for calculations but limiting the
        display to the original −5 to 5 or V to E axes;
        establishing a second graph or adjusted axes to show scaled values exceeding
        default limits.

TABLE 24

EXEMPLARY SECONDARY CALCULATIONS GENERATED BY UNIFORM SCALING

Assigning points to uniform scaling wherein the point assignment with increasing scaled value may be linear, exponential or by another means of mathematical conversion
Assigning points to calculated bins in accordance with the distance of a given bin from baseline and wherein the point assignment may be linear, exponential or by another means of mathematical conversion
Summating scores or points (as shown in original disclosure for airway score and integrative scores)
establishing cutoffs based on scaled scores and/or points and determining whether a scaled value or mathematically derived score and/or score-generated points reaches a predetermined threshold or cutoff for a given action.

TABLE 25

EXEMPLARY FEATURES OF CONCATENATION

Linking.
    Via virtual conversion digit-ictionary:
        Linking sites with the same scored variable
        Linking sites with equivalent variables
        Linking sites with coding related to a given condition [e.g., laboratory tests
        which are coded so as designate relation a cardiac condition or a parent
        category (e.g., Ischemic Heart Disease cardiac subsystem or overall Cardiac
        system]
    Denoting and linking sources of a condition with the condition (see Table of
    Prefixes)
    Denoting and linking impacts by a condition with the condition (see Table of
    Suffixes)
    Linking related information with a parent category wherein linking of parent category
    includes region, system, subsystem or feature category, multisystem condition or
    event.
    Denoting and linking information related to a condition, such as test results and flow
    sheets, with the condition.
    Denoting and linking copopulation of identical or related information
Integration:
    Commonly scaled multi-issue score integration.
    Compilation of related uniformly scaled scores to generate an integrated score.
    Integrated commonly scaled score-based display (as per the SHICCT List described
    in text and Table 8;
    Integrated commonly scaled data storage;
    Integrated commonly scaled score-based communication;

TABLE 26

PREFIXES

Prefix indicates "From . . . : i.e., the causes and insults contributing to a given
condition, with options for simply entering the letter code for the system of
the source condition and/or adding row# of the source condition (often
automatically by the computerized program).
Exemplary Endogenous Sources
    From another Condition: e.g., "à ###" (whereà is the 3-4 letter abbreviation for the
    system and ### is the numeric code of the source condition within that system)

TABLE 26-continued

PREFIXES

From a system, subsystem or region (in the absence of knowing a specific condition):
  e.g., "Fromȧ ###." "From . . . row of Chief Complaint
  From a multisystem condition - e.g.,, malignancy, multiorgan autoimmune condition
  From a score or value (e.g., lab results) that impacts the
  receiving row.
  FromTest result
Exemplary Exogenous (e.g., iatrogenic) Factors:
  From negative impact of meds: "MED####" or "CHEMO####
  From negative impact of surgery: "SURG####"
  From negative impact from procedure: "PROC####"
  FromTrauma or Insult "TRAU####")

TABLE 27

EXEMPLARY SUFFIXES

Suffixes indices "To . . . ": refer to outputs (links, actions, outcomes)
  Links:
    "To rowȧ ####" identifies condition(s) affected by the given condition.
    #> rowȧ ####" identifies condition(s) affected by the given multisystem condition.
    "ToMalign###" indicates that details about a malignancy (or possible malignancy),
    including its potential spread and chemotherapy are listed in the Malignancy system . . . (to
    Neoplasm system)
    "ToInf####" indicates that the given condition has caused, or has the potential to cause,
    widespread infection that is detailed in the Infection system.
    "To Heme###" indicates that the given condition has impacted the Hematologic system.
    "To Pain###" indicates that the given condition has impacted the Pain syndrome and that
    the scores for pain are included in the Pain### row.
    Copopulation of risk indices, criteria for testing
    "To Lab###" indicates that the given condition is driving lab test(s)
    "To Tests###" indicates that the given condition is driving other tests
  Actions:
    Initiating or changing therapy,
    pursuing additional testing,
    notifying care giver(s)
    caregiver or patient alerts
  Outputs
    Inclusion on SHICCT (Scaled Health Information Calculation and Concatenation
    Tool) List. This displays and links components of the patient's active record and
    database for display, linking and additional calculation and concatenation and output
    (FIG. 4) and it can be arranged in a variety of ways:
      By bodily system or region
      Chronologically
      Selected for a given provider or type of provider or type of note
      In hierarchal order based on acuity ranking
      In hierarchal order based on severity
      So as to identify times of change
    Stored database
    Given provider's note
    Inclusion on and ranking within a Handoff List between/among care providers
    Printed summary
    Electronic Wallet card or chip:
      Contains summary data (e.g., as displayed on SHICCT List)
      Can access data via wired terminal or internet Further, Table 28 summarizes an embodiment of the common scale for cardiovascular parameters included in the system disclosed above with reference to FIGS. 1-32 as described in Tables 22 and 23.

TABLE 28

|  | <−5 | >−5to ≤−4 | >−4to ≤−3 | >−3to ≤−2 | >−2to ≤−1 | >−1to <0 | 0 |
|---|---|---|---|---|---|---|---|
|  | ≤V.0 | W.9toW.0 | X.9toX.0 | Y.9toY.0 | Z.9toZ.1 | −Φ.1to −Φ.9 | Φ |
| HR | <19 | 20to29 | 30to39 | 40to49 | 50to59 | 60to69 | 70 |
| SBP | <60 | 60to69 | 70to79 | 80to89 | 90to99 | 100to109 | 110 |
| ST segment | <−5 | −5to −4.1 | −4to −3.1 | −3to −2.1 | −2to −1.1 | −1to −0.1 | 0 |
| CVP | <5 | 5to5.9 | 6to6.9 | 7to7.9 | 8to8.9 | 9to9.9 | 10 |

|  | >0to<1 | ≥1to <2 | ≥2to <3 | ≥3to <4 | ≥4to <5 | >5 |
|---|---|---|---|---|---|---|
|  | Φ.1toΦ.9 | A.0toA.9 | B.0toB.9 | C.0toC.9 | D.0toD.9 | ≥E.0 |
| HR | 71to79 | 80to89 | 90to99 | 100to119 | 120to129 | >130 |
| SBP | 111to119 | 120to129 | 130to139 | 140to149 | 150to159 | >160 |

TABLE 28-continued

| | | | | | | |
|---|---|---|---|---|---|---|
| ST segment | 0.1to0.9 | 1.0to1.9 | 2.0to2.9 | 3.0to3.9 | 4.0to4.9 | >5.0 |
| CVP | 10.1to10.9 | 11to11.9 | 12to12.9 | 13to13.9 | 14to14.9 | >15 |

Table 28 illustrates application of the inventive proposed common scale for monitoring parameters which otherwise have markedly disparate data ranges that would limit multiparameter graphical display and interparameter comparison. Each is centered at its consensus "normal" value.

Difference of Given value from normal value determined by the formula:

Difference=Given value−Normal value

% Difference of Given value from normal determined by the formula:

100×(Given value−Normal value)/Normal value

Values determined in accordance with predefined bin boundaries, determined by consensus agreement for the present example (Table 28) are: increments of 10 from a consensus normal of 70 for HR (heart rate), 10 from 110 for SBP (systolic blood pressure), 1.0 from 0 for ST segments (indicative of ischemia on electrocardiogram) and 1.0 from 10 for CVP (central venous pressure).

Looking at Table 28 in detail, the top row shows the bins allotted for the scaled values. The second row shows the alternative options for labeling these bins with successive letters as opposed to successive numbers so as to avoid potential confusion of a scaled value with a raw value (as per Table 23).

Consistent with the embodiment disclosed with reference to FIGS. 1-32, this provides common scaling of variables which otherwise have markedly disparate data ranges that would limit interparameter comparison. Each is centered at its consensus "normal" value; commonly accepted normal ranges are encompassed by −Φ.9 to +Φ.9. Subsequent bins (identified by numbers or alphanumerics) denote multiples beyond the normal range for the given variable.

One has the option to select the centering value, here shown as consensus normal; alternative options include normalizing to single reading or multiple readings at baseline. For simplicity, the table is limited to serial integers; however, within each bin, values can be expressed in decimal increments; e.g., a heart rate of 82 would be +A.2) (Table 23). Decimals may be progressive values within each ordinal (e.g. A to B, B to C) increment or progressive fractions of the increment).

Table 29 shows an embodiment for scaling tests that are reported in the context of the normal median and 95% confidence intervals. Here, the bins are defined as multiples of the "distance" between the median and the 5th or 95th percentile.

FIGS. 33 and 34 illustrate the application of scaling based bin application discussed above in reference to Tables 23, 28 and 29. [FIG. 33 was published as a component of an Abstract at the October 2011 meeting of the American Society of Anesthesiologists in Chicago Ill. and was included as part of U.S. Provisional Patent Application Ser. No. 61/529,636, filed Aug. 31, 2011, entitled "ASA Scores," which is incorporated herein by reference]. In a subsequent Abstract presented at the October 2012 meeting of the American Society of Anesthesiologists and which was included in U.S. patent application Ser. No. 13/459,836, which is incorporated herein, increasing points were assigned for progressive bin distance from normal: in the example shown, 1, 2, 4, 8, 16, and 32 were assigned to bins +1 to +6 and to bins −1 to −6 (wherein 6 represents scaled values<5 (FIG. 35)).

Referring now in detail to FIG. 33, it is shown how the scaling facilitates concurrent display of the frequency distributions of heart rate and blood pressure on common axes. The histograms not only facilitate display but enable determination of the % of readings that differ by a certain degree from normal (or baseline) for subsequent calculation of "lability scores". One has the option to select the denominator for normalization: here shown as consensus normal; alternative options include normalizing to single reading or multiple readings at baseline. For simplicity, the table is limited to serial integers; however, within each bin, values can be expressed in decimal increments; e.g., a heart rate of 82 would be +A.2 (where A corresponds to a 10 mmHg increment and 0.2 corresponds to an additional 2 mmHg increment).

TABLE 29

| Test (Range) | −5 | −4 | −3 | −2 | −1 | 0 | +1 | +2 | +3 | +4 | +5 |
|---|---|---|---|---|---|---|---|---|---|---|---|
| Na+ 135-145 | <115 | 115-120 | 120-125 | 125-129 | 130-134 | 134-145 | 146-150 | 151-155 | 156-160 | 161-165 | >165 |
| K+ 3.5-4.5 | <1.5 | 1.5-1.9 | 2.0-2.4 | 2.5-2.9 | 3.0-3.4 | 3.5-4.5 | 4.6-5.0 | 5.1-5.5 | 5.6-6.0 | 6.1-6.5 | >6.5 |

FIG. 34 illustrates continuous recording of four scaled indices during major surgery; x-axis relates successive time points; left y-axis=sequential + and − numerical categories shown for bins away from normal as shown in top row of Tables 28 and 29; right y axis=sequential+ and − letter categories for bins away from normal as shown in second row of Table 21. The lettered option is introduced for scaled values so as to eliminate any chance of confusing raw values and scaled values. While this use of dual y-axes is helpful for the present explanation, users may prefer to establish the y-axis as a logarithmic scale so as to facilitate display of the very high unscaled (original) values described with respect to Table 23. One also could adjust the y-axis for each parameter so that it corresponds to the inventive means of scaling, thereby enabling parameters to be viewed on a common graph.

FIG. 34 shows how multiple parameters with markedly disparate clinical ranges (e.g. arterial systolic normally ranges from 100 to 150 mmHg while ST segments typically are 0±1 mm) can be displayed, compared and analyzed on common axes. Shading shows how values beyond a predetermined (or adjustable) cutoff can be readily identified for viewing, sending alerts, etc. This may be especially applicable to patients reviewing laboratory results (Table 27) as summarized in Table 29. The provider and/or patient would simply be alerted to values beyond a certain range or serial ranges which can be coded for level of concern. Parameters can be assessed individually or in groups such as a series of liver function tests. Note the option to extend beyond −V to +E range on right axis.

FIG. 35 shows composite scoring of heart rate, blood pressure and estimated blood loss (with the points assigned as described above) compared to a score which assigned points for highest heart rate, lowest blood pressure and blood loss. As shown by the inset, the present method offers far more detail as to the cardiovascular responses.

FIG. 36 illustrates the difficulty viewing laboratory tests with disparate ranges, in this case sodium (normal median=140) and potassium (normal median 4). Plotting raw data on traditional axes obscures vital relationships. The four data points represent: 1) Values at time of diagnosis of hyperaldosteronism (Conn's disease), a disorder which causes high sodium and low potassium. 2) After replenishment of potassium, the impact of which is not appreciated on the potassium tracing. 3) After administration of a diuretic, which lowers both sodium and potassium 4) After excessive replacement of potassium after treatment of the underlying disorder. In all phases, the changes in potassium (include pronounced hyperkalemia at point "4" are barely discernible. and the changing relationship between sodium and potassium cannot be appreciated.

FIG. 37 illustrates how the disparate ranges of sodium and potassium can be converted k to −V to +E based upon 95% confidence interval (CI) increments for each parameter. They now can be viewed on the same scale.

FIG. 38 shows how scaling according the increments of FIG. 37 delineates the changing relationship between sodium and potassium in the context of the hyperaldosteronism described with respect to FIG. 36.

FIG. 39 is designed to show how SHICCT can revolutionize record keeping, providing the "missing link" for assessment, quantification, display, and integration. A main focus of this embodiment is the mechanism of displaying the uniformly scaled data via the SHICCT List (alluded to in Tables 25, 26). This replaces the classic, oft-criticized listing of the currently used Problem List; the classic Problem List is simply a listing of conditions that typically fails to include current activity status, severity (chronic vs acute), or treatments; nor does it provide links among conditions or chart entries pertinent to these vital aspects of the condition.

In contrast, the inventive SHICCT List provides and concatenates calculated scores (numbers, alphanumerics and "symbolnumerics" as described in Table 22) for Activity Status, Chronic Signs & Symptoms, Chronic Composite scores, Acute Signs & Symptoms, Acute Composite scores, and Physiologic and Functional impact—the scores provide a reliable list that you can always "count" on. The use of symbols and letters provide inventive symbol-numerics and inventive alphanumerics that augment the information that is displayed. As described above with reference to FIGS. 1-32, scoring can be applied to local as well as systemic and to acute as well as chronic conditions, to test results, to causes and effects of conditions. The inventive uniform scoring also can be applied to disparate existing condition-specific scores so that they too are amenable to uniform scaling on the SHICCT list.

A preferred SHICCT List embodiment is shown in FIG. 39. It is appreciated the SHICCT List shown with reference to FIG. 39 may be modified to meet user (e.g., institutional) preferences with respect to what information is included and how it is displayed so long as they do not forsake uniform scoring.

The present embodiment, expands the conversion dictionary described above with reference to FIGS. 1-32 to one that is score-based and row number-(alphanumeric) based for linking: items that are scored or are responsible for a given score (another condition, test results, medication which may be expressed as prefixes in our inventive alphanumerics) or affected by the score (e.g., copopulated because of the score; lab tests to be obtained, which may be expressed as suffixes in our inventive alphanumerics).

Referring now to the columns of FIG. 39, an explanation is provided below. Column 1—Row # of Condition on FIG. 39 is the inventive # assigned to a condition based on its parent system/subsystem or region. Similar branched logic coding was described in my original submission. The present description applies it to facilitate display and concatenation via the SHICCT List and related SHICCT components and to achieve the goals of the conversion dictionary disclosed in the original submission: equivalent terms (e.g., for conditions or for signs or for symptoms) appear as the same row #; similar conditions may be grouped according to subsystem row # (s), system or region.

The letters and numbers shown in Table 30 constitute a sample numbering embodiment. Parent bodily system or region denoted by 2-digit number as well as an easily recognizable letter code (e.g., abbreviation for system name; e.g., 02CARD for the Cardiac System). A condition's alphanumeric can be hardcoded in the EHR for common (and even uncommon) conditions or it can be assigned sequentially for the given patient within the range of # s associated with the parent system/subsystem or region. The sequence of numbers is consistent among systems and subsystems. The specific code represents a condition or hardcoded signs and symptoms or freetyping.

TABLE 30

| System, Subsystem, Condition and Related Entries | Row # |
|---|---|
| 00OVERALL | |
|     HARDCODED LISTING OF SIGNS&SYMPTOMS and TEST RESULTS (SST) for UNCERTAIN SYSTEM, SUBSYSTEM AND CONDITION | 1/sst1 to sst##### |
|     FREE TYPE (TYPE) for UNCERTAIN SYSTEM, SUBSYSTEM AND CONDITION | 2/type1 to type#### |
|     CHIEF COMPLAINT (CC) (link in actual note to the appropriate system/subsystem/condition) | CC003 |
|         sst (pertaining to cc) | CC/s# |
|         type (pertaining to cc) | CC/t# |
|     MEDICATIONS, ALLERGIES, PRIOR SURGERIES: coded comparably on a separate list that can be merged with the SHICT Problem List | |

TABLE 30-continued

| System, Subsystem, Condition and Related Entries | Row # |
|---|---|
| 01 CARDIAC (CARD) SYSTEM | 01CARD0-999 |
|    Score for Overall CARD | 01CARD0 |
|    CARDIAC SIGNS AND SYMPTOMS IN ABSENCE OF KNOWN SUBSYSTEM OR CONDTION | 01CARD1-19 |
|       sst (pertaining to overall CARD System) | |
|       type (pertaining to overall CARD System) | |
|    TYPE FOR SUBSYSTEM or CONDITION FOR WHICH THERE IS NO HARDCODED ENTRY | 01CARD20-99 |
|    CORONARY ARTERIES SUBSYSTEM | 01CARD100-199 |
|       SCORE FOR CORONARY ARTERY DISEASE SUBSYSTEM | 01CARD100-s |
|       SIGNS AND SYMPTOMS FOR UNCERTAIN CONDITION WITHIN THIS SUBSYSTEM | 01CARD101-119 |
|          e.g. of sst (pertaining to overall card/cad) | 01CARD101.s# |
|          e.g. of # type (pertaining to overall card/cad) | 01CARD101.t# |
|       HARDCODED CONDITIONS w/in CARD/CAD | 01CARD120-199 |
|       $1^{ST}$ HARDCODED CONDITION | 01CARD121 |
|          sst (pertaining to given condition within card/cad) | 01CARD121.s# |
|          e.g. of type (pertaining to given condition within card/cad) | 01CARD121.t# |
|       $2^{ND}$ HARDCODED CONDITION | 01CARD122 |
|          sst (pertaining to given condition within card/cad) | |
|          type (pertaining to given condition within card/cad) | |
|    VALVULAR DISEASE SUBSYSTEM | 01CARD200-299 |
| 02 RESPIRATORY (RESP) SYSTEM | 02RESP0-999 |
|    Score for Overall RESP | 02RESP0 |
| 03-~20 OTHER SYSTEMS | |
| LABORATORY (LAB) VALUES | LABS0-999 |
|    SODIUM ACTUAL VALUE | LABSrow# |
|    SODIUM SCALED VALE | LABSrow# |
|    TROPONIN ACTUAL VALUE | 01LABSrow# |
|    TROPONIN SCALED VALUE | 01LABSrow# |
| VITAL SIGNS & PHYSIOLOGIC INDICES (VS AND PHYSIOLOGIC INDICES (PHYS) | |
|    BLOOD PRESSURE | |
|    CENTRAL VENOUS PRESSURE | |
|    TEMPERATURE | |

In addition, the list of systems may be preceded by OVERALL, which has specific rows and ranges for Chief Complaint, Other Urgent Issues, Medications, Allergies, Prior Surgeries and related general items and groups. In accordance with a preferred embodiment, all signs & symptoms are listed alphabetically but each may have a code in front to identify the system that the given items typically is associated with—so as to facilitate sorting, finding and displaying. The list of systems is then followed by groupings for Laboratory Tests (LABS) and monitoring (MONIT) values that may pertain to multiple systems. Likewise, this can be done for Laboratory Values. In a preferred embodiment, the default presentation is with the prefix hidden.

As noted above with reference to the embodiment disclosed in FIGS. 1 to 32, coding may be compatible with established means of ICD coding. The designation of a "row #" offers the added advantages of consistency and, consistent with the aims of the conversion dictionary, enables one to readily locate a given condition on the SHICCT list and locate its links to other entries.

Date/Time stamp facilitates separation of multiple entries for the same Condition; in preferred embodiments, this would be entered automatically by the EHR.

In Column 2 of the SHICCT List disclosed in FIG. 4, the Provider Code is the unique #, letter code or preferably α# assigned to each user. In addition to the prior art purpose of identifying the given user, the provider code in the inventive program also designates a provider level which:

determines if and where the given provider may enter/edit inventive scores, and enables sorting/viewing of entries based upon provider status.

This, too, can be scaled in accordance with uniform (e.g., 0 to 5) scaling with 0="best" or, in this case, maximal access (can enter and edit official scores into SHICCT database independently and without the need for a co-sign) and 5=no access. A provider's level may be made readily identifiable by a common formatting technique such as color, shading, font size or by annotating the provider code. Alternatively, one could delineate the provider level code in a separate column.

In Column 3 of the SHICCT List disclosed in FIG. 39, the column for Condition is configured for hardcoded entry and/or freetype (TYPE) entry of a given condition (one per row). User can enter directly onto the SHICCT list but it generally is preferred to populate this column via the Review of Systems (ROS). As information is entered in the ROS, row # s for hardcoded conditions and signs/symptoms are automatically assigned. User is prompted to enter scores (for acuity and severity as described with respect to subsequent columns) or to confirm default score or a prior score. SHICCT list and ROS entries are linked by common row #.

In Column 4 of the SHICCT List disclosed in FIG. 39, Additional Information: alerts the reader that there is additional information pertaining to the condition listing and its scores. "Text" would be selected by default if there is a new or changed score (since it is likely that there would be an explanation for the score in the chart).

In Column 5 of the SHICCT List disclosed in FIG. 39, Prefix: Causes & Inputs provides options, such as those listed in Table 26, for providing information about the source of the given scored Condition or other sites that share the same Condition (i.e., are copopulated as would be the case for a Condition which has been entered as the Chief Complaint) and, if indicated, links to said sources and sites. Default is abbreviated name of system and the source row # (e.g., CARD121) which, as shown on Table 30, indicates a hardcoded condition (e.g., exertional angina) on row #121 within CARD system. Autoentry of α#### codes for paired "From" and "To" sites can be accomplished by a means such as successive clicking the "From . . . " source (Table 26) and the "To . . . " (Table 27) recipient sites in the SHICCT database. These may be linked by a mouse click.

In Column 6 of the SHICCT List disclosed in FIG. 39, Rx ȧ0-5

TABLE 31

Treatments and Their Effectiveness

| Treatment | Treatment ȧ # Code | Decrease of Signs & Symptoms 0-5 Severity Score* | Decrease of Composite 0-5 Severity Score*. |
|---|---|---|---|
| Medical prophylaxis to prevent worsening or complications, but no impact on severity scores | MED####-0 | No impact | No impact |
| Medical reduction of signs & symptoms but not of underlying disorder | M1 | Dec by 0-4 | Dec by 0-1 |
| Medical elimination of signs & symptoms but not of underlying disorder | M2 | Dec by 1-5 | Dec by 0-1 |
| Medical incomplete cure of disorder | M3 | Dec by 0-5 | Dec by 0-4 |
| Medical complete cure of the disorder with sequelae | M4 | Dec by 0-5 | Dec by 0-4 |
| Medical complete cure of the disorder, no sequelae | M5 | Dec by 1-5 | Dec by 1-5 |
| Device prophylaxis to prevent worsening or complications, but no impact on severity scores | | | |
| Device reduction of signs & symptoms but not of underlying disorder | D1 | Dec by 0-4 | Dec by 0-1 |
| Device elimination of signs & symptoms but not of underlying disorder | D2 | Dec by 1-5 | Dec by 0-1 |
| Device incomplete cure of disorder | D3 | Dec by 0-5 | Dec by 0-4 |
| Device complete cure of the disorder with sequelae | D4 | Dec by 0-5 | Dec by 0-4 |
| Device complete cure of the disorder, no sequelae | D5 | Dec by 1-5 | Dec by 1-5 |
| Surgical prophylaxis to prevent worsening or complications, but no impact on severity scores | | | |
| Surgical reduction of signs & symptoms but not of underlying disorder | S1 | Dec by 0-4 | Dec by 0-1 |
| Surgical elimination of signs & symptoms but not of underlying disorder | S2 | Dec by 1-5 | Dec by 0-1 |
| Surgical incomplete cure of disorder | S3 | Dec by 0-5 | Dec by 0-4 |
| Surgical complete cure of the disorder with sequelae | S4 | Dec by 0-5 | Dec by 0-4 |
| Surgical complete cure of the disorder, no sequelae | S5 | Dec by 1-5 | Dec by 1-5 |
| Procedure(nonsurgical) prophylaxis to prevent worsening or complications, but no impact on severity scores | | | |
| Procedure (nonsurgical) reduction of signs&symptoms but not of underlying disorder | P1 | Dec by 0-4 | Dec by 0-1 |
| Procedure (nonsurgical) elimination of signs&symptoms** but not underlying disorder | P2 | Dec by 1-5 | Dec by 0-1 |
| Procedure (nonsurgical) incomplete cure of disorder | P3 | Dec by 0-5 | Dec by 0-4 |
| Procedure (nonsurgical) complete cure of the disorder with sequelae | P4 | Dec by 0-5 | Dec by 0-4 |
| Procedure (nonsurgical) complete cure of the disorder, no sequelae***( | P5 | Dec by 1-5 | Dec by 1-5 |

Potential treatments and their progressive degrees of effectiveness are summarized separately in Table 31. The listings combine potential treatments with progressive degrees of Rx effectiveness.

In Column 7 of the SHICCT List disclosed in FIG. 39, Activity Status provides 1-5 alphanumeric to relate status as to whether resolved, chronic, recently or currently acute and/or acute at a prior date; see Table 32. Activity Status is maintained from the preceding visit. As for scores (described below), information prepopulated from a prior (typically immediately preceding) entry date may initially appear in parentheses. These disappear if the entry is accepted or modified. If the modification involves the Activity Status, then the change is in bold (no italics) for the given date of entry.

Again, the default is to identify that there is additional information in the chart for the same row or range of rows or other sources of information (e.g. Labs, Monitoring which are coded for linking

TABLE 32

ACTIVITY STATUS RANKINGS & ASSOCIATED ALPHANUMERICS FOR CONDITIONS

| Description of Activity Rank for a documented Condition or for Signs/Symptoms of an Undiagnosed Condition | # |
|---|---|
| Negative entry for given potential condition, feature or system | 0 |
| Resolved condition or isolated event without residual dysfunction or continued need for meds | 0 |

TABLE 32-continued

ACTIVITY STATUS RANKINGS & ASSOCIATED ALPHANUMERICS FOR CONDITIONS

| Description of Activity Rank for a documented Condition or for Signs/Symptoms of an Undiagnosed Condition | # |
|---|---|
| Remission with no current evidence of recurrence; not on continued treatment | 1 |
| Chronic (longstanding) Condition; 2P if acute in the distant past; 2F if tends to have minor nonacute fluctuations (e.g. as chronicled by↑, ↓, or ± on severity scores) | 2 |
| New Chronic (nonacute, without flareup) condition; 3F if minor nonacute fluctuations | 3 |
| Acute flareup of a Chronic condition: 4R if recent; 4C if current | 4 |
| New Acute condition: 5R if recent; 5C if current | 5 |

In Columns 8 to 14 of the SHICCT List disclosed in FIG. 4, SCORES: based on activity status (described above), scores in accordance with Table 33 will be entered for:

Chronic Signs & Symptoms and Chronic Composite Score; and/or

Acute Signs & Symptoms and Acute Composite Scores; and

Physiologic Impact and Implications

Functional Impact

If scores available from a prior entry, then they will prepopulate the appropriate cells; otherwise, the user will enter (or modify).

The present disclosure distinguishes between "Signs & Symptoms" and "Composite" so that a user (e.g., a covering care giver who has received a handoff from another care giver) can know whether signs and symptoms are preexisting as well as have an appreciation of underlying severity. Such a simplified score-based breakdown provides a universal means for relating the presence of a condition and its severity.

Scores from the preceding visit appear in parentheses. If the current Activity Status is chronic, then only the chronic cells are prepopulated. If the current Activity Status is acute (e.g., 3R or 3C), then, if available, the chronic as well as acute cells are prepopulated.

Column 8—Chronic Signs & Symptoms: Current chronic (i.e., not acute) score (0 to 5) based solely on patient's signs and symptoms and vital signs at this time as would be obtained during a history and physical. It can be viewed as the typical daily score in the context of the present therapies (Rx).

Column 9—Chronic Composite: Current chronic (i.e., not acute) score (0 to >5) based on the composite severity as evidenced by Chronic Signs & Symptoms+known Underlying Pathology+nature and frequency of flareups+Laboratory tests. so long as they do not justify a change from Chronic to Acute. As noted above, the Composite score is more indicative of a conditions underlying severity than "Signs & Symptoms."

Column 10—Acute Signs & Symptoms: Score (0 to 5) during an acute episode [new (recent or current) Condition or flareup, new treatment or major change in treatment] based solely on patient's signs and symptoms and vital signs at this time.

Column 11—Acute Composite: Score (0 to >5) during an acute episode (new or flareup; recent or current) based on the composite severity as evidenced by Acute (recent or current) Signs&Symptoms+known Underlying Pathology+Laboratory tests.

Column 12—Physiologic Impact: As detailed for the system-specific ASA (American Society of Anesthesiologists) physical status score in my original filing, the Physiologic Impact amounts to what may be considered a condition-specific ASA score: the user assigns a score as if this were the only condition, subsystem, or system exerting physiologic impact on the patient.

If there are multiple conditions within a system, then the default is simply to display the physiologic score for the given system (and not its component conditions which, however, would be readily accessible).

Column 13—Functional Impact: recorded if functional impairment attributed to a nonphysiologic etiology.

Column 14—Scaled established specialty score (as per Table 23).

TABLE 33

Scoring Values and Symbols

|   | Chronic Signs & Symptoms | Chronic Composite | Acute Signs & Symptoms | Acute Composite | Overall Physiologic Impact & Implications |
|---|---|---|---|---|---|
| Values | | | | | |
| 0 | | | | | |
| 1 | Negligible | Negligible | Negligible | Negligible | Negligible |
| 2 | Mild | Mild | Mild | Mild | Mild |
| 3 | Moderate | Moderate | Moderate | Moderate | Moderate |
| 4 | Severe | Severe | Severe | Severe | Severe |
| 5 | Characteristic of organ and/or system failure | Organ and/or system failure | Characteristic of organ and/or system failure | Organ and/or system failure | Life-threatening |
| Symbols | | | | | |
| ≥ | Score assigned is an estimate that, when all information has been acquired, has a good chance of being raised to a higher integer value. | | | | |
| ≤ | | | | | |
| ↑ | Worsening not sufficient to warrant change in score | | | | |
| ↓ | Improvement not sufficient to warrant change in score | | | | |
| ± | Change deemed to be temporary due to transient factors (e.g., if the following prefixes caused transient change as opposed to a new condition or lasting change in an existing condition: surgical insult, procedural insult, accident) | | | | |

↑ and ↓ are not intended to provide subdivisions of the numerical values; instead they are designed to relate worsening or improvement (i.e., relative change) within a given score for the given date of entry; e.g., if a patient with chronic renal insufficiency was assigned a chronic composite score of 3 for a creatinine of 2.5, s/he could be scored 3↑ if the creatinine increased to 2.9; similarly a score of 3 would change to 3↑ if the creatinine increased from 3 to 3.6.
If ± precedes a value, it means that the score likely is temporarily changed to that value (e.g., ±4 means score temporarily changed to 4)
If scores already have been entered from a prior date/time of entry for a given Condition, then the scores for Acuity and Severity appear in parentheses. The user has the option to skip, review or edit Column 15—Suffix: "To . . . ": (Outputs): relates outputs (links) to other areas of the SHICCT list and remaining chart (Table 27)

Column 16—Date of Original Onset will be entered automatically by the computer or should be entered by the user, who first enters information about the problem Columns 17 & 18—Worst Signs&Sympt (<5)(Date) are adjoining columns for entering (typically automatically) the most severe Signs&Symptoms ranging from 1 toy (without discrimination among Chronic or Acute) and the accompanying date Columns 19 &20—Worst Composite (<5)(Date) are adjoining columns for entering (typically automatically) the worst Composite score ranging from 1 to 5 (without discrimination among Chronic or Acute) and the accompanying date Additional Potential Columns include: Patient-specific risks for Anesthesia, Patient-Specific risks for Surgery (e.g. column 21 on FIG. 36).

In summary, the inventive SHICCT provides a heretofore unavailable means of calculating and concatenating multiple components of a patient's health information. The inventive SHICCT List overcomes the limitations of a standard problem list. Furthermore, the SHICCT list provides easy transition to score based features, including:

Ordering of lab tests;
Determination and ranking of items for a handoff list;
Assessment of questionnaires (especially if items on said questionnaire are based on hard-coded conditions and/or signs and symptoms as per Table 4;
Flow sheets of change during a rapid changing clinical state; and
Identification of transient effects (such as transient adverse response to a medication) that otherwise would be buring or paper or lost within an electronic record.
The basis for the wallet card described above with reference to FIGS. 1-32, wherein the SHICCT list or selected components can always be with the patient and, if desired, electronic linkage can be provided (smart card, internet, etc).

The aforementioned embodiments thus have thereby addressed what Anesthesiology News referred to in its article "Towers of Babel in Hospitals as Record Systems Struggle to Communicate" (March 2012).

The present multi-dimensional system and method for assessing, consistently coding, quantifying, displaying, integrating and communicating information relating to patient health and perioperative risk as described above may be implemented using a platform as described below for applying the previously disclosed method and system (and herein described modifications thereof). As will be appreciated based upon the following disclosure, new scaling embodiments are introduced and a platform is provided for universal entry (at the level of universal targets) of universal scores quantifying the activity status (ACT) and severity (SEV) of a patient's conditions at herein-introduced "targets," of which there are approximately 5 to 15 for each of the body's approximately 30 bodily systems. With reference to Tables 34 to 36, the integration of the scaling and formatting (with focus at the bodily system (e.g. cardiac) or region (e.g., leg) level and target level) provides unique embodiments that constitute much-needed re-engineering of the electronic health records. This is complemented by embodiments for applying universal scaling to laboratory test values and physiologic indices with respect to Tables 28 and 29 and FIGS. 25, 33-38.

As will be explained below in greater detail, the previously described system and method is modified to assess ACT as well as SEV of each condition at two specific scoring "sites": first, at the level of the encompassing bodily system or region (SorR) similar to the system-specific score described in above; second, this is achieved in a way that captures local ACT and SEV at the presently introduced "target" level. The "target" level is uniquely designed to capture local impact while avoiding the overwhelming task of trying to apply uniform scaling to thousands of potential patient conditions of varying nature and risk. This "target" provides a unique dimension to the electronic health record, providing a unique way to focus scoring so as to avoid the extremes of vagueness (failure to capture local disorders or the local impact of a widespread condition) and bewildering granularity (overwhelming number of conditions). These now get scored based upon target and encompassing bodily system or region impacts according to heretofore unavailable universal criteria that are amenable to concatenation and calculation within and among different electronic health records. Table 34 displays a preferred embodiment of the conversion dictionary for calculating 0-5 scaled values for Overall Physiologic Status, encompassing bodily system or region overall (pansystemic) impact, Activity Status (ACT) of each condition, Current severity (SEV) at target level, optional entry of Relative Condition SEV (vs. worst possible for given condition) for conditions deemed to be of special importance. The valuable flexible nature of the present inventive uniform scaling is further shown in the right hand column, where it is applied to rate the malignancy of tumors (benign and malignant neoplasms).

More particularly, the present platform is universal and interoperable for quantitative assessment, universal real time communication and interoperable information retrieval across the gamut of a patient's health profile. The foundation for the scaling is provided with reference to the system and method for assessing, consistently coding, quantifying, displaying, integrating and communicating information relating to patient health and, if deemed indicated, perioperative risk as described above. The present platform allows for generalizable scaling of ACT status and SEV. ACT is applied for each condition. SEV is applied first at the level of the encompassing bodily system or region and then at the "target" level. As shown in Table 34, when deemed indicated (for reasons described below), the health care provider has the option to also score the condition's relative SEV. SEV of a condition or disorder means how severe the condition or disorder is relative to its greatest potential severity (which would be "5"). SEV at target is a requisite score that rates severity at the target (regardless of condition's relative severity). Overall Physiologic Disturbance may be determined by calculation (e.g., adding bodily system or region scores) or by clinical judgment (as is the case for the American Society of Anesthesiologists Physical Status score discussed above).

The bodily system or region and "target" levels are scaled by applying a two-component universal template composed of (1) Scaling with a universal range of numerics, in accordance with ScaleMED conversion dictionary (per Table 34) and (2) Applying scaling to universal bodily systems or regions and universal "targets" (Table 35). In particular, such universal assessment of encompassing bodily system or region and template is achieved accordance with the Template for Uniform Numeric Annotation with ScaleMED® (TUNAS) shown in Table 36 by:

first determining if a given System or Region (SorR) has positive condition and if so scoring with scaled value≥1.

If the SorR is ≥1, then the electronic platform (in the form the TUNAS template of Table 36) sequentially prompts the health care provider to enter name of condition in one of two ways:

Option A: Mouseclick Selection from Dropdown Menu of Hardcoded Conditions (per Table 35)
select a condition that is hardcoded per Table 35. (with option for additional description). This not only populates column "Condition Name" with the positive conditions within the given SorR but also automatically enters ###0 and name of the condition(s)' associated target (or #### and name for subtarget—for purposes of simplicity, target and subtarget are collectively referred to a "target"). Said target code is automatically appended with M #, Q # or C # suffix as defined in Table 35.

Option B: Free-type Entry (if condition not on the limited hardcoded list of conditions, e.g. Table 35):
  enter the name of each positive condition (as per typical problem list and/or medical history entry during routine workflow) on successive lines within the SorR;
  select a target from the listings of Table 35. In preferred electronic embodiment, the targets of a given SorR would appear as a dropdown menu; alternatively the limited number of targets (in contrast to thousands of potential conditions) enables all potential targets for a given SorR to be included in the right hand column of the TUNAS template (which may be helpful if one is using a printed template.

If condition is a neoplasm (e.g., mass or tumor), then enter condition's neoplasm score per Table 34.

enter the score for ACT enter the score for SEV at target level, with options for scoring with greater granularity:
  if target identification codec has Q # suffix (per above), then target score is followed by "/" so that health care provider can enter score for the given condition's relative SEV (compared to its worst possible severity as per Table 34), regardless of its impact on the target.
  if target identification codec has M # suffix (per above), then target score is followed by "/" so that health care provider can enter score for the given condition's relative multisystem severity as per Table 34, regardless of its impact on target.
  if target identification codec has C # suffix (per above), then there is not an automated prompt to provide a condition score (which the provider or group of providers has the option of adding). C # is included primarily for providing consistent means of entering—and hence viewing, linking, integrating and retrieving—conditions deemed important (e.g., because of their frequency, impact).

Nothing in the current art approaches the sensitivity, flexibility, universally achievable generalizable granularity of the present invention, encompassing real-time overall physiologic status, system or regional status, impact on targets as well as the widespread impact of multisystem conditions. By scoring target and conditions independently, granularity is achieved without disproportionate weighting (e.g., by a severe form of a relatively harmless condition). #### coding augments universality and interoperability within and among electronic health records for one-time and serial assessments using the universal numeric language. The embodiments described herein (e.g. Tables 34, 35 and 36) and the encompassing Conversion Dictionary (Table 37) are amenable to: inclusion in the electronic health record's core: import as an ancillary platform that is interoperable among different systems, and/or use as a printed template for handwritten entries. With potential links to (or written inclusion of) text and other vital information about the patient's health (if indicated), TUNAS can serve as the main basis for communication among providers, between provider and patient, and with data bases. Flexibility is further achieved by lack of restrictions by check boxes and other forms of rigid criteria (where a new finding about a disease might invalidate prior records relying on rigid criteria). In addition, if deemed indicated after TUNAS is implemented, additional conditions can be tagged with C # (with recommendation that numbering start with C99 and progress backwards). The hierarchy also permits addition of subtargets without compromising universality at the target level. In column for Therapy, provider enters Letter code for different forms of therapy; with (automatic) time-stamp.

Hence, the operability and universality of this two-component universal template is based not only on the uniform means of scaling but also on the grouping and hence scoring of conditions at 5-15 targets for each of approximately 30 encompassing bodily systems or regions. Regardless of the condition, its basic scoring is based on impact on the given target. This allows the impact of all conditions to be recorded, but to not have disproportionate weighting of conditions of relatively minor impact.

With the foregoing in mind, as facilitated by the multiple features of the conversion dictionary (summarized in Table 37), the present invention combines the scaling described above, that is, universal 0 to 5 scaling of a patient's morbidities (herein termed ScaleMED™) with the assignment of the scaled scores in the context of an interoperable platform (Template for Uniform Numeric Annotation with ScaleMED™=TUNAS) and comparable scaling of other indices to provide uniformity among health care providers, institutions, databases, regulatory agencies and patient communication tools. As noted above with reference to Tables 28 and 29 and FIGS. 25, 33, 34, 35, 37 and 38 the uniform scaling of ScaleMED also is introduced for calculation of numerics for laboratory values and physiologic measurements (Scaled Annotation of Labs and Monitoring Outputs with Ordinal Numerals=SALMON).

The present invention therefore unifies vital qualities (e.g., ACT and SEV) with the universal scaling as described above. Table 34 shows uniform 0-5 scaling that is applicable at the time of care at the systemic and local levels. Without trespassing on the vendor-protected, do-not-access (DNA) core, such conversion-generated real-time numeric annotation (cgRNA) tags each entry with universal ordinal numbers for ACT and SEV that are substitutable among different health care providers, different morbidities and different languages [e.g., moderate, medium, "中等" (Mandarin), "moderada" (Spanish) and "modérée" (French) all→"3"].

TABLE 34

CONVERSION DICTIONARY for Numeric Annotation of System or Region (SorR) and Its Potential Targets with ScaleMED ®

| Scaled Value | System or Region (SorR) and Overall (Pansystemic) Impact by condition w/in SorR | Activity Status (ACT) of Given Condition | Current Severity (SEV) @ Target or subTarget | Relative Condition SEV (vs. worst possible for given condition) 1 | Neoplasm Score (N0 to N5) |
|---|---|---|---|---|---|
| 0 | No conditions within SorR | RESOLVED | NONE @ present | RESOLVED | Biopsy negative |

TABLE 34-continued

CONVERSION DICTIONARY for Numeric Annotation of System or Region (SorR) and Its Potential Targets with ScaleMED ®

| Scaled Value | System or Region (SorR) and Overall (Pansystemic) Impact by condition w/in SorR | Activity Status (ACT) of Given Condition | Current Severity (SEV) @ Target or subTarget | Relative Condition SEV (vs. worst possible for given condition) 1 | Neoplasm Score (N0 to N5) |
|---|---|---|---|---|---|
| 1 | SorR contains condition(s) but no/negligible current SorR impact | REMISSION | NEGLIGIBLE | MINIMAL | Apparently resolved |
| 2 | SorR currently impacted; MILD overall impact | CHRONIC - established | MILD | MILD | Suspected to be malignant |
| 3 | SorR currently impacted: MODERATE overall impact | CHRONIC-new nonacute onset | MODERATE | MODERATE | Malignant, Local Primary or from a remote site |
| 4 | SorR currently impacted: SEVERE overall impact | ACUTE EXACERBATION of CHRONIC or RECURRENT | SEVERE | SEVERE | Malignant, Local spread or single metastasis |
| 5 | SorR currently impacted: LIFE-THREATENING, TOTALLY INCAPACITATING | ACUTE ONSET of NEW CONDITION | DESTRUCTION of TARGET or subTarget | WORST POTENTIAL SEVERITY | Malignant, Diffuse spread &/or widespread metastases |

Legend:
Universal 0-5 numeric vocabulary of System or Region (SorR), and the morbidities within, herein termed ScaleMED ®. The sensitivity of scoring may be increased without disturbing consistency: if there is a change in status that does not merit a change in score, it can be identified with an ↑ or ↓.
1 = Although requisite scaling of all conditions is not a feature of preferred embodiments, it may be deemed indicated for selected conditions (as denoted in Tables 35 and 36). In such cases, the relative severity of the condition is scored; this may not correspond to its impact on a given target; e.g., a bad respiratory infection may have a relative severity = 4 or 5 but its impact on its target (the lungs) may be mild or moderate (2 or 3). Condition score may be based on clinical assessment (e.g., signs and symptoms), established criteria for the given condition or, where nonScaleMED scoring has been developed for a specific disorder [as per prior art described above for asthma or for Model for End stage Liver Disease (MELD)], conversion of the prior art condition score to 0 to 5 scale. (As per text, one can avoid potential confusion upon conversion of numbers to scaled values by expressing these scaled values as successive letters (e.g., A to E to represent 1-5). 0 (e.g., signs and symptoms), established criteria for the given condition or, where nonScaleMED scoring has been developed for a specific disorder [as per prior art described above for asthma or for Model for End stage Liver Disease (MELD)], conversion of the prior art condition score to 0 to 5 scale. (As per text, one can avoid potential confusion upon conversion of numbers to scaled values by expressing these scaled values as successive letters (e.g., A to E to represent 1-5).

TABLE 35

| System or Region (SorR) | | Targets and hardcoded subtargets | | Hardcoded Conditions (M#,C#) |
|---|---|---|---|---|
| ##00 | (SorR) Name | ###0 or #### | Name | Within Target or Coded Subtarget |
| 1100 | Central Nervous System -- (Brain) & Psychiatric | 1110 | Brain Parenchyma | C1 = Alzheimer's, c2 = Traumatic Brain Injury, c3 = concussion, c4 = encepaloapthy, c5 = other Confusion, c6 = Parkinsonism, c7 = seizures; c8 == TIA, c9 = Stroke, c10 = autism, c11 = Congenital or birth defect causing neurocognitive dysfunction |
| | | 1120L,R | Myelin and Sheaths | C12 = multiple sclerosis, |
| | | 1130 | Cerebral Vasculature | c13 = Intracerebral hemorrhage |
| | | 1140L,R | Carotid artery(s) | |
| | | 1141L,R | Vertebrobasilar | |
| | | 1142 | Cerebro-venous | c14 = subdural hematoma |
| | | 1143 | CSF & ICP | c15: hydrocephalus |
| | | 1150 | Neuro-Psychiatric | |
| | | 1151 | Situational Anxiety | |
| | | 1152 | Psychiatric Disorder | |
| | | 1153 | Alcohol Dependence | |
| | | 1154 | Drug Dependence | |
| | | 1155 | Eating Disorders | C16 = Anorexia, c17 = bulimia, c18 = BMI >60 |
| 1200 | Spinal Cord & Nerves | 1210 | Spinal Cord | c1 = Quadrapareris; c2 = Quadraplegia; c3 = Paraparesis; c4 = Paraplegia; c5 = ALS; c6 = Autonomic Hyperreflexia, c7 = myelocele |
| | | 1211 | Cervical | |
| | | 1212 | Thoracic | |
| | | 1213 | Lumbosacral | |
| | | 1220 | Peripheral Nerves | c8 = polyneuropathy, c9 = nerve injury |
| | | 1230 | Autonomic Nerves | c10 = autonomic neuropathy |
| 1300 | Eyes, Ears, Face, Head | 1310 | Eyes | C1 = decreased Vision. C2 = cataract, c3 = diabetic retinopathy, c4 = retinal detachment |
| | | 1320L,R | Ears | c5 = decreased hearing, c6 = tinnitus, c7 = Meniere's |
| | | 1330 | Face | |
| | | 1340 | Head | |
| | | 1350 | Cranial nerves | |
| 1400 | Nose, Mouth, Throat, Larynx, Trachea | 1410 | Nose and Sinuses | c1 = infection, c2 = nose bleed |
| | | 1420 | Mouth | c3 = infected tooth, c4 = loose tooth |
| | | 1430 | Throat | |
| | | 1440 | Larynx | C5 = vocal inflammation, C6 = vocal cord injury (BLR), |
| | | 1450 | Trachea | c7 = tracheostomy in place |

TABLE 35-continued

| System or Region (SorR) | Targets and hardcoded subtargets | | Hardcoded Conditions (M#,C#) |
|---|---|---|---|
| ##00 (SorR) Name | ###0 or #### | Name | Within Target or Coded Subtarget |
| 1500 Pulmonary & Intrathoracic | 1510 | Overall Lungs | M1 = flu; c2 = COPD, c3 = ARDS, c4 = pneumonia, c tuberculosis |
| | 1520L,R | Lung Parenchyma | |
| | 1530 | Airways | c1 = asthma, |
| | 1540L,R | Pulmonary Artery | C6 = pulmonary embolism |
| | 1550L,R | Pleura | C7 = pleural effusion |
| | 1560L,R | Diaphragm | |
| 1600 Cardiac | 1610 | Overall Heart | C1 = cardiac arrest, C2 = chf, C3 = dec ejection fraction, C4 = chest pain, c5 = pulmonary edema, C6 = SOB likely card; |
| | 1620 | Myocardium | C7 = infarct, c8 = ischemic region, C9 = LV aneurysm, C10 = diastolic dysfunction,. |
| | 1630 | Coronary Arteries | |
| | 1640 | Valves | |
| | 1641 | Aortic Valve | |
| | 1642 | Mitral Vale | |
| | 1643 | Pulmonary Valve | |
| | 1644 | Tricuspid Valve | |
| | 1650 | Septa | C11 = ASD, C12-VSD |
| | 1640 | Conduction System | C13 = pacemaker; C14 = ICD, C15 = electromechanical dissociation |
| | 1651 | Atrial Conduction | C16 = symptomatic sinus bradycardia, C17 = Atrial fib, C18 = other SVT; |
| | 1652 | Nodal Conduction | C19 = $1^{st}$ dg AVB; C20 = $2^{nd}$ deg AVB; C21 = $3^{rd}$ deg block. |
| | 1653 | Ventricular Conduction | C22 = Vent tach; C23 = Vent fib |
| | 1660 | Pericardium | |
| 1700 Blood Pressure & Vascular | 1710 | Blood Pressure | M1 = hypertension; M2 = hypotension |
| | 1720 | Arterial | C1 = atherosclerotic cardiovascular disease; C2 = ischemia |
| | 1730 | Aorta | |
| | 1740L,R | Renal Arteries | |
| | 1750 | Peripheral arteries | |
| | 1751L,R | UE arteries | |
| | 1752L,R | LE arteries | |
| | 1753 | Intra-abdominal | |
| | 1760 | Venous | C3 = deep vein thrombosis, C4 = phlebitis |
| | 1761L.R | UE veins | |
| | 1762L.R | LE veins | |
| 1800 Endocrine & Glucoregulatory | 1810 | Pancreatic Endocrine & Glucoregulatory | M1 = diabetes mellitus, C1 = other glucose disturbance |
| | 1820 | Pituitary | |
| | 1830L,R | Thyroid | C2 = hyperthyroidism, C3 = hypothyroidism |
| | 1840 | Parathyroid | C4 = hyperparathyroidism |
| | 1850L,R | Adrenal Glands | C5 = Cushing's dis C6 = Addison's dis. C7 = Conn's dis. |
| | 1860 | Neuroendocrine | M2 = pheocromocytoma, M3 = carcinoid |
| 1900 Gastro-Intestinal | 1910 | Upper GI | C1 = nausea, C2 = vomiting; |
| | 1911 | Esophagus and EG junction | C3 = GERD, C4 = Barrett's esoph, C5 = varices, C6 = dysphagia |
| | 1912 | Stomach | C7 = peptic ulcer |
| | 1920 | Lower Gi | C8 = inflamm bowel disease, C9 = diarrhea, C10 = constipation |
| | 1921 | Small Intestine | |
| | 1922 | Large Intestine | |
| | 1923 | Anus | |
| | 1924 | Appendix | |
| 2000 Liver, Pancreas, Spleen | 2010 | Liver | c1 = hepatitis, c2 = cirrhosis, c3 = fatty liver, c4 = liver failure |
| | 2020 | Biliary Tree | C5 = gall stones |
| | 2021 | Gall bladder | C6 = cholecystitis |
| | 2022 | Bile ducts | |
| | 2030 | Portal vessels | C7 = portal hypertension |
| | 2340 | Pancreas (non-endocrine) | C8 = pancreatitis |
| | 2350 | Spleen | |
| 2100 KUBU | 2110L,R | Kidney | C1 = renal insufficiency, c2 = end stage renal disease |
| | 2120L,R | Urinary Tracts | |
| | 2121L,R | Ureter | |
| | 2122 | Bladder | C3 = cystitis |
| | 2123 | Urethra | C4 = Incontinence |
| 2200 Fluids & Electrolytes | 2210 | Fluids | C1 = hypervolemia, c2 = hypovolemia |
| | 2220 | Electrolytes | |
| 2300 Female & Male | 2310 | Pregnancy | C1 = eclampsia, c2 = preeclampsia, c3 = premature labor, c4 = fetal demise |

TABLE 35-continued

| System or Region (SorR) | Targets and hardcoded subtargets | | Hardcoded Conditions (M#,C#) |
|---|---|---|---|
| ##00 (SorR) Name | ###0 or #### | Name | Within Target or Coded Subtarget |
| | 2311 | Female Reproductive | C4 = female infertility, c5 = endometriosis |
| | 2312 | Vagina | |
| | 2313 | Cervix | |
| | 2314 | Uterus | |
| | 2315L,R | Ovaries | |
| | 2330L,R | Breasts | |
| | 2340 | Male Reproductive | C7 = male infertility |
| | 2341 | Penis | |
| | 2342 | Testes | |
| | 2343 | Prostate | C8 = bph, c9 = high PSA |
| 2400 Other Intra-Abdom & Pelvic | 2410 | Mesentery & Peritoneum | |
| | 2420 | Nodes | |
| 2500 Infection & Hematologic | 2510 | Systemic Infection | c1 = HIV, c2 = sepsis |
| | 2510 | WBC | c3 = high WBC, c4 = low WBC |
| | 2520 | RBC | C5 = acute anemia, c6 = chronic anemia, c7 = abnormal RBC |
| | 2530 | Platelets | C8 = high platelets, c9 = low platelets, c10 = antiplatelet therapy |
| | 2540 | Coagulation | C11 = DIC, c12 = decreased coagulation, c13 = increased coagulation, c14 = anticoagulation therapy |
| 2600 Skin, Muscle, Bone, Joints, Connective Tissue & Inflammatory | 2610 | Inflammatory Syndrome | C1 = Lupus, c2 = systemic rheumatoid arthritis, c3 = Sjogren's syndrome |
| | 2620 | Connective Tissue | |
| | 2630 | Joints | C4 = Arthritis |
| | 2640 | Muscles | C5 = myasthenia gravis, c6 = fibromyalgia |
| | 2650 | Skin | |
| | 2660 | Bones | C7 = Osteoporosis |
| 2700 Central Body Regions | 2710 | Neck | |
| | 2720 | Chest Wall | |
| | 2730 | Abdominal Wall | |
| | 2731 | Inguinal LR | |
| | 2740 | Back | |
| | 2741 | Cervical Vertebrae | |
| | 2742 | Thoracic Vertebrae | |
| | 2743 | Lumbosacral Vertebrae | |
| | 2740 | Buttocks | |
| 2800 Upper Extremities | 2910L,R | Arm | C1 = fracture |
| | 2811 L,R | Shoulder | |
| | 2812 L,R | Proximal Arm | |
| | 2813 L,R | Elbow | |
| | 2814 L,R | Forearm | |
| | 2815 L,R | Wrist | |
| | 2816 L,R | Hand | |
| | 2817 L,R | Fingers | |
| 2900 Lower Extremities | 2910 L,R | Leg | C1 = fracture, c2 = amputation |
| | 2911 L,R | Hip | |
| | 2912 L,R | Thigh | |
| | 2913 L,R | Knee | |
| | 2914 L,R | Distal Leg | |
| | 2915 L,R | Ankle | |
| | 2916 L,R | Foot | |
| | 2917 L,R | Toes | |

Legend:
Systems or Regions (SorR), Targets, SubTargets and their corresponding numeric identification codes: ##00, ###0, and ####, with annotations when deemed indicated for hard-coded conditions (C# and names in right-hand column).
M# indicates a condition with multisystem impact (e.g., diabetes).
C# indicates a condition of potential importance (because of features such as frequency or impact and its relevance to clinical care, research and/or quality metrics).

As evident in Tables 34 and 35 and the preceding text, the integrated application of ScaleMED, TUNAS and SALMON addresses heretofore limiting electronic health record deficiencies, succinctly and universally capturing and organizing vital features of virtually any and all patient morbidities and/or laboratory values and physiologic indices. The embodiments shown overcome prior art deficiencies with respect to the extremes of vagueness and overwhelming granularity and lack of generalizability and interoperability.

Furthermore, in addition to aforementioned grouping of physiologic impact at the encompassing bodily system or region level, TUNAS constitutes a foundation for assignment and organization of scaled assessment of severity at the local level that avoids the virtually unaddressable need to otherwise have universal scores for thousands of individual conditions. Hence, two tables (Tables 34 and 35) detail virtually all of the components of universal cgRNA-tagging of virtually every condition; Table 36 shows their application.

TABLE 36

Template for Uniform Numeric Annotation with ScaleMED ® (TUNAS)

| System or Region (SorR) | CONDITION: Free-type per typical routine unless given condition is hardcoded (M# or C# appended to target). If neoplasm, follow condition name with NA (per Table 34). | TARGETS or SUBtargets and Conditions: Select (eg, mouseclick) from SoR-specific menu (e.g., dropdown of targets within given SorR, per Table 35). Target or hard-coded subtarget always scored. Score for hard-coded conditions (M# and C# as per Table 35) should be entered as second value preceded by "/" so as to distinguish from target score.[1] | | | | |
|---|---|---|---|---|---|---|
| ##00 = Name Score | Condition Name N# | Menu Selection: (###0 or ####) Target or Subtarget Name | ACT # | SEV # | Therapy[2] | Optional column for Code and Name of all targets, subtargets and coded conditions per Table 35 |
| 1100 = CNS & Psych 0 1 2 3 4 5 | | | | | | |
| 1200 = SPINAL CORD & NERVES 0 1 2 3 4 5 | | | | | | |

Template for Uniform Numeric Annotation with ScaleMED ® based on universal scaling and System or Region and Target delineation introduced herein. All entries are time-stamped. First 2 of the 29 SorR shown. If given SorR is negative, it can be reduced to one line. Shading shows additional entries to be made by health care provider to populate TUNAS.
[1]Option to achieve additional granularity when deemed indicated by scoring a portion of the target or an actual condition when neither is not hard-coded. User can tag target ### with "sub" and: provide subtarget score after "/" so as leave target store undisturbed. One can identify presence of an otherwise uncoiled condition by appending target with "C" and providing condition score after "/".
[2]Select letter(s) for relevant therapies" C = Chemotherapy, D = device, M = Medication, R = Revascularization, P = nonsurgical Procedure, S = Surgery, T = Transplant; X = Xray therapy.

As shown in Table 35, each target and coded subtarget has an SorR-specific "###0 or ####" identification number (ID). Virtually effortless real time numeric annotation with scores for ACT and SEV can be attached to coded target for real-time linking among chart entries within TUNAS and throughout the electronic health record, as well as for archiving and retrieval for expanded applications. Attaching the code to the universal targets, rather than relying on assignment on a per-vendor or per-program basis, virtually ensures interoperability.

As noted above, the inventive mechanism for tagging each target with an identification number and score enables retrieving and linking that are vastly simplified, especially for use with a computer. That linking can be to other targets and conditions which either cause or are caused by the problem at the given target and/or to laboratory values (as shown above) and medications, etc. For example, if one had a patient with renal disease, s/he can link to the lab values that would be most relevant and even to run charts where they would select the relevant variables. This can form groupings of universally coded variables (e.g., a renal

TABLE 37

Summary of Features of Conversion Dictionary

Conversion of text to uniform scaling of activity status (ACT) (Table 34)
Conversion of text to uniform scaling of severity: overall physiologic status, system or region (SorR), target (and subtargets) within SorR (Table 34)
Conversion of text to uniform scaling of relative severity of conditions (compared to their worst possible severity = 5) (Table 34)
Conversion of patient assessments (e.g., negligible pain = 1, as per text)
Conversion of scoring indices to uniform scaling of SEV*. These may be included as an optional "Prior Art Scoring Indices" column on the TUNAS template and/or wherever the indices are cited in the patient's record. Examples of such conversion include:
    0 to 15 Glasgow coma scale (per FIG. 32.2) to uniform scale
    hypertensive rating (e.g., Report of the Joint National Committee on Prevention,
    Detection, Evaluation, and Treatment of High Blood Pressure, as per text) to
    uniform scale
    Childs-Pugh score of severity of liver disease (FIG. 32.10) to uniform scale
Conversion of test score groupings to uniform scaling
    Obstructive apnea score based upon Apnea Hypoxia Index (FIG. 32.9)
    Scaling of cardiac ejection fraction (FIG. 32.6)
    Scaling of METS (metabolic equivalents during treadmill study) at which time
    patient develops chest pain (FIG. 32.6)
    Conversion of other assessments such as habits and related risk factors to
    uniform scale (e.g., FIG. 11b)
Assignment of tentative scores (potentially more than one) based on text entry in condition column; e.g, Pickwickian = 4 or 5; thyroid storm = 4 or 5; status asthmaticus = 5; inclusion of term "coma" in listing of diabetes (e.g., as "diabetic coma) = 5 (FIG. 32)
Assignment of tentative scores based on study results; e.g. Forced Expiratory Volume in 1 second (FEV1 <800 = 4 or 5) (FIG. 32.9)
Conversion of laboratory data and physiologic measurements to uniform scale according to predetermined criteria (Tables 23, 28 and 29, FIGS. 33-38).
Identification of system or region and target from hard-coded conditions (Tables 35 and 36) as well as from recognition of free-text (FIG. 10) - thereby provide vital consolidation as per Table 35
Matching of text with established coding (FIG. 10, Table 35)

*= To avoid confusion between raw values and scores with scaled values of present invention, conversion dictionary may assign A to E instead of 1 to 5 and −V to E instead of −5 to +5 grouping might include lab tests such as "blood urea nitrogen," creatinine, and potassium). Optional columns can be added for lab links and monitoring links and medication links, as well as other examples of scaling, linking, integrating and applying, shown herein. By providing identifiers for the lab tests and monitoring indices, they too can be readily linked and grouped as deemed indicated. Targets can also be linked to billing and quality assurance codes.

The annotation of the present invention can be expanded by adding new columns to the TUNAS template. At the bodily system or region level, one can add scoring of functional impact, which may be considerably greater than physiologic impact in a bodily region. At the target level, expansion may include universal dropdown menus that list: a) universal features that may be applicable to any target (e.g., infection, ischemia, malignancy, inflammatory, congenital); b) exogenous causes (e.g., habits, trauma, prior anesthetic complication, surgery, adverse event or other iatrogenic); c) another bodily system or region and its targets that impact or are impacted by the given condition and target. It thereby provides unique detail as to the impact of exogenous challenges, e.g., the severity of an adverse event. As noted above, the scaling system and method as described above also can be applied to anesthesia-specific issues, including 0-5 scaled assessments of the patient's airway and of anticipated or resultant surgery. Columns also may be dedicated to easily understood, universal bidirectional provider-patient scaling of status. Patient self-assessment may include self-assessment of pain in accordance with inventive uniform scale: 0=none, 1=negligible, 2=mild, 3=moderate, 4=severe, 5—worst pain imaginable. In selected cases, one may elect to include the condition (as opposed to only target) score (Tables 34-36) to facilitate patient communication.

In addition, as it gains support within an institutional network and hopefully cooperation among vendors, conversion to a numeric scale can be expanded to test results and physiologic indices, replacing flags and "high'/"low" with more meaningful data as addressed with respect to Tables 28 and 29 and FIGS. 25, 34, 35, 36, 37, and 38 (as described above).

Thus, it is anticipated that, in virtually all settings, scaling in accordance with the present invention uniquely can achieve the goals put forth in Table 1. ACT # and SEV # provide universal assessment at universal targets, succinctly and interoperably providing vital information about the status of patient morbidities in accordance with objectives 1 and 2. Scoring of the encompassing bodily system or region, as well as overall, provides physiologic impact. The real time interoperable scaled annotation and coding can be tagged to a condition (e.g., #### C #) for linking throughout the electronic health record(s) and subsequent databases. Supplementing the numeric tag with an abbreviation for treatments and procedures provides additional information as to presence and type(s) of therapy, the timing of which may be provided by formatting (e.g., bold if new) and time-stamping (in accordance with means of time-stamping within given electronic health record. Serial tagging on subsequent encounters (each of which is dated and sequentially numbered) identifies persistence or change of condition's local status and encompassing bodily system or region impact; serial scaling also will enable distinction between new and preexisting morbidities, of particular value in the perioperative setting when there has been an intervening challenge or treatment.

Additionally, scaling in accordance with the present invention will facilitate filtering based on ACT # and SEV # and enable ranking with optional sequestering of inactive/ insignificant conditions Linking may be achieved with optional dropdown menu of etiologies and ID # of the encompassing bodily system or region and targets within TUNAS. In addition, conversion-generated real-time numeric annotation can identify changes associated with adverse events and generate cutoffs for notifications and actions, including alerts and provide a foundation for ICD coding and handoffs. The common scaling language of the present invention facilitates patient-health care provider and patient-electronic health record interaction. Furthermore, the present scaling annotation and TUNAS ID numbering are interoperable among different languages.

In addition, conversion of text to numerals harvests the computing power of electronic health records for cumulative and interval assessments of morbidities and risk assessment indices and outcomes. Scaling in accordance with the present invention when combined with TUNAS thereby would achieve recommendations for both "feed-forward information" in real time perioperative care and for "feedback information" that can be used for future management of the given patient and incorporated into databases for evidence-based practice. (Nelson E C, Fisher E S, Weinstein J N. A perspective on patient-centric, feed-forward "collaboratories." Engineering a Learning Healthcare System: A Look at the Future: Workshop Summary Institute of Medicine (US) and National Academy of Engineering (US) Roundtable on Value & Science-Driven Health Care. Washington (DC): National Academies Press (US); 2011. Pages 149-169; Available at: https://www.asahq.org/sitecore/content/PSH/ learning %20collaborative/. Accessed Sep. 9, 2014. The Perioperative Surgical Home (PSH) A Comprehensive Literature Review for the American Society of Anesthesiologists. (Kash B, Cline K, Menser T, Zhang Y)

The benefits to clinical care passively extend to evidence-based medicine and cost-effectiveness research, addressing the recommendation that data be collected in a consistent format which is maintained throughout reporting processes (Kush R D, Helton E, Rockhold F W, Hardison C D: Electronic Health Records, Medical Research, and the Tower of Babel. N Engl J Med 2008; 358(16):1738-1740 Apr. 17, 2008). TUNAS promotes the interoperability that is vital to this process, including archiving for data registries and applications of "big data." Especially within the TUNAS platform, scaling in accordance with the present invention would optimize propensity matching, a vital component of bias reduction (Cimino J J Improving the electronic health record—are clinicians getting what they wished for? JAMA. 2013 Mar. 13; 309(10):991-2. doi: 10.1001/jama.2013.890) and it would ensure capture of anticipated as well as unanticipated outcomes (that may be missed by selective data forms, checkboxes or post-discharge administrative coding) and thereby avoid such recent failures as delayed ability to appreciate the risk of noncardiac complications associated with increased beta blockers (when the drug was administered to protect the heart) or underreporting of cardiac complications attributable to rofecoxib (when the drug was administered for noncardiac indications). These may be missed if one relies on arbitrary criteria.

Moreover, TUNAS can be adapted to exceed the objectives put forth in Table 1. In accordance with the question raised more than 10 years ago—"is it time for our specialty (anesthesiology) to develop a standardized preoperative assessment . . . and postoperative visit?" (T1116) TUNAS can provide the foundation for universal preoperative and post-operative notes as well as notes throughout a patient's healthcare management. One also can provide for additions (e.g., nonscaled descriptors) so TUNAS can generate a standalone document for handoffs, morning rounds or even discharge summaries as well as wallet card and chips based on cutoffs (individual and integrated). This can drive testing as well as prompt review of relevant textual descriptions (as per current progress notes) and potentially link to relevant entries within TUNAS and throughout the electronic health record. In addition, TUNAS can provide the patient with a succinct, readily viewable scaling "selfie." It thus achieves (and exceeds) Center for Medicare and Medicaid Services' recommendations/requirements for meaningful clinical, administrative and investigative electronic health record use (Blumenthal D, Tavenner M. The "meaningful use" regulation for electronic health records. N Engl J Med. 2010; 363(6):501-4).

Scoring according to the preferred embodiments essentially entails transparent conversion of clinical documentation to generate numeric representation of ACT and SEV at systemic as well as local (target and, when indicated, condition levels. The limited numeric vocabulary provides health care provider—and electronic health record—friendly tagging that is generalizable, substitutable and interoperable. Although varied means of prior art scoring previously has been and continues to be applied to specific settings, no existing method provides a dynamic platform akin to ScaleMED™ arrayed in TUNAS for uniform universal assessment of the gamut of morbidities nor a platform for universal assessment of physiologic and laboratory measurements akin to SALMON—without restrictive (arbitrary yes/no, normal/abnormal) checkboxes for fixed variables. The introduction of scaling in accordance with the present invention and TUNAS thus constitutes the means to achieve integration of features to effectively provide a dynamic platform that chronicles morbidities, test values and physiologic variables. Scaling in accordance with the present invention and its encompassing structure address the extremes of vagueness vs excessive granularity as well as lack of interoperability within and among electronic health records and between health care providers speaking different languages—without need for specially trained professionals for chart review and coding. The embodiments described herein are suitable for incorporation by vendors in their "do-not-access" core, as an imported platform or as a printed template.

While the preferred embodiments, indices and acronyms have been shown and described, it will be understood that there is no intent to limit the invention by such disclosure, but rather, is intended to cover all modifications and alternate constructions falling within the spirit and scope of the invention.

ABBREVIATIONS, ACRONYMS AND TERMS

Inventive Designs and Methods with Respect to ScaleMED, TUNAS and SALMON
ScaleMED™=term introduced for conversion of descriptions of a patient's morbidities at the system or region (SorR), target (designated divisions of each SOR for assessment of impact) and selected conditions with a uniform numeric scale
TUNAS=Template for Uniform Numeric Annotation with ScaleMED™
SALMON=Scaled Annotation of Labs and Monitoring with Ordinal Numerals
00=cording for bodily system and region (SorR)
0=coding for targets within SorR
=coding subtarget within target
0M # and #### M #=target (or subtarget) with suffix with code for multisystem condition
0Q # or #### Q #=target (or subtarget) with suffix with code for hardcoded condition that should be quantified with ScaleMED
0C # or #### C #=target (or subtarget) with suffix with code for hardcoded condition that typically is not quantified with ScaleMED
Inventive Designs and Methods:
SHAPE™=Silverman-Holt Aggregate Preoperative (or, for more general use, Patient) Evaluation method which is generally the present inventive integrative mechanism of quantitative assessment and communication for assessing, coding, quantifying, displaying, integrating and communicating information relating to patient health and perioperative risk. This technique is implemented by displaying various scores relating to bodily functions.
ASPIRIN™=acronym for display or template representing modified ASA score (SISS™), Surgical risk/invasiveness (SOCU™ or SICU™), Physical factors affecting mask ventilation, indicators of Intubation difficulty, special Risk indicators, Interim information & issues, and Needs for the particular case which is used in conveying the various components making up the SHAPE™ score, that is, the present mechanism of quantitative assessment and communication.
SHICCT™=Scaled Health Information Calculating and Concatenating Tool.
SISS™ (or SIS™) score=SHAPE™ Individual Systems Status score, which is the individual body system status score used in the present mechanism of quantitative assessment and communication.
SOCU™ score=SHAPE™ Overall Cutting Upset score (pronounced "sock you"), which is the score relating to surgical risk and invasiveness used in the present mechanism of quantitative assessment and communication.
SICU™ score=SHAPE™ Itemized Cutting Upset score, which is the score relating to delineate the inter-system impact of the planned surgical procedure regardless of the patient's underlying condition used in the present mechanism of quantitative assessment and communication.
SAD™ score=SHAPE™ Aggregate Disorder score, which is the score relating to body systems and their degree of dysfunction used in the present mechanism of quantitative assessment and communication.
SMASH™=SHAPE™ Multifaceted Assessment of Surgical Harm, which is an integration of physical status (ASA score) and Surgical risk and invasiveness (SOCU™ score) used in the present mechanism of quantitative assessment and communication.
SPICE™=SHAPE™ Physical factor and Intubation Composite Evaluation, which is an airway index that typically integrates scores for "Physical factors primarily affecting ventilation" and "Intubation predictors" used in the present mechanism of quantitative assessment and communication.
SMIRC™=SHAPE™ Mask score, Intubation score, and Report score Composite, which is a score based on reports of prior intubations used in the present mechanism of quantitative assessment and communication.
SASRI™=SHAPE™ Alphanumeric Score for Risk Indicators, which is a letter/alphanumeric scored code for such issues that may have an that is disproportionate to their physical status or physical factors affecting mask ventilation, and often depends on the context (e.g., it may be higher for pre-anesthetic care than it would be for chronic medical care).

SCRAP™=SHAPE™ Cardiac Risk Assessment Points, which is scoring converting cardiac risk index to common language and scoring used in the present mechanism of quantitative assessment and communication.

ICD-9$_{SHAPE™}$=ICD-9 (version 9 of International Classification of Diseases) code modified by inventive code and/or score.

CPT$_{SHAPE™}$=CPT (Current Procedural Terminology) code modified by inventive code and/or score.

SHAPE™$_{ICD-9}$=SHAPE™ code and inventive score with inclusion of ICD-9 code.

SHAPE™$_{CPT}$=SHAPE™ code and inventive score with inclusion of CPT code.

TCS Indexionary™=text, code and score conversion index and dictionary

A ### B ### C # D # Z ###=designation of inventive code for system/subsystem/feature category/feature/subfeature and descriptor S/sS/FC/F/sF/ssF/D=system/subsystem/feature category/feature/subfeature/subsubfeature/descriptor $#=inventive score assigned to the given item at the given level of branching

$# A ###$# B ###$# C #$# D #$# Z ###=designation of inventive code and score for system/subsystem/feature category/feature/subfeature and descriptor (which is not scored)

Healthcare providers, Societies and Sources of Information:
PCP=primary care provider
Lab=laboratory
ACC=American College of Cardiology
AHA=American Heart Association
ASA=American Society of Anesthesiologists
ICD-9=International Classification of Diseases (9$^{th}$ edition)
CPT=Clinical Procedure Code
Tests and Indices:
Lytes=blood levels of electrolytes (e.g., sodium, potassium)
LFTs=liver function tests (blood)
BUN=measurement of blood urea nitrogen level
CBC=complete blood count (red blood cells, white blood cells, platelets)
PT/PTT=prothrombin and partial thromboplastin clotting times
EKG=electrocardiogram
BP=blood pressure
HR=heart rate
Other Common Abbreviations:
H&P=history and physical examination
DOS=day of surgery
HPI=history of present illness
AICD=automatic intracardiac defibrillator
Bodily Systems and Subsystems:
   Central Nervous System & Cognitive Disorders (CNS)
   Seizure disorder (CNS$_{seiz}$)
   Cerebral Ischemia (CNS$_{isch}$)
   Nonischemic Cerebrovascular Disorders (CNS$_{nonishcerebvasc}$)
   Nonmalignant Intracranial Mass (CNS$_{nonmalig}$)
   Malignant Intracranial Mass (CNS$_{malig}$)
   Head Trauma (CNS$_{trauma}$)
   Infection (CNS$_{infect}$)
   ICP/Hydrocephalus (CNS$_{ICP}$)
   Cognitive Disorders (CNS$_{cognif}$)
   Parkinsonism & Related Movement Disorders (CNS$_{park}$)
   Other (CNS$_{other}$)
   Psychiatric (PSYCH) & Pain
   Pysch
   Pain
   Endocrine (ENDO)
   Diabetes Mellitus (ENDO$_{diab}$)
   Thyroid mass or dysfunction (ENDO$_{thy}$)
   Parathyroid (ENDO$_{parathy}$)
   Pituitary (ENDO$_{pit}$)
   Steroids/Adrenals (ENDO$_{ster}$)
   Pheochromocytoma (ENDO$_{pheo}$)
   Carcinoid (ENDO$_{carc}$)
   Other (ENDO$_{other}$)
   Cardiac (CARD)
   Ischemic Heart Disease (CARD$_{isch}$)
   Nonischemic Cardiomyopathy (CARD$_{myop}$)
   Congestive Heart Failure (CARD$_{chf}$)
   Exercise Tolerance (CARD$_{exercise}$)
   Valvular Heart Disease (CARD$_{valv}$)
   Septal Defects (CARD$_{septal}$)
   EKG (CARD$_{ekg}$)
   Stress Test (CARD$_{StressEKG}$; CARD$_{scan}$)
   Echocardiogram (CARD$_{echo}$)
   Cardiac Catheterization (CARD$_{cath}$)
   Bradycardia (unless "normal" for patient) (CARD$_{brady}$)
   Tachy Atrial or Nodal Dysrhythmia (CARD$_{atrial}$)
   Ventricular Dysrhythmia (CARD$_{vent}$)
   Other (CARD$_{other}$)
   Hypertension (↑BP)
   Vascular (VASC)
   Peripheral Vascular Disease (VASC$_{pvd}$)
   Venous Disease (VASC$_{ven}$)
   Anomolous Vasculature
   Other (VASC$_{other}$)
   Respiratory (RESP)
   Bronchospastic Disease (RESP$_{spasm}$)
   Restrictive Pulmonary Disease (RESP$_{restrict}$)
   Mixed Obstructive/Restrictive Pulmonary Disease (RESP$_{mixed}$)
   Lung or Mediastinal Malignancy (RESP$_{malig}$)
   Other Lung or Mediatinal Mass (RESP$_{mass}$)
   Obstructive Sleep Apnea (RESP$_{osa}$)
   Injury/Dysfunction (RESP$_{inj}$)
   Upper Respiratory Infection (RESP$_{uri}$)
   Tuberculosis (RESP$_{tb}$)
   Other (RESP$_{other}$)
   Liver, Pancreas & Spleen (LPS)
   Liver Disorder (LPS$_{liver}$)
   Gall Bladder Disorder (LPS$_{gallblad}$)
   Pancreas Disorder (LPS$_{panc}$)
   Spleen Disorder (LPS$_{spleen}$)
   Other (LPS$_{other}$)
   Gastrointestinal (GI)
   Gastroesophageal Reflux (GI$_{gerd}$)
   Other Stomach (GI$_{stom}$)
   Intestinal Disorder (GI$_{int}$)
   Other (GI$_{other}$)
   Kidney, Ureter, Bladder, and Urethra (KUBU)
   Renal Insufficiency (KUBU$_{RENinsuf}$)
   Stones (KUBU$_{stones}$)
   Other Kidney (KUBU$_{RENother}$)
   Other Ureter, Bladder, Urethra (KUBU$_{UBUother}$)
   Female (GYN)
   Pregnancy (PREG)
   Breast (GYN$_{breast}$)
   Fibroids (GYN$_{fibroid}$)
   GYN tumor (GYN$_{tumor}$)
   Other GYN (GYN$_{other}$)
   Male GU
   Prostate (MALE$_{prost}$)
   Penis and Testes (MALE$_{pen\&test}$)

Other Male ($MALE_{other}$)
Neuro-Musculo-Skeletal & Skin (NMS)
Lumbar & Thoracic Spine ($NMS_{spine}$)
Cervical Spine ($NMS_{cerv}$)
Bone ($NMS_{bone}$)
Arthritis ($NMS_{arth}$)
Neural Disorder ($NMS_{neur}$)
Neuromuscular Disorder (NMSnm)
Myopathy ($NMS_{myop}$)
Skin ($NMS_{skin}$)
Soft Tissues & Membranes ($NMS_{soft\ tissue}$)
Burns ($NMS_{burn}$)
Other ($NMS_{other}$)
Eyes, Ear, Nose, and Throat (ENT)
Airway Mass ($ENT_{mass}$)
Vocal Cords and Larynx (nontumor)
Mouth, Nose and Sinuses ($ENT_{nose}$)
Ears ($ENT_{ears}$)
Parotid ($ENT_{parot}$)
Eyes ($ENT_{eyes}$)
Other ($ENT_{other}$)
Hematologic (HEME)
Hypercoagulable State ($HEME_{clot}$)
Bleeding Diathesis ($HEME_{bleed}$)
RBC & Hb Disorders ($HEME_{Hb}$)
WBC Disorders ($HEME_{wbc}$)
Other ($HEME_{other}$)
Fluid & Electrolytes (F&E)
Hypervolemia ($F\&E_{fluid}$)
Hypovolemia ($F\&E_{hypo}$)
Lytes ($F\&E_{lytes}$)
Multisystem Disorders
(see listing at bottom of FIG. 32—text, code and score conversion index and dictionary)

The invention claimed is:

1. A multi-dimensional system that quantitatively organizes otherwise non-quantified and independently quantified information with respect to a patient's medical issues by utilizing commonly scaled numeric rankings comprising:
a computer station comprising:
a graphical user interface for inputting patient information to a database;
a conversion dictionary providing a uniform numeric vocabulary for assessment of text and measurements pertaining to a patient's health status with a common scale associated with a patient's medical condition across multiple variables, the conversion dictionary providing for conversion of patient information input via the graphical user interface to provide common numeric coding and scoring across myriad conditions and bodily systems; and
a processor which calculates health assessments based upon a template and uniform scaling in accordance with the conversion dictionary, activity status for each condition and severity of a patient's condition at a level of an encompassing bodily system and at a target level;
the processor further co-populates information entered for one disorder or body system throughout multiple database fields for various other disorders or body systems by linking the one disorder or body system to various other disorders or body systems so as to integrate clinical, investigative, quality improvement research and administrative functions with common data entry, coding and scoring, the co-populated information being exported for communication, diagnostic and treatment algorithms, quality assurance and quality improvement databases based on identical terminology common terminology based on universal language or common significance based upon text and/or code+score as mediated by the conversion dictionary;
the processor presenting an output to the graphical user interface for providing information relating to health of the patient, which is viewable by the user via the graphical user interface, and includes a score for the physical condition of the patient, a score for the degree of expected surgical risk and invasiveness or a score for other vital assessments of perioperative complexity;
wherein, when graded assessment of the health of the patient is indicated, the output includes one-time or uniformly scaled assessments regarding conditions, targets, systems and/or regions within and among patients presented at the time patient information is input to the database to succinctly and universally capture and organize vital features of patient morbidities and/or laboratory values and physiologic indices.

2. The multi-dimensional system according to claim 1, wherein the conversion dictionary provide common numeric coding and scoring for conditions and bodily systems selected from the group consisting of overall physiologic status, impact of conditions at bodily systems and regions, impact of affected system or region on overall physiologic status, assessment of activity status and severity of conditions and at hardcoded structural and functional targets within each specific system or region, graded assessment of neoplasms scaled assessment of patient risk factors, scaled assessment of challenges and interventions scaled assessment of test results, and scaled assessment of values generated by monitoring a patient's physiologic indices.

3. The multi-dimensional system according to claim 1, wherein the conversion dictionary converts test values and physiologic indices to uniform scaling for multiple parameter display and comparative assessment.

4. The multi-dimensional system according to claim 1, wherein the activity status is categorized with a scaling range encompassing a RESOLVED, REMISSION, CHRONIC-established, CHRONIC-new nonacute onset, ACUTE EXACERBATION of CHRONIC or RECURRENT, and ACUTE ONSET of NEW CONDITION.

5. The multi-dimensional system according to claim 3, wherein severity is categorized with a numeric range encompassing no problem, negligible, mild, moderate, severe, or organ or system failure.

6. The multi-dimensional system according to claim 1, wherein the target level is determined by applying a two-component universal template composed of (1) scaling with a universal range of numerics and (2) applying scaling to universal bodily systems or regions and universal targets.

7. The multi-dimensional system according to claim 1, wherein the output of the processor includes one-time or serial:
uniformly scaled numeric scored assessments regarding health of the patient, including conditions and related patient categories, wherein the related patient categories include bodily regions, bodily systems, subsystems, structural or functional targets, or feature categories;
uniformly scaled numeric score-based information display; and
uniformly scaled numeric score-based information storage.

8. The multi-dimensional system according to claim 1, wherein the commonly scaled numeric rankings are of severity, impact or concern ranging from lowest score akin to "normal, healthy, no problem" to highest score akin to "life-threatening, moribund, critical, total loss of function, or not expected to survive."

9. The multi-dimensional system according to claim 1, wherein calculated and concatenated data are displayed on a scale-based interactive problem list.

10. The multi-dimensional system according to claim 9, wherein concatenation entails commonly scaled multi-issue score integration, enabling compilation of related uniformly scaled scores to generate an integrated score.

11. The multi-dimensional system according to claim 1, wherein decisions with respect to patient care are score-guided by the output, wherein the decisions are selected from the group consisting of assessments relating to laboratory testing, assessments relating to triaging, patient monitoring or treatment, and nature and extent of subsequent patient care.

12. The multi-dimensional system according to claim 1, wherein the output includes a specific report, a score-focused printed summary, a focused electronic summary, a risk assessment index, established guidelines for diagnosis and treatment, patient instructions or an alert to a caregiver or patient.

13. The multi-dimensional system according to claim 1, wherein the conversion dictionary provides common language, coding and scoring for Chronic Signs & Symptoms based solely on patient's signs and symptoms and vital signs obtained during a history and physical.

14. The multi-dimensional system according to claim 1, wherein the conversion dictionary provides common language, coding and scoring for Chronic Composite scores based on the composite severity as evidenced by Chronic Signs & Symptoms+known Underlying Pathology+nature and frequency of flareups+Laboratory tests.

15. The multi-dimensional system according to claim 1, wherein the conversion dictionary provides common language, coding and scoring for Acute Signs & Symptoms based on an acute episode based solely on patient's signs and symptoms and vital signs at this time.

16. The multi-dimensional system according to claim 1, wherein the conversion dictionary provides common language, coding and scoring for Acute Composite based upon an acute episode based on composite severity as evidenced by Acute Signs & Symptoms+known Underlying Pathology+Laboratory tests.

17. The multi-dimensional system according to claim 1, wherein the processor co-populates data fields and performs text matching, code matching and score matching based upon uniform scaling in accordance with the conversion dictionary.

* * * * *